US012729190B2

(12) United States Patent
Chamakuri et al.

(10) Patent No.: US 12,729,190 B2
(45) Date of Patent: Sep. 8, 2026

(54) CORONAVIRUS MAIN PROTEASE INHIBITORS AND METHODS USING SAME

(71) Applicant: Baylor College of Medicine, Houston, TX (US)

(72) Inventors: Srinivas Chamakuri, Houston, TX (US); Shuo Lu, Houston, TX (US); Melek Nihan Ucisik, Medford, MA (US); Ying-Chu Chen, Acton, MA (US); John C. Faver, Medford, MA (US); Ravikumar Jimmidi, Houston, TX (US); Martin M. Matzuk, Houston, TX (US); Timothy Palzkill, Houston, TX (US); Zhifeng Yu, Wayland, MA (US); Damian W. Young, Houston, TX (US)

(73) Assignee: Baylor College of Medicine, Houston, TX (US)

(*) Notice: Subject to any disclaimer, the term of this patent is extended or adjusted under 35 U.S.C. 154(b) by 401 days.

(21) Appl. No.: 18/580,321

(22) PCT Filed: Jul. 18, 2022

(86) PCT No.: PCT/US2022/073853

§ 371 (c)(1),
(2) Date: Jan. 18, 2024

(87) PCT Pub. No.: WO2023/004291

PCT Pub. Date: Jan. 26, 2023

(65) Prior Publication Data

US 2025/0276955 A1 Sep. 4, 2025

Related U.S. Application Data

(60) Provisional application No. 63/223,381, filed on Jul. 19, 2021.

(51) Int. Cl.

| | |
|---|---|
| ***C07D 401/04*** | (2006.01) |
| ***A61K 31/40*** | (2006.01) |
| ***A61K 31/416*** | (2006.01) |
| ***A61K 31/4439*** | (2006.01) |
| ***A61K 31/4725*** | (2006.01) |
| ***A61P 31/14*** | (2006.01) |
| ***C07D 207/12*** | (2006.01) |
| ***C07D 231/56*** | (2006.01) |
| ***C07D 401/14*** | (2006.01) |
| ***C07D 403/12*** | (2006.01) |
| ***C07D 405/04*** | (2006.01) |

(52) U.S. Cl.

CPC ............ *C07D 401/04* (2013.01); *A61K 31/40* (2013.01); *A61K 31/416* (2013.01); *A61K 31/4439* (2013.01); *A61K 31/4725* (2013.01); *A61P 31/14* (2018.01); *C07D 207/12* (2013.01); *C07D 231/56* (2013.01); *C07D 401/14* (2013.01); *C07D 403/12* (2013.01); *C07D 405/04* (2013.01)

(58) Field of Classification Search

CPC .. C07D 401/04; C07D 207/12; C07D 231/56; C07D 401/14; C07D 403/12; C07D 405/04; A61P 31/14; A61K 31/40; A61K 31/416; A61K 31/4439; A61K 31/4725

USPC .......................................................... 514/307

See application file for complete search history.

(56) References Cited

U.S. PATENT DOCUMENTS

| | | | |
|---|---|---|---|
| 2008/0280891 | A1 | 11/2008 | Kelly et al. |
| 2016/0185785 | A1 | 6/2016 | Ioannidis |
| 2017/0050939 | A1 | 2/2017 | Stewart et al. |

FOREIGN PATENT DOCUMENTS

| | | | |
|---|---|---|---|
| WO | 2011109254 | A1 | 9/2011 |
| WO | 2013165606 | | 11/2013 |
| WO | 2017197051 | | 11/2017 |

OTHER PUBLICATIONS

Extended European Search Report issued Sep. 25, 2025 in European Patent Application No. 22846776.7. 11 pages.

St. John, S.E., et al., "Targeting zoonotic viruses: Structure-based inhibition of the 3C-like protease from bat coronavirus HKU4—The likely reservoir host to the human coronavirus that causes Middle East Respiratory Syndrome (MERS)", Bioorganic & Medicinal Chemistry, vol. 23, No. 17, Sep. 1, 2015 (Sep. 1, 2015), pp. 6036-6048, XP055826372, Amsterdam, NL C07D, ISSN: 0968-0896, DOI: 10.1016/j.bmc.2015.06.039.

Supplementary Partial European Search report issued Jul. 2, 2025 in European Patent Application No. 22846776.7. 14 pages.

International Search Report and Written Opinion dated Dec. 6, 2022 for International Application No. PCT/US22/73853.

Chamakury , et al., "DNA-encoded chemistry technology yields expedient access to SARS-COV-2 Mpro inhibitors", PNAS, vol. 118 No. 36 e2111172118, Jul. 21, 2021.

*Primary Examiner* — Kristin A Vajda

(74) *Attorney, Agent, or Firm* — Saul Ewing LLP; Kathryn Doyle; Domingos J. Silva

(57) ABSTRACT

In one aspect, the present disclosure provides compounds which inhibit a coronavirus main protease. In another aspect, the present disclosure provides a method of treating, ameliorating and/or preventing a coronavirus infection in a subject, the method comprising administering to the subject a therapeutically effective amount of a compound of the disclosure. In some embodiments, the method prevents or treats COVID-19 in the subject.

20 Claims, 38 Drawing Sheets

Specification includes a Sequence Listing.

CDD-1714
24.4 nM

CDD-1712
inactive

CDD-1713
64.8 nM

CDD-1793
inactive

CDD-1776
inactive

CDD-1886
inactive

CDD-1976
42 nM

CDD-1847
inactive

CDD1713-1 (1404601) CDD1976-1 (1682271)
CDD1713-2 (1428076) CDD1976-2 (1368146)
CDD1713-3 (1132297) CDD1976-3 (1468100)

MPro melting temperature shift, ΔTm°C

| Compound | 12.5 µM | 25 µM | 50 µM | 100 µM |
|---|---|---|---|---|
| CDD-1733 | 056 ± 0.21 | 2.74 ± 0.63 | 8.90 ± 0.02 | 9.89 ± 0.31 |
| CDD-1819 | 3.06 ± 0.39 | 10.1 ± 0.24 | 14.9 ± 0.17 | 16.1 ± 0.38 |
| CDD-1845 | 8.86 ± 0.17 | 12.9 ± 0.35 | 16.3 ± 0.42 | 18.6 ± 0.23 |

| Assay (half-life) | JQ1 | Alprazolam | CDD-1733 | CDD-1819 | CDD-1845 |
|---|---|---|---|---|---|
| MLM $t_{1/2}$ (min) | 16.4 | 260.1 | 30.1 | 4.85 | N/A |
| HLM $t_{1/2}$ (min) | 9.4 | 978 | 27 | 4.80 | 5.5 |
| MLM $CL_{int}$ (µM/min/mg) | 84.3 | 5.32 | 46.1 | 285.3 | N/A |
| HLM $CL_{int}$ (µM/min/mg) | 146.9 | 1.41 | 51.4 | 285.4 | 250.6 |

SEQUENCE LISTING

```
Sequence total quantity: 9
SEQ ID NO: 1           moltype = DNA  length = 48
FEATURE                Location/Qualifiers
source                 1..48
                       mol_type = other DNA
                       organism = synthetic construct
SEQUENCE: 1
ggtggctcat atgtcggcag tgctgcaatc cggctttcgc aaaatggc                48

SEQ ID NO: 2           moltype = DNA  length = 59
FEATURE                Location/Qualifiers
source                 1..59
                       mol_type = other DNA
                       organism = synthetic construct
SEQUENCE: 2
gccacctgga tccttaatga tgatgatgat gatggggacc ctggaaggtt acaccagag   59

SEQ ID NO: 3           moltype = AA  length = 10
FEATURE                Location/Qualifiers
source                 1..10
                       mol_type = protein
                       organism = synthetic construct
SEQUENCE: 3
SAVLQSGFRK                                                          10
```

-continued

```
SEQ ID NO: 4            moltype = AA  length = 8
FEATURE                 Location/Qualifiers
source                  1..8
                        mol_type = protein
                        organism = synthetic construct
SEQUENCE: 4
SGFTFQGP                                                  8

SEQ ID NO: 5            moltype = AA  length = 14
FEATURE                 Location/Qualifiers
source                  1..14
                        mol_type = protein
                        organism = synthetic construct
SEQUENCE: 5
KTSAVLQSGF RKME                                           14

SEQ ID NO: 6            moltype = DNA  length = 12
FEATURE                 Location/Qualifiers
source                  1..12
                        mol_type = other DNA
                        organism = synthetic construct
SEQUENCE: 6
acacttgctg gt                                             12

SEQ ID NO: 7            moltype = DNA  length = 12
FEATURE                 Location/Qualifiers
source                  1..12
                        mol_type = other DNA
                        organism = synthetic construct
SEQUENCE: 7
cagcaagtgt ga                                             12

SEQ ID NO: 8            moltype = DNA  length = 56
FEATURE                 Location/Qualifiers
source                  1..56
                        mol_type = other DNA
                        organism = synthetic construct
SEQUENCE: 8
tatgatacta aagtaagtca cacacaattg gagcagtcct gagtgaatac ctgcat      56

SEQ ID NO: 9            moltype = DNA  length = 58
FEATURE                 Location/Qualifiers
source                  1..58
                        mol_type = other DNA
                        organism = synthetic construct
SEQUENCE: 9
atgcaggtat tcactgagga ctgctccaat tgtgtgtgac ttactttagt atcatatc    58
```

CORONAVIRUS MAIN PROTEASE INHIBITORS AND METHODS USING SAME

CROSS-REFERENCE TO RELATED APPLICATIONS

This application is a 35 U.S.C. § 371 national phase application from, and claims priority to, PCT International Patent Application No. PCT/US2022/073853, filed Jul. 18, 2022, which claims priority under 35 U.S.C. § 119(e) to U.S. Provisional Patent Application No. 63/223,381, filed Jul. 19, 2021, which applications is are hereby incorporated herein by reference in their entirety.

STATEMENT REGARDING FEDERALLY SPONSORED RESEARCH OR DEVELOPMENT

This invention was made with government support under P20CA221729 awarded by National Cancer Institute. The government has certain rights in the invention.

SEQUENCE LISTING

The ASCII text file named "046641-7049WO1—Sequence Listing," created on Jul. 15, 2022, comprising 8.9 Kbytes, is hereby incorporated by reference in its entirety.

BACKGROUND OF THE DISCLOSURE

On Mar. 11, 2020, the World Health Organization recognized the coronavirus disease 2019 (COVID-19) outbreak caused by severe acute respiratory syndrome coronavirus 2 (SARS-CoV-2) as a pandemic. Although vaccines are being approved for emergency use to fight COVID-19, there is an urgent need for effective new drug treatments to reduce the morbidity and/or mortality for patients who have already contracted COVID-19, not yet received the vaccine, are infected with SARS-COV-2 variants that are more resistant to the vaccines, and/or for future coronavirus pandemics.

Currently, there is no effective, specific treatment regimen for COVID-19. The statistics show that the lethal outcomes of the infection worsen with age and underlying conditions like diabetes, hypertension, asthma, and chronic obstructive pulmonary disease (COPD), among others. Immunocompromised individuals and people from disadvantaged socioeconomic backgrounds are also in great danger of detrimental results. The world has already suffered a heavy death toll of nearly 3 million people, with the US ranking first with its about 570,000 casualties. The lack of specific treatments led the Food and Drug Administration (FDA) to issue emergency use authorizations (EUA) for a few existing therapies. Among these, Remdesivir, originally an Ebola treatment, and convalescent plasma from recovered patients have been effective in shortening the recovery times of hospitalized patients in critical condition. In contrast, the EUAs for hydroxychloroquine sulfate and chloroquine phosphate were revoked due to cardiac side effects and lack of efficacy. Clearly, there is an extremely urgent need worldwide for a specific and effective treatment.

While several vaccines against COVID-19 have received an EUA, a recent NBC poll showed that only 44% of the American population would agree to be vaccinated with a government-approved coronavirus vaccine. Moreover, some of the approved vaccines have led to severe blot clots in a small population of vaccinated individuals. Further questions of what population groups can safely receive the vaccine (not yet approved for use in children), whether all vaccinated individuals would develop immunity for an elongated time, and whether such a vaccine could be safely distributed to especially underdeveloped parts of the world remain unanswered. Even following the rapid development of an effective COVID-19 vaccine against the current strains of SARS-COV-2, there has to be a constant global monitoring effort for the emerging strains akin to the monitoring of the influenza strains. Potential seasonal mutations of viral strains limit the effectiveness of developed vaccines, as they can only capture the known strains at the time of formulation. A case in point, the influenza vaccine effectiveness was only about 40% effective for the 2019-2020 season according to the Centers for Disease Control and Prevention. Thus, safe, orally bioavailable drugs that are stable at room temperature and hence straightforward to distribute and store would provide a huge opportunity in treating already symptomatic infections, for prophylactic use, and for emerging coronavirus infections.

There is thus a need in the art for novel compounds that treat, ameliorate, and/or prevent coronavirus infections and methods of using these compounds. The present disclosure addresses these needs.

BRIEF SUMMARY OF THE INVENTION

The present disclosure provides certain compounds of formula (I) and/or (II), or a salt, solvate, stereoisomer, tautomer, isotopically labeled derivative, or geometric isomer thereof, wherein the substituents in (I) and/or (II) are defined elsewhere herein:

(I)

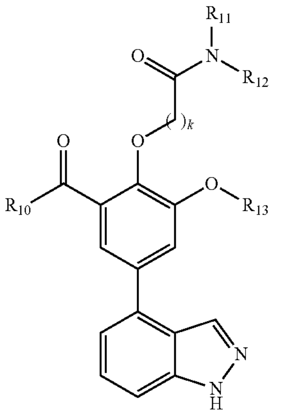

and (II)

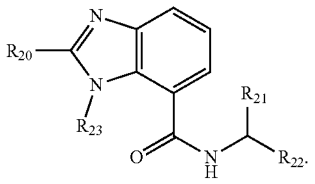

The present disclosure further provides pharmaceutical compositions comprising at least one compound of the present disclosure. In certain embodiments, the pharmaceutical composition further comprises at least one pharmaceutically acceptable carrier. In other embodiments, the pharmaceutical composition further comprises at least one additional agent useful for treating, ameliorating, and/or preventing a coronavirus infection.

The present disclosure further provides methods of treating, ameliorating, and/or preventing a coronavirus infection in a subject. In certain embodiments, the method comprises administering to the subject a therapeutically effective amount of at least one compound of the present disclosure. In certain embodiments, the coronavirus is at least one of 229E, NL63, OC43, HKU1, MERS-COV, SARS-COV, and SARS-COV-2. In certain embodiments, the compound and/or pharmaceutical composition is administered to the subject orally or intravenously. In certain embodiments, coronavirus main protease ($M^{pro}$) is inhibited in the subject.

BRIEF DESCRIPTION OF THE DRAWINGS

The following detailed description of exemplary embodiments of the disclosure will be better understood when read in conjunction with the appended drawings. For the purpose of illustrating the disclosure, non-limiting embodiments are shown in the drawings. It should be understood, however, that the disclosure is not limited to the precise arrangements and instrumentalities of the embodiments shown in the drawings.

FIG. 5A: Concentration-dependent inhibition curve of CDD-1713. FIG. 5B: Concentration-dependent inhibition curve of CDD-1714. FIG. 5C: Concentration-dependent inhibition curve of CDD-1976.

FIG. 8A: Structure of $M^{pro}$ with CDD-1713. The $F_o$-$F_c$ density map is shown for the inhibitor with contouring level at 30. The catalytic site is located within the square. FIG. 8B: Magnified view of the catalytic center. The $M^{pro}$ amino acid residues involved in CDD-1713 binding are shown as stick models and labeled. $M^{pro}$ residues that form hydrogen bonds (dashed black lines) and van der Waals interactions with CDD-1713 are indicated. One water molecule involved in hydrogen bond was indicated. The side chain of Asn142 is not shown to avoid obstruction of the view of hydrogen bonds on the aldehyde group. FIG. 8C: $F_o$-$F_c$ omit maps showing electron density of the covalent bond formed between Cys145 and CDD-1713 contoured at 3 s. Continuous electron density is present between C13 on the aldehyde group of CDD-1713 and thiol on the side chain of Cys145. FIG. 8D: 2D diagram of the $M^{pro}$ interaction with CDD-1713 generated by Ligplot$^+$. Carbon atoms, nitrogen atoms, and oxygen atoms are shown. Hydrogen bonds are represented as black dashed lines and hydrophobic contacts are represented as spoke arcs. Water molecule was presented as spheres. The length of each hydrogen bond is labeled.

FIG. 13A: Gel chromatogram of the purified SARS-COV-2 $M^{pro}$ sample. FIG. 13B: Purified SARS-COV-2 $M^{pro}$ exhibited protease activity in the FRET-based assay. "PP" stands for pure substrate peptide.

FIG. 14A: CDD-1713 was found to have an apparent $K_i$ of 64.8 nM. FIG. 14B: CDD-1714 was found to have an apparent $K_i$ of 24.4 nM. FIG. 14C: CDD-1733 was found to have an apparent $K_i$ of 14.9 nM. FIG. 14D: Inhibition of human thrombin, a Ser-protease, by CDD-1713, CDD-1714, and CDD-1733. No inhibition was associated with these compounds in a fluorescence assay. CDD-1472, a 1 nM thrombin inhibitor, was used as control.

FIG. 15A: Structure of $M^{pro}$ (Tan) with CDD-1733 (pink). The $F_o$-$F_c$ density map is shown for the inhibitor with contouring level at 36. The catalytic site is located within the square. FIG. 15B: Magnified view of the catalytic center. The $M^{pro}$ amino acid residues involved in CDD-1733 binding are shown as stick models and labeled. $M^{pro}$ residues that form hydrogen bonds (dashed black lines) and van der Waals interactions with CDD-1713 are indicated.

DETAILED DESCRIPTION OF THE DISCLOSURE

Figure 1:
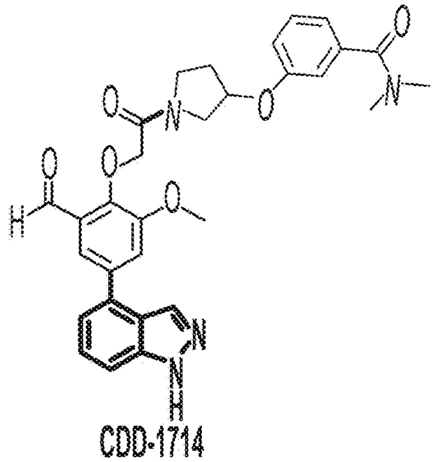
FIG. 1 depicts certain small molecules contemplated within the disclosure.
Figure 1:
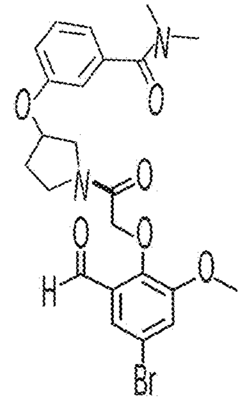
Figure 1:
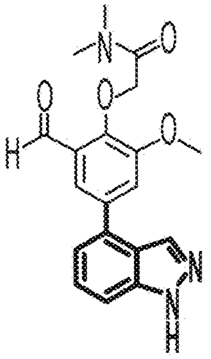
Figure 1:
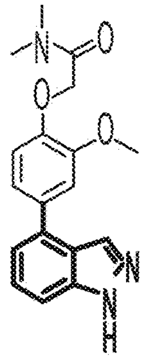
Figure 1:
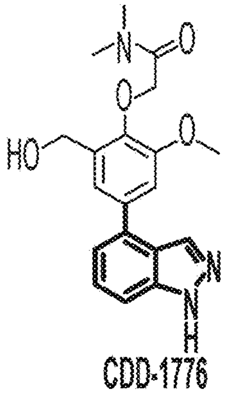
Figure 1:
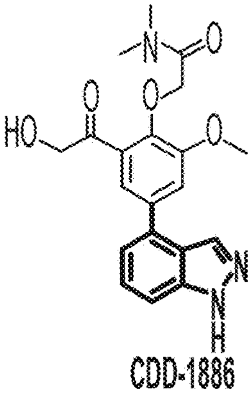
Figure 1:
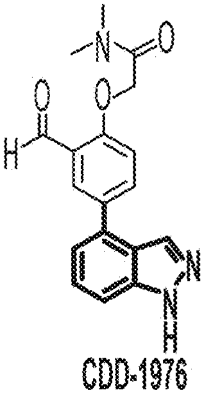
Figure 1:
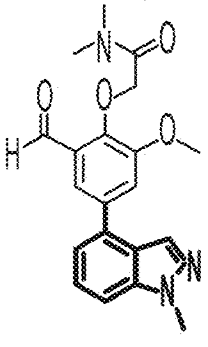

SARS-COV-2 is a positive-stranded, enveloped RNA virus, which was first evidenced in the bronchoalveolar lavage fluid of patients in Wuhan hospitals. Its genome comprises six major open-reading frames (ORF), like many other coronaviruses, along with some other accessory genes. The polyproteins encoded by ORF 1a and 1ab are used to create functional proteins by extensive proteolytic processing, which perform essential tasks pertaining to viral replication, transcription, viral assembly and immune response modulation. This processing is mainly achieved by the main protease ($M^{pro}$ or $3CL^{pro}$). Hence, $M^{pro}$ is indispensable for the viral lifecycle and thus a key therapeutic target.

The present disclosure provides, in one aspect, compounds that inhibit coronavirus main proteases. In some embodiments, the compounds inhibit the SARS-COV-2 $M^{pro}$. In certain embodiments, the compound is a compound of formula (I), or a salt, solvate, stereoisomer, tautomer, isotopically labelled derivative, or geometric isomer thereof. In other embodiments, the compound is a compound of formula (II), or a salt, solvate, stereoisomer, tautomer, isotopically labelled derivative, or geometric isomer thereof.

The present disclosure further provides a method of treating, ameliorating, and/or preventing a coronavirus infection in a subject. In certain embodiments, the method comprises administering to the subject a therapeutically effective amount of a compound of the disclosure. In certain embodiments, the compound of the disclosure is administered to the subject prophylactically to prevent a coronavirus infection. In other embodiments, the compound of the disclosure is administered to a subject with a symptomatic or asymptomatic coronavirus infection to treat the infection. In some embodiments, the coronavirus infection is COVID-19. In some embodiments, the compound of the disclosure is orally administered to the subject.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, $-CH{=}C{=}CCH_2$, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, cyclohexenyl, cyclopentenyl, cyclohexadienyl, butadienyl, pentadienyl, and hexadienyl among others.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, —NHR, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "aminoalkyl" as used herein refers to amine connected to an alkyl group, as defined herein. The amine group can appear at any suitable position in the alkyl chain, such as at the terminus of the alkyl chain or anywhere within the alkyl chain.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

As used herein, the term "composition" or "pharmaceutical composition" refers to a mixture of at least one compound described herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

The terms "halo," "halogen," or "halide" group, as used herein, by themselves or as part of another substituent, mean, unless otherwise stated, a fluorine, chlorine, bromine, or iodine atom.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heteroarylalkyl" as used herein refers to alkyl groups as defined herein in which a hydrogen or carbon bond of an alkyl group is replaced with a bond to a heteroaryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise, a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, wherein $X^1$, $X^2$, and $X^3$ are all different, wherein $X^1$ and $X^2$ are the same but $X^3$ is different, and other analogous permutations.

The term "monovalent" as used herein refers to a substituent connecting via a single bond to a substituted molecule. When a substituent is monovalent, such as, for example, F or Cl, it is bonded to the atom it is substituting by a single bond.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, $CF_3$, $OCF_3$, R, C(O), methylenedioxy, ethylenedioxy, N(R)$_2$, SR, SOR, $SO_2R$, $SO_2N(R)_2$, $SO_3R$, C(O)R, C(O)C(O)R, C(O)$CH_2$C(O)R, C(S)R, C(O)OR, OC(O)R, C(O)N(R)$_2$, OC(O)N(R)$_2$, C(S)N(R)$_2$, $(CH_2)_{0-2}$N(R)C(O)R, $(CH_2)_{0-2}$N(R)N(R)$_2$, N(R)N(R)C(O)R, N(R)N(R)C(O)OR, N(R)N(R)CON(R)$_2$, N(R)$SO_2$R, N(R)$SO_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted ($C_1$-$C_{100}$) hydrocarbyl, wherein R can be hydrogen (in examples that include other carbon atoms) or a carbon-based moiety, and wherein the carbon-based moiety can be substituted or unsubstituted.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term “pharmaceutically acceptable” refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language “pharmaceutically acceptable salt” refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds described herein include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term “pharmaceutically acceptable carrier” or “pharmaceutically acceptable excipient” means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound described herein within or to the patient such that it may perform its intended function. Typically, such compounds are carried or transported from one organ, or portion of the body, to another organ, or portion of the body. Each carrier must be “acceptable” in the sense of being compatible with the other ingredients of the formulation, including the compound(s) described herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, “pharmaceutically acceptable carrier” also includes any and all coatings, antibacterial and antifungal agents, and absorption delaying agents, and the like that are compatible with the activity of the compound(s) described herein, and are physiologically acceptable to the patient. Supplementary active compounds may also be incorporated into the compositions. The “pharmaceutically acceptable carrier” may further include a pharmaceutically acceptable salt of the compound(s) described herein. Other additional ingredients that may be included in the pharmaceutical compositions used with the methods or compounds described herein are known in the art and described, for example in Remington's Pharmaceutical Sciences (Genaro, Ed., Mack Publishing Co., 1985, Easton, PA), which is incorporated herein by reference.

The term “solvent” as used herein refers to a liquid that can dissolve a solid, liquid, or gas. Non-limiting examples of solvents are silicones, organic compounds, water, alcohols, ionic liquids, and supercritical fluids.

The term “substantially” as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term “substantially free of” as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term “substantially free of” can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term “substituted” as used herein in conjunction with a molecule or an organic group as defined herein refers to the state in which one or more hydrogen atoms contained therein are replaced by one or more non-hydrogen atoms. The term “functional group” or “substituent” as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, $OC(O)N(R)_2$, CN, NO, $NO_2$, $ONO_2$, azido, $CF_3$, $OCF_3$, R, O (oxo), S (thiono), C(O), S(O), methylenedioxy, ethylenedioxy, $N(R)_2$, SR, SOR, $SO_2R$, $SO_2N(R)_2$, $SO_3R$, C(O)R, C(O)C(O)R, C(O)

$CH_2C(O)R$, $C(S)R$, $C(O)OR$, $OC(O)R$, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, $N(R)N(R)C(O)R$, $N(R)N(R)C(O)OR$, $N(R)N(R)CON(R)_2$, $N(R)SO_2R$, $N(R)SO_2N(R)_2$, $N(R)C(O)OR$, $N(R)C(O)R$, $N(R)C(S)R$, $N(R)C(O)N(R)_2$, $N(R)C(S)N(R)_2$, $N(COR)COR$, $N(OR)R$, $C(=NH)N(R)_2$, $C(O)N(OR)R$, and $C(=NOR)R$, wherein R can be hydrogen or a carbon-based moiety; for example, R can be hydrogen, $(C_1-C_{100})$ hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

A "therapeutic" treatment is a treatment administered to a subject who exhibits signs of pathology, for the purpose of diminishing or eliminating those signs.

The term "thioalkyl" as used herein refers to a sulfur atom connected to an alkyl group, as defined herein. The alkyl group in the thioalkyl can be straight chained or branched. Examples of linear thioalkyl groups include but are not limited to thiomethyl, thioethyl, thiopropyl, thiobutyl, thiopentyl, thiohexyl, and the like. Examples of branched alkoxy include but are not limited to iso-thiopropyl, sec-thiobutyl, tert-thiobutyl, iso-thiopentyl, iso-thiohexyl, and the like. The sulfur atom can appear at any suitable position in the alkyl chain, such as at the terminus of the alkyl chain or anywhere within the alkyl chain.

The terms "treat," "treating" and "treatment," as used herein, means reducing the frequency or severity with which symptoms of a disease or condition are experienced by a subject by virtue of administering an agent or compound to the subject.

Throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

In one aspect, the present disclosure relates to a coronavirus inhibitor. In certain embodiments, the coronavirus inhibitor inhibits the main protease ($M^{pro}$) of a coronavirus. Exemplary coronaviruses include, but are not limited to, 229E, NL63, OC43, HKU1, MERS-CoV, SARS-COV, and SARS-COV-2. In certain embodiments, the coronavirus inhibitor inhibits the SARS-COV-2 $M^{pro}$. The coronavirus inhibitor will also inhibit the main protease of known SARS-COV-2 variants including, but not limited to, B.1.1.7 identified in the United Kingdom, B.1.427 and B.1.429 identified in California, and the P.1 variant from Brazil. Although not wishing to be limited by theory, it is believed that the coronavirus inhibitors of the present disclosure will inhibit the $M^{pro}$ of the B.1.1.7, B.1.427, B.1.429, and P.1 variants of SARS-COV-2, as well as other known variants, because there are no changes in the $M^{pro}$ amino acid sequence in these variants. The coronavirus inhibitor will also inhibit new variants for which there are no amino acid changes in the protease. In some embodiments, the coronavirus inhibitor will also inhibit new variants having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the current sequence of the $M^{pro}$ found in all currently known SARS-COV-2 variants. In certain embodiments, the coronavirus inhibitor inhibits the main proteases of the major coronavirus groups including the alpha, beta, gamma, and delta coronaviruses.

In some embodiments, the coronavirus inhibitor is a compound of formula (I), or a salt, solvate, stereoisomer, tautomer, isotopically labelled derivative, or geometric isomer thereof:

(I)

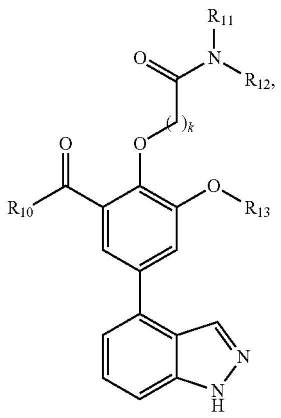

wherein:

$R_{10}$ is selected from the group consisting of H, D, OH, and $C_1$-$C_6$ hydroxyalkyl; and $R_{11}$ and $R_{12}$ are each independently $C_1$-$C_6$ alkyl; or $R_{11}$ and $R_{12}$ combine with the N atom to which they are bound to form an optionally substituted heterocyclyl;

$R_{13}$ is $C_1$-$C_6$ alkyl; and k is an integer from 1 to 10.

In certain embodiments, $R_{10}$ is H. In other embodiments, $R_{10}$ is $C_1$-$C_6$ hydroxyalkyl. In certain embodiments, $R_{10}$ is $(CH_2)_n$—OH wherein n is an integer from 1 to 6. In some embodiments, $R_{10}$ is $(CH_2)_n$—OH wherein n is 1.

In certain embodiments, $R_{11}$ and $R_{12}$ are each $C_1$-$C_6$ alkyl. In some embodiments, $R_{11}$ and $R_{12}$ are each methyl.

In other embodiments, $R_{11}$ and $R_{12}$ combine with the N atom to which they are bound to form an optionally substituted heterocyclyl. In certain embodiments, the heterocyclyl is a saturated $C_3$-$C_7$ heterocyclyl. In some embodiments, the heterocyclyl is a saturated $C_4$ heterocyclyl. In certain embodiments, $R_{11}$ and $R_{12}$ combine with the N atom to which they are bound to form a substituted pyrrolidine ring. In certain embodiments, the pyrrolidine ring is substituted with

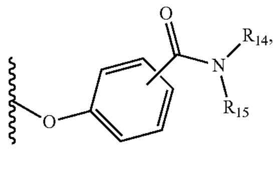

wherein  indicates the point of attachment to the pyrrolidine ring, and $R_{14}$ and $R_{15}$ are each independently $C_1$-$C_6$ alkyl. In certain embodiments, $R_{13}$ and $R_{14}$ are each methyl. In some embodiments, the pyrrolidine ring is substituted with

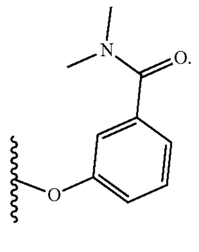 [SMILES: *Oc1cccc(C(=O)N(C)C)c1]

Therefore, in some embodiments, $R_{11}$ and $R_{12}$, together with the nitrogen atom to which they are attached, combine to form

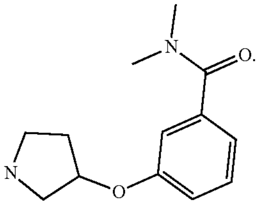 [SMILES: CN(C)C(=O)c1cccc(OC2CCNC2)c1]

In certain embodiments, $R_{13}$ is $C_1$-$C_6$ linear alkyl. In some embodiments, $R_{13}$ is methyl.

In certain embodiments, k is 1.

In some embodiments, the compound of formula (I) is selected from:

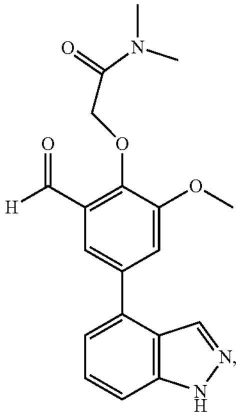

-continued

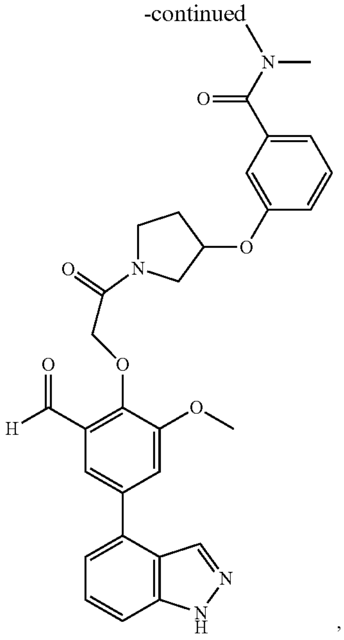

, and

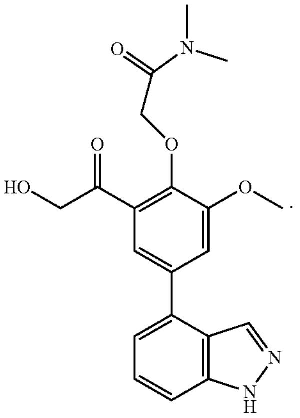

In other embodiments, the coronavirus inhibitor is a compound of formula (II), or a salt, solvate, stereoisomer, tautomer, isotopically labelled derivative, or geometric isomer thereof:

(II)

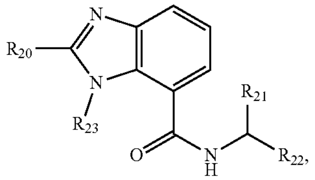

wherein:

$R_{20}$ is selected from the group consisting of

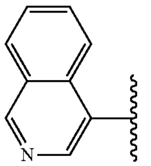 [SMILES: *c1cncc2ccccc12]

and $C_5$ heteroaryl optionally substituted with $C_1$-$C_6$ alkyl;

$R_{21}$ is selected from the group consisting of H, D, and $C_1$-$C_{12}$ alkyl;

$R_{22}$ is selected from the group consisting of unsubstituted $C_6$-$C_{12}$ aryl, unsubstituted $C_4$-$C_{10}$ heteroaryl, and phenyl aryl substituted with one or more substituents selected from the group consisting of $CF_3$, $CCl_3$, $CBr_3$, $CI_3$, $C_1$-$C_6$ alkyl, and $C_1$-$C_6$ haloalkoxy;

$R_{23}$ is selected from $(CH_2)_mC(=O)NHR_{24}$, $(CH_2)_nC(=O)OH$, $(CH_2)_pC(=O)OR_{24}$, $C_3$-$C_7$ cycloalkyl, and $C_3$-$C_7$ heterocyclyl, wherein the $C_3$-$C_7$ cycloalkyl and the $C_3$-$C_7$ heterocyclyl are each optionally substituted with $C(=O)NHR_{25}$;

$R_{24}$ and $R_{25}$ are each independently a $C_1$-$C_6$ alkyl; and m, n, and p are each independently an integer from 1 to 10;

wherein, when $R_{20}$ is an unsubstituted $C_5$ heteroaryl, $R_{23}$ is $(CH_2)_nC(=O)NHR_{24}$; and wherein, when $R_{22}$ is unsubstituted $C_6$ aryl, $R_{21}$ is methyl.

In some embodiments,  indicates the point of attachment of $R_{20}$, $R_{21}$, $R_{22}$, or $R_{23}$ to formula (II).

In certain embodiments, $R_{20}$ is

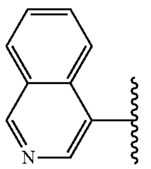

.

In other embodiments, $R_{20}$ is unsubstituted pyridine. In certain embodiments, $R_{20}$ is 3-pyridyl. In yet other embodiments, $R_{20}$ is pyridine substituted with $C_1$-$C_6$ alkyl. In certain embodiments, $R_{20}$ is pyridine monosubstituted with methyl. In certain embodiments, $R_{20}$ is

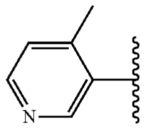

.

In certain embodiments, $R_{21}$ is H. In other embodiments, $R_{21}$ is $C_1$-$C_{12}$ alkyl. In certain embodiments, $R_{21}$ is a linear $C_1$-$C_{12}$ alkyl. In some embodiments, $R_{21}$ is methyl, ethyl, or propyl. In certain embodiments, the carbon atom of formula (II) comprising $R_{21}$ and $R_{22}$ is a stereocenter.

In certain embodiments, $R_{22}$ is unsubstituted $C_6$-$C_{12}$ aryl. In some embodiments, $R_{22}$ is naphthyl. In certain embodiments, $R_{22}$ is 2-naphtyl. In certain embodiments, $R_{22}$ is phenyl. In other embodiments, $R_{22}$ is unsubstituted $C_4$-$C_{10}$ heteroaryl. In some embodiments, $R_{22}$ is quinolinyl. In some embodiments, $R_{22}$ is

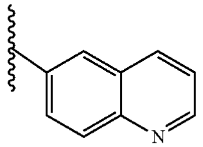

.

In yet other embodiments, $R_{22}$ is $C_6$ aryl substituted with one or more substituents selected from $CF_3$, $CCl_3$, $CBr_3$, $CI_3$, $C_1$-$C_6$ alkyl, and $C_1$-$C_6$ haloalkoxy. In some embodiments, $R_{22}$ is phenyl monosubstituted with $CF_3$. In certain embodiments, $R_{22}$ is

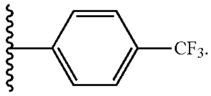

In other embodiments, $R_{22}$ is

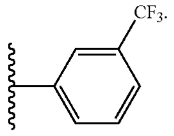 [SMILES: *c1cccc(C(F)(F)F)c1]

In some embodiments, $R_{22}$ is phenyl monosubstituted with $C_1$-$C_6$ alkyl. In certain embodiments, $R_{22}$ is phenyl monosubstituted with methyl. In certain embodiments, $R_{22}$ is

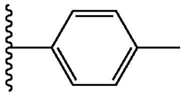

.

In some embodiment, $R_{22}$ is phenyl monosubstituted with $C_1$-$C_6$ haloalkoxy. In certain embodiments, $R_{22}$ is phenyl monosubstituted with $OCHF_2$. In certain embodiments, $R_{22}$ is

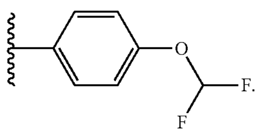 [SMILES: *c1ccc(OC(F)F)cc1]

In certain embodiments, $R_{23}$ is $(CH_2)_nC(=O)NHR_{24}$. In some embodiments, $R_{23}$ is $(CH_2)_mC(=O)NHR_{24}$ wherein m is 3. In some embodiments, $R_{23}$ is $(CH_2)_mC(=O)NHR_{24}$ wherein m is 3 and $R_{24}$ is methyl. In other embodiments, $R_{23}$ is $(CH_2)_nC(=O)OH$ wherein n is 3. In other embodiments, $R_{23}$ is $(CH_2)_pC(=O)OR_{24}$ wherein p is 3 and $R_{24}$ is methyl. In other embodiments, $R_{23}$ is unsubstituted $C_3$-$C_7$ cycloalkyl. In some embodiments, $R_{23}$ is cyclobutyl. In yet other embodiments, $R_{23}$ is $C_3$-$C_7$ cycloalkyl monosubstituted with $C(=O)NHR_{25}$. In some embodiments, $R_{23}$ is cyclobutyl monosubstituted with $C(=O)NHR_{25}$. In some embodiments, $R_{23}$ is cyclobutyl monosubstituted with $C(=O)NHR_{25}$ wherein $R_{25}$ is methyl. In certain embodiments, $R_{23}$ is

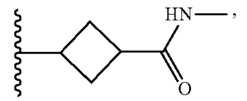

wherein $R_{23}$ may comprise one or more stereocenters. In certain embodiments, $R_{23}$ is

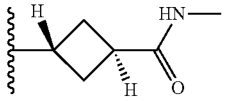 or 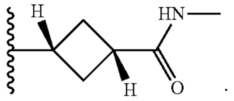 .

In other embodiments, $R_{23}$ is cyclopentyl monosubstituted with C(=O)$NHR_{25}$. In some embodiments, $R_{23}$ is cyclopentyl monosubstituted with C(=O)$NHR_{25}$ wherein $R_{25}$ is methyl. In certain embodiments, $R_{23}$ is

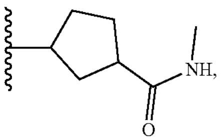 [SMILES: *C1CCC(C(=O)NC)C1]

wherein $R_{23}$ may comprise one or more stereocenters. In certain embodiments, $R_{23}$ is

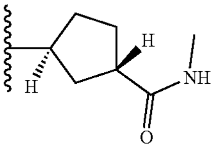 or 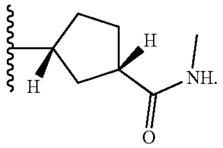

In yet other embodiments, $R_{23}$ is an unsubstituted $C_3$-$C_7$ heterocyclyl. In some embodiments, $R_{23}$ is a saturated $C_5$ heterocyclyl. In certain embodiments, $R_{23}$ is a saturated $C_5$ heterocyclyl comprising one nitrogen atom. In certain embodiments, $R_{23}$ is

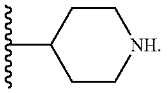

In some embodiments, the compound of formula (II) is selected from:

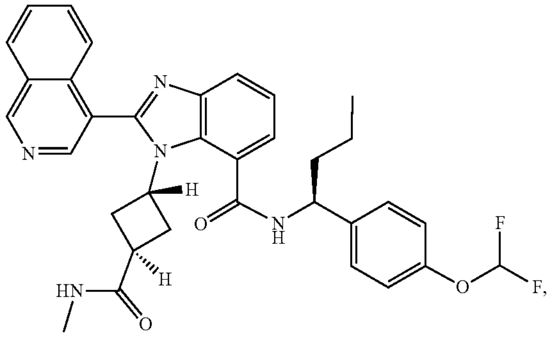

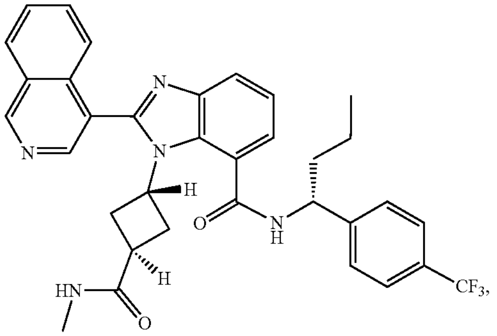

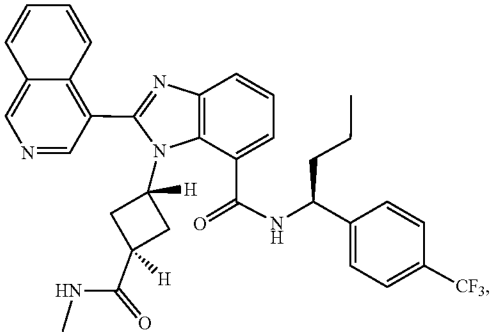

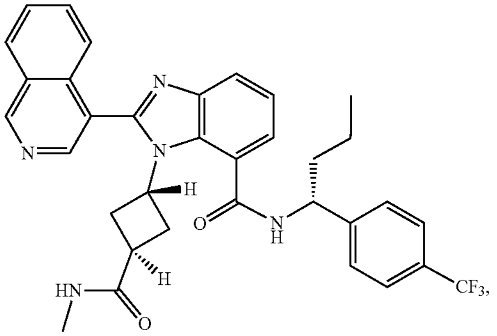

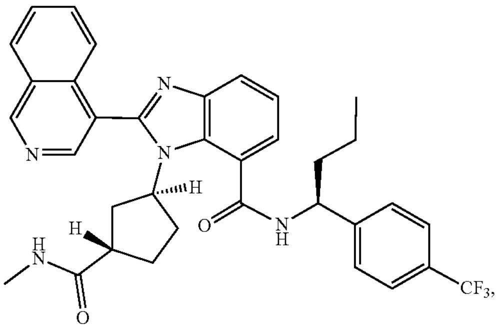

-continued
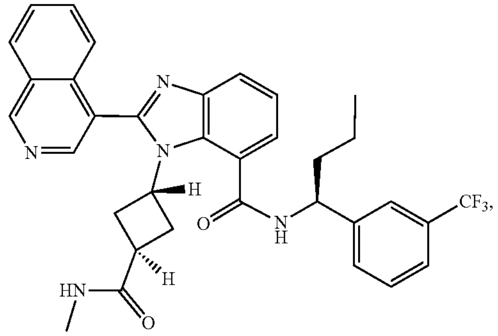
,
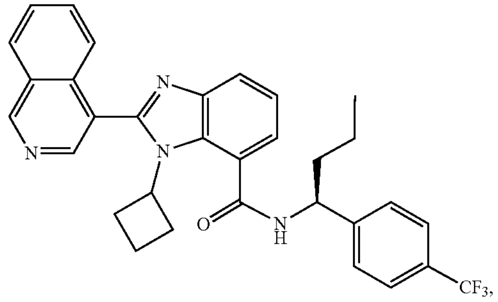
,
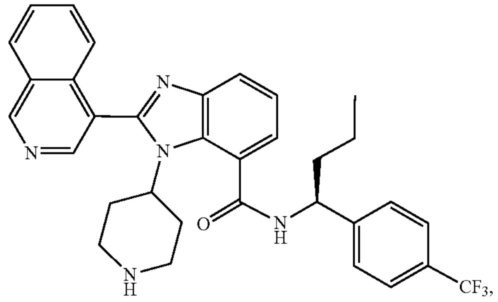
,
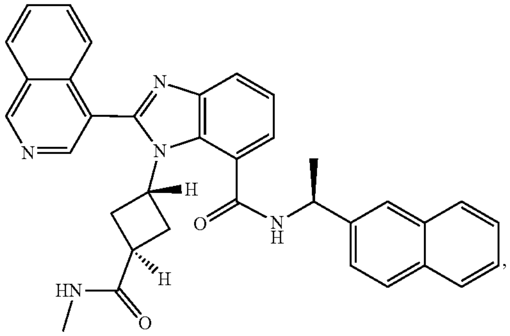
,
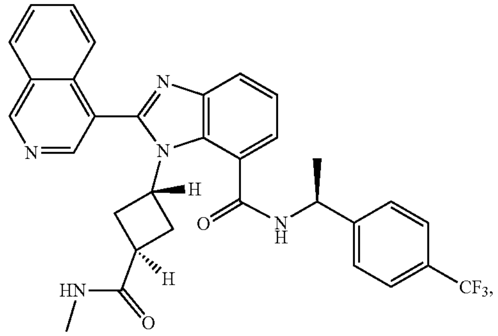
,
-continued
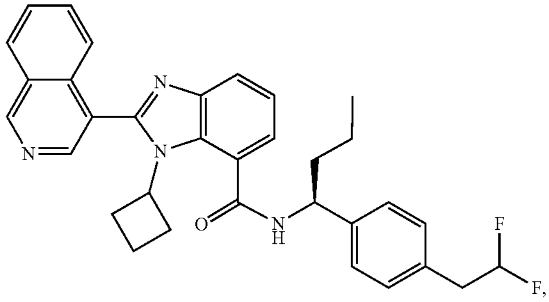
,
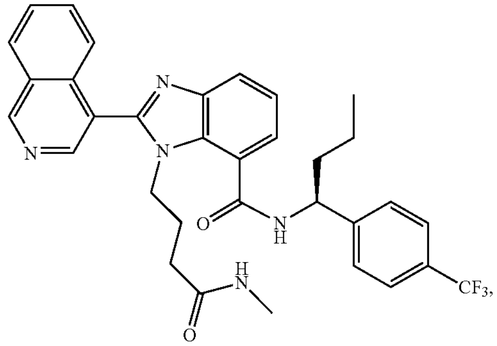
,
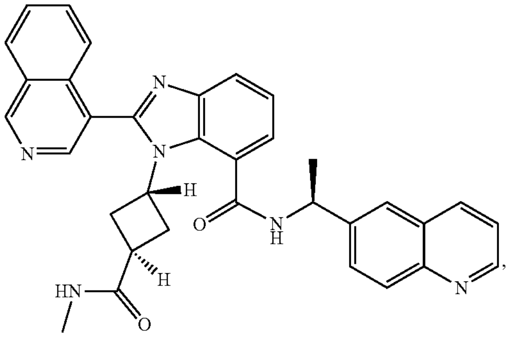
,
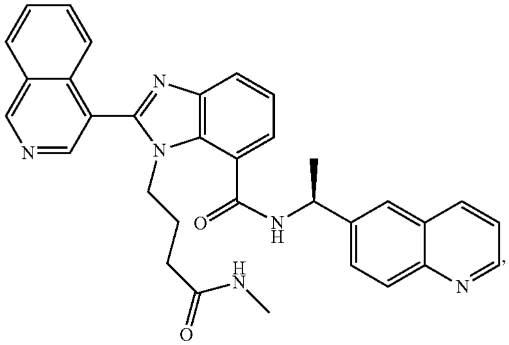
,
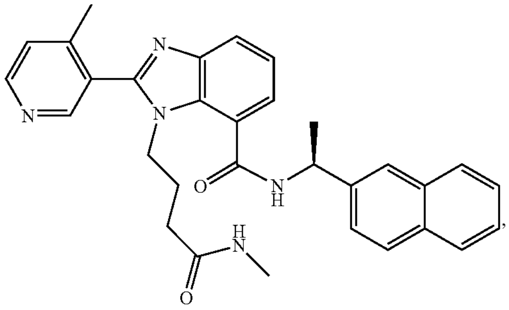
, -continued

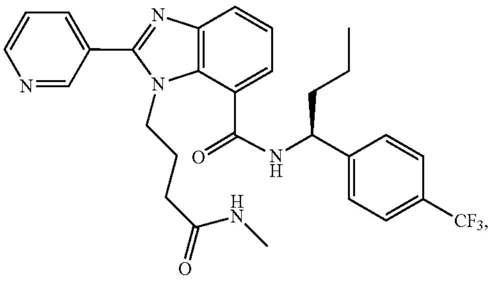

,

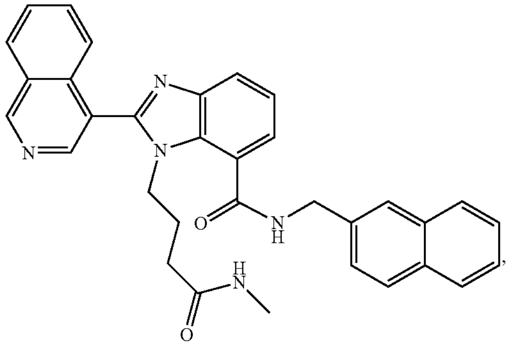

,

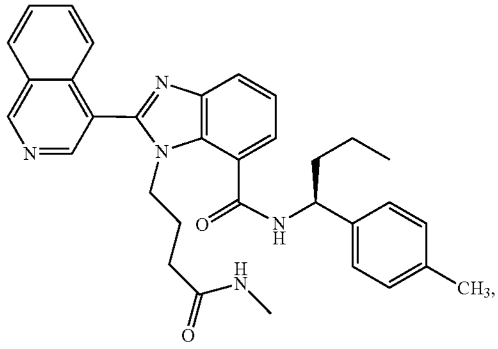

,

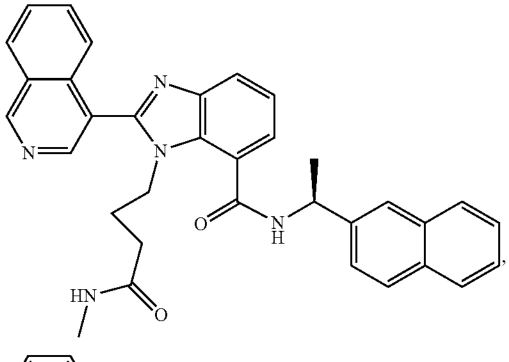

,

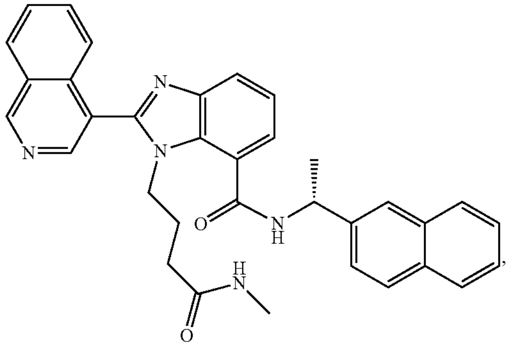

,

-continued

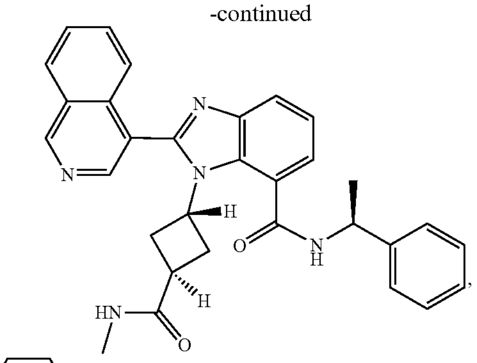

,

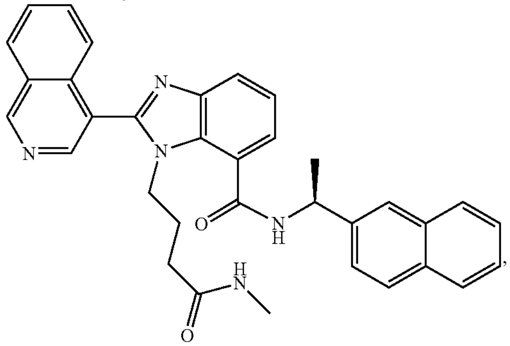

, and

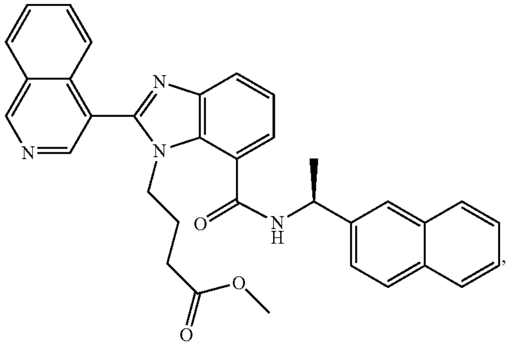

,

The compounds described herein can possess one or more stereocenters, and each stereocenter can exist independently in either the (R) or(S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound(s) described herein, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compound(s) described herein can exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compound(s) described herein are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$, and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

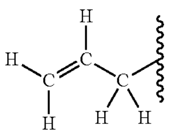
allyl

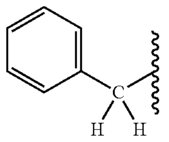
Bn

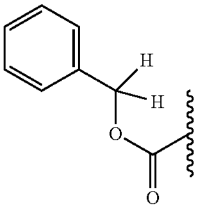
Cbz

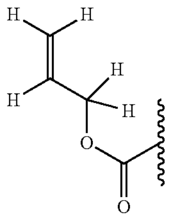
Alloc

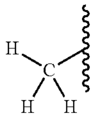
Me

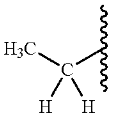
Et

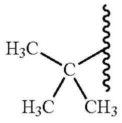
t-butyl

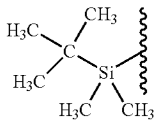
TBDMS

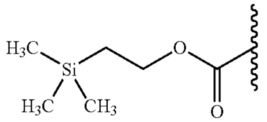
Teoc

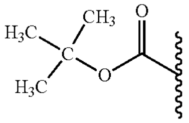
Boc

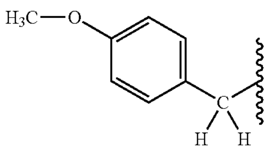
PMB

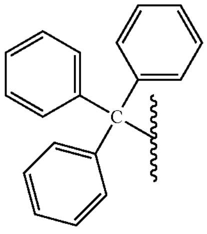
trityl

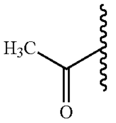
acetyl

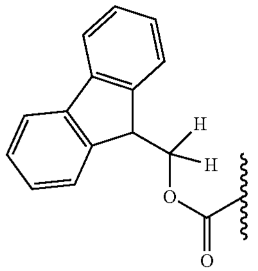
FMOC

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions

The compositions containing the compound(s) described herein include a pharmaceutical composition comprising at least one compound as described herein and at least one pharmaceutically acceptable carrier. Exemplary pharmaceutically acceptable carriers are described elsewhere herein.

In some embodiments, the composition comprises a compound of formula (I) and/or a compound of formula (II), or a salt, solvate, stereoisomer, tautomer, isotopically labelled derivative, or geometric isomer thereof. In some embodiments, the composition comprising a compound of formula (I) and/or a compound of formula (II), or a salt, solvate, stereoisomer, tautomer, isotopically labelled derivative, or geometric isomer thereof, is co-administered with a second composition comprising a pharmaceutically active compound. The pharmaceutically active compound can be any compound known to a person of skill in the art to aid in the treatment of a subject with a coronavirus infection. In certain embodiments, the pharmaceutically active compound is a coronavirus inhibitor other than the inhibitors of formula (I) and formula (II). In certain embodiments, the pharmaceutically active compound is a SARS CoV-2 inhibitor. In some embodiments, the SARS-COV-2 inhibitor is a polymerase inhibitor. Although not wishing to be limited by theory, it is believed that the co-administration of a compound of formula (I) and/or formula (II) with another coronavirus inhibitor may enhance the anti-viral effect and, as importantly, limit the evolution of inhibitor-resistant variants.

In certain embodiments, the composition is formulated for an administration route such as oral or parenteral, for example, transdermal, transmucosal (e.g., sublingual, lingual, (trans) buccal, (trans) urethral, vaginal (e.g., trans- and perivaginally), (intra) nasal and (trans) rectal, intravesical, intrapulmonary, intraduodenal, intragastrical, intrathecal, subcutaneous, intramuscular, intradermal, intra-arterial, intravenous, intrabronchial, inhalation, and topical administration. In some embodiments, the composition is formulated as a pill, tablet, gelcap, or capsule for oral administration. In other embodiments, the composition is formulated for intravenous administration.

Methods of Treatment

In another aspect, the present disclosure relates to a method of treating, ameliorating, and/or preventing a coronavirus infection in a subject. In certain embodiments, the method comprises administering to the subject a therapeutically effective amount of a compound of formula (I) or a compound of formula (II), or a salt, solvate, stereoisomer, tautomer, isotopically labelled derivative, or geometric isomer thereof.

In some embodiments, the subject is administered a compound of formula (I). Exemplary compounds of formula (I), or salts, solvates, stereoisomers, tautomers, isotopically labelled derivative, or geometric isomers thereof are described elsewhere herein. In other embodiments, the subject is administered a compound of formula (II). Exemplary compounds of formula (II), or salts, solvates, stereoisomers, tautomers, isotopically labelled derivative, or geometric isomers thereof are described elsewhere herein. In yet other embodiments, the subject is administered a compound of formula (I) and a compound of formula (II). In some embodiments, the compound of formula (II) comprises one or more stereocenters.

In some embodiments, the compound of formula (I) or formula (II), or the salt, solvate, stereoisomer, tautomer, isotopically labelled derivative, or geometric isomer thereof is administered to the subject prophylactically to prevent a coronavirus infection. In other embodiments, the compound of formula (I) or formula (II), or the salt, solvate, stereoisomer, tautomer, isotopically labelled derivative, or geometric isomer thereof is administered to subject who has a symptomatic or asymptomatic coronavirus infection in order to treat the infection. The compound of formula (I) or formula (II), or the salt, solvate, stereoisomer, tautomer, isotopically labelled derivative, or geometric isomer thereof can be administered to the subject using any administration route known to a person of skill in the art. Exemplary routes of administration are described elsewhere herein. In some embodiments, a composition comprising a compound of formula (I) or formula (II), or a salt, solvate, stereoisomer, tautomer, isotopically labelled derivative, or geometric isomer thereof is orally administered to the subject. In some embodiments, a pill, tablet, gelcap, or capsule comprising a compound of formula (I) or formula (II), or a salt, solvate, stereoisomer, tautomer, isotopically labelled derivative, or geometric isomer thereof is orally administered to the subject. In other embodiments, a composition comprising a compound of formula (I) or formula (II), or a salt, solvate, stereoisomer, tautomer, isotopically labelled derivative, or geometric isomer thereof is intravenously administered to the subject.

The coronavirus infection can be any coronavirus infection known to a person of skill in the art. In certain embodiments, the coronavirus infection is caused by SARS-COV-2. In certain embodiments, the coronavirus infection is COVID-19.

The compound of formula (I) or formula (II), or a salt, solvate, stereoisomer, tautomer, isotopically labelled derivative, or geometric isomer thereof can be administered to the subject in any dosage with any timing of dosage administration necessary to treat or prevent a coronavirus infection in the subject. In certain embodiments, the compound of formula (I) or formula (II), or a salt, solvate, stereoisomer, tautomer, isotopically labelled derivative, or geometric isomer thereof is administered to a subject with a symptomatic or asymptomatic coronavirus infection. In some embodiments, compound of formula (I) or formula (II), or a salt, solvate, stereoisomer, tautomer, isotopically labelled derivative, or geometric isomer thereof is administered to a subject with symptomatic or asymptomatic COVID-19. In certain embodiments wherein the subject has a symptomatic coronavirus infection, the compound formula (I) or formula (II), or a salt, solvate, stereoisomer, tautomer, isotopically labelled derivative, or geometric isomer thereof treats the coronavirus infection in the subject by reducing, alleviating, stopping, or preventing one or more symptoms of the coronavirus infection in the subject.

In certain embodiments, the subject is a mammal. In other embodiments, the mammal is a human.

In some embodiments, the step of administering a compound of formula (I) or a compound of formula (II), or a salt, solvate, stereoisomer, tautomer, isotopically labelled derivative, or geometric isomer inhibits the main protease ($M^{pro}$) of the coronavirus and therefore disrupts the coronavirus lifecycle in the subject. Although not wishing to be limited by theory, it is believed that in all coronaviruses, extensive proteolytic processing of polyproteins encoded by open reading frame (ORF) 1a and 1ab by the coronavirus main protease creates functional proteins which perform essential tasks pertaining to viral replication, transcription, viral assembly and immune response modulation. Therefore, it is believed that $M^{pro}$ of a coronavirus is indispensable for the viral lifecycle. In some embodiments, the compound of formula (I) or a compound of formula (II), or a salt, solvate, stereoisomer, tautomer, isotopically labelled derivative, or geometric isomer thereof interacts with the S pocket of the coronavirus $M^{pro}$. In certain embodiments, the compound of formula (I) or a compound of formula (II), or a salt, solvate, stereoisomer, tautomer, isotopically labelled derivative, or geometric isomer thereof interacts with the S pocket of the SARS-COV-2 $M^{pro}$. In some embodiments, the method further comprises administering to the subject a therapeutically effective amount of a pharmaceutically active compound. In some embodiments, the pharmaceutically active compound is administered after the administration of the compound of formula (I) and/or formula (II), or a salt, solvate, stereoisomer, tautomer, isotopically labelled derivative, or geometric isomer thereof. In other embodiments, the pharmaceutically active compound is co-administered with the compound of formula (I) and/or formula (II), or a salt, solvate, stereoisomer, tautomer, isotopically labelled derivative, or geometric isomer thereof. In certain embodiments, the pharmaceutically active compound is known or believed to treat, ameliorate, and/or prevent a coronavirus infection in the subject. Exemplary compounds believed to aid in the treatment, amelioration, and/or prevention of a coronavirus infection include, but are not limited to, interferons such as IFN-alpha, IFN-beta, and IFN-lambda, remdesivir, dexamethasone, hydroxychloroquine, chloroquine, azithromycin, tocilizumab, acalabrutinib, tofacitinib, ruxolitinib, baricitnib, anakinra, canakinumab, apremilast, marillimumab, sarilumab, lopinavir, ritonavir, oseltamivir, favipiravir, umifenovir, galidesivir, colchicine, ivermectin, vitamin D, a coronavirus polymerase inhibitor, and combinations thereof.

Administration/Dosage/Formulations

The regimen of administration may affect what constitutes an effective amount. The therapeutic formulations may be administered to the subject either prior to or after the onset of the disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation. Administration of the compositions described herein to a patient, preferably a mammal, more preferably a human, may be carried out using known procedures, at dosages and for periods of time effective to treat the disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat the disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound described herein is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the compound(s) described herein are dictated by and directly dependent on (a) the unique characteristics of the therapeutic compound and the particular therapeutic effect to be achieved, and (b) the limitations inherent in the art of compounding/formulating such a therapeutic compound.

In certain embodiments, the compositions described herein are formulated using one or more pharmaceutically acceptable excipients or carriers. In certain embodiments, the pharmaceutical compositions described herein comprise a therapeutically effective amount of a compound described herein and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions described herein are administered to the patient in dosages that range from one to five times per day or more. In other embodiments, the compositions described herein are administered to the patient in range of dosages that include, but are not limited to, once every day, every two, days, every three days to once a week, and once every two weeks. It is readily apparent to one skilled in the art that the frequency of administration of the various combination compositions described herein varies from individual to individual depending on many factors including, but not limited to, age, disease or disorder to be treated, gender, overall health, and other factors. Thus, administration of the compounds and compositions described herein should not be construed to be limited to any particular dosage regime and the precise dosage and composition to be administered to any patient is determined by the attending physician taking all other factors about the patient into account.

The compound(s) described herein for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound described herein is from about 1 mg and about 2,500 mg. In some embodiments, a dose of a compound described herein used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, a composition as described herein is a packaged pharmaceutical composition comprising a container holding a therapeutically effective amount of a compound described herein, alone or in combination with a second pharmaceutical agent; and instructions for using the compound to treat, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions described herein include oral, nasal, rectal, intravaginal, parenteral, buccal, sublingual or topical. The compounds for use in the compositions described herein can be formulated for administration by any suitable route, such as for oral or parenteral, for example, transdermal, transmucosal (e.g., sublingual, lingual, (trans) buccal, (trans) urethral, vaginal (e.g., trans- and perivaginally), (intra) nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions described herein are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compound(s) described herein can be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compounds as described herein may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or similar alcohol.

Additional Administration Forms

Additional dosage forms suitable for use with the compound(s) and compositions described herein include dosage forms as described in U.S. Pat. Nos. 6,340,475; 6,488,962; 6,451,808; 5,972,389; 5,582,837; and 5,007,790. Additional dosage forms suitable for use with the compound(s) and compositions described herein also include dosage forms as described in U.S. patents application Ser. Nos. 20030147952; 20030104062; 20030104053; 20030044466; 20030039688; and 20020051820. Additional dosage forms suitable for use with the compound(s) and compositions described herein also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations described herein can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use with the method(s) described herein may be administered in the form of microparticles, for example, by injection or in the form of wafers or discs by implantation.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions described herein. Thus, single unit dosage forms suitable for oral administration, such as tablets, capsules, gelcaps, and caplets that are adapted for controlled-release are encompassed by the compositions and dosage forms described herein.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" is defined herein as a compound or compounds, including, but not limited to, polymers, polymer matrices, gels, permeable membranes, liposomes, or microspheres or a combination thereof that facilitates the controlled-release of the active ingredient. In some embodiments, the compound(s) described herein are administered to a patient, alone or in combination with another pharmaceutical agent, using a sustained release formulation. In some embodiments, the compound(s) described herein are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound described herein depends on the age, sex and weight of the patient, the current medical condition of the patient and the progression of the disease or disorder in the patient being treated. The skilled artisan is able to determine appropriate dosages depending on these and other factors.

A suitable dose of a compound described herein can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound(s) described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds described herein can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXPERIMENTAL EXAMPLES

The disclosure is further described in detail by reference to the following experimental examples. These examples are provided for purposes of illustration only, and are not intended to be limiting unless so specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present disclosure, and are not to be construed as limiting in any way the remainder of the disclosure.

Materials and Methods

All starting materials and reagents were purchased from commercial sources and used without further purification. Solvents were purchased as either anhydrous grade products in sealed containers or reagent grade and used as received. All reactions were carried out in dry glassware under a nitrogen atmosphere using standard disposable or gastight syringes, disposable or stainless steel needles, and septa. Stirring was achieved with magnetic stir bars. Flash column chromatography was performed with $SiO_2$ (230-400 mesh) or by using an automated chromatography instrument with an appropriately sized column. Thin layer chromatography was performed on silica gel $60F_{254}$ plates (E. Merck). Non-UV active compounds were visualized on TLC using one of the following stains: $KMnO_4$, ninhydrin, p-anisaldehyde. $^1H$ and $^{13}C$ NMR spectra were recorded on an instrument operating at either 600 MHz or 151 MHz, respectively. LCMS data were collected using an HPLC instrument coupled to a low resolution mass spectrometer with single quadrupole ionization operating in either positive or negative ion mode. The analytical method utilized a $C_{18}$ column (2.1×50 mm, 1.8 μm) eluting with a linear gradient of 95%/5% water/$CH_3CN$ (modified with 0.05% formic acid; T=0 min flow=0.35 mL/min) to 95%/5% $CH_3CN$/water (T=3.5 min flow=0.5 mL/min) then 95%/5% $CH_3CN$/water to T=5 min (0.5 mL/min). Peak detection was done at 254 nm and 230 nm for UV active compounds. High-resolution mass spectrometry (HRMS) spectra were obtained on a Thermo Scientific Q Exactive hybrid quadrupole-Orbitrap mass spectrometer equipped with a HESI source and using lock masses for correction. Samples were introduced into the HRMS via reversed phase HPLC on an Accucore Vanquish C18+ column (2.1×100 mm, 1.5 μm) eluting with a linear gradient of 95%/5% water/acetonitrile (modified with 0.1% formic acid) to 10%/90% water/acetonitrile over 8 min.

Plasmid Construction

The *E. coli* strain XL1-Blue [recA1, endA1, gyrA96, thi-1, hsdR17, supE44, relA1, lac, [F9 proAB lacIq lacZΔM15, Tn10 (tetr)]] (Stratagene, Inc., La Jolla, CA) was used as the host for the plasmid construction. The *E. coli* strain BL21 (DE3) (fhuA2 [lon] omp Tgal (λDE3) [dcm] ΔhsdS λ E3=λsBamHIo ΔEcoRI-B int::(lacI::PlacUV5::T7gene1) i2I Δnin5) was used as the host for protein expression.

The gene encoding SARS-Cov-2 $M^{pro}$ (ORF1ab polyprotein residues 3264-3569, GenBank code: MN908947.3) was codon-optimized for *Escherichia coli* expression and synthesized by GenScript Biotech (NJ, USA). The synthesized gene was amplified by PCR using the forward primer 5'-GGTGGCTCATATGTCGGCAGTGCTGCAATCCGGC TTTCGCAAAATGGC-3' (SEQ ID NO: 1) and reverse primer 5'-GCCACCTGGATCCTTAATGATGAT GATGATGATGGGGACCCTGG AAGGTTACACCAGAG-3' (SEQ ID NO: 2) to introduce the N-terminal $M^{pro}$ cleavage-site (SAVLQ↓SGFRK (SEQ ID NO: 3); arrow indicates the cleavage site) and the C-terminal PreScission cleavage site (SGVTFQ↓GP; (SEQ ID NO: 4)) followed by a 6×His-tag. The PCR fragment was then inserted into the pSumo plasmid using NdeI and BamHI restriction sites to generate an N-terminal Sumo-$M^{pro}$ fusion construct pSUMO-SARS-COV-2-$M^{pro}$. The DNA sequences of the plasmids with the corresponding gene insertion were confirmed by Sanger sequencing (Eurofins, Luxembourg, KY).

Protein Expression and Purification

SARS-COV-2 $M^{pro}$ with a C-terminal 6×His-tag was expressed and purified from the *E. coli* BL21 (DE3) strain. *E. coli* cells were cultured in LB medium at 37° C. to an OD600 absorbance of 0.8 and protein over-expression was induced by with 0.4 mM Isopropyl β-d-1-thiogalactopyranoside (IPTG) for 20 h at 20° C. The N-terminal Sumo-fusion was auto-cleaved while active $M^{pro}$ was expressed, generating an authentic N-termini of $M^{pro}$. The next day cells were harvested by low speed centrifugation and resuspended in binding buffer (25 mM Tris-HCl pH=8.0, 150 mM NaCl, 5 mM β-mercaptoethanol, 20 mM imidazole and Xpert protease inhibitor cocktail (GenDEPOT, Katy, TX). Sonication was used to disrupt cells and cell debris were removed by centrifugation at 10,000×g for 10 min at 4° C. The supernatant was mixed with binding buffer pre-equilibrated $Ni^{2+}$ Sepharose 6 Fast Flow resin (GE Healthcare, Stockholm, Sweden) for 30 min at 4° C. and then loaded onto the column. After washing, protein was eluted by adding buffer A (25 mM Tris-HCl pH-8.0, 150 mM NaCl, 5 mM β-mercaptoethanol and Xpert protease inhibitor cocktail) supplemented with 40 mM, 60 mM, 80 mM and 100 mM imidazole, respectively. The purity of $M^{pro}$ in each fraction was visualized by SDS-PAGE followed by Coomassie Brilliant Blue (CBB) staining. Protein fractions containing >95% pure $M^{pro}$ were pooled and buffer exchanged with buffer B (20 mM Tris-HCl pH=7.3, 150 mM NaCl, 1 mM EDTA and 1 mM DTT) using a Amicon® Ultra-15 Centrifugal Filter Unit (MilliporeSigma, Burlington, MA). Purified $M^{pro}$ was then mixed with PreScission protease (GenScript Biotech, NJ, USA) at a ratio of 1 mg protein to 10 units protease based on manufacturer recommendations and incubated for 20 h at 4° C., resulting in $M^{pro}$ with authentic N- and C-termini. GST Bind™ Resin (Novagen, NJ, USA) and $Ni^{2+}$ Sepharose 6 Fast Flow resin was applied sequentially to remove GST-tagged PreScission protease and remaining $M^{pro}$-His. To further eliminate protein contamination from the PreScission protease, uncleaved $M^{pro}$-His and 6×His tag, $M^{pro}$ was concentrated and loaded on to a Superdex™ 75 increase 10/300GL size exclusion column (GE Healthcare, Stockholm, Sweden) pre-equilibrated with buffer B. The elution profile of $M^{pro}$ protein was visualized by SDS-PAGE followed by CBB staining and pure $M^{pro}$ protein was combined for further use.

Dec-Tec Affinity Selection with $M^{pro}$

To identify $M^{pro}$ binding compounds, the DEC-Tec library pool was screened in two tubes: 1) absence of $M^{pro}$ protein (bead binding no-target control, NTC), 2) presence of His-$M^{pro}$ at 1 μM. Before the screen was initiated, the DEC-Tec libraries were quantitated using qPCR and pooled together to let each compound have 1 million copies. Three rounds of DEC-Tec selection have been performed to improve ligand enrichment. The DNA barcode from the last round of selection was PCR amplified and sequenced to identify the linked drug-like binders. In brief, DEC-Tec screen and sequencing were performed as follows: 1) His-$M^{pro}$ at 1 μM was incubated with DEC-Tec libraries in 50 mM Tris-HCl buffer, pH 8.0, containing 150 mM NaCl, 10 mM imidazole, 1 mM TCEP, 1 mM CHAPS, and 0.1 mg/ml sheared salmon sperm DNA for 45 min at room temperature with continuous shaking; 2) His-$M^{pro}$ along with binding molecules were immobilized by HisPur Ni-NTA magnetic beads through brief vortex; 3) Beads were washed 1 time with the aforementioned selection buffer without the addition of sheared salmon sperm DNA by brief and vigorous vortex; 4) Binding DEC-Tec molecules were dissociated form His-$M^{pro}$ by heating beads at 80° C. for 10 min with continuous shaking; 5) The resulting eluent containing protein binding molecules was further incubated with fresh His-$M^{pro}$ to initiate another round of selection following the same protocol described above; 6) After the last round of selection, the eluted encoding oligonucleotides were amplified using Platinum Taq DNA Polymerase High Fidelity using primers that incorporate complementary sequences to the library headpiece or tailpiece along with the Illumina READ 1 or READ 2 sequences required for clustering and Illumina sequencing; 7) The amplified DNA were cleaned by Agencourt AMPure XP beads and quantitated by Agilent high sensitivity DNA kit using a Bioanalyzer; 8) DNA was then denatured and sequenced along with a 3% PhiX spike-in in a single-read, 105-cycle sequencing on an Illumina NextSeq 500 instrument; 9) The FASTQ format sequencing data was generated through Illumina BaseSpace and decoded and analyzed.

Enzyme Inhibition Assay and $K_i$ Values Determination

To evaluate the potency of synthesized compounds against $M^{pro}$, the proteolytic activity of 50 nM $M^{pro}$-His and $M^{pro}$ was first measured in the presence and absence of 25 μM compound using the fluorescent peptide Dabcyl-KT-SAVLQSGFRKM-E(Edans)-$NH_2$ (SEQ ID NO: 5) (GenScript Biotech NJ, USA) as the reporter substrate at a concentration of 15 μM. Compounds were incubated with $M^{pro}$ for 20 min at room temperature in reaction buffer composed of 20 mM Tris-HCL, pH 7.3, 100 mM NaCl, 1 mM EDTA, 1 mM DTT and 0.02% Tween-20. Hydrolysis of the fluorescent peptide was monitored at an emission wavelength of 460 nm with excitation wavelength at 360 nm, using a TECAN M200 plate reader (TECAN, Männedorf, Switzerland). Compounds that inhibited $M^{pro}$ activity by less than 50% were considered inactive (Table 1).

To determine the $K_i$ values of active compounds, 25 nM $M^{pro}$ was mixed with increasing concentrations of compounds (from 40 nM to 4000 nM with two-fold dilutions) and hydrolysis of 15 μM fluorescent peptide was monitored. Initial hydrolysis rates of fluorescent peptide were plotted as a function of compound concentrations and $K_i$ values were obtained by fitting the data into the Morrison equation with standard error from triplicates. The $K_m$ value used for $K_i$ calculations is 17 μM.

Morrison Equation used:

$$Y=V_o*(1-((((E_t+X+(K_i*(1+(S/K_m))))-(((E_t+X+(K_i*(1+(S/K_m))))\hat{}2)-4*E_t*X)\hat{}0.5))/(2*Et)))$$

(Y, Enzyme activity; X, Concentration of inhibitor; $E_t$, Enzyme concentration; $K_m$, Michealis-Menten constant of enzyme; S, substrate concentration)

Crystallography and Data Collection

To obtain the structure of $M^{pro}$ in complex with CDD-1713, Mpro and CDD-1713 were mixed at a 1:2 molar ratio and incubated at 4° C. overnight to facilitate complex formation. Crystal screening was performed using commercially available crystal screening suites PEGs, PEGII, PACT and JCSGI from Qiagen (Valencia, CA) in 96-well format. Hanging drops were set up by an in-house TTP LabTech Mosquito instrument (TTP Labtech Ltd, Melbourn, UK) and crystals were obtained through the vapor diffusion method. Crystals were obtained in a condition of 20% (w/v) PEG3350 and 0.2 M sodium acetate at room temperature were picked and 25% glycerol was used as the cryoprotectant.

X-ray diffraction data was collected using an Advanced Light Source synchrotron beam line. Reflection data were indexed, integrated, and scaled using the iMosflm and the CCP4i Suite. Molecular replacement was performed using the $M^{pro}$ structure (PDB: 7K3T) as the search model. Structures were further refined several rounds using PHENIX.refine and Crystallography Object-Oriented Toolkit (Coot). The electron densities of CDD-1713 and the covalent bond between residue $M^{pro}$ Cy145 and CDD-1713 in the crystal structure were further examined by creating a polder mFo-Fc OMIT map using the PHENIX software.

Thermal Shift Assay

The dye SYPRO Orange (ThermoFisher Scientific, USA) was used to perform the protein thermal shift assay. The assay was set up on a 384-well Roche plate where the SARS-CoV-2 main protease at a concentration of 1.5 μM was incubated with the test compound at various concentrations, and SYPRO Orange dye at 5× in a 10 μL reaction. The melting curve experiment and data analysis was run on a Roche Lightcycler 480 real-time PCR instrument.

Human Protease Assays

Cathepsin B Assay

A kit from BPS Bioscience (#79590) was used with adjustments to the manufacturer's protocol as follows: The activated enzyme was diluted 250-fold just before use, and the reaction was run at RT in black 96 half-area plates in a total reaction volume of 50 uL containing 0.01% Tween-20. Instead of measuring endpoints at 60 min the increase in fluorescence (Ex 360 nm, Em 460 nm) per second (RFU/s) was obtained from linear progress curves over 10 min. Fractional activities were calculated from reactions with no inhibitors. E-64 was used as a positive control.

Thrombin Assay

A kit from Sigma-Aldrich (MAK243) was used with adjustments to the manufacturer's protocol as follows: Thrombin reconstituted according to protocol and then diluted 10-fold with assay buffer just before use. The unknown AMC-peptide substrate was further diluted 3-fold with the provided buffer. The reaction was run at RT in kinetic mode for 10 min in white 96 half-area plates in a total reaction volume of 100 uL containing 0.01% Tween-20. The increase in fluorescence (Ex 350 nm, Em 450 nm) per second (RFU/s) was obtained from linear progress curves. Fractional activities were calculated from reactions with no inhibitors. CDD-1472, a potent thrombin inhibitor identified by using DEC-Tec, was used as a positive control.

Renin Assay

A kit from BPS Bioscience (#80211) was used with adjustments to the manufacturer's protocol as follows: The reaction was run at RT in black 96 half-area plates in a total reaction volume of 50 uL containing 0.01% Tween-20. Instead of measuring endpoints at 30 min the increase in fluorescence (Ex 490 nm, Em 520 nm) per second (RFU/s) was obtained from linear progress curves over 10 min. Fractional activities were calculated from reactions with no inhibitors. Aliskiren was used as a positive control.

MMP-1 Assay

A kit from Biovision (#K794-100) was used with adjustments to the manufacturer's protocol as follows: The enzyme was reconstituted according to protocol and then diluted 5-fold with assay buffer just before use. The unknown fluorogenic substrate was further diluted 10-fold with the provided assay buffer. The reaction was run at 37 C in black 96 half-area plates in a total reaction volume of 50 μL containing 0.01% Tween-20. The increase in fluorescence (Ex 490 nm, Em 520 nm) per second (RFU/s) was obtained from linear progress curves over 10 min. Fractional activities were calculated from reactions with no inhibitors. GM 6001 was used as a positive control.

Metabolic Stability Assay in Liver Microsomes

Compound CDD-1713 and CDD-1976 (2.0 μM) was incubated in mouse or human liver microsomes (0.5 mg protein/mL) at 37° C. The samples were collected at specific time-points 0, 30, and 60 min in duplicate. The reactions were terminated by adding an equivalent volume of ice-cold methanol and vortexed. The reaction mixtures were centrifuged at rcf 15,000 for 15 min. Three μL of the supernatant was analyzed by UHPLC-Q Exactive Orbitrap MS (Thermo Fisher Scientific, USA) equipped with 50 mm×4.6 mm column (XDB C-18, Agilent Technologies, USA). The column temperature was maintained at 40° C. The flow rate was at 0.3 mL/min with a 30% mobile phase (acetonitrile containing 0.1% formic acid). Q Exactive MS was operated in positive mode with electrospray ionization. Ultra-pure nitrogen was applied as the sheath (45 arbitrary unit), auxiliary (10 arbitrary unit), sweep (1.0 arbitrary unit) and the collision gas. The capillary gas temperature was set at 275° C. and the capillary voltage was set at 3.7 kV. MS data were acquired from 80 to 1,200 Da in profile mode. JQ1 and alprazolam were used as the short and long half-life control, respectively.

Cell Uptake Assay and Cytotoxicity Assay in HepG2

The HepG2 cells maintained in DMEM (containing 1 g/L glucose, 10% fetal bovine serum and 1% penicillin/streptomycin) were seeded in a 12-well plate (a final density of $5\times10^5$/well) for cell uptake assay and 96-well plate for cytotoxicity assay (a final density of $5\times10^4$/well). The plate was incubated at 37° C. for 24 h.

Cell Uptake

The cells in 12-well plate were treated with CDD-1713 or CDD-1976 (final concentration: 10 μM). The plate was incubated at 37° C. for another 2 hr. The medium in the plate was decanted and the cells were rinsed with 1 mL of 1×DPBS for three times. 0.5 mL of 0.25% Trypsin was added into each well and incubated for 3.5 min (at 37° C.). 1 mL of complete medium was added into each well to quench the reaction. After spinning at 350×g for 5 min, the cell pellet was reconstituted in MeOH/$H_2O$ (v/v 1/1) and CDD-1713 or CDD-1976 was extracted from 100 μL of the resulting mixture with 100 μL of ice-cold methanol. The mixtures were centrifuged at rcf 15,000 for 15 min. Three μL of the supernatant was analyzed by UHPLC-Q Exactive Orbitrap MS (Thermo Fisher Scientific, USA) equipped with 50 mm×4.6 mm column (XDB C-18, Agilent Technologies, USA). The column temperature was set at 40° C. Ultra-pure nitrogen was applied as the sheath (45 arbitrary unit), auxiliary (10 arbitrary unit), sweep (1.0 arbitrary unit) and the collision gas. The capillary temperature was 275° C., and the auxiliary gas temperature was 380° C. The spray voltage was 3.75 kV. MS data were acquired from 80 to 1,200 Da in profile mode. The mobile phase system was (A) water (containing 0.1% formic acid)-(B) acetonitrile (containing 0.1% formic acid), with a flow rate of 0.3 mL/min. The gradient elution program was as follows: 0-0.25 min, 40% B; 0.25-1.5 min, 40-98% B; 1.5-3.5 min, 98% B; 3.5-3.8 min, 98-40% B; 3.8-5 min, 40% B. Doxorubicin and dacarbazine were used as positive and negative controls, respectively. The experiments were performed in triplicate.

Cytotoxicity Assay

The cells in 96-well plate were treated by CDD-1713 or CDD-1976 at the final concentrations of 0, 10, 20, 50, 100 μM (n=3 replicates/concentration level/drug). After 24 h incubation at 37° C., the medium in the plate was decanted and 100 μL of DMEM (without phenol red) was added into each well. The cell variability was measured using XTT method. The absorbance at 475 nm was read with a Tecan M1000 pro machine, with a reference wavelength of 660 nm. The reading was normalized by vehicle with final 0.5% DMSO for each drug.

Plasma Stability Assay

Compound CDD-1713 and CDD-1976 were incubated in human and mouse plasma respectively at a concentration of 10 μM in duplicate (n=2) at 37° C. At time-points of 0, 30, 60 and 120 min, 15 μL of sample were taken out and the reactions terminated by adding 75 μL of ice-cold methanol. The reaction mixtures were then vortexed for 30 sec and centrifuged at rcf 15,000 for 15 min. Following centrifugation, 3 μL of the supernatant was analyzed using UHPLC-Q Exactive Orbitrap MS. The percentage of test compound remaining at the individual time points relative to the 0 min sample was then determined.

Real-Time Cell Analysis (RTCA) Assay for Evaluating In Vitro Inhibition of SARS-COV-2 Replication by $M^{pro}$ Inhibitors Inhibition of SARS-COV-2 replication in VERO E6 and HEK hACE2 cells was measured using an xCELLigence RTCA HT Analyzer (Agilent Technologies), tracking the virus-induced cytopathic effect (CPE) on the cellular growth kinetics. Applied methods were similar as recently described elsewhere (Zost, S. J. et al. "Rapid isolation and profiling of a diverse panel of human monoclonal antibodies targeting the SARS-COV-2 spike protein," Nature Medicine, 2020 26:1422-1427). After a background reading of the 96-well E-plate using 50 μL only of media, $1\times10^4$ cells were seeded in each well, using 100 μL of culture media (VERO E6 cells: DMEM+1× pen/step+10% FBS or HEK-hACE2 cells: DMEM+1× pen/strep+10% FBS+10 mM HEPES). The E-plate was incubated for 30 min at room temperature to minimize edging effects. After the cells settled, the E-plate was transferred to xCELLigence instrument for real-time analysis of cell proliferation for 24 h. Drug candidates dissolved in DMSO were two-fold serially diluted in cell culture media in a 96-well plate (deep). Drug samples were prepared in duplicate and DMSO was included as buffer control. An equal volume of cell culture media containing SARS-COV-2 (USA_WA1/2020 isolate) was added to the drugs. Final concentrations of small drug tested ranged from 0.2 μM to 50 μM, and wells containing virus only or cell culture media only were added as controls. The plate was incubated for 1 h at 37° C. 5% $CO_2$. After the incubation, the E-plate was removed from the xCELLigence instrument and the cell culture media in the E-plate was replaced by 250 μL of the drugs candidates/virus mixture from the deep well plate. The E-plate was then transferred back to the xCeL-Ligence instrument and real-time analysis of the CPE was continued for an additional 75 h.

Data were analyzed using the RTCA software (Agilent Technologies). Duplicate wells were averaged, and the cell index was normalized to the last measured time-point before the addition of the drugs/virus mixture Using Prism9 software (GraphPad) the normalized cell index data was plotted versus time, and the half maximal inhibitory concentration ($IC_{50}$) of each drug candidate was calculated.

DECL Methods

General Information of DECL

The general materials, procedures, and equipment utilized can be found in DECL publications.

Materials and Equipment Used for the DNA-Encoded Chemical Libraries

Figure 28:
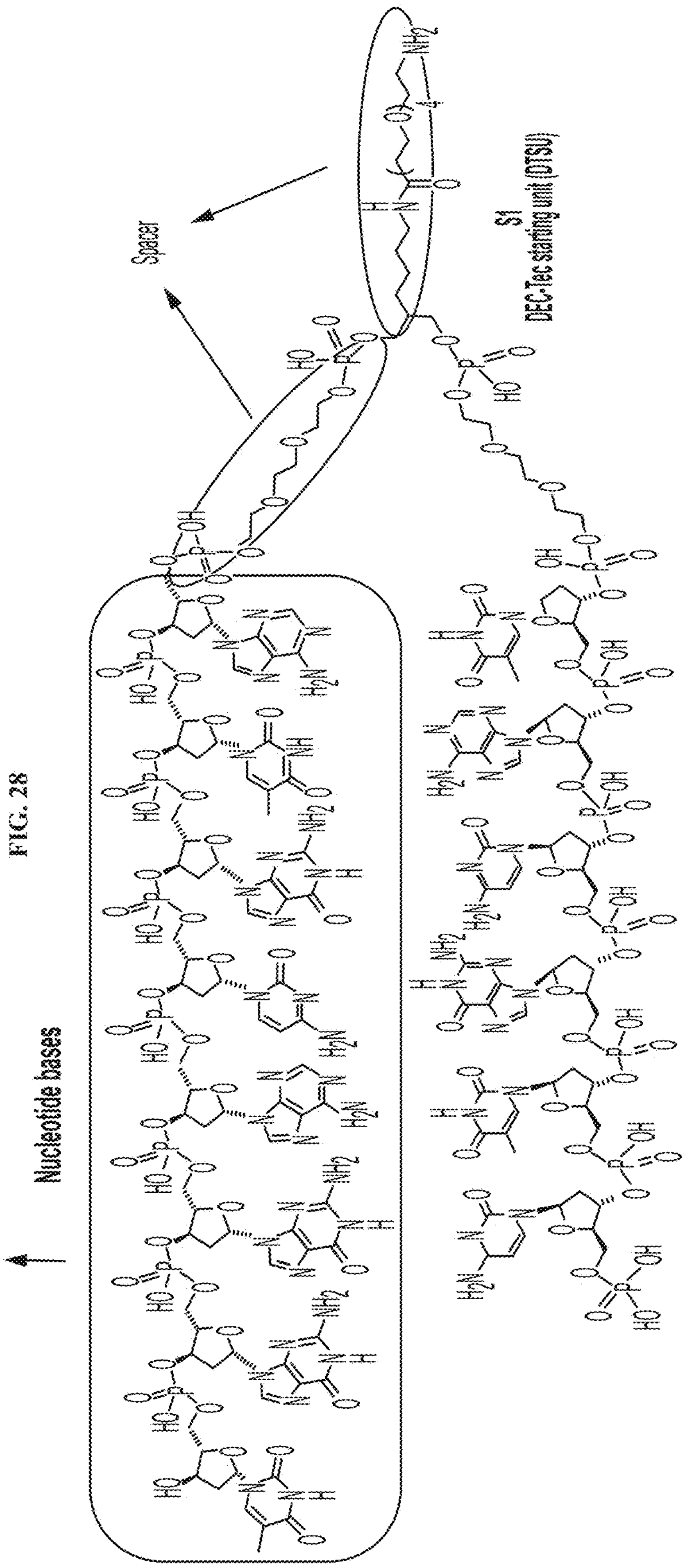
FIG. 28 depicts the structure of DECTec starting unit (DTSU) S1 (5'-Phos-CTGCAT-Spacer 9-Amino C7 plus AOP-Spacer 9-ATGCAGGT 3').

The starting unit dsDNA oligonucleotide with modified phosphates with PEG4 linker and terminal amine (DEC-Tec Starting Unit/DTSU, FIG. 28) and encoding 5'-phosphorylated oligonucleotides were purchased from LGC Biosearch Technologies. A "spike-in" with 10-mer DNA oligonucleotide featuring a cholesterol tag and terminal amine was purchased from LGC Biosearch Technologies to charge with pooled library to assess chemical reaction progress. T4 DNA ligase in high concentration was obtained from Qiagen Enzymatics. DNAse/RNAse-free ultrapure water from Invitrogen, HPLC-grade acetonitrile from Fisher and high-purity absolute ethanol from Koptec were used to prepare buffer solutions. LC/MS-grade water from Fisher, Optima LC/MS-grade methanol from Fisher, hexafluoroisopropanol (99+% purity) from Sigma-Aldrich and HPLC-grade triethylamine from Fisher were used to prepare LC/MS running solvent. All listed buffer solutions were prepared in-house, including HEPES 10× ligation buffer (300 mM 2-[4-(2-hydroxyethyl) piperazin-1-yl]ethanesulfonic acid, 100 mM adenosine triphosphate, 100 mM dithiothreitol, 10 mM $MgCl_2$, aq. NaCl (5 M), aq. NaOH, and basic borate buffer (250 mM sodium borate/boric acid, pH 10). Chemical building blocks and reagents were purchased from various vendor sources and used without further purification. Building blocks were purchased from a variety of manufacturer and generally prepared in acetonitrile (MeCN), dimethyl sulfoxide (DMSO) or mixed aqueous acetonitrile. The stock solution of building blocks were stored in 2D barcoded tubes from Phenix with septa-caps from Phenix at −80° C. and aliquots were taken for each use. Solutions were transferred using Fisherbrand pipette tips. Polypropylene PCR tubes from Genemate, tubes from Eppendorf, 96-well PCR plates from ThermoFisher and 96-well deep-well plates from USA Scientific were used to perform chemical reactions or DECL production. Large volume of chemical reactions or ethanol precipitations were performed in polypropylene 15-mL, 50-mL centrifuge tubes or 250 mL screw-cap bottles from various manufacturers. Heated reactions were performed on Mastercycler nexus gradient from Eppendorf, benchtop heating blocks from ThermoFisher, or TS-DW deep well plate themoshaker from Grant, or laboratory ovens from Fisher. Solutions were centrifuged in 5424R centrifuge from Eppendorf, or Lynx 4000 centrifuges from ThermoFisher. Optical density measurements were made using a Biophotometer from Eppendorf. A Vanquish UHPLC system was integrated with LTQ XL ion trap mass spectrometer (ThermoFisher Scientific) for LC/MS analysis of DNA oligonucleotides. DNA ligation was assessed by gel electrophoresis analysis and visualized with Molecular Imager Gel Doc XR system from BIO-RAD after staining in an ethidium bromide solution.

General Procedure for the Analysis of DNA Oligonucleotides

DNA sample or reaction mixture were diluted to 10 μM final concentration and injected in amounts of 5-10 μL on a Vanquish/LTQ system.

LC/MS Parameters for Thermo Vanquish UHPLC with LTQ Ion Trap MS Instrument:

(i) LC Settings

Column: Thermo DNAPac RP (2.1×50 mm, 4 μm)

Solvent A: 15 mM triethylamine (TEA)/100 mM hexafluoroisopropanol (HFIP) in water Solvent B: 15 mM TEA/100 mM HFIP in 50% methanol Solvent C: Methanol Flow rate: 0.65 mL/min Run time: 2 mins (gradient)

Column temperature: 100° C. (post column cooler at 40° C.)

Eluent: 15 mM TEA/100 mM HFIP in a water/methanol solvent system (ii) MS settings Source: ESI in negative mode Spray voltage: 4100 V Source heater temperature: 390° C.

Sheath Gas: 28 (instrument units)

Auxiliary Gas: 8 (instrument units)

Sweep Gas: 2 (instrument units)

Capillary temperature: 350° C.

Capillary voltage: −33.0 V

Tube lens: −92.0 V

MS Scan: 500-2000 m/z

DNA samples were analyzed on a Thermo Vanquish UHPLC system coupled to an electrospray LTQ ion trap mass spectrometer. An oligonucleotide column (Thermo DNAPac RP, 2.1×50 mm, 4 μm) was used with ion-pairing mobile phase for all the separations. Full scan negative-ion mode over the m/z range of 500-2000 was acquired for mass spectra. Data analysis was performed by processing the raw data with the automated biomolecule deconvolution with Promass and reporting software using ZNova novel algorithm to produce artifact-free mass spectra.

General Procedure for DNA Ligation (Preparation of Headpiece S2 from DTSU S1)

To DTSU S1 (100 nmol, 100 μL, 1.0 equiv) (FIG. 28) was added primer_foward (5'-ACACTTGCTGGT-3' (SEQ ID NO: 6), 105 nmol, 105 μL, 1.05 equiv), primer_reverse (5'-CAGCAAGTGTGA-3' (SEQ ID NO: 7), 105 nmol, 105 μL, 1.05 equiv), and nuclease-free water (62.9 μL), followed by the addition of 10×HEPES buffer (41.7 μL) and T4 DNA ligase (2.1 μL) to make the final concentration of DNA 0.24 mM. Incubate the reaction mixture at room temperature overnight. The ligation progress was monitored with LC/MS analysis and gel electrophoresis. Gel electrophoresis was executed with a 12-well 10% TBE acrylamide gel from Invitrogen in 1×TBE buffer prepared in-house. The DNA loading sample was prepared by adding 10 μL of the diluted DNA sample and 2 μL of 6×DNA loading dye to a final concentration of 12 ng/μL. Gels were run at 120 V for 45 min and stained with 0.5 ng/ml ethidium bromide in 1×TBE buffer for 40 min before visualizing. After completion of the ligation, the reaction mixture was purified by ethanol precipitation to yield the headpiece S2 for further use in chemical validation and library production. The procedure described above was followed to complete the remaining ligations utilized for library production. An exemplary final DNA sequence includes 5' d TAT GAT ACT AAA GTA AGT CAC ACA CAA TTG GAG CAG TCC TGA GTG AAT ACC TGC AT (SEQ ID NO:8)-Spacer 9-Amino C7-Spacer 9-ATG CAG GTA TTC ACT GAG GAC TGC TCC AAT TGT GTG TGA CTT ACT TTA GTA TCA TAT C 3' (SEQ ID NO: 9).

General Procedure for Ethanol Precipitation and DNA Reconstitution

Mixtures from chemical reactions or ligation were added 4% v/v of 5 M NaCl solution and 3 times of the reaction volume of absolute ethanol to crash out the DNA material. The mixture was pipet mixed thoroughly before storing at −20° C. overnight. The slurry was then centrifuged at 4000×G for an hour, removed the supernatant and added another portion of pre-chilled 75% ethanol solution to wash the pellet. The pellet was centrifuged at 4000×G for another hour before decanting the supernatant. The DNA pellet was air dried and nuclease-free water was added to reconstitute the DNA material. In general, ethanol precipitation was carries out after each chemical reactions or ligations and multiple 75% ethanol wash can be applied while needed.

Pharmacokinetics of CDD-1733, CDD-1819, and/or CDD-1845 in Mice

WT mice (n=4) were administered with CDD-1733, CDD-1819, or CDD-1845 (50 mg/kg, intraperitoneal injection) dissolved in 0.5% (w/v) methyl cellulose at a dose of 10 μL/g, individually. About 20 μL of blood (anticoagulated by sodium heparin) were collected via the tail vein at 5 min, 10 min, 0.25, 0.5, 1.0, 2.0, 4.0, 6.0, 8.0, and 24 h time points post dose. The whole blood samples were span at 2,000 rcf for 5 min for the separation of plasma. The plasma samples were stored at −80° C. before analysis. All the samples were analyzed with a Q Exactive orbitrap MS (Thermo Fisher Scientific, San Jose, CA) coupled with Vanish UHPLC (Thermo Fisher Scientific, San Jose, CA). LC-Q Exactive MS was operated in the same parameters used in metabolic stability assay above. The concentration of these compounds in plasma were quantified using a calibration curve. The calibration curve was regressed with a weight of 1/x2 with high linearity (r2>0.99) and accuracy (RSD<15%).

Calculation of Pharmacokinetic Parameters

PK parameters such as half-time ($T_{1/2}$), area under the plasma concentration-time curve during the period of observation ($AUC_{0-t}$), area under the plasma concentration-time curve from zero to infinity ($AUC_{0-\infty}$), clearance (CL), and the mean residence time (MRT) were calculated by WinNonlin software (Certara, Princeton, NJ) by noncompartmental analysis. The plasma concentration-time curves were plotted in Prism 7 (GraphPad, San Diego, CA) as mean±S.E.M.

Example 1: DNA-Encoded Chemistry Technology Yields Breakneck Access to SARS-COV-2 $M^{pro}$ Inhibitors The conventional process of drug discovery is based on automated high-throughput screening (HTS). HTS requires a complex infrastructure, the development a miniaturized assay tailored to the individual target, and generally the need for extensive medicinal chemistry to optimize modestly potent hits that arise from the screen. The development of such screening method is therefore sluggish and not well suited to meet the present public health demands imposed by the COVID-19 pandemic. A process which circumvents these challenges would significantly accelerate the pace for identification of clinical candidate compounds.

DNA-Encoded Chemistry Technology (DEC-Tec) is a screening paradigm that addresses these pitfalls related to HTS by screening of billions of DNA-tagged small molecules as a single mixture using an affinity selection assay. The expanded chemical space afforded by billions of drug-like small molecules allows the identification of high-affinity ligands in a practical affinity-based selection protocol that is both cost-effective and rapid. Therefore, as a more expeditious approach toward generating SARS-COV-2 therapeutics, the application of DEC-Tec to critical viral proteins was favored.

The genome of SARS-COV-2 comprises six major open-reading frames including two polyproteins that undergo extensive proteolytic processing to create functional proteins that perform tasks essential for viral propagation. This processing is largely achieved by SARS-CoV-2 main protease ($M^{pro}$ or $3CL^{pro}$), a cysteine protease enzyme indispensable for the virus lifecycle and a key therapeutic target.

DNA-encoded chemistry technology (DEC-Tec) is an increasingly attractive strategy to explore chemical space to identify small-molecules and high-affinity binders for a multitude of protein targets. DEC-Tec involves the creation of libraries of drug-like molecules covalently attached to a unique DNA barcode that enables identification of binders for a target in a pool of millions to billions of compounds. The collection of over 55 DEC-Tec libraries (4 billion unique molecules) including protease-biased libraries and various libraries utilizing DNA-compatible reactions developed in-house, provides the operational capacity to support emergent action at the onset of pandemics. The hypothesis was that SARS-COV-2 $M^{pro}$ screening of billions of DNA-encoded molecules, generation of small molecule-$M^{pro}$ co-crystals, and minimal medicinal chemistry follow-up would generate drug-like inhibitors of $M^{pro}$ for emergent use in patients infected with SARS-COV-2, related variants, and related coronaviruses.

Figure 2:
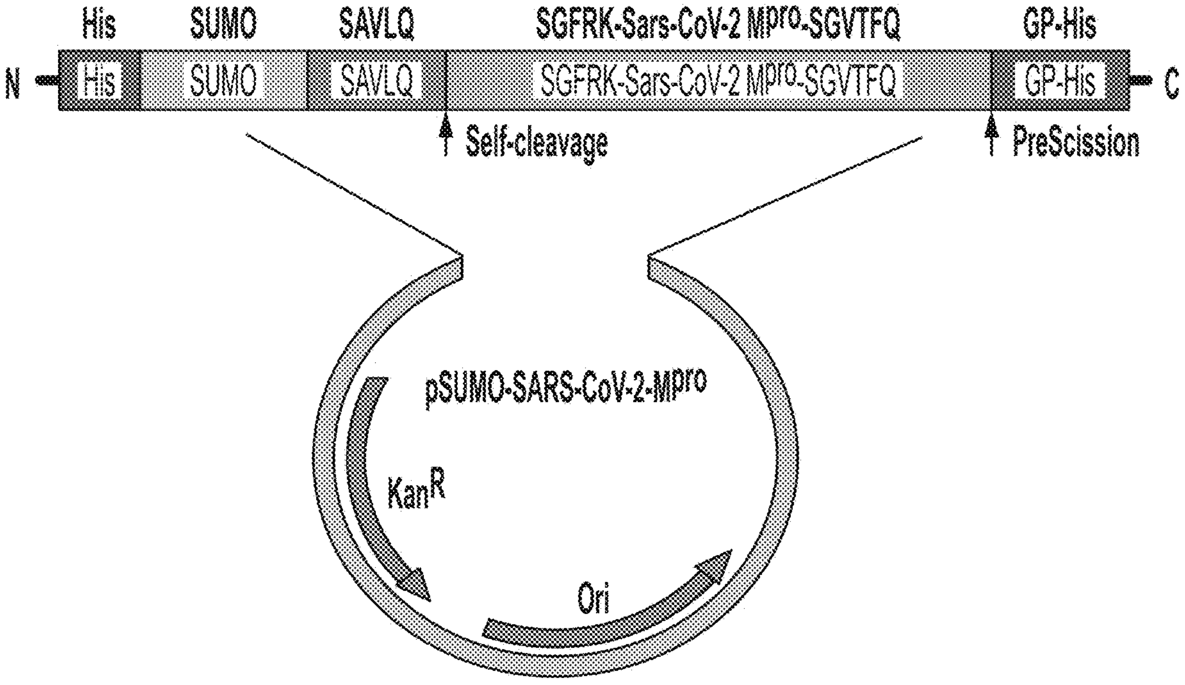
FIG. 2 is a schematic representation of pSUMO-SARS-COV-2-$M^{pro}$ construction. 6×His-tag SUMO was fused to the N-terminus of $M^{pro}$ gene through $M^{pro}$ cleavage-site (SAVLQ↓SGFRK; arrow indicates the cleavage site). PreScission cleavage site (SGVTFQ↓GP) followed by a 6×His-tag was introduced to the C-terminus of $M^{pro}$.
Figure 3:
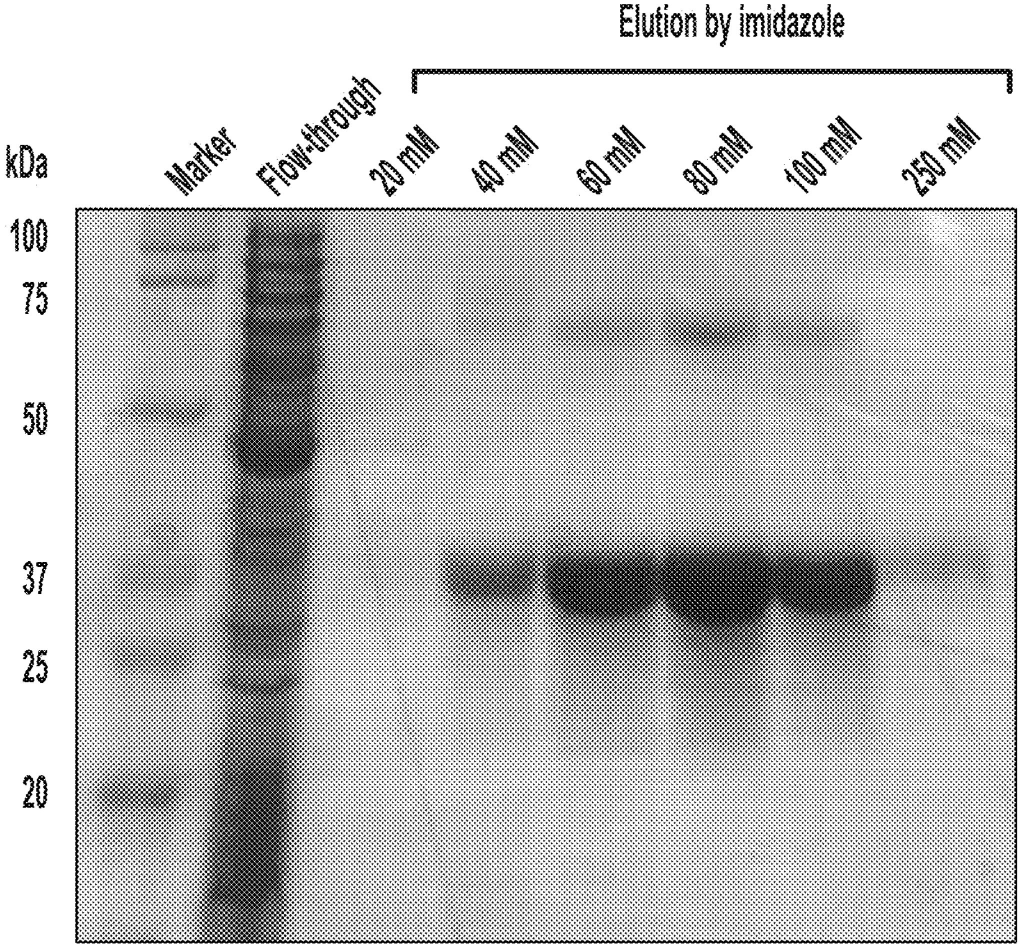
FIG. 3 is the $M^{pro}$-His6 purification profile. Cell lysate was mixed with binding buffer pre-equilibrated $Ni^{2+}$ Sepharose 6 Fast Flow resin and $M^{pro}$-His6 was eluted with increasing concentrations of imidazole (20 mM-250 mM). The elution profile of $M^{pro}$-His6 protein was visualized by SDS-PAGE followed by CBB staining. Two bands of $M^{pro}$-His6 on the gel are approximately 35 kDa (monomer) and 70 kDa (dimer).

To screen the DEC-Tec collection, the pSUMO-SARS-COV-2-$M^{pro}$ plasmid carrying the SUMO-$M^{pro}$-His6 tag was constructed (FIG. 2). The $M^{pro}$ open reading frame sequence was flanked on the N-terminus by its endogenous cleavage-site (SAVLQ↓SGFRK) (SEQ ID NO: 3) and on its C-terminus by a PreScission cleavage site (SGVTFQ↓GP) (SEQ ID NO: 4). The SUMO-$M^{pro}$-His6 recombinant fusion protein was expressed from *E. coli* BL21 (DE3), and the $M^{pro}$ enzyme with its authentic N-terminus and the His6 tag was purified as described in FIG. 3. Because the nickel magnetic screen capture test requires a His-tag, the $M^{pro}$-His6 protein was used for DEC-Tec library screening. For crystallography and enzymatic assays, the $M^{pro}$-His6 protein was treated with PreScission enzyme to remove the C-terminal 6-His tag, and the $M^{pro}$ was further purified by gel filtration chromatography. Using a fluorescent peptide, Dabcyl-KTSAVLQSGFRKM-E(Edans)-$NH_2$ (SEQ ID NO: 5), as a reporter substrate, it was confirmed that the purified recombinant $M^{pro}$-His6 and the $M^{pro}$ ("native") lacking the His6 tag were very active and demonstrated nearly identical bioactivity in vitro.

Forty unique DNA-encoded chemical libraries (DECLs) cumulatively containing 3.987 billion drug-like compounds were pooled together for the screen of $M^{pro}$-His6 binding compounds. Each library was pre-quantitated by quantitative polymerase chain reaction (qPCR), and the library pooling was conducted to have one million copies of each compound present in the pool. The selection for $M^{pro}$-His6 binders comprised a 3-round affinity selection with an $M^{pro}$-His6 protein concentration of 1 μM. An independent affinity selection was performed in parallel without protein to serve as a no-target control to identify any non-protein specific enrichment.

Figure 4:
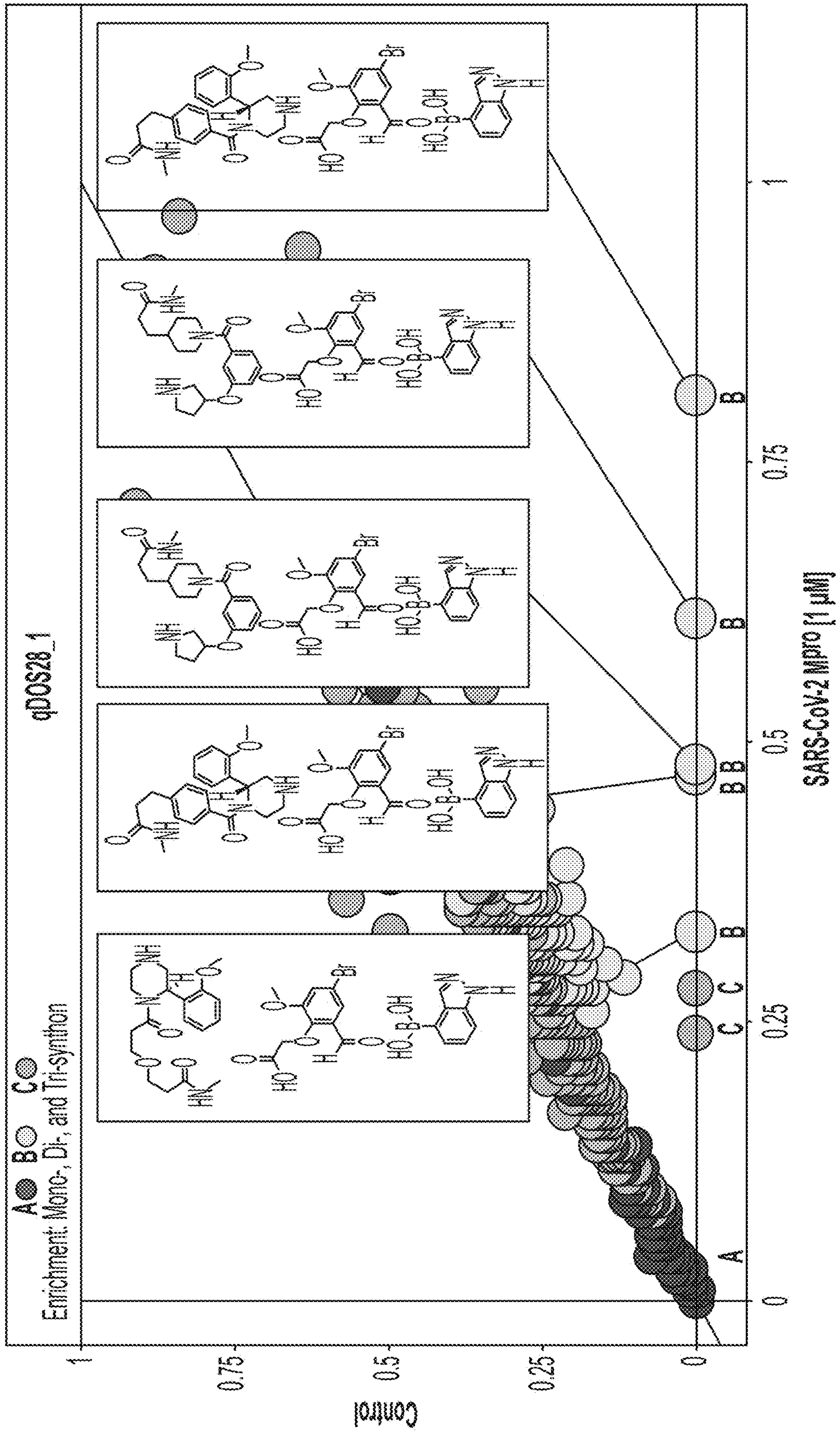
FIG. 4 depicts the enrichment profile of the DNA-encoded chemical library (qDOS28_1) against SAR-COV-2 $M^{pro}$ at 1 μM. This selection data has shown the enrichment of the same BB2 (middle of each box) and BB3 (bottom of each box) with various BB1 (top of each box), where the BB1 features di-substituted amine.

Illumina next-generation sequencing identified a chemical series consistently enriched with excellent structure-enrichment relationships (SER) from qDOS28_1, one of the DEC-Tec libraries (FIG. 4). The process of modern HTS screening has the capability to interrogate the activity of ~100K small molecules per day in a specialized well-based assay. Here, DEC-Tec was used to evaluate nearly 4 billion small-molecules as a single mixture in a day against $M^{pro}$, a rate of 40,000 times faster than conventional HTS. Thus DEC-Tec, through its breakneck rate of screening offers a tremendous advantage to infectious disease targets of pathogens that pose both present and imminent public health threats.

The DNA sequences resulting from the $M^{pro}$ selection were analyzed to determine structural features that were enriched to prioritize compounds to be synthesized without the DNA barcode (off DNA). Compounds within DECLs are generally constructed from the union of 3-building blocks (tri-synthons). Compounds enriched from the selection can be analyzed for those sharing one or two building blocks (mono-synthons vs. di-synthons) in common, leading to the identification of critical structure-enrichment relationships. The consideration of these SER leads to potent compounds in an efficient manner, supplanting the need for many rounds of laborious medicinal chemistry.

Based on the $M^{pro}$ selection analysis, the tri-synthon CDD-1714 ("hit" molecule) and its smaller di-synthons CDD-1712, CDD-1713 (FIG. 1) were synthesized off DNA in 2-4 steps from commercially available materials.

Figure 5A:
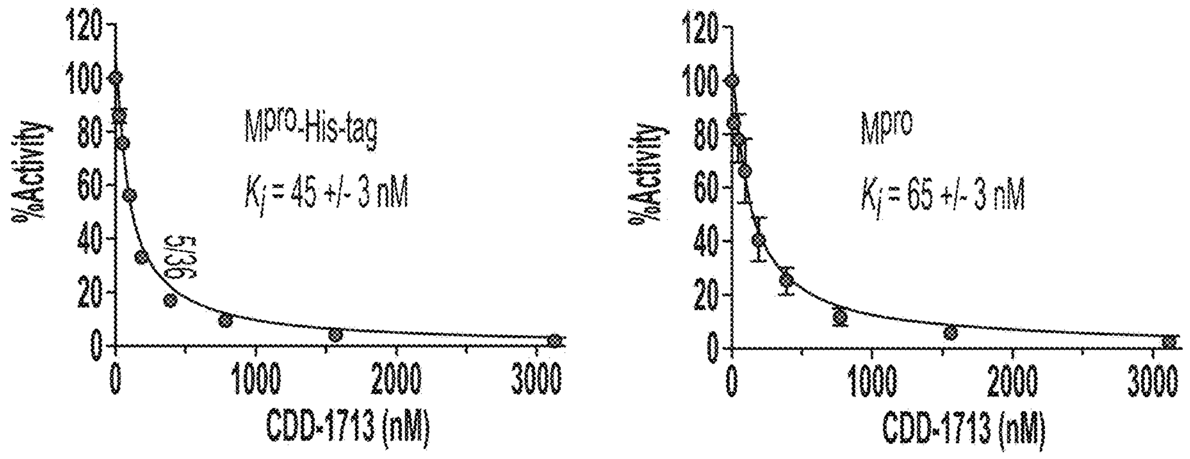
FIGS. 5A-5C depict the inhibition $K_i$ value determination against $M^{pro}$. 25 nM of $M^{pro}$-His6 or $M^{pro}$ cefotaxime was mixed with increasing concentrations of CDD-1713, CDD-1714, and CDD-1976. The remaining activities (dots) of $M^{pro}$ towards fluorescent peptide were plotted as a function of compound concentrations and $K_i$ values were calculated by fitting the data into Morrison equation with standard error from triplicates.
Figure 5B:
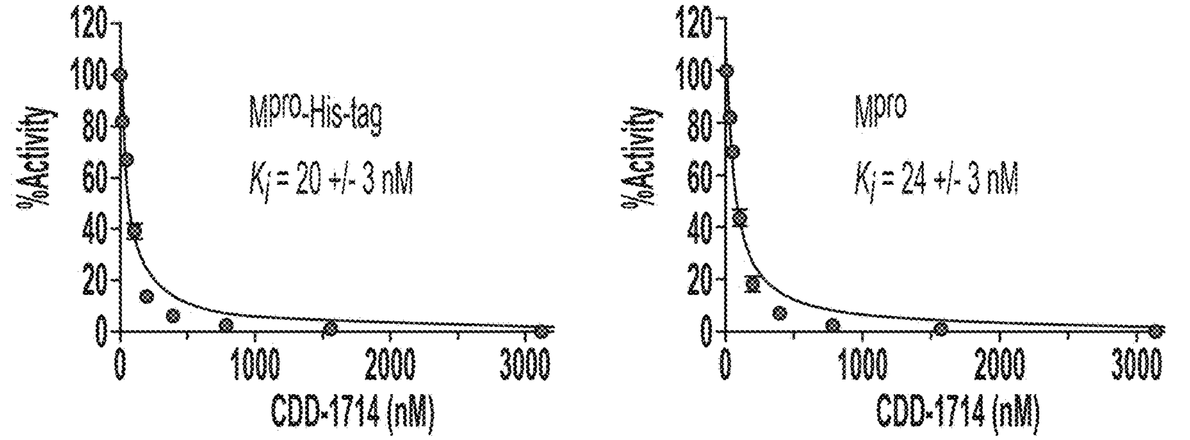
Figure 5C:
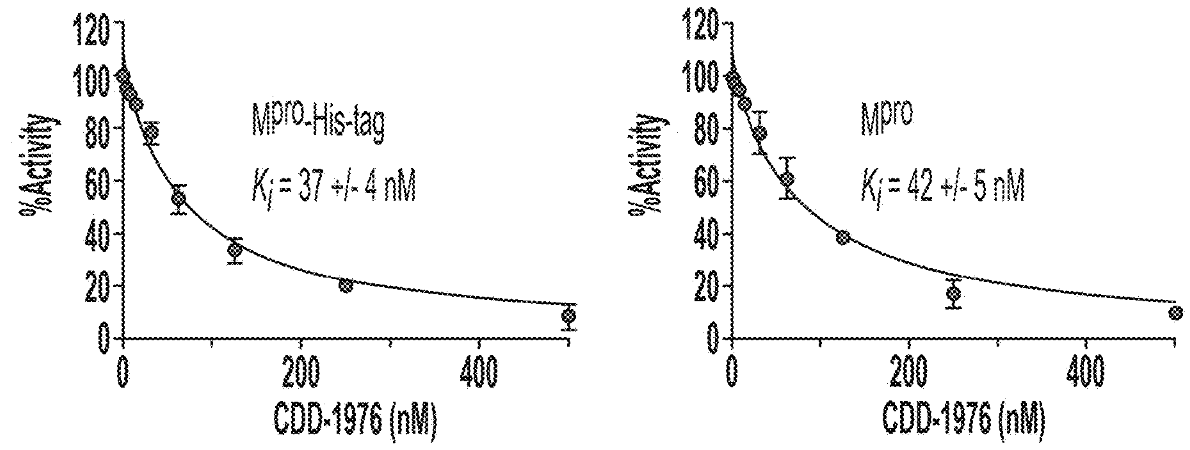

To characterize the potency of selected compounds towards $M^{pro}$, the above described fluorescent peptide reporter assay was utilized. For initial compound screening, 25 μM of compound was incubated with $M^{pro}$ and only compounds which inhibited $M^{pro}$ proteolytic activity >90%, were considered as candidates. The $K_i$ values of these compounds were determined with concentrations ranging from 4 nM to 4000 nM (FIGS. 5A-5C).

Since $M^{pro}$-His6 was used in library screening, parallel enzyme inhibition assays were performed using either $M^{pro}$-His6 or $M^{pro}$ to evaluate the potency of compounds towards $M^{pro}$ proteolytic activity in the presence and absence of His-tag. Using this protease inhibition assay, it was found that CDD-1713 and CDD-1714 inhibited $M^{pro}$ with $K_i$ values of 64.8 nM and 24.4 nM, respectively (FIGS. 5A-5C and Table 1).

TABLE 1

Selected compounds and $M^{pro}$ inhibition data

| Compound | Structure | $M^{pro}$-His $K_i$ (nM) | $M^{pro}$ $K_i$ (Nm) |
|---|---|---|---|
| CDD-1712 | 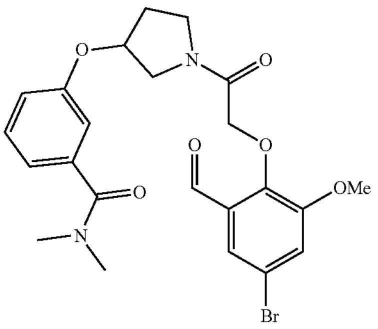 [SMILES: COc1cc(Br)cc(C=O)c1OCC(=O)N1CCC(Oc2cccc(C(=O)N(C)C)c2)C1] | Inactive | Inactive |
| CDD-1713 | 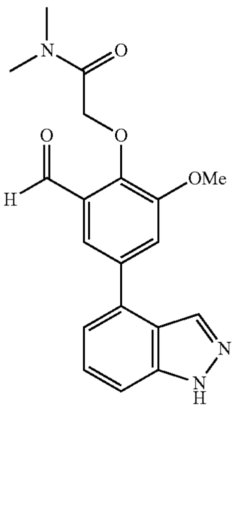 [SMILES: COc1cc(-c2cccc3[nH]ncc23)cc(C=O)c1OCC(=O)N(C)C] | 44.8 ± 2.9 | 64.8 ± 4.9 |

TABLE 1-continued
| Selected compounds and $M^{pro}$ inhibition data | | | |
|---|---|---|---|
| Compound | Structure | $M^{pro}$-His $K_i$ (nM) | $M^{pro}$ $K_i$ (Nm) |
| CDD-1714 | 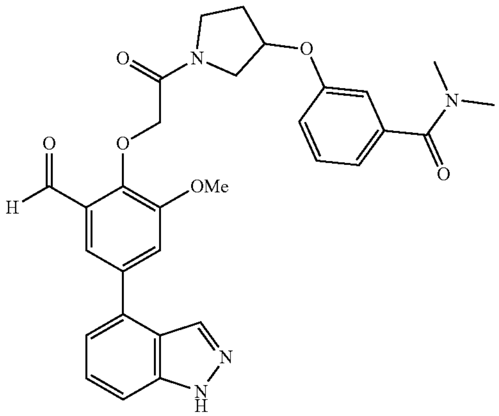 [SMILES: COc1cc(-c2cccc3[nH]ncc23)cc(C=O)c1OCC(=O)N1CCC(Oc2cccc(C(=O)N(C)C)c2)C1] | 20.2 ± 3 | 24.4 ± 3.2 |
| CDD-1776 | 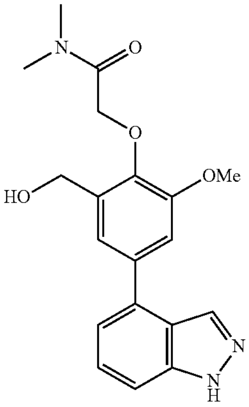 [SMILES: COc1cc(-c2cccc3[nH]ncc23)cc(CO)c1OCC(=O)N(C)C] | Inactive | Inactive |
| CDD-1777 | 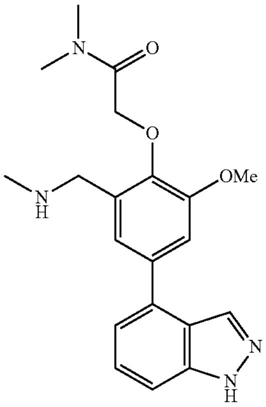 [SMILES: CNCc1cc(-c2cccc3[nH]ncc23)cc(OC)c1OCC(=O)N(C)C] | Inactive | Inactive |

TABLE 1-continued
| Selected compounds and $M^{pro}$ inhibition data | | | |
|---|---|---|---|
| Compound | Structure | $M^{pro}$-His $K_i$ (nM) | $M^{pro}$ $K_i$ (Nm) |
| CDD-1793 | 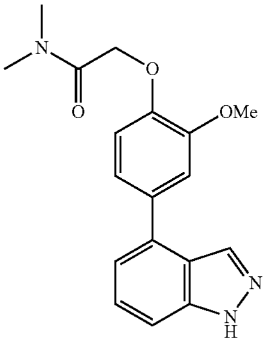 [SMILES: COc1cc(-c2cccc3[nH]ncc23)ccc1OCC(=O)N(C)C] | Inactive | Inactive |
| CDD-1847 | 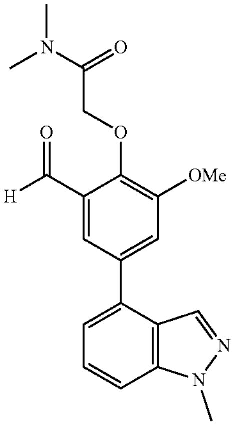 [SMILES: COc1cc(-c2cccc3c2cnn3C)cc(C=O)c1OCC(=O)N(C)C] | Inactive | Inactive |
| CDD-1883 | 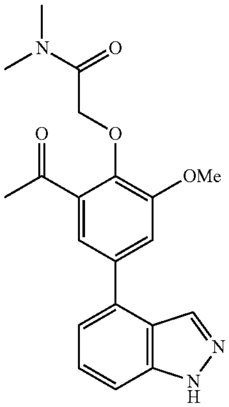 [SMILES: COc1cc(-c2cccc3[nH]ncc23)cc(C(C)=O)c1OCC(=O)N(C)C] | Inactive | Inactive |

TABLE 1-continued
| Selected compounds and $M^{pro}$ inhibition data | | | |
|---|---|---|---|
| Com-pound | Structure | $M^{pro}$-His $K_i$ (nM) | $M^{pro}$ $K_i$ (Nm) |
| CDD-1886 | 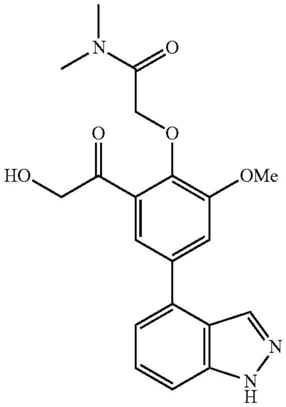 [SMILES: COc1cc(-c2cccc3[nH]ncc23)cc(C(=O)CO)c1OCC(=O)N(C)C] | 15700 ± 1200 | 21200 ± 1500 |
| CDD-1971 | 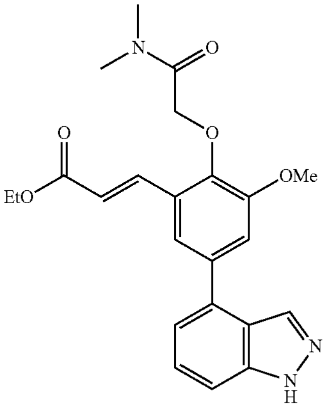 [SMILES: CCOC(=O)/C=C/c1cc(-c2cccc3[nH]ncc23)cc(OC)c1OCC(=O)N(C)C] | Inactive | Inactive |
| CDD-1976 | 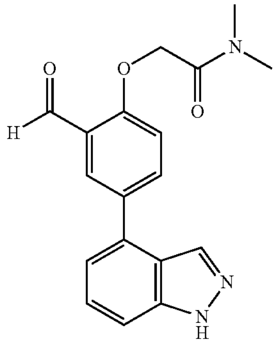 [SMILES: CN(C)C(=O)COc1ccc(-c2cccc3[nH]ncc23)cc1C=O] | 37 ± 4 | 42 ± 5 |

TABLE 1-continued

| Selected compounds and $M^{pro}$ inhibition data | | | |
|---|---|---|---|
| Compound | Structure | $M^{pro}$-His $K_i$ (nM) | $M^{pro}$ $K_i$ (Nm) |
| CDD-1982 | 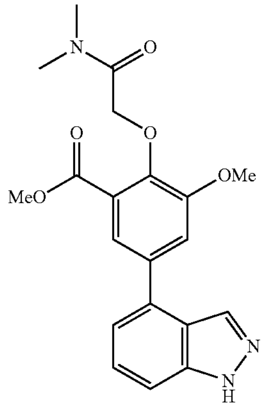 [SMILES: COC(=O)c1cc(-c2cccc3[nH]ncc23)cc(OC)c1OCC(=O)N(C)C] | Inactive | Inactive |
| CDD-2037 | 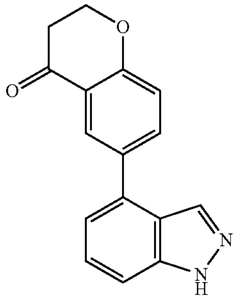 [SMILES: O=C1CCOc2ccc(-c3cccc4[nH]ncc34)cc21] | Inactive | Inactive |
| CDD-2038 | 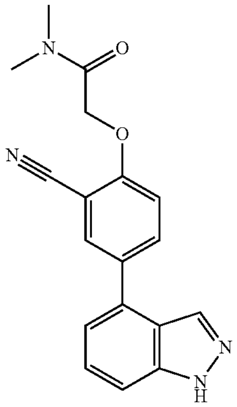 [SMILES: CN(C)C(=O)COc1ccc(-c2cccc3[nH]ncc23)cc1C#N] | Inactive | Inactive |

Figure 6A:
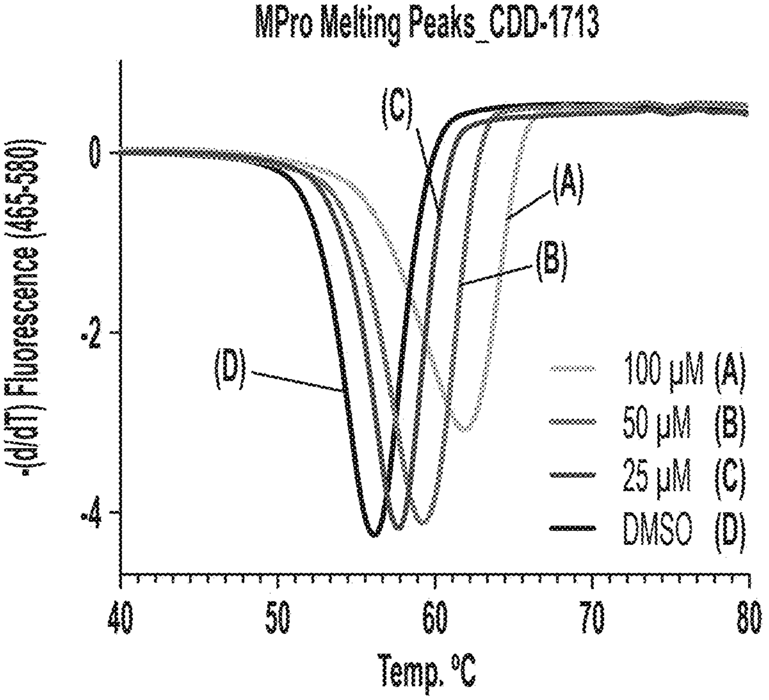
FIGS. 6A-6C show that CDD-1713 (FIG. 6A), CDD-1714 (FIG. 6B), and CDD-1976 (FIG. 6C) stabilized the SARS-COV-2 main protease ($M^{pro}$) in the protein thermal shift stability assay. Data analysis and protein melting temperature (Tm) calculation were run on a Roche Lightcycler 480 real-time PCR instrument (n=2). The plot was generated using a GraphPad Prism software.
Figure 6B:
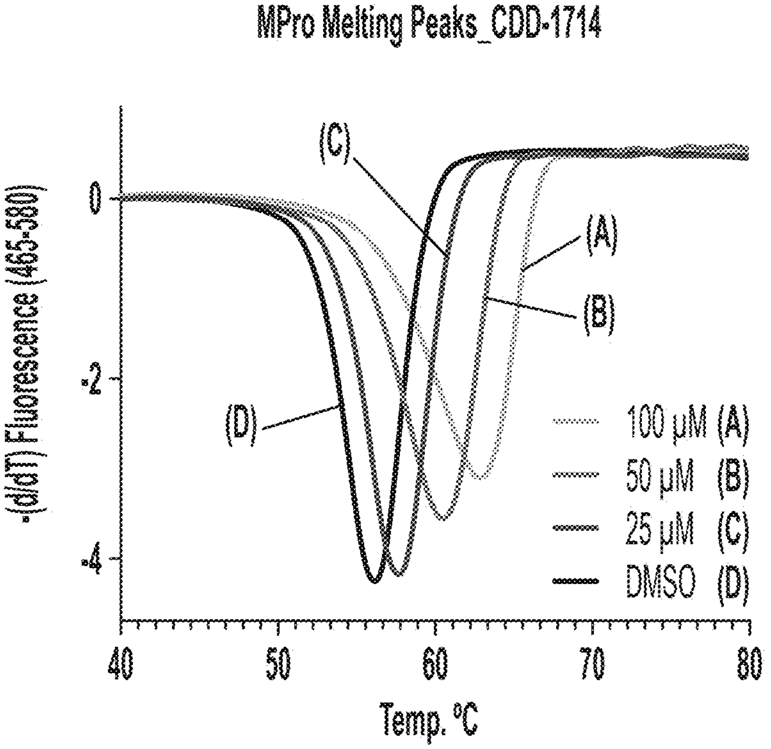
Figure 6C:
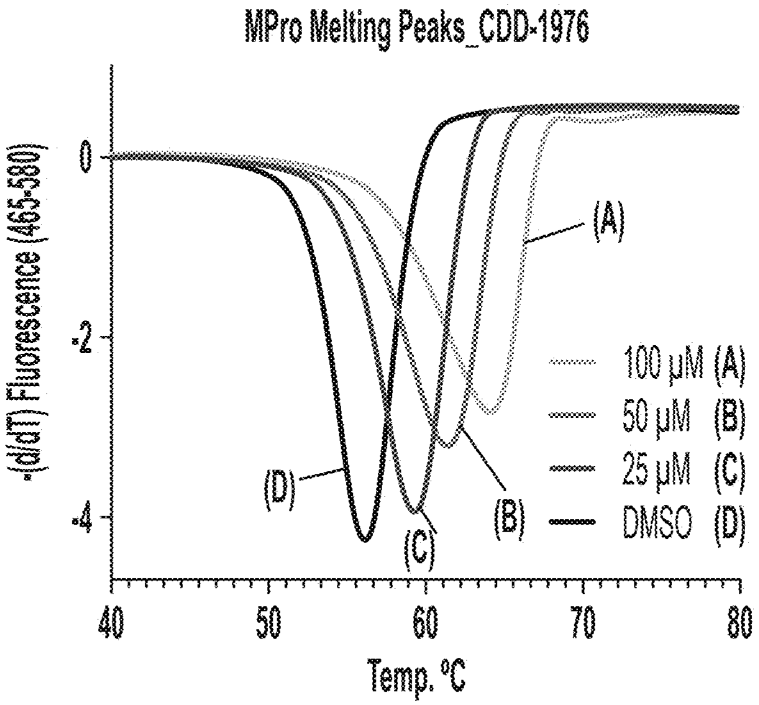
Figure 7A:
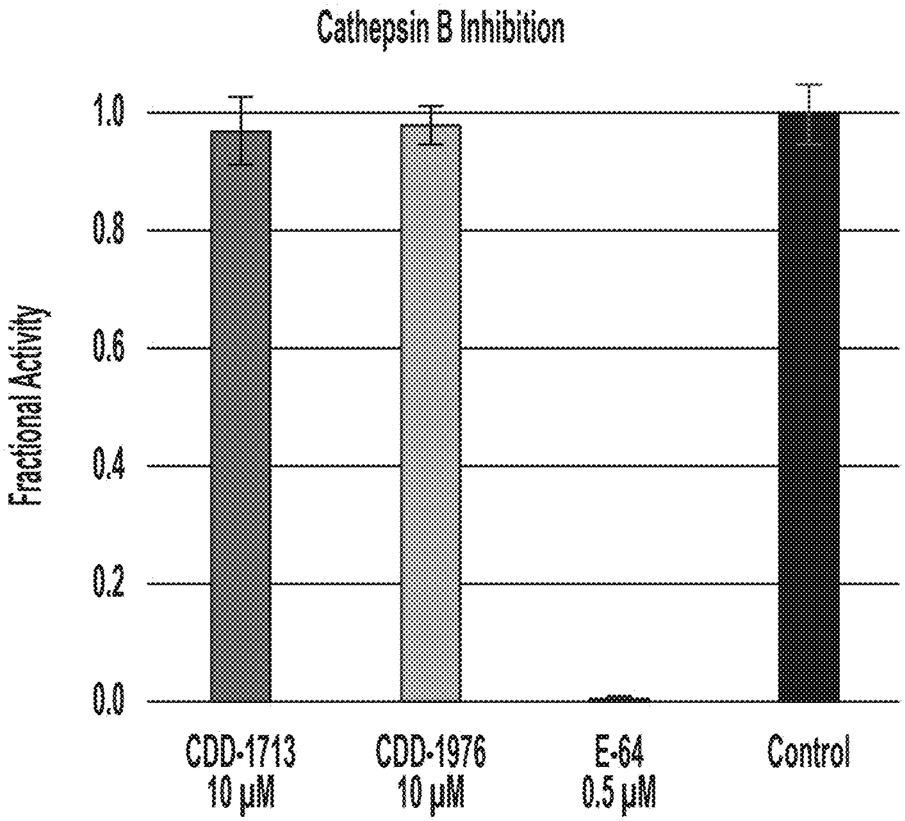
FIGS. 7A-7D show that the potential off-target inhibition of major proteases, i.e., cathepsin B (a cysteine protease like $M^{pro}$), thrombin (a serine protease), renin (an aspartic protease), and matrix metallopeptidase 1 (MMP-1), was evaluated with compounds CDD-1713 and CDD-1976, and control inhibitors, as indicated. The best inhibition was observed with renin by CDD-1713, with an estimated $K_{iapp}$ of 53 μM, calculated as described in methods section.
Figure 7B:
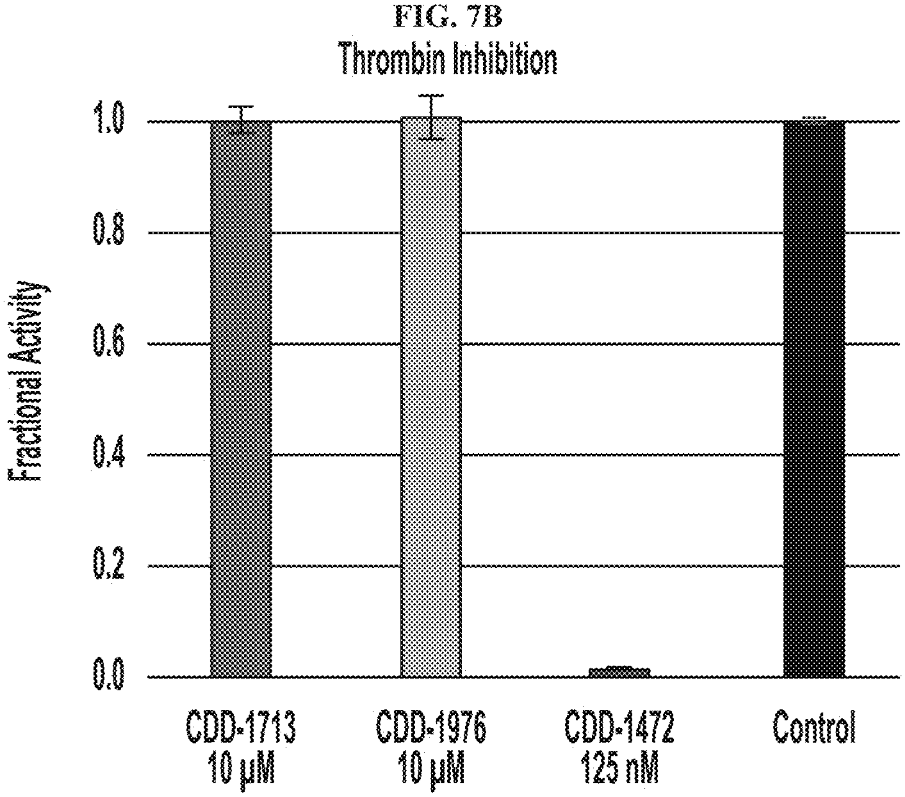
Figure 7C:
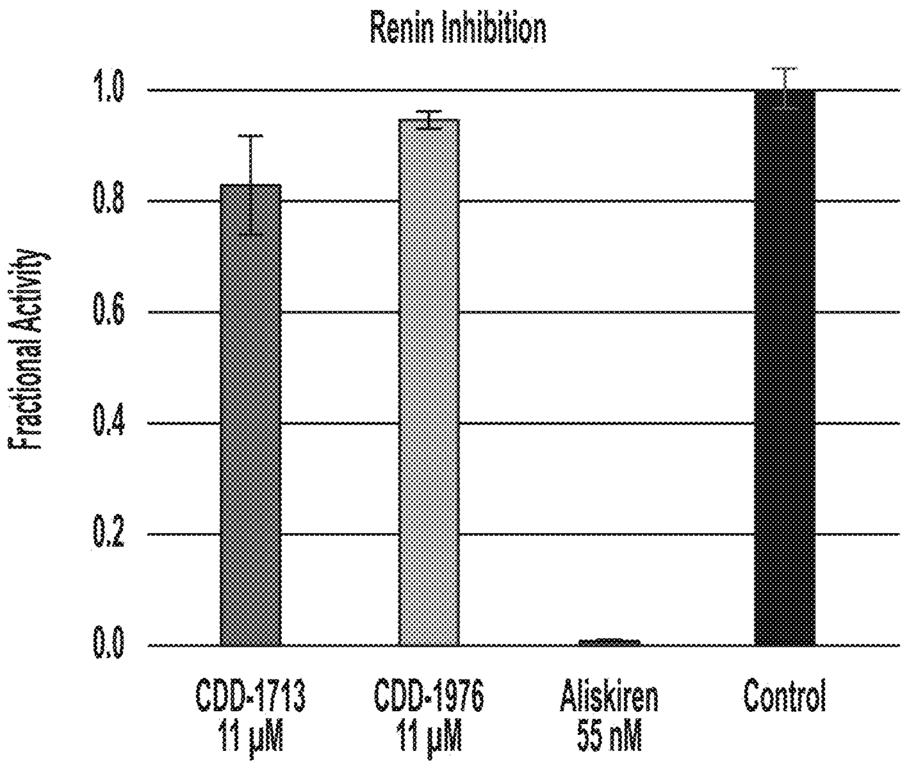
Figure 7D:
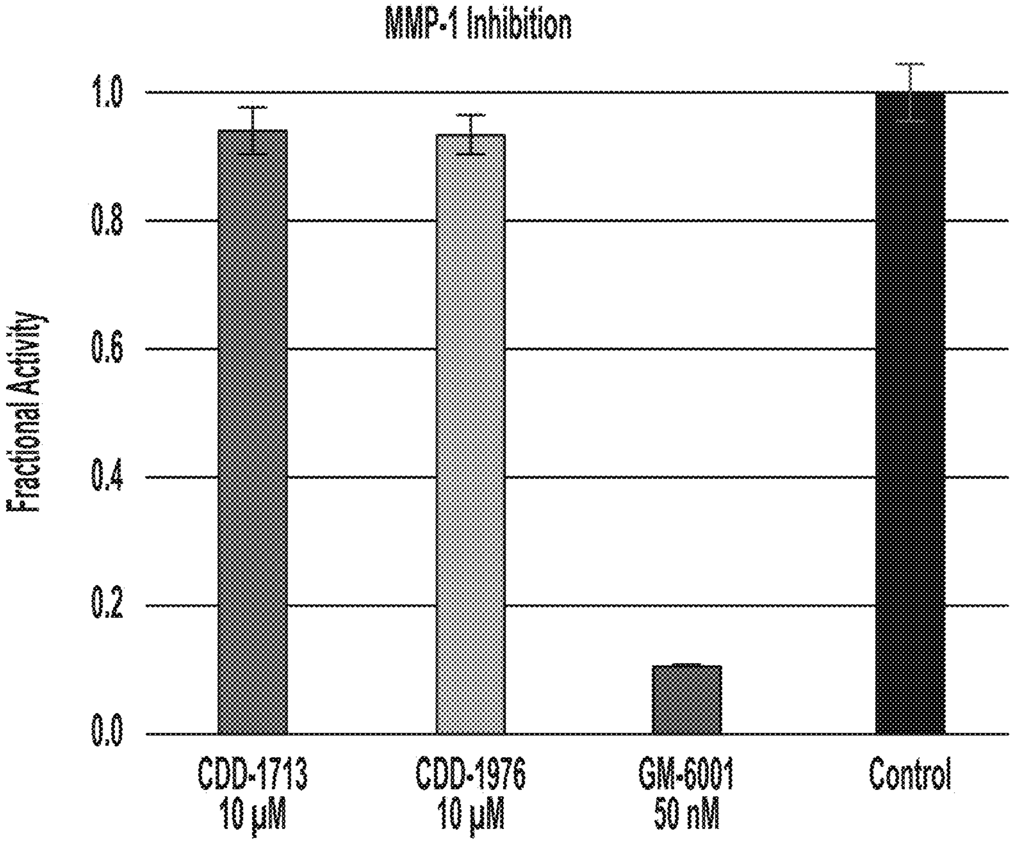

These results indicated that building block 1 (BB1), closest to the DNA attachment site, was less critical for binding and inhibition; CDD-1713 was chosen for optimization efforts based on its low molecular weight (353.3 g/mol) and good cLog P (2.01). CDD-1713 contains a reactive aldehyde functional group capable of forging covalent bonds with proteins, and thus initially the importance of the aldehyde moiety was examined. Deleting the aldehyde (CDD-1793) or replacing with hydroxymethyl (CDD-1776) completely abolished the activity, while replacing the aldehyde with hydoxymethyl ketone (CDD-1886) drastically decreased $M^{pro}$ inhibition by greater than 100-fold (FIG. 1). It was therefore concluded that the aldehyde was important for activity and next its electrophilic nature was probed. Generation of the more electron deficient des-methoxy analog (CDD-1976) showed better inhibition compared to CDD-1713. Aldehydes have the propensity to react non-selectively; however, CDD-1712 did not show any activity, additionally CDD-1847 was synthesized, which incorporates an N-methylindazole, and it was found that this compound completely lost activity. Given this remote substitution to the aldehyde, it is likely that the $M^{pro}$ inhibitory activity of CDD-1713 and related analogs results from a specific binding interaction with $M^{pro}$. To confirm that the potent inhibitors bound tightly to MPIO, a protein thermal shift stability assay (thermofluor assay) was performed. CDD-1713, CDD-1714, and CDD-1976 cause a concentration-dependent stabilization of $M^{pro}$ with CDD-1976 showing the most pronounced temperature shift at all three protein concentrations (FIGS. 6A-6C). Taken altogether, the DEC-Tec process involving affinity selection of 4-billion DNA-encoded compounds against $M^{pro}$, analysis of SER, and synthesis of the exemplary compounds off DNA yielded potent and selective inhibitors of $M^{pro}$. CDD-1713, which was inferred directly from the selection, was synthesized in rapid fashion (10 weeks from start to finish), highlighting DEC-Tec's ability to produce potent compounds without extensive synthetic optimization.

Figure 8A:
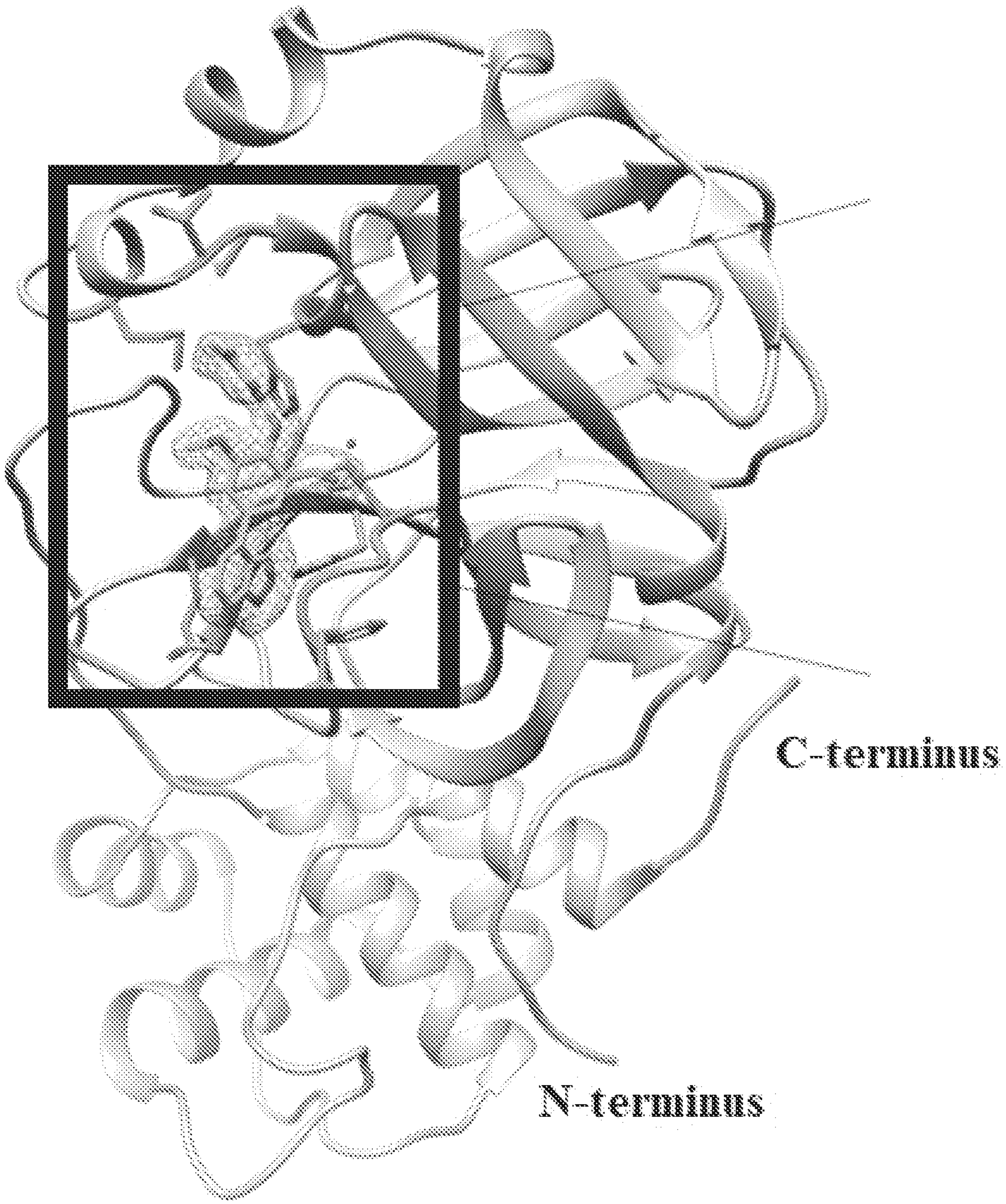
FIGS. 8A-8D depict the crystal structure of $M^{pro}$ in complex with CDD-1713.
Figure 8B:
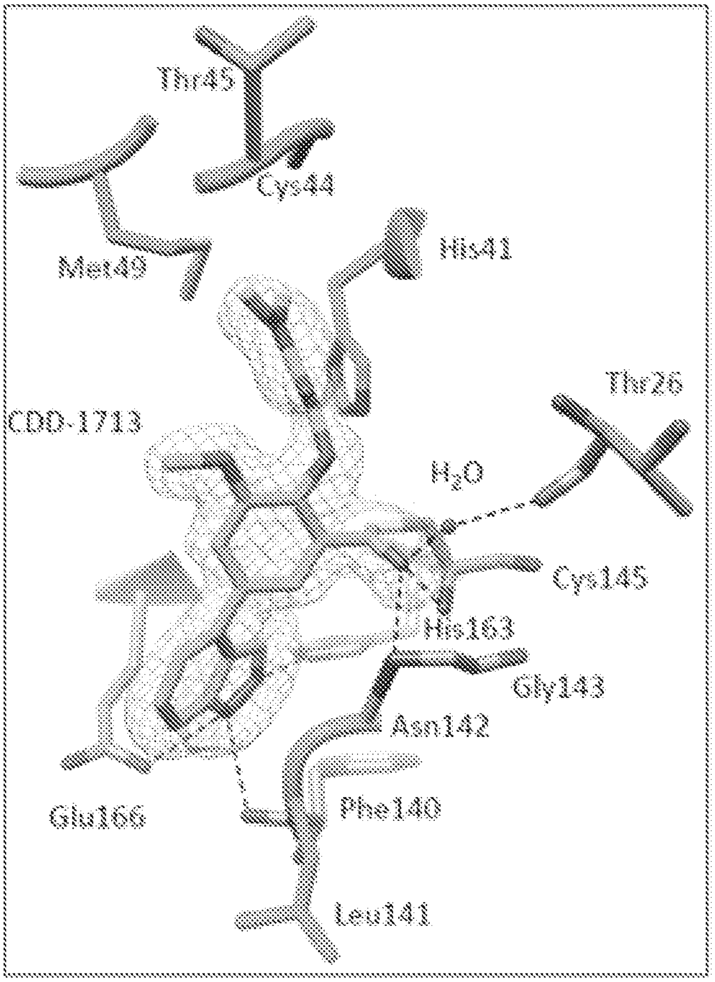
Figure 8C:
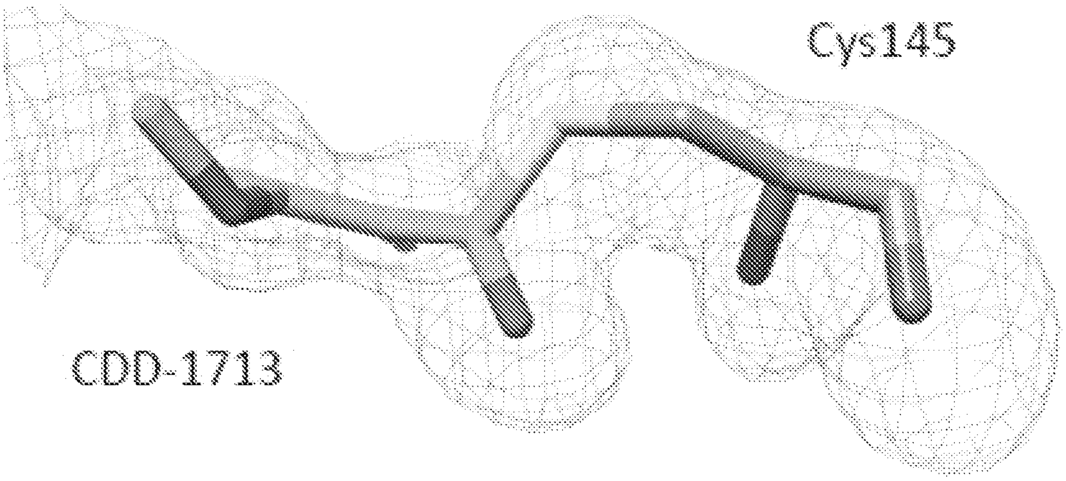
Figure 8D:
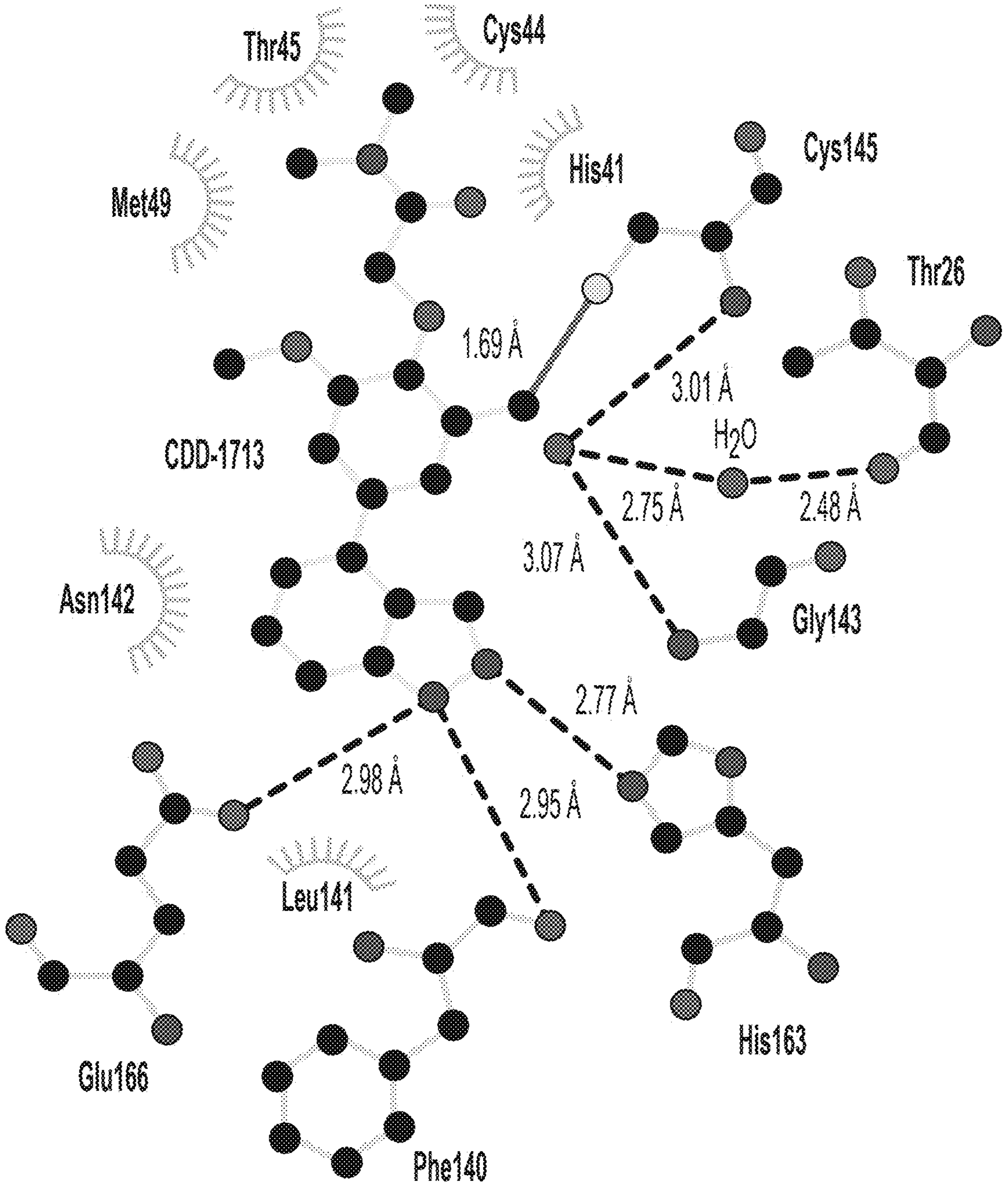

Using the $M^{pro}$ sequence, BLAST search analysis of the reference proteins encoded by the human genome shows no significant similarity. To confirm that the $M^{pro}$ inhibitors do not show any potential off-target inhibition of major proteases in humans, their effects were tested on four important proteases representing four classes of human protease enzymes. As might be expected from the BLAST search, none of the inhibitors block the enzymatic activity of cathepsin B (a cysteine protease like $M^{pro}$), thrombin (a serine protease), renin (an aspartic protease), or matrix metallopeptidase-1 (MMP-1) (FIGS. 7A-7D). Thus, the potent molecules are anticipated to have specific effects on inhibition of viral protein processing in vivo without altering human cellular activity.

suggesting CDD-1713 may exhibit broad $M^{pro}$ specificity. The central phenyl ring of CDD-1713 makes hydrophobic interactions with Asn142 and positions the aldehyde group for interaction with Cys143. The O-alkyl chain on the central phenyl ring occupies a region between the S2 and S1' subsites. The terminal methyl groups of the dimethylamide make hydrophobic interactions with His41, Cys44, Thr45, Ser46, and Met49 (FIG. 8D). Finally, the methoxy group attached to the central phenyl ring is solvent-exposed and does not interact with $M^{pro}$.

Figure 9:
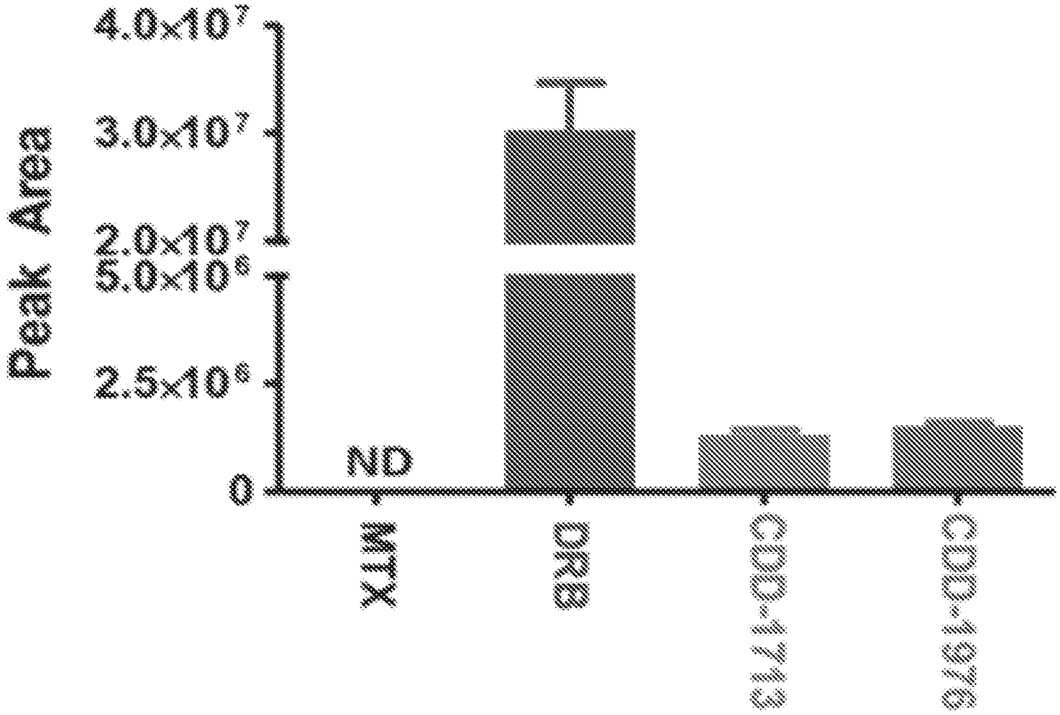
FIG. 9 depicts HepG2 cell uptake of CDD-1713 and CDD-1976. The HepG2 cell uptake capacities of CDD-1713 and CDD-1976 were expressed as the intracellular concentrations (peak areas) of these two compounds. Methotrexate (MTX) and doxorubicin (DRB) were used as the negative and positive controls, respectively. The HepG2 cells were incubated with the compounds and controls (final concentration 10 μM) for 2 hours at 37° C., harvested and homogenized. The intracellular concentrations were measured with UHPLC-Q Exactive Orbitrap MS. ND stands for "not detected".
Figure 10:
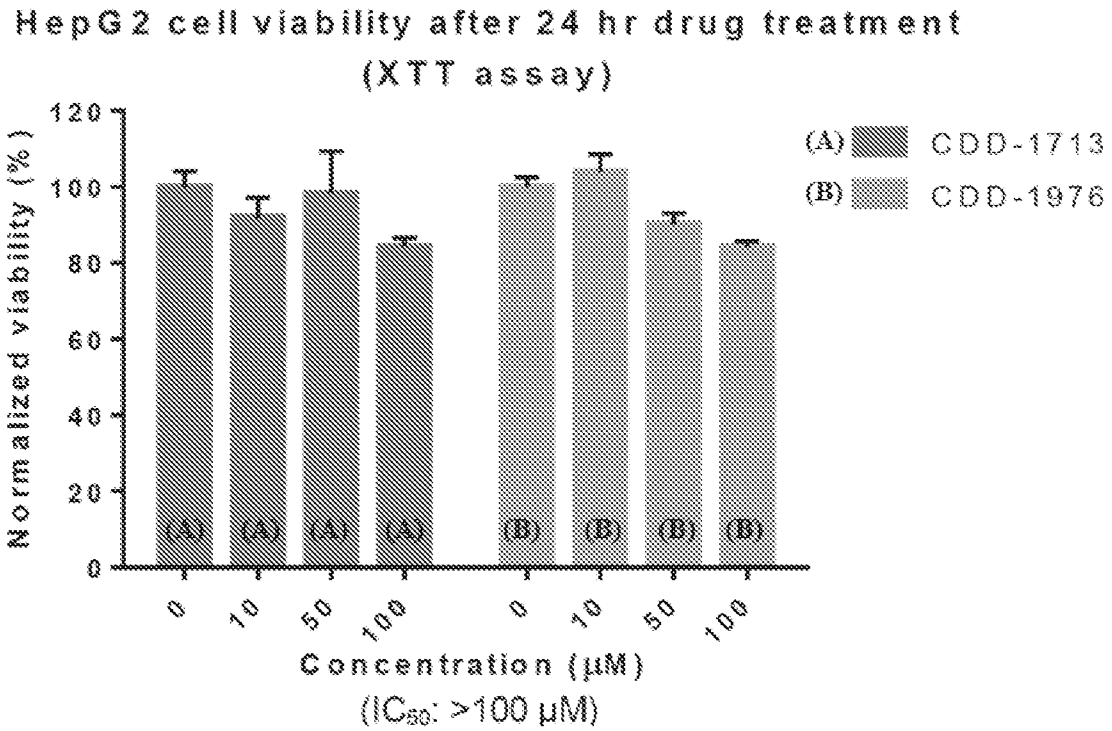
FIG. 10 depicts HepG2 cell viability after incubation with CDD-1713 and CDD-1976 for 24 hours. The HepG2 cells were incubated with CDD-1713 and CDD-1976 (0-100 μM) for 24 hours at 37° C. Cell viability was measured with XTT assay. XTT readings were normalized by the control group (DMSO) to give the normalized viabilities. The $IC_{50}$ values were expressed as ">100 μM" for CDD-1713 and CDD-1976, as the cell viabilities were larger than 80% in the 100 μM group for both compounds.
Figure 11A:
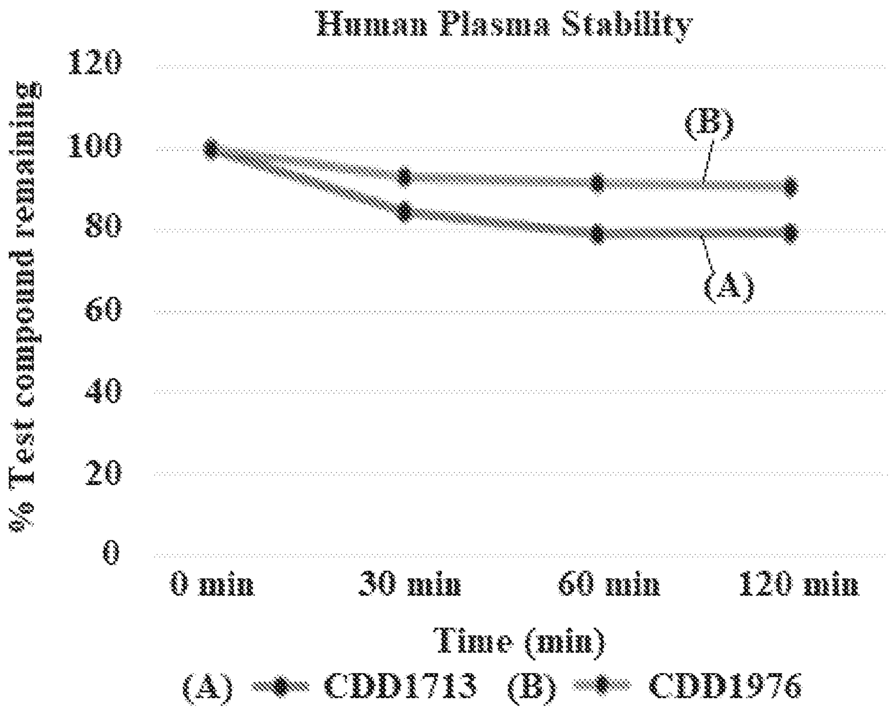
FIGS. 11A-11B depict plasma stability of CDD-1713 and CDD-1976 in human (FIG. 11A) and mouse plasma (FIG. 11B). CDD-1713 and CDD-1976 were incubated in human and mouse plasma respectively at a concentration of 10 μM in duplicate (n=2) at 37° C. The reactions were terminated at time points of 0, 30, 60 and 120 min by adding ice-cold methanol. Following centrifugation, the supernatant was analyzed using UHPLC-Q Exactive Orbitrap MS. The percentage of test compound remaining at the individual time points relative to the 0 min sample was determined.
Figure 11B:
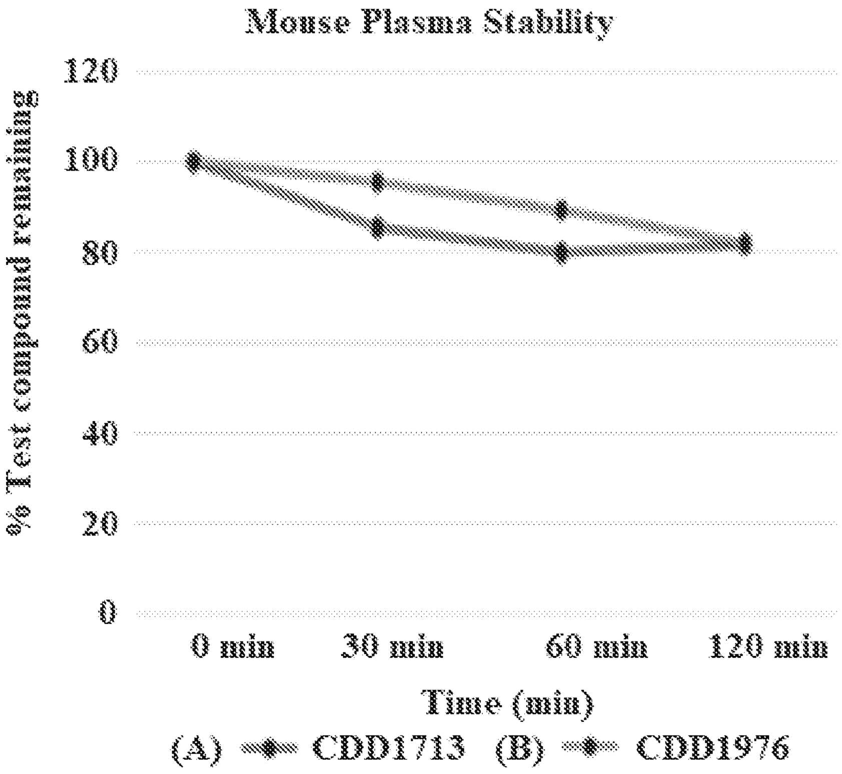

Using mouse and human liver microsomes, CDD-1713 was found to be metabolically labile in both mouse and human assays, while CDD-1976 is more stable in human liver microsomes, but not mouse (Table 2). CDD-1713 and CDD-1976 displayed moderate cell permeability in an uptake assay of HepG2 cells (FIG. 9) and no obvious cytotoxicity in HepG2 cells was observed for both compounds at 100 μM (FIG. 10). Both CDD-1713 and CDD-1976 are relatively stable in human and mouse plasma, 80% of compounds remained in plasma after 2 h incubation (FIGS. 11A-11B).

TABLE 2

Metabolic stability[a] of selected compounds in MLM[b] and HLM[c]

| Entry | Assay (half-life) | JQ1 | Alprazolam | CDD-1713 | CDD-1976 |
|---|---|---|---|---|---|
| 1 | MLM $t_{1/2}$ | 11.8 | 296 | 8.4 | 10.2 |
| 2 | HLM $t_{1/2}$ | 9.7 | 832 | 15.3 | 41.4 |

[a]Conditions: liver microsome concentration (0.5 mg protein/mL), compound concentration (2.0 μM), and NADPH concentration (1.0 mM); JQ1 was used as a short half-life control and Alprazolam was used as a long half-life control; measurements were obtained in duplicate at 0, 30, and 60 min;
[b]Mouse liver microsomes;
[c]Human liver microsomes.

Figure 12:
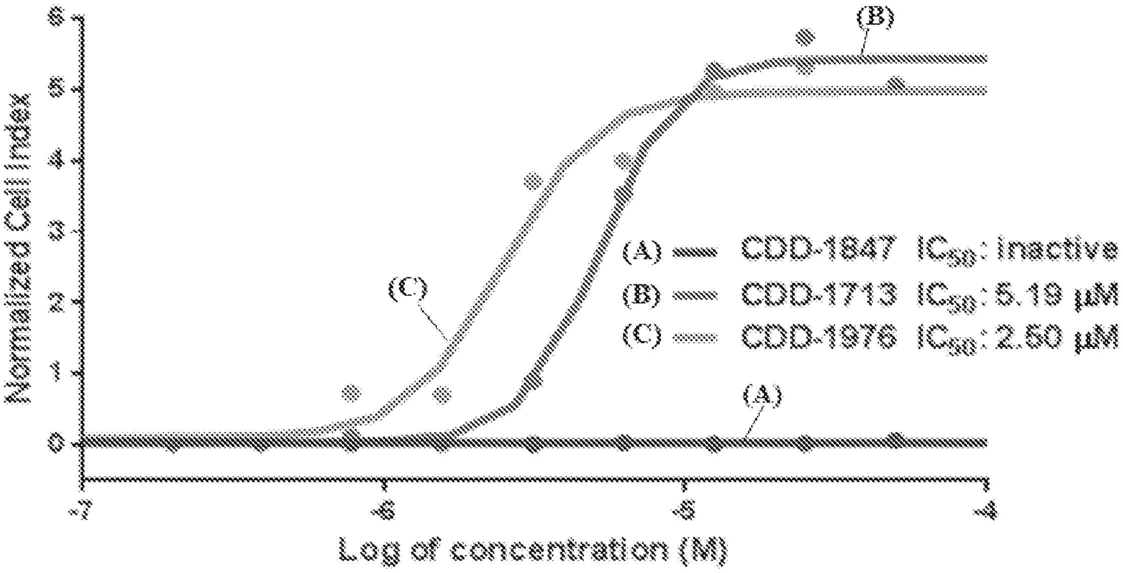
FIG. 12 depicts normalized cell index plotted versus concentration (Log) of $M^{pro}$ drug compounds measured using the xCELLigence RTCA. Average data points from duplicate measurements. A sigmoidal dose-response curve was fitted to determine $IC_{50}$ values for each $M^{pro}$ drug compound (lines).

To understand the interactions of CDD-1713 with $M^{pro}$, the X-ray crystal structure of the enzyme in complex with the inhibitor was determined. For this purpose, the purified enzyme was co-crystallized with CDD-1713. The structure was determined in space group C121 at 1.8 Å resolution with a single monomer in the asymmetric unit (FIGS. 8A-8D). The biological dimer is formed by the monomer and its symmetry-related monomer across the crystallographic 2-fold axis, as seen previously in $M^{pro}$ structures. Examination of the structure reveals CDD-1713 is positioned in the active site of $M^{pro}$ with the electron density clearly showing a 1.7 Å covalent bond from the aldehyde of CDD-1713 to Sγ of the catalytic residue Cys145 (FIGS. 8B-8C). The carbonyl oxygen of the aldehyde forms hydrogen bonds with the main chain nitrogen atoms of Gly143 and Cys145 that form the oxyanion hole of the enzyme. Similar interactions have been reported for bicyclopropane-containing inhibitors of $M^{pro}$ with an aldehyde warhead. The active site of $M^{pro}$ contains four sub-sites (S1', S1, S2, S3) that accommodate the amino acids of the peptide substrate or peptidomimetic inhibitors (P1', P1, P2, P3). $M^{pro}$ has a stringent requirement for a P1 glutamine occupying the S1 sub-site. The indazole ring of CDD-1713 inserts into the S1 pocket (FIGS. 8A-8D). The NH of the indazole group forms hydrogen bonds with the sidechain Oε of Glu166 and the main chain O of Phe140 while the N of the indazole forms a hydrogen bond with the Nε2 of His163 (FIGS. 8A-8D). In addition, the indazole group makes hydrophobic interactions with Phe140, Leu141, Asn142, and Glu166 (FIGS. 8A-8D). The extensive interactions of the indazole with residues in the S1 pocket is of note in that the residues in the S1 pocket are largely conserved among Coronavirus $M^{pro}$ enzymes, The viral inhibitory capacity of compounds CDD-1713 and CDD-1976 was demonstrated using a Real-Time Cell Analysis (RTCA) Assay. To evaluate viral inhibition, different concentrations of the $M^{pro}$ inhibitors were added to VERO E6 cells incubated with a live strain of the SARS-COV-2 virus. Subsequently, the growth kinetics of the cells were followed over 75 h. In the positive control group, SARS-COV-2 effectively caused cell death, which was observed as a decrease in the normalized cell index compared to the negative control group (no virus). CDD-1713 and CDD-1976 successfully reduced cell death in a dose-dependent manner, indicating that virus replication was stopped (FIG. 12). CDD-1976 was found to be most effective, with a calculated $IC_{50}$ of 2.50 μM, followed by CDD-1713 with an $IC_{50}$ of 5.19 μM. CDD-1847, a closely related analog that abolishes binding to $M^{pro}$, was unable to prevent cell death by the SARS-COV-2 virus.

In summary, using a DEC-Tec based strategy, CDD-1713 and CDD-1976 were identified as potent and selective inhibitors of SAR-COV-2 $M^{pro}$ that block viral reproduction in a short span of 20 weeks. X-ray crystallography was further deployed to elucidate the structural details of $M^{pro}$ inhibition by CDD-1713 and this information should enable further development of drug-like $M^{pro}$ inhibitors. These studies support DEC-Tec as an expedient and effective paradigm for generating therapeutics against critical targets within the SARS-COV-2 genome.

Example 2: Targeting the Main Protease of SARS-COV-2 for Treatment of COVID-19

Figure 13A:
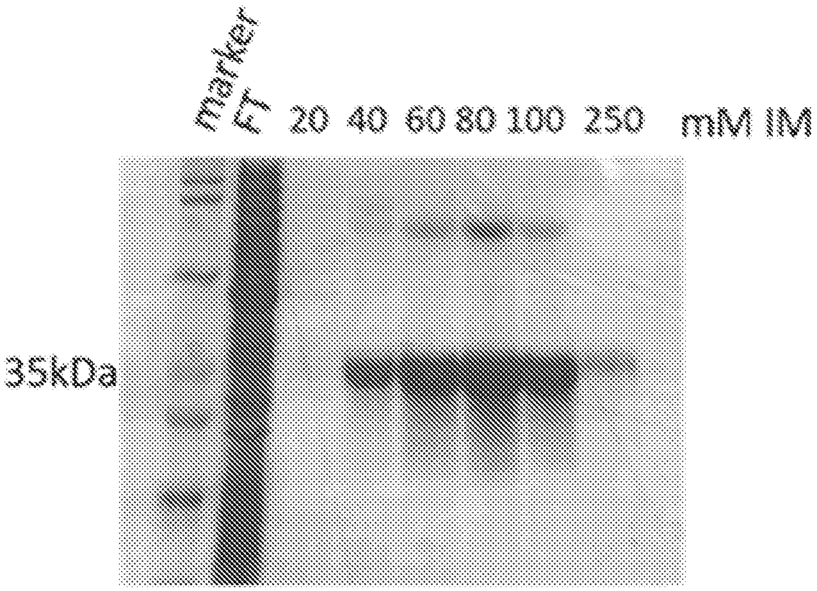
FIGS. 13A-13B depict SARS-COV-2 $M^{pro}$ purification and activity.
Figure 13B:
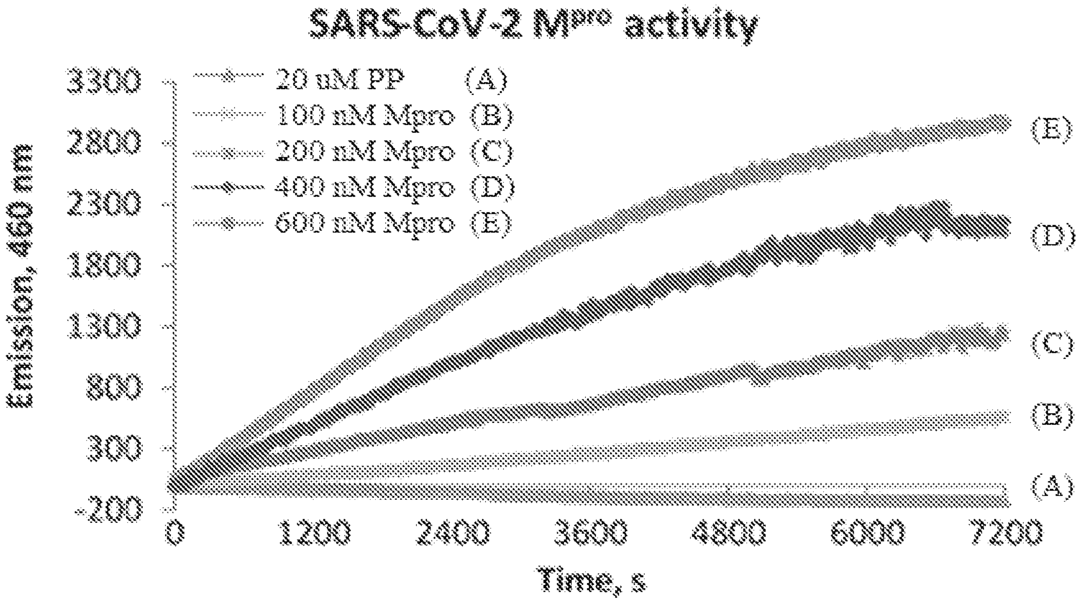

Inhibition of the SARS-COV-2 $M^{pro}$ with small molecules will disrupt the viral lifecycle in human host cells, which will attenuate the infection. The rapid discovery of novel inhibitors of SARS-COV-2 $M^{pro}$ is a great opportunity for developing therapeutics in treating COVID-19 and emerging coronavirus infections. Four protein expression plasmids were constructed to produce the SARS-COV-2 $M^{pro}$ in *E. coli*. The $M^{pro}$-SUMO and $M^{pro}$-GST expression systems were used with subsequent protein purification strategies to obtain milligram quantities of $M^{pro}$ with authentic N- and C-termini (FIG. 13A). The protease activity of the protein was further validated using a Förster Resonance Energy Transfer (FRET)-based assay with the fluorescent substrate Dabcyl-KTSAVLQ|SGFRKM-E(Edans)-$NH_2$ (FIG. 13B). This assay is also used to verify the inhibition of SARS-COV-2 $M^{pro}$ by the small molecules of the present disclosure (Table 3).

TABLE 3

Structure-activity relationships of the compounds in the CDD-1730 hit series

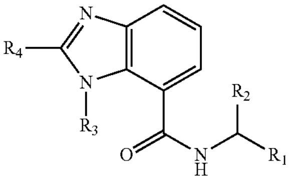

| Cmpd | $R_1$ | $R_2$ | $R_3$ | $R_4$ | $K_{iapp}$ (nM)[a] | $K_{iapp}$ (nM)[b] |
|---|---|---|---|---|---|---|
| CDD-1732 | 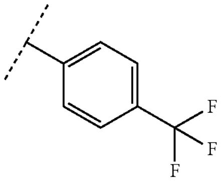 | 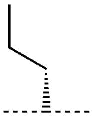 | 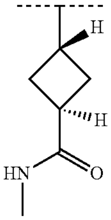 | 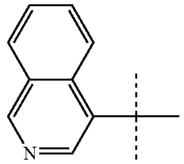 | 656.8 ± 56.5 | 806 ± 124.4 |
| CDD-1733 | 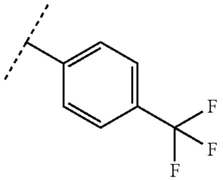 | 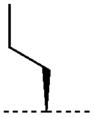 | 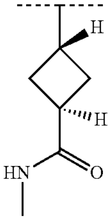 | 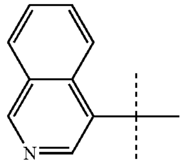 | 12 ± 2.2 | 18.1 ± 4.3 |
| CDD-1829 | 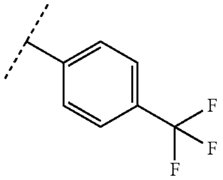 | 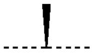 | 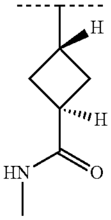 | 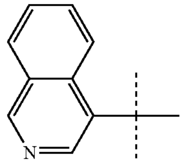 | 45.7 ± 3.7 | 47.9 ± 4.7 |
| CDD-1780 | 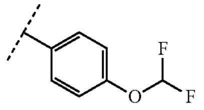 | 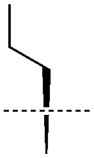 | 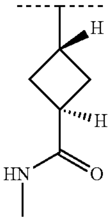 | 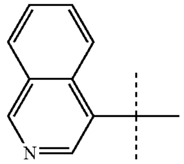 | 13.7 ± 1.5 | 15.7 ± 1.6 |
| CDD-1795 | 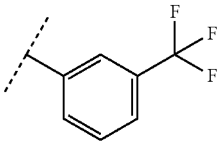 | 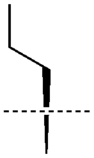 | 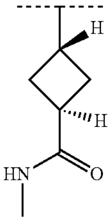 | 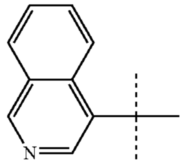 | 29.4 ± 4.3 | 35.2 ± 4.9 |

TABLE 3-continued
Structure-activity relationships of the compounds in the CDD-1730 hit series
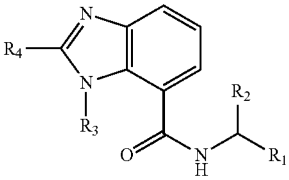
| Cmpd | $R_1$ | $R_2$ | $R_3$ | $R_4$ | $K_{iapp}$ (nM)[a] | $K_{iapp}$ (nM)[b] |
|---|---|---|---|---|---|---|
| CDD-1841 | 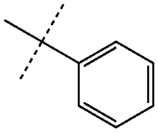 | 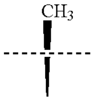 | 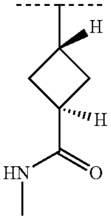 | 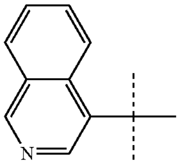 | 570.9 ± 72.7 | 564.8 ± 55.3 |
| CDD-1843 | 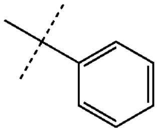 | 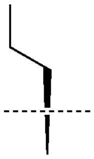 | 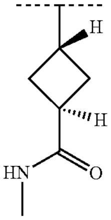 | 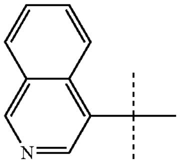 | Inactive | Inactive |
| CDD-1790 | 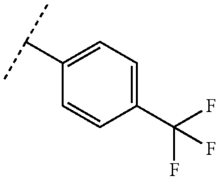 | 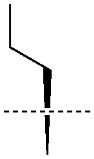 | 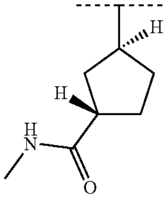 | 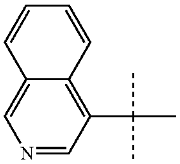 | 620.5 ± 46 | 663.3 ± 66 |
| CDD-1806 | 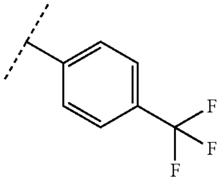 | 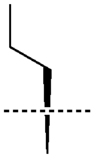 | 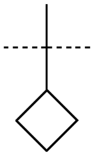 | 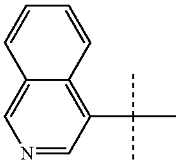 | 164.9 ± 12.9 | 137 ± 11.6 |
| CDD-1820 | 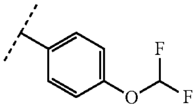 | 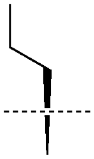 | 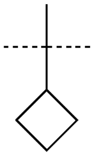 | 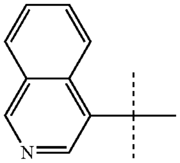 | 66.7 ± 5.8 | 71 ± 6.2 |
| CDD-1789 | 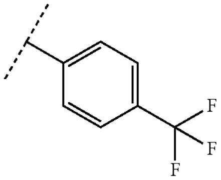 | 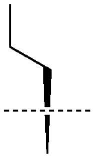 | H | 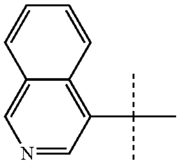 | Inactive | Inactive |

TABLE 3-continued
Structure-activity relationships of the compounds in the CDD-1730 hit series
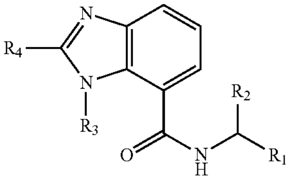
| Cmpd | $R_1$ | $R_2$ | $R_3$ | $R_4$ | $K_{iapp}$ (nM)[a] | $K_{iapp}$ (nM)[b] |
|---|---|---|---|---|---|---|
| CDD-1804 | 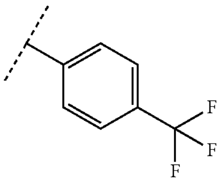 | 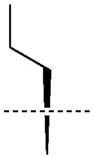 | 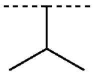 | 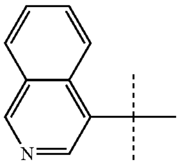 | Inactive | Inactive |
| CDD-1818 | 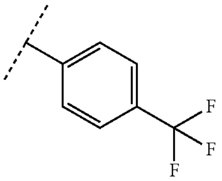 | 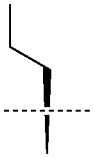 | 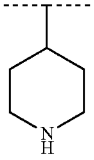 | 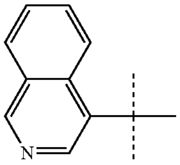 | 1470 ± 152 | 1714 ± 128 |
| CDD-1830 | 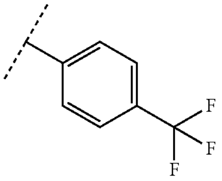 | 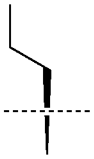 | 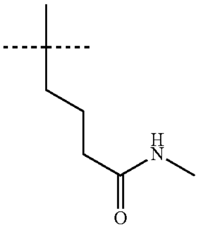 | 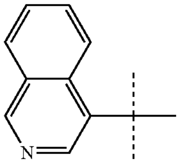 | 5.6 ± 0.5 | 6.5 ± 1 |
| CDD-1831 | 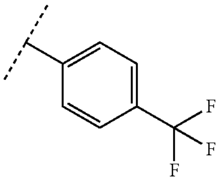 | 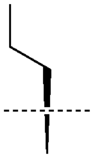 | 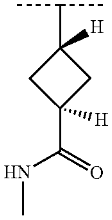 | 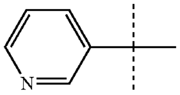 | Inactive | Inactive |
| CDD-1846 | 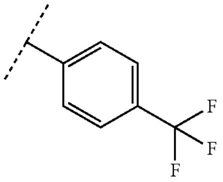 | 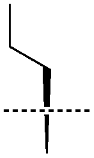 | 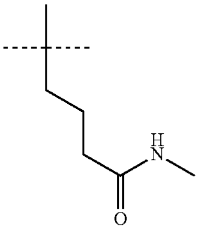 | 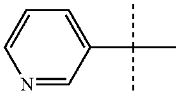 | 669.6 ± 59.1 | 805.5 ± 65.4 |
| CDD-1819 | 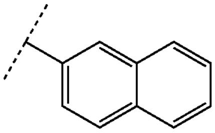 | 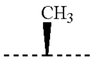 | 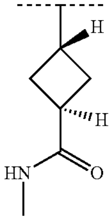 | 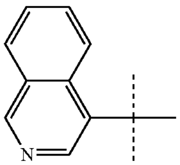 | 4.9 ± 1 | 4.2 ± 0.7 |

TABLE 3-continued
Structure-activity relationships of the compounds in the CDD-1730 hit series
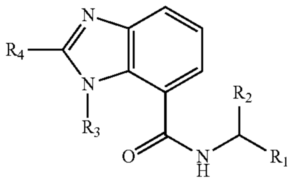
| Cmpd | $R_1$ | $R_2$ | $R_3$ | $R_4$ | $K_{iapp}$ (nM)[a] | $K_{iapp}$ (nM)[b] |
|---|---|---|---|---|---|---|
| CDD-1845 | 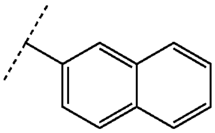 | 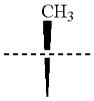 | 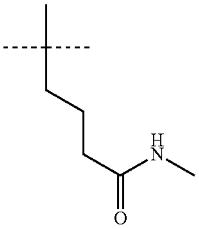 | 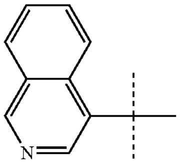 | — | 3.5 |
| CDD-1884 | 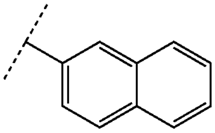 | 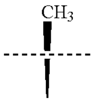 | 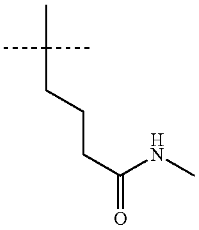 | 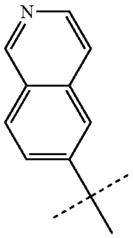 | Inactive | Inactive |
| CDD-1885 | 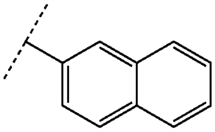 | 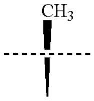 | 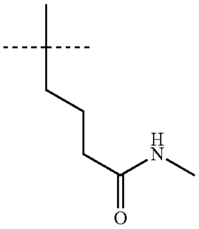 | 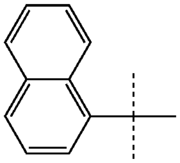 | Inactive | Inactive |
| CDD-1906 | 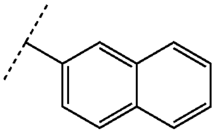 | 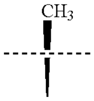 | 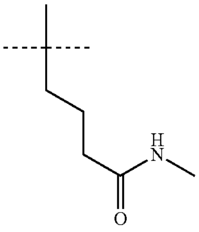 | 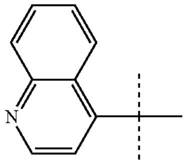 | Inactive | Inactive |
| CDD-1905 | 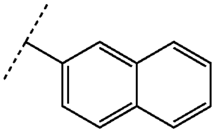 | 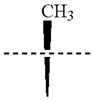 | 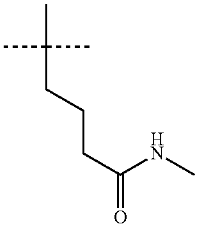 | 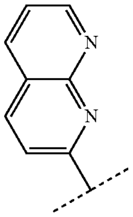 | Inactive | Inactive |

TABLE 3-continued
Structure-activity relationships of the compounds in the CDD-1730 hit series
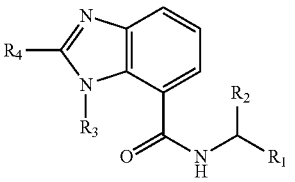
| Cmpd | $R_1$ | $R_2$ | $R_3$ | $R_4$ | $K_{iapp}$ (nM)[a] | $K_{iapp}$ (nM)[b] |
|---|---|---|---|---|---|---|
| CDD-1907 | 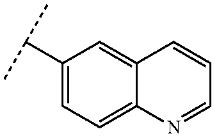 | 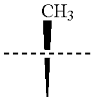 | 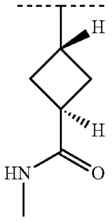 | 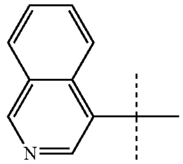 | 1187 ± 119.6 | 1330 ± 84.4 |
| CDD-1908 | 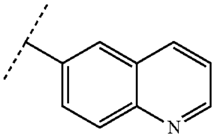 | 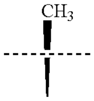 | 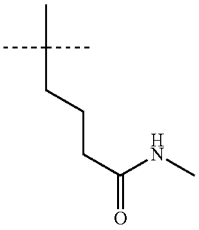 | 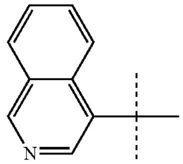 | 764.3 ± 66.2 | 852.1 |
| CDD-1924 | 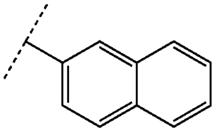 | 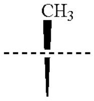 | 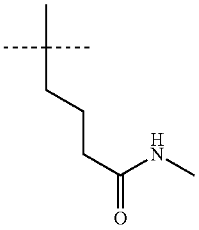 | 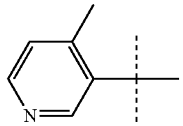 | 373.9 ± 22.8 | 426.4 ± 46.4 |
| CDD-1925 | 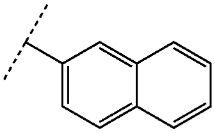 | H | 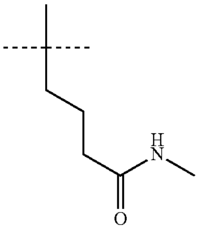 | 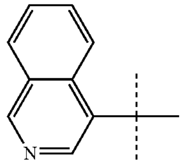 | 51.3 ± 7.5 | 42.5 |
| CDD-1926 | 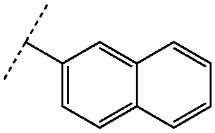 | 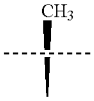 | 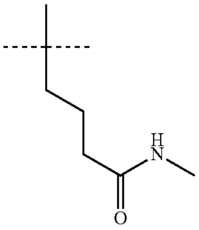 | 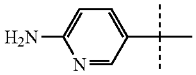 | Inactive | Inactive |

TABLE 3-continued

Structure-activity relationships of the compounds in the CDD-1730 hit series

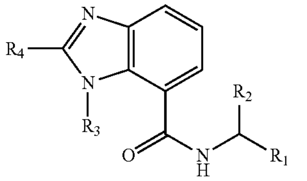

| Cmpd | $R_1$ | $R_2$ | $R_3$ | $R_4$ | $K_{iapp}$ (nM)[a] | $K_{iapp}$ (nM)[b] |
|---|---|---|---|---|---|---|
| CDD-1934 | 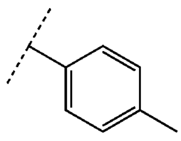 | 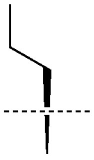 | 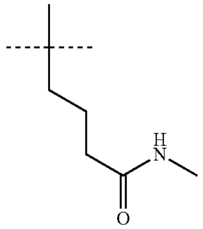 | 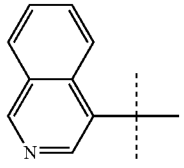 | 29.1 ± 3 | 27.4 ± 2.4 |
| CDD-1935 | 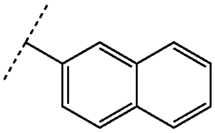 | 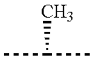 | 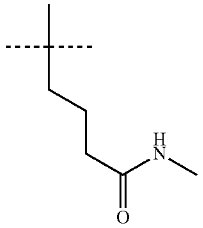 | 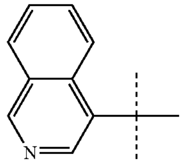 | 2275 ± 197.5 | 2301 ± 201.1 |
| CDD-1972 | 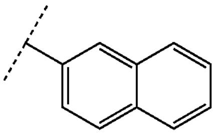 | 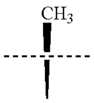 | 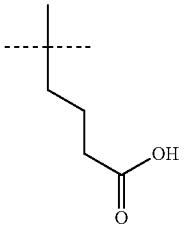 | 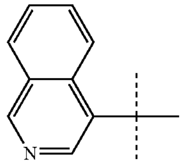 | 84.7 ± 9.4 | 87.9 ± 8.4 |
| CDD-1842 | 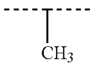 | 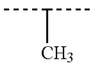 | 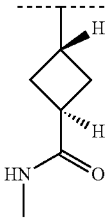 | 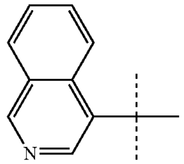 | Inactive | Inactive |

Figure 14A:
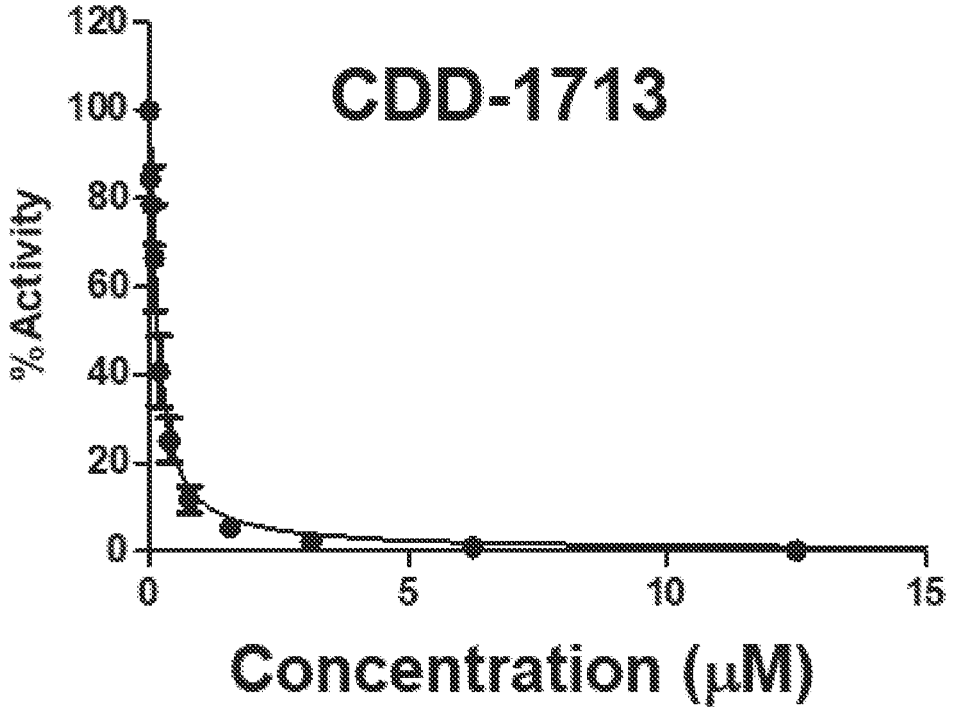
FIGS. 14A-14D show dose response curves for the confirmed initial hits CDD-1713, CDD-1714, and CDD-1733. The apparent $K_i$ values were calculated using the Morrison equation.
Figure 14B:
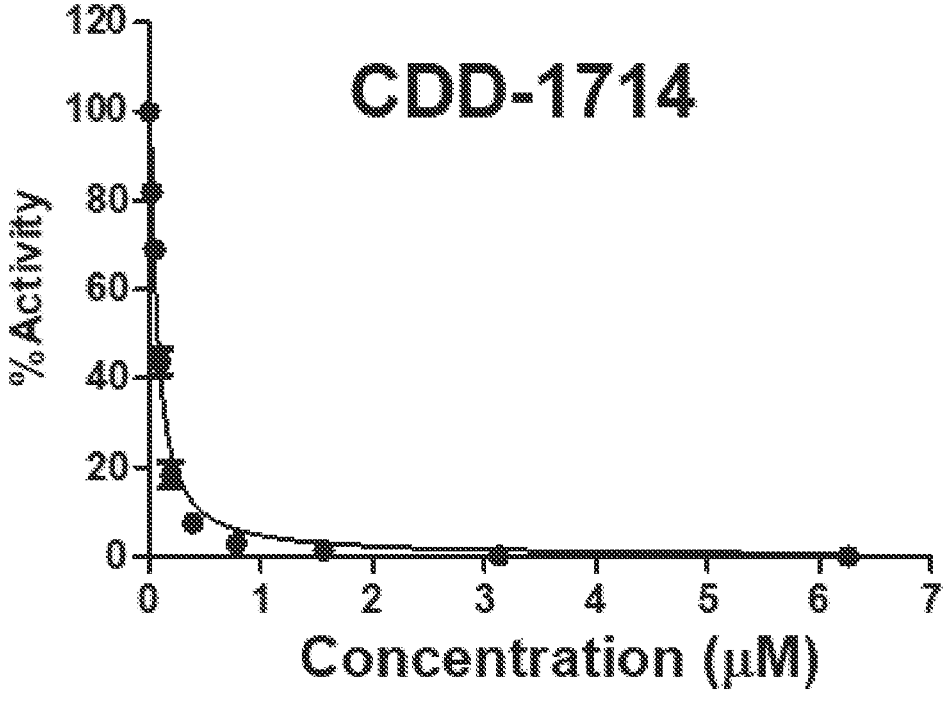
Figure 14C:
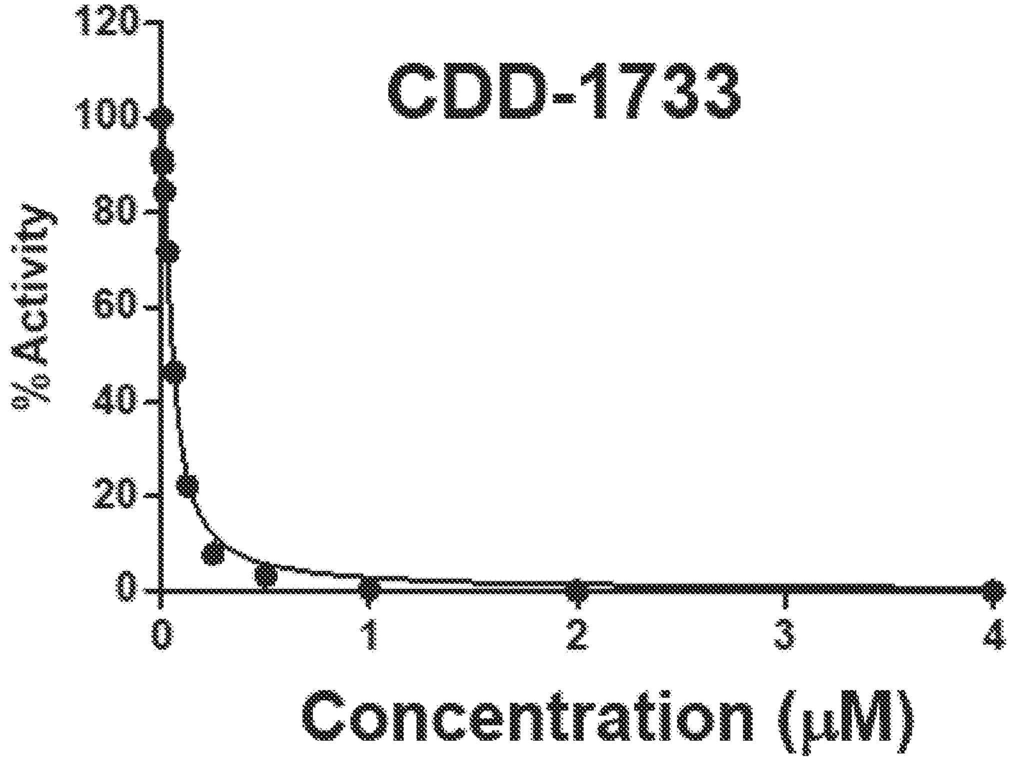
Figure 14D:
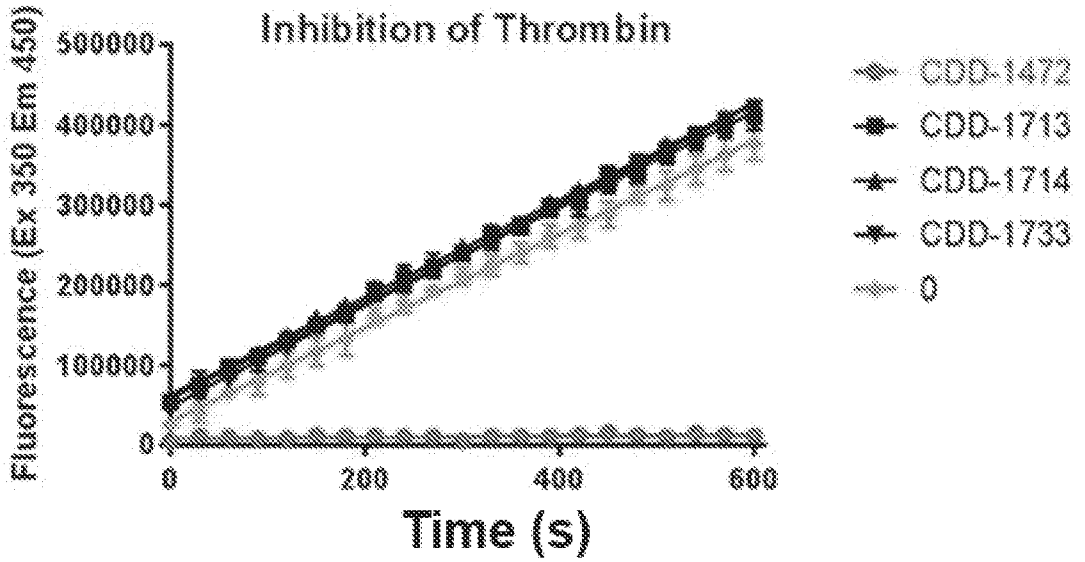

A screen of an in-house compound collection discovered inhibitors of SARS-COV-2 $M^{pro}$ which were confirmed for inhibition against SARS-COV-2 $M^{pro}$ via the described FRET-based assay. Three compounds displayed potent inhibition in a dose-dependent fashion (FIGS. 14A-14C). The promising compounds were also tested for cross-inhibition of human thrombin, a Ser-protease, and human cathepsin B, a Cys-protease, and displayed no inhibition (Table 4, FIG. 14D).

TABLE 4

Selected data for confirmed DEL hits and their analogs thereof

| Compound | CDD-1713 | CDD-1714 | CDD-1732 | CDD-1733 | CDD-1777 | CDD-1780 | CDD-1790 | CDD-1795 | CDD-1806 |
|---|---|---|---|---|---|---|---|---|---|
| M. Wt. (g/mol) | 353 | 543 | 600 | 600 | 368 | 598 | 614 | 600 | 525 |
| Measured apparent solubility in | 156.8 | 54.4 | 26.9 | 30.3 | 194.6 | 41.8 | 52.1 | 50.4 | 0.1 |

TABLE 4-continued

| Selected data for confirmed DEL hits and their analogs thereof | | | | | | | | | |
|---|---|---|---|---|---|---|---|---|---|
| Compound | CDD-1713 | CDD-1714 | CDD-1732 | CDD-1733 | CDD-1777 | CDD-1780 | CDD-1790 | CDD-1795 | CDD-1806 |
| PBS buffer (2% DMSO) (μM) $K_{i,\ app}$ towards SARS-CoV-2 $M^{pro,\ athentic\ termini}$ (nM) | 64.8 | 24.4 | 806 | 14.9 | 2427 | 15.7 | 663 | 35.2 | 137 |
| ΔTm of Mpro at 50 μM compound conc. (° C.) | 2.99 | 2.93 | 0.61 | 7.75 | 1.00 | 9.19 | | | |
| ΔTm of HOVPro-Gi.1 at 50 μM compound conc. (° C.) | −0.09 | −0.11 | −0.82 | −0.74 | | −0.18 | | | |
| ΔTm of HOVPro-Gii.4 at 50 μM compound conc. (° C.) | −0.73 | −0.41 | −1.24 | −1.2 | | −1.23 | | | |
| Thrombin inhibition | None | None | None | None | | None | | | |
| Human Cathepsin B, Fractional Remaining Activity | 0.97 | 0.92 | | 0.91 | | 0.95 | | 1.07 | 0.94 |
| HLM $t_{1/2}$ (min) | 15.3 | 10.5 | | | | 18 | | | |
| MLM $t_{1/2}$ (min) | 8.4 | 10.7 | | | | 35.1 | | | |
| HLM CLint (μL/min/mg) | 90.6 | 131.5 | | | | 76.1 | | | |
| MLM CLint (μL/min/mg) | 146.7 | 130 | | | | 39.5 | | | |
| 293T day 3 relative cell viability (% inhibition at 10 μM) | None | 21 | 30 | 16 | 4 | 6 | | | |

The SARS-COV-2 $M^{pro}$ construct used in the FRET inhibition assay had the authentic termini, while the construct used in the thermal shift assay had the His-tag, like in the initial compound screen. Thrombin inhibition was measured via a fluorescence assay.

Figure 15A:
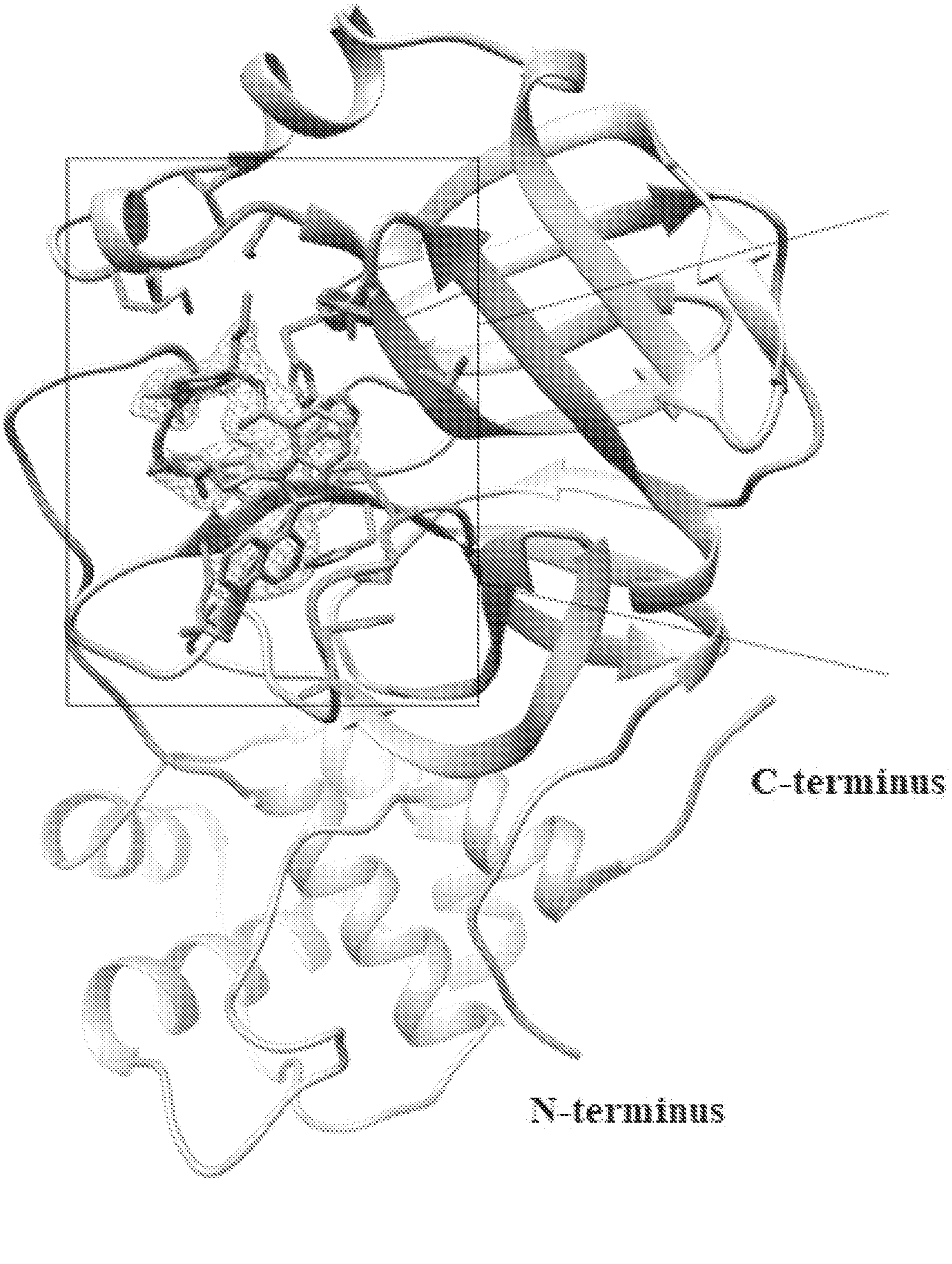
FIGS. 15A-15B depict the crystal structure of $M^{pro}$ in complex with CDD-1733.
Figure 15B:
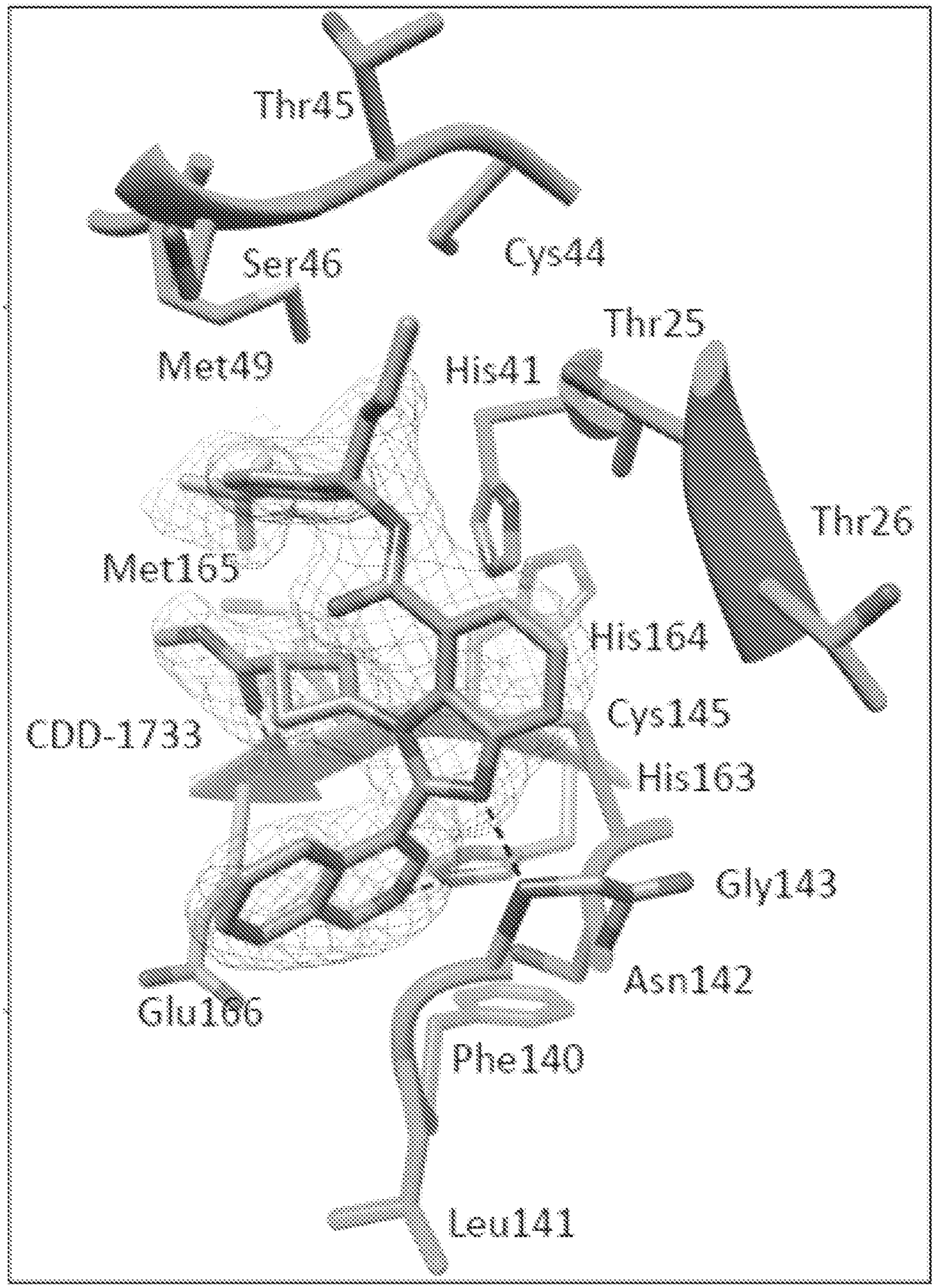
Figure 16:
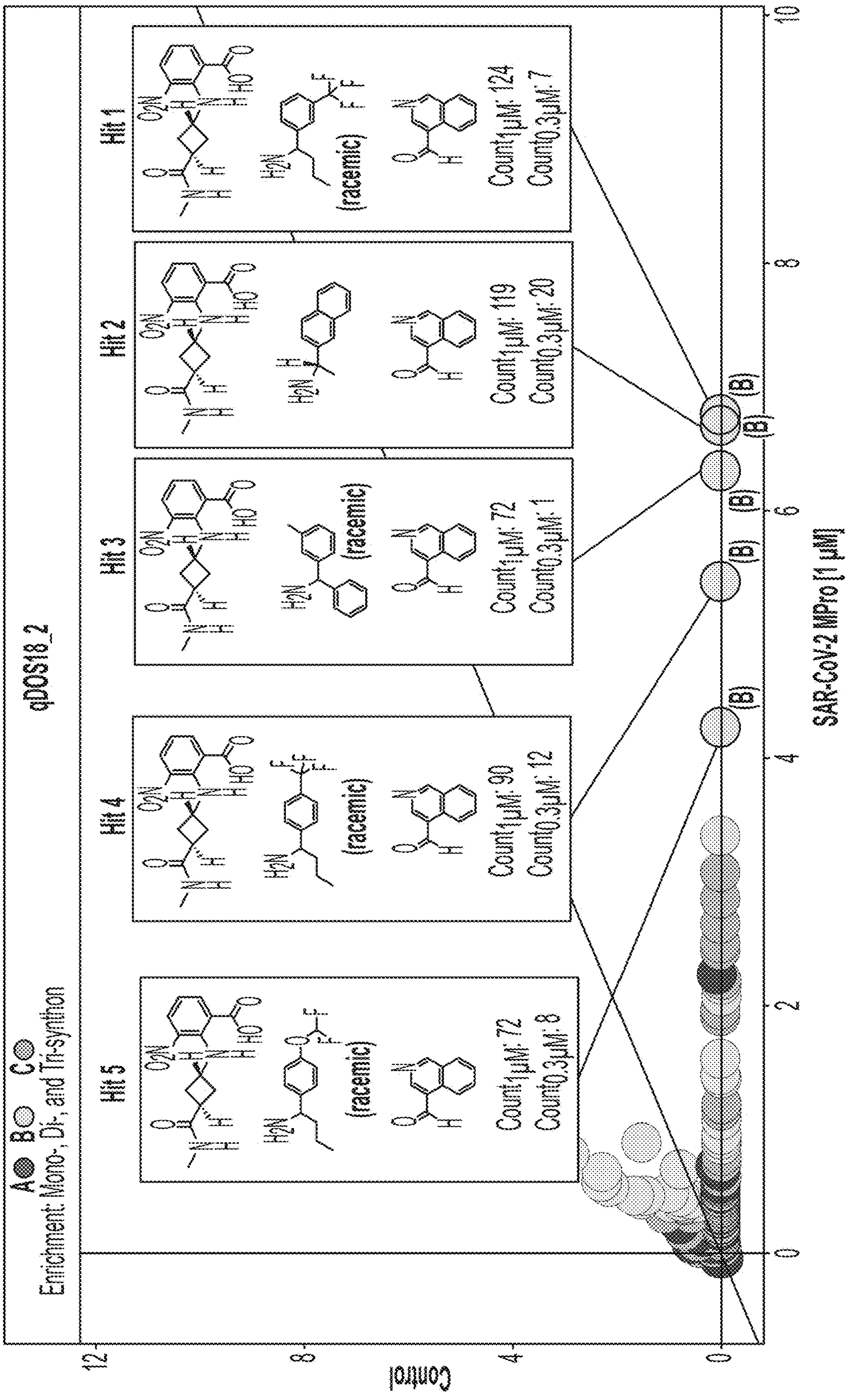
FIG. 16 depicts the enrichment profile of the DNA-encoded chemical library (qDOS18_2) against SAR-COV-2 $M^{pro}$ at 1 μM. The selection data has shown a series of enrichment with the same BB1 (top of each box) and BB3 (bottom of each box) with various BB2 (middle of each box), where BB2 participated in cycle 3 aldehyde condensation to form benzimidazole core. $Count_{1\ \mu M}$ and $Count_{0.3\ \mu M}$ indicate the number of counts in affinity selection at 1 μM and 0.3 μM protein concentration, respectively.
Figure 17A:
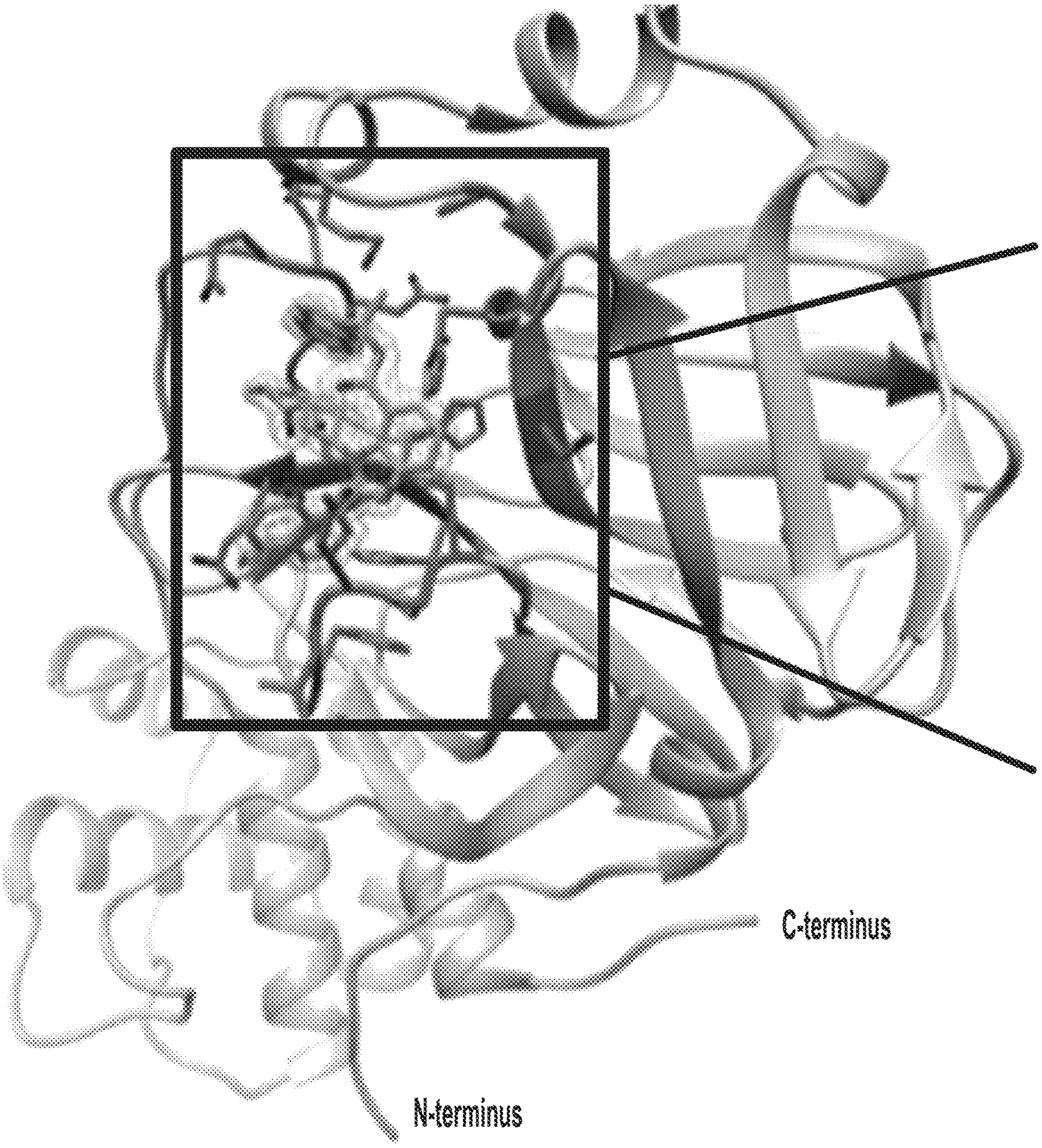
FIGS. 17A-17B depict the crystal structure of $M^{pro}$ in complex with CDD-1819.
Figure 17B:
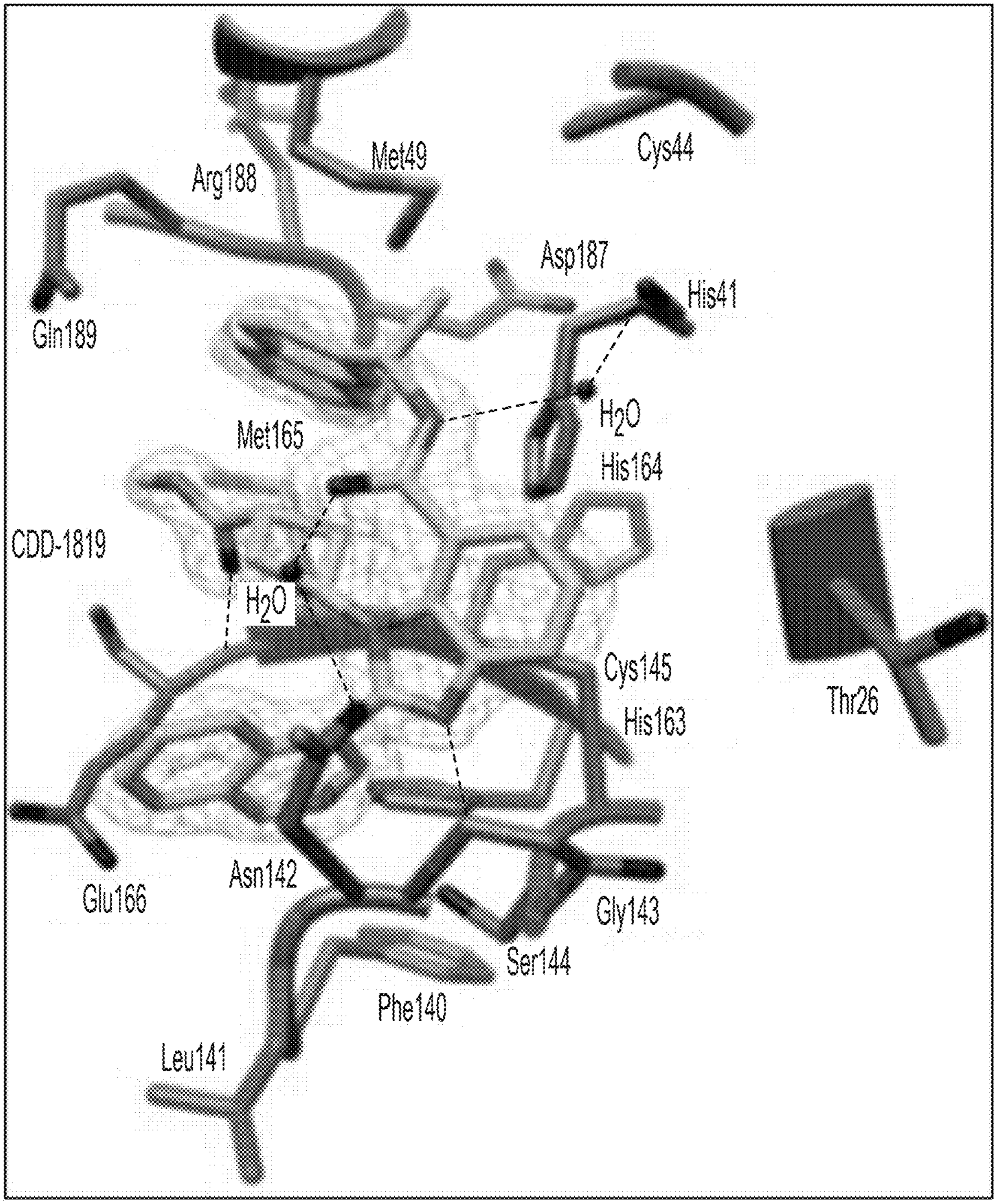
Figure 18A:
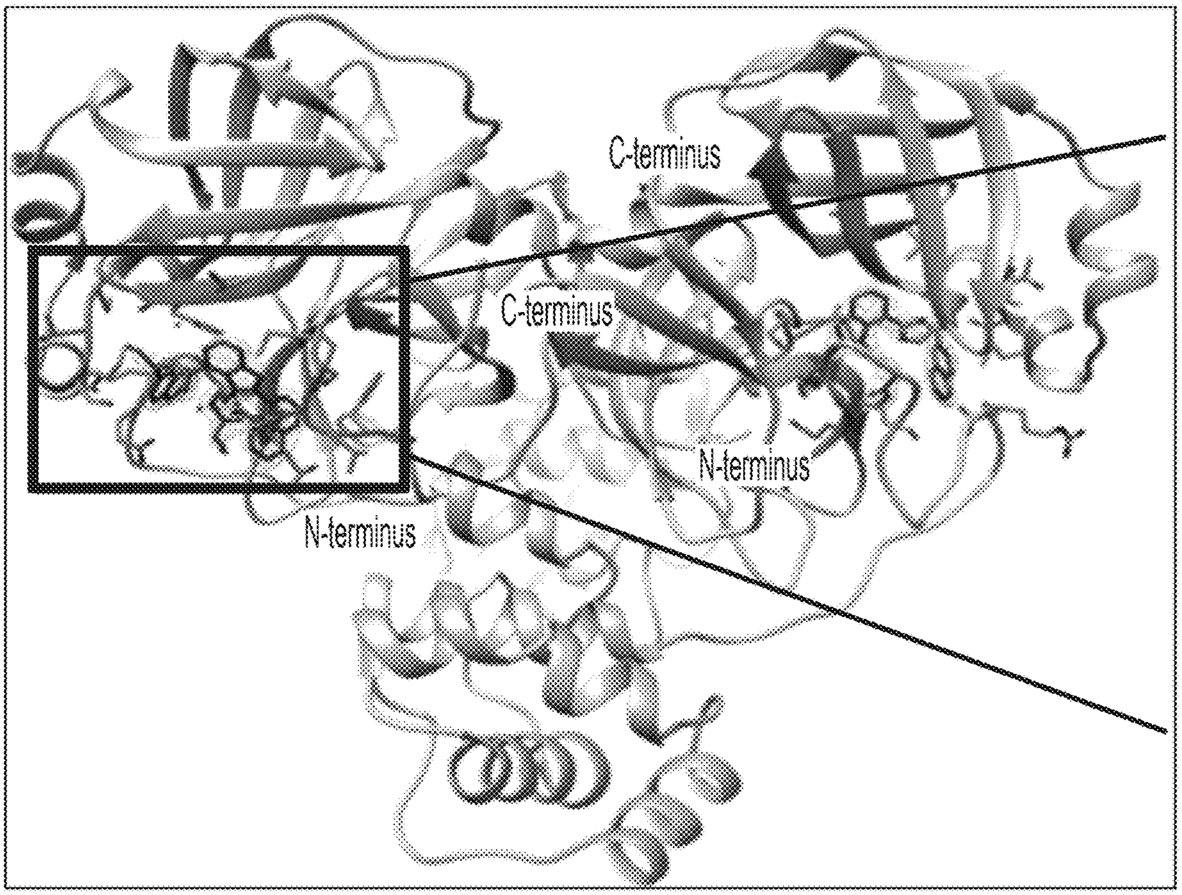
FIGS. 18A-18B depict the crystal structure of $M^{pro}$ in complex with CDD-1845.
Figure 18B:
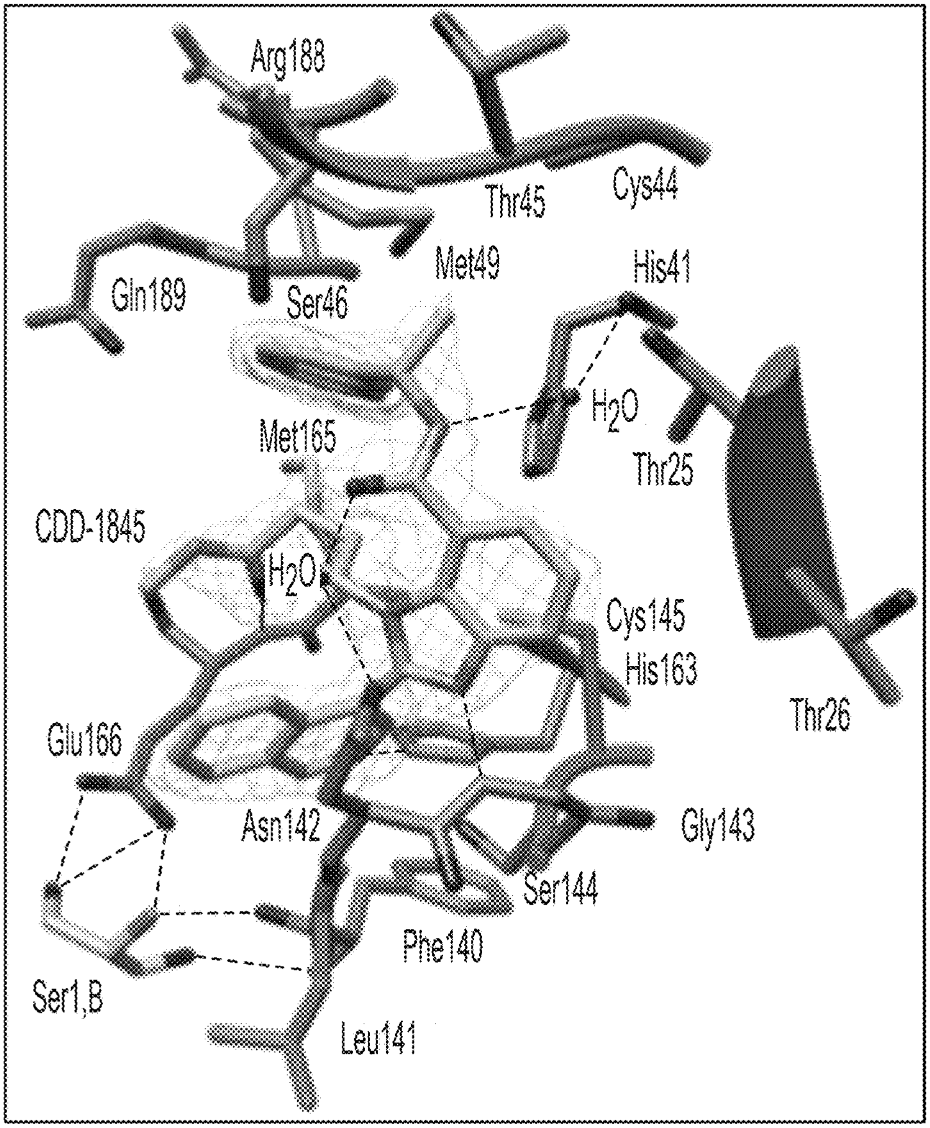
Figure 19A:
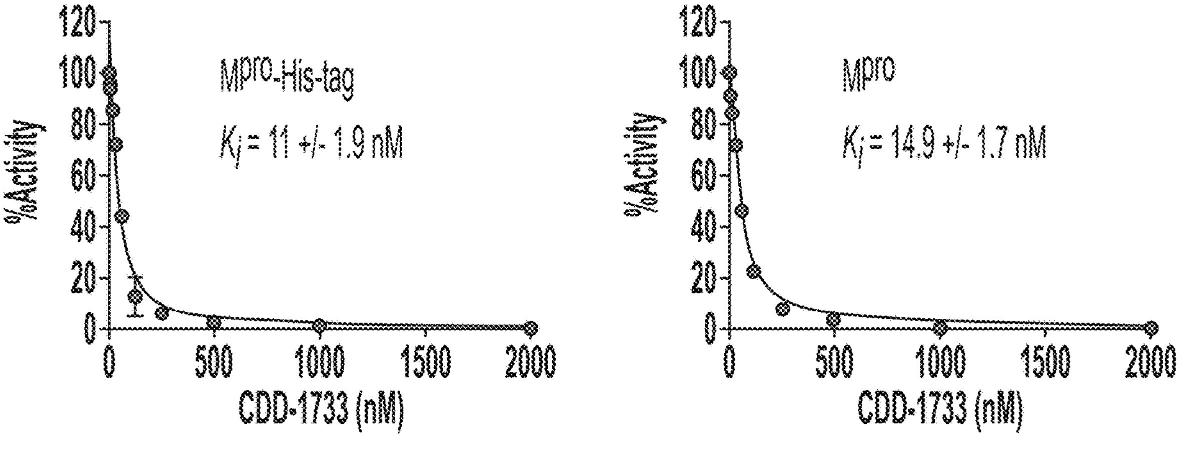
FIGS. 19A-19L depict inhibition $K_i$ value determination for CDD-1733 series against $M^{pro}$. 25 nM of $M^{pro}$-His6 or $M^{pro}$ cefotaxime was mixed with increasing concentrations of the CDD-1733 series compound. The remaining activities (dots) of $M^{pro}$ towards fluorescent peptide were plotted as a function of compound concentrations and $K_i$ values was calculated by fitting the data into Morrison equation with standard error from triplicates.
Figure 19B:
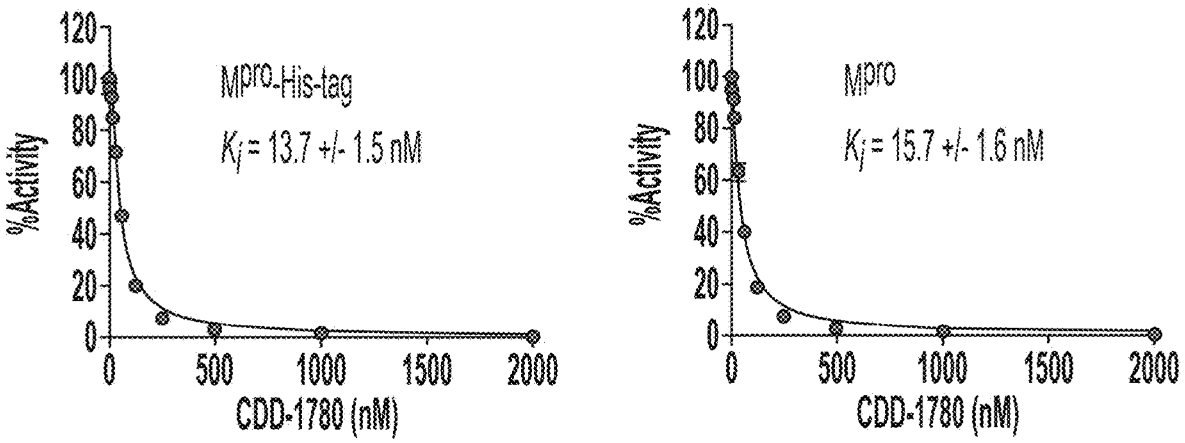
Figure 19C:
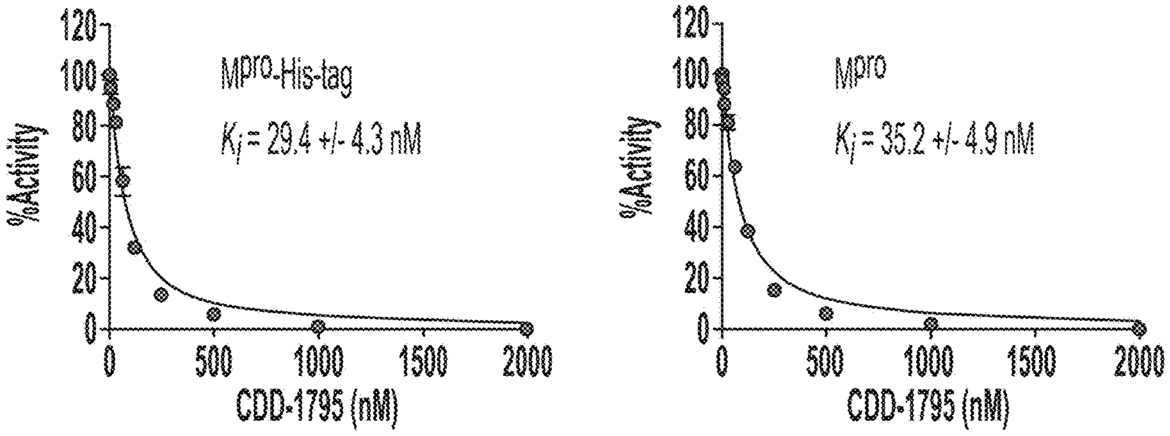
Figure 19D:
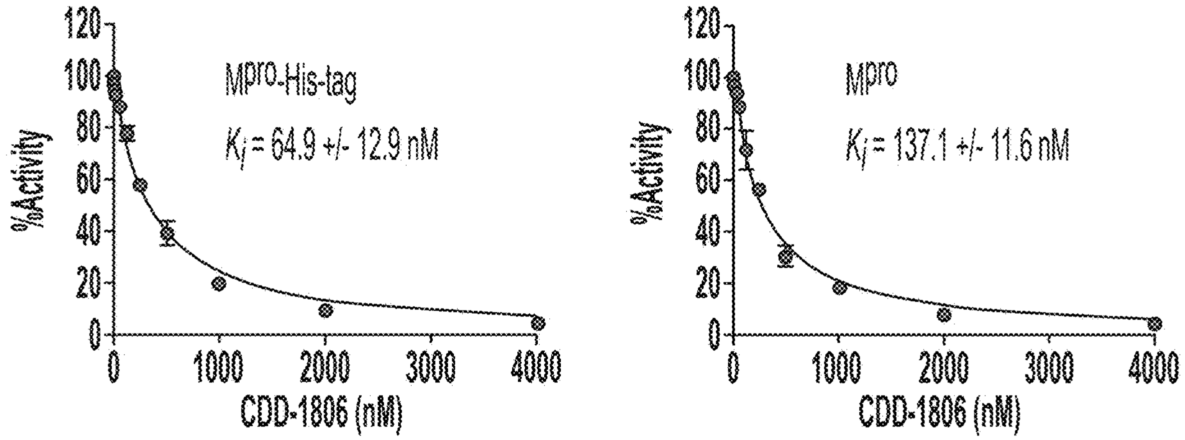
Figure 19E:
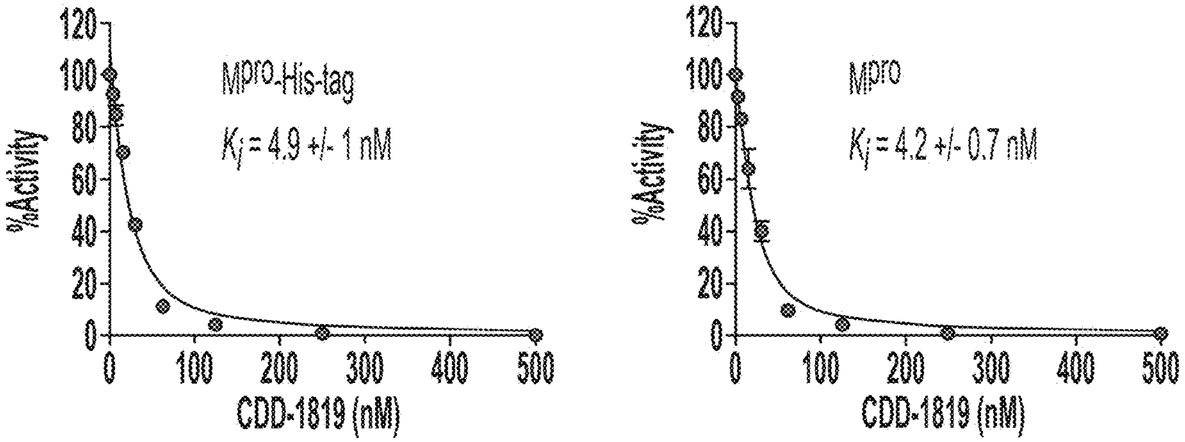
Figure 19F:
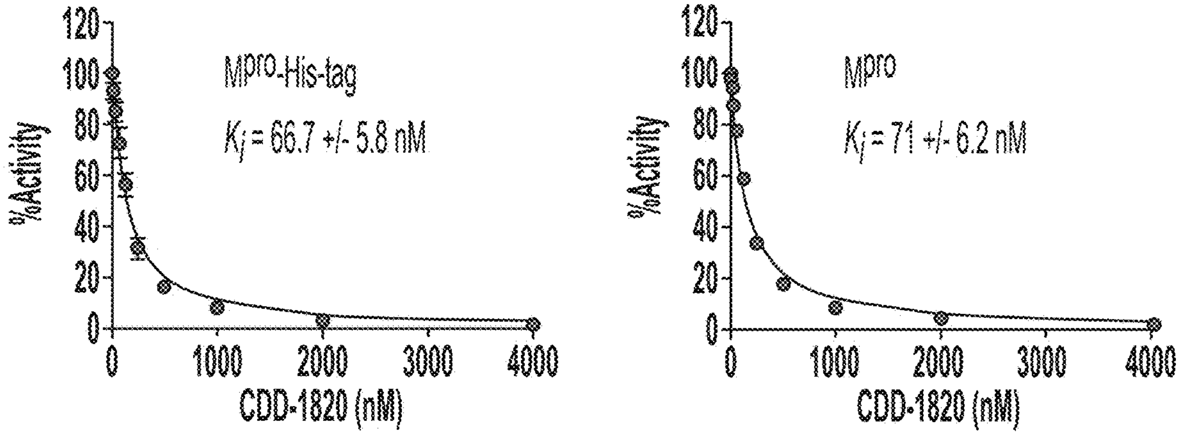
Figure 19G:
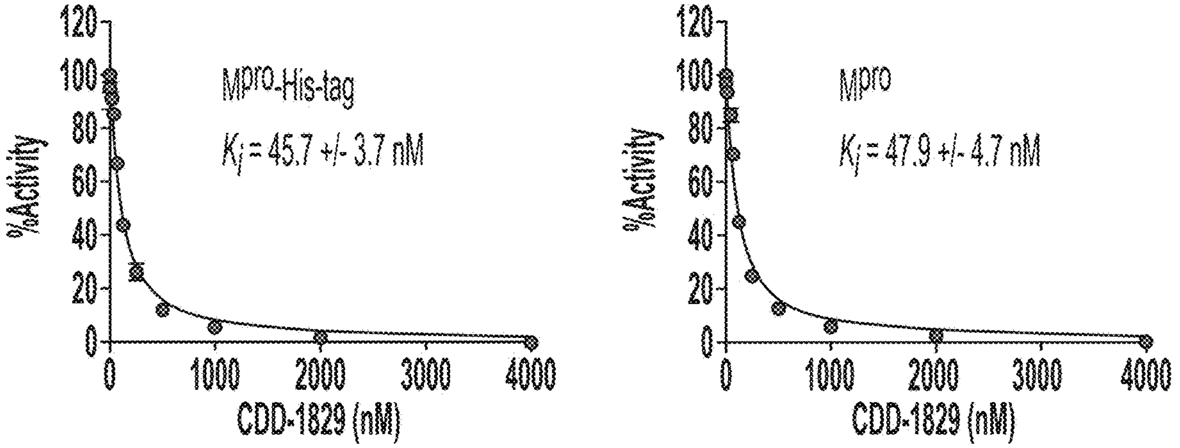
Figure 19H:
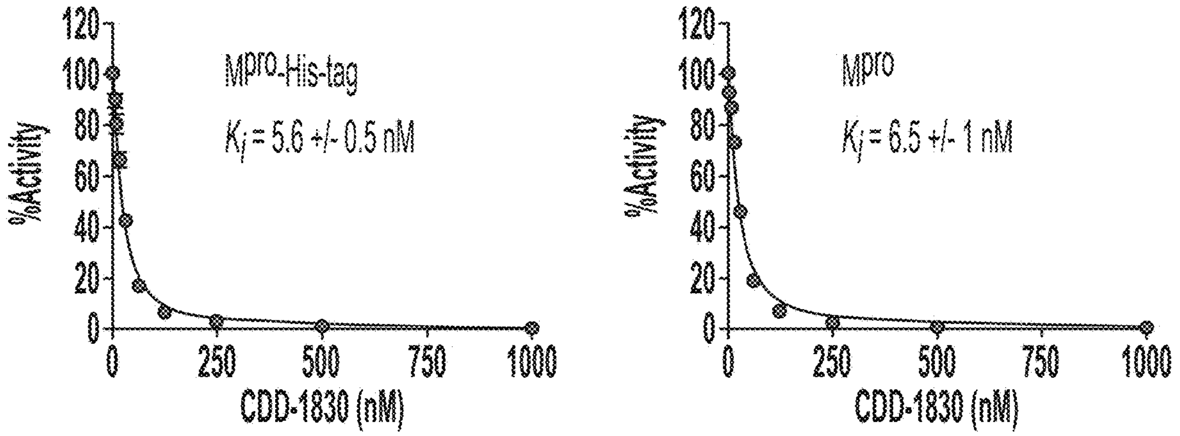
Figure 19I:
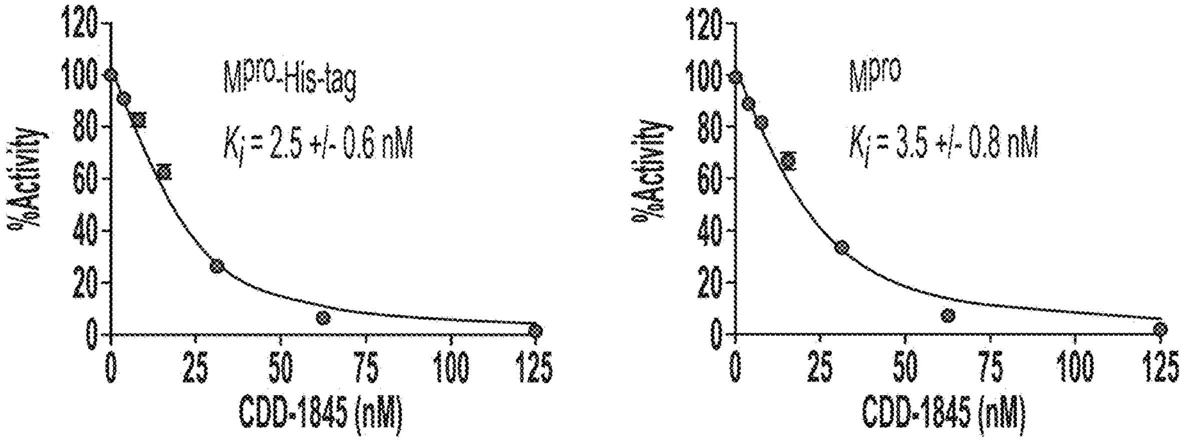
Figure 19J:
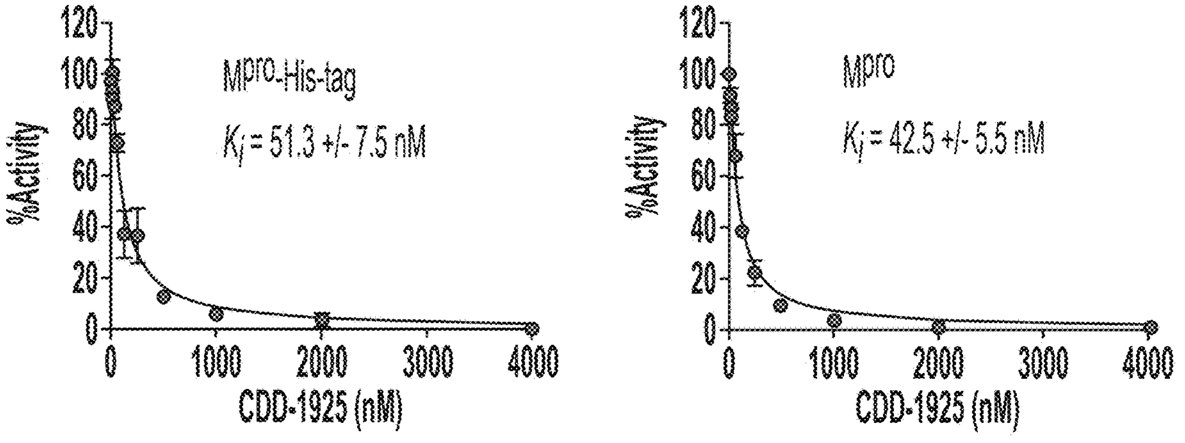
Figure 19K:
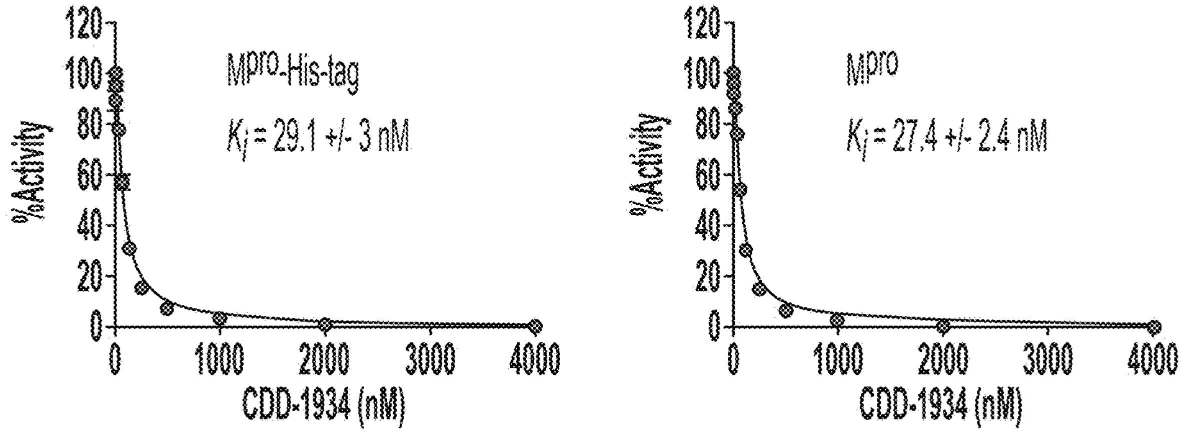
Figure 19L:
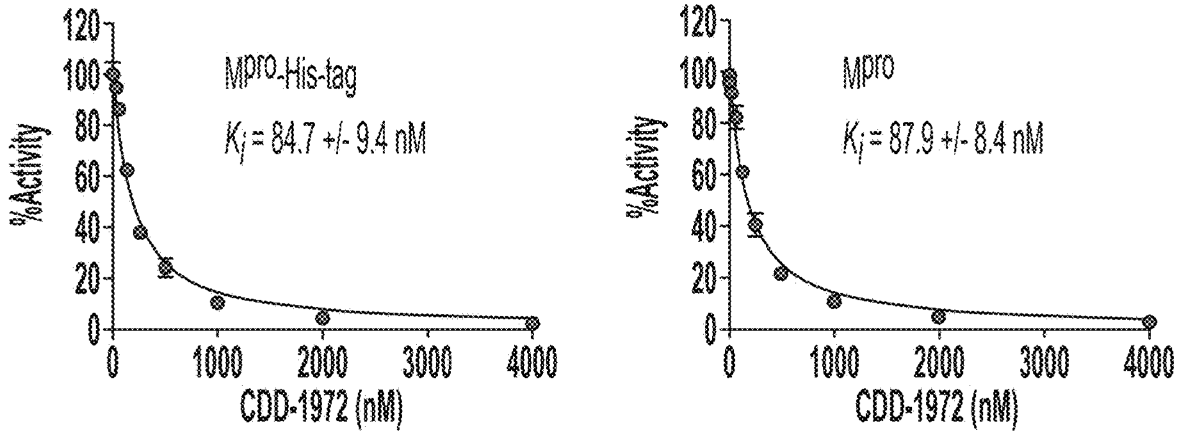
Figure 20A:
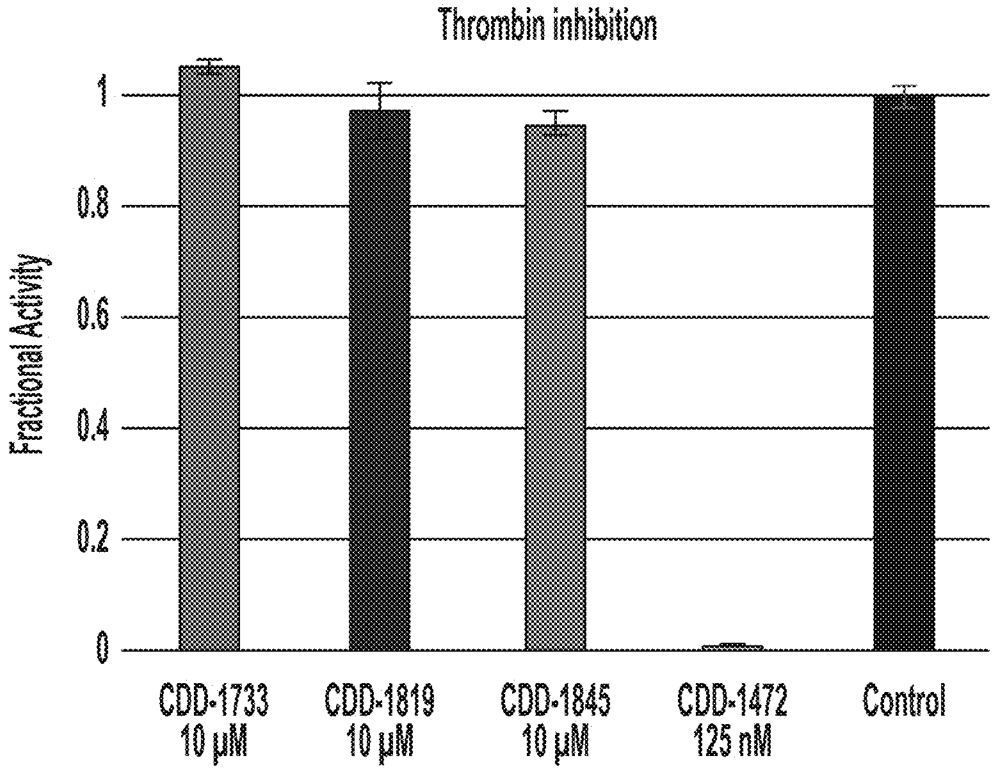
FIGS. 20A-20D show negative human protease data. Potential off-target inhibition of major proteases, i.e., cathepsin B (a cysteine protease like $M^{pro}$), thrombin (a serine protease), renin (an aspartic protease), and matrix metallopeptidase 1 (MMP-1), was tested with all active compounds with CDD-1733, CDD-1819 and CDD-1-845 shown in the figure and control inhibitors as indicated.
Figure 20B:
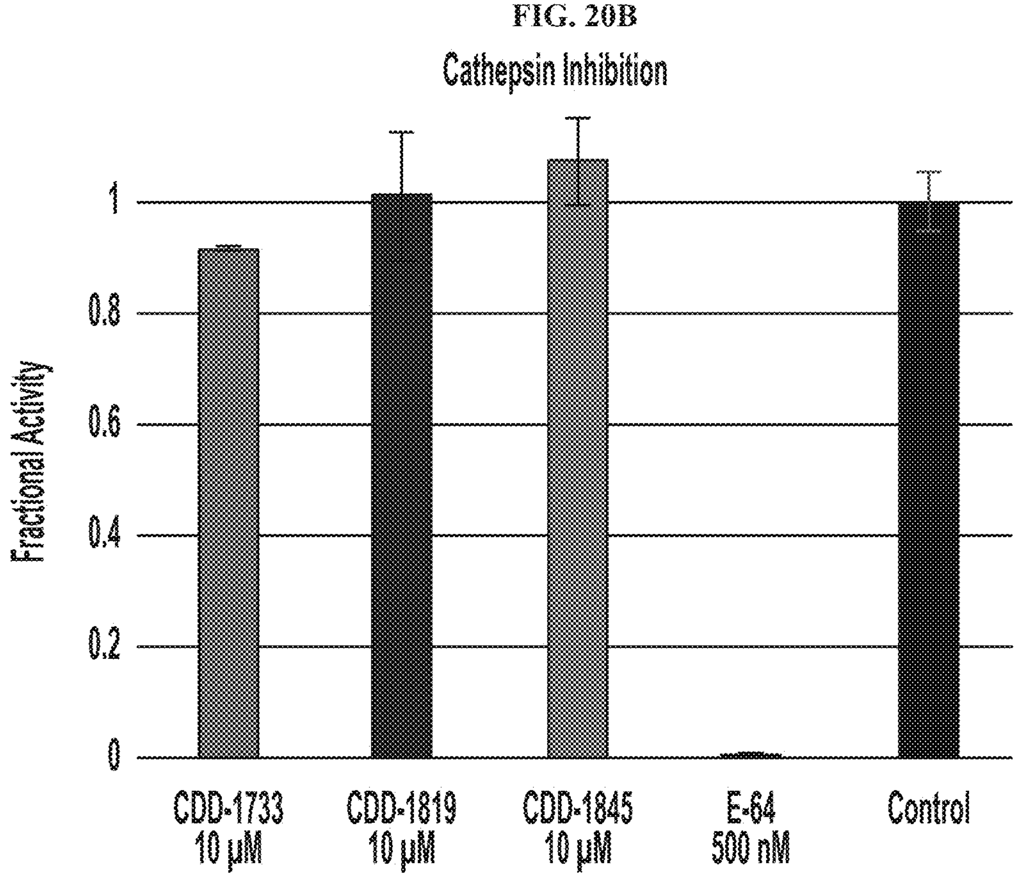
Figure 20C:
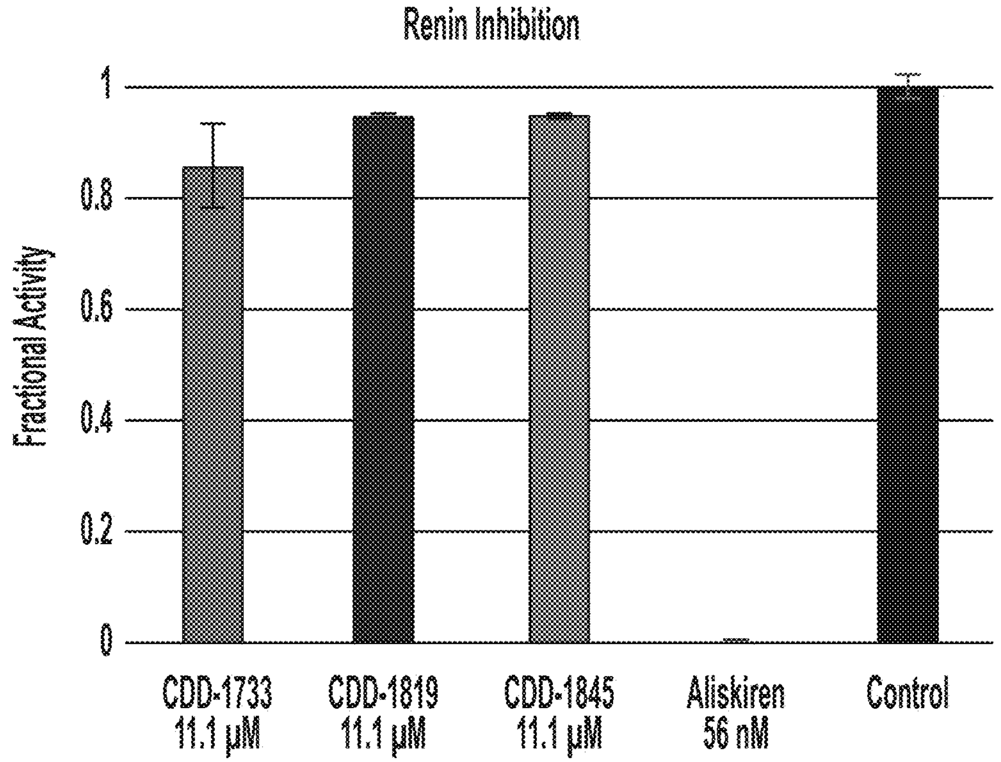
Figure 20D:
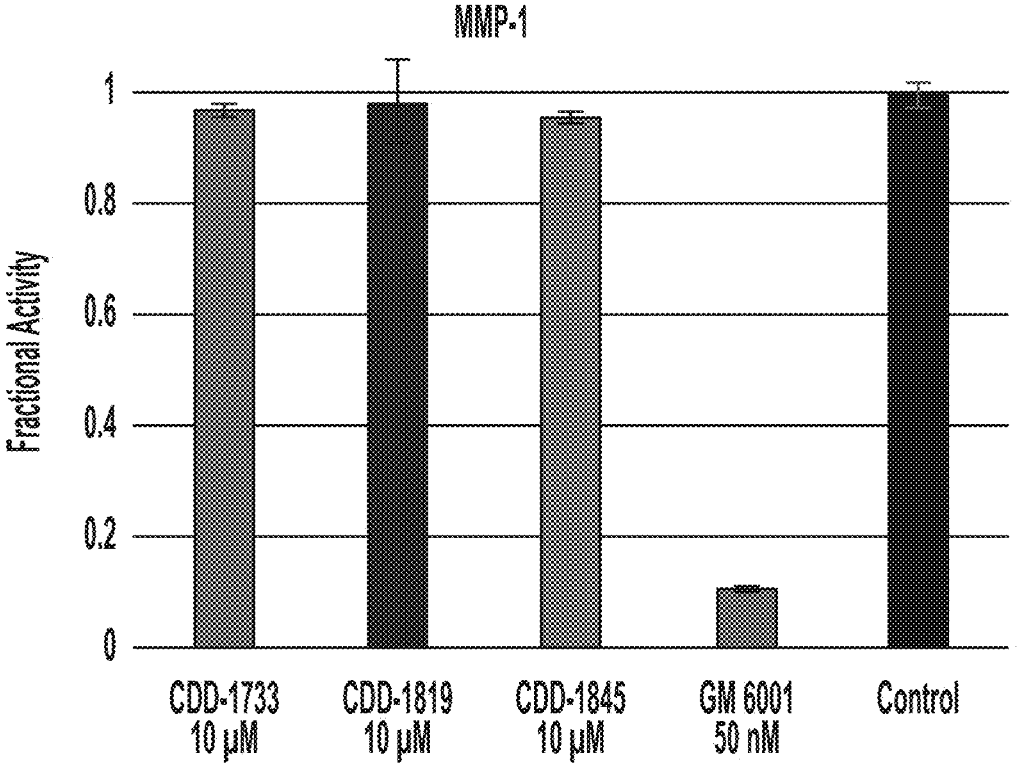
Figure 21A:
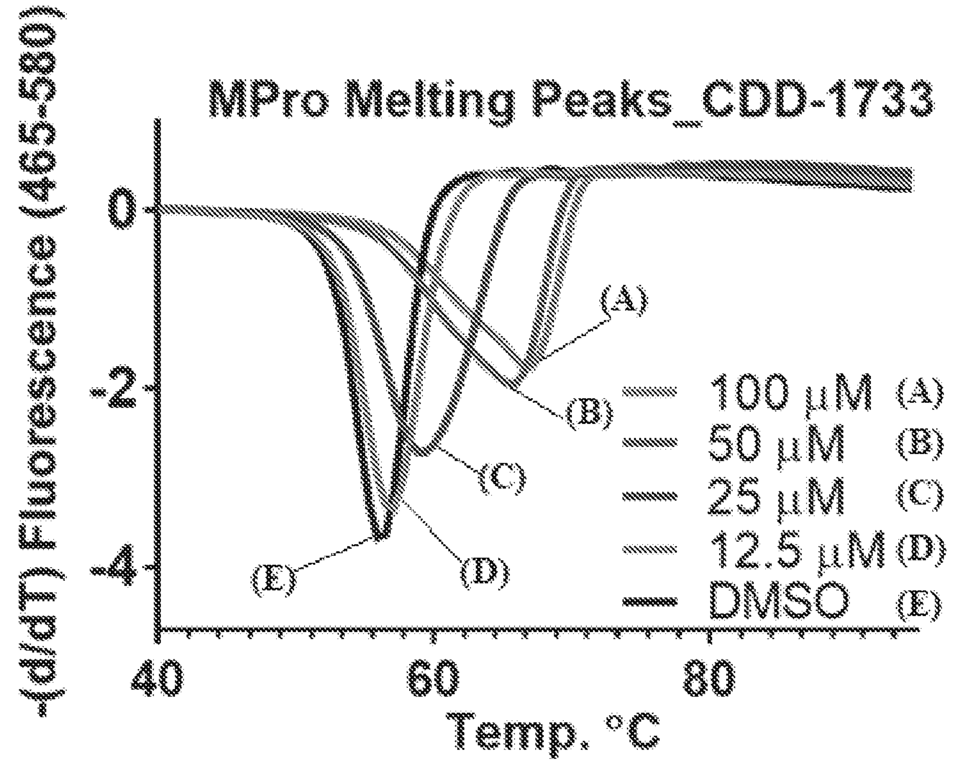
FIGS. 21A-21D show that CDD-1733, CDD-1819, and CDD-1845 stabilized the SARS-CoV-2 main protease ($M^{Pro}$) in the protein thermal shift stability assay. Data analysis and protein melting temperature (Tm) calculation were run on a Roche Lightcycler 480 real-time PCR instrument (n=2). The plot was generated using a GraphPad Prism software.
Figure 21B:
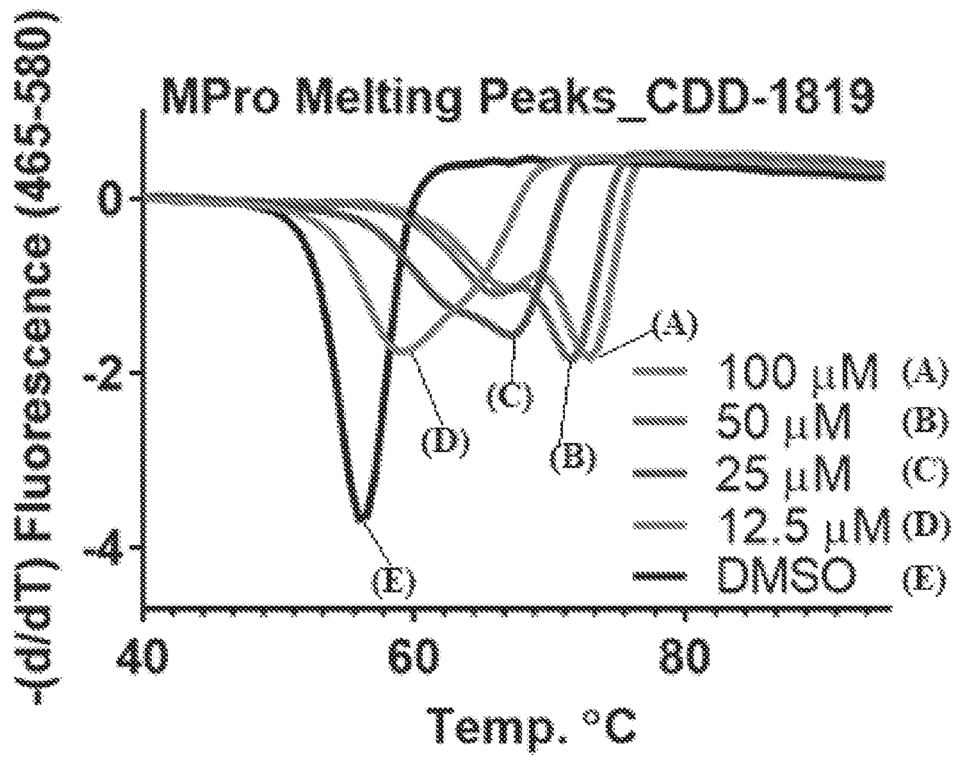
Figures 21C, 21D, 22:
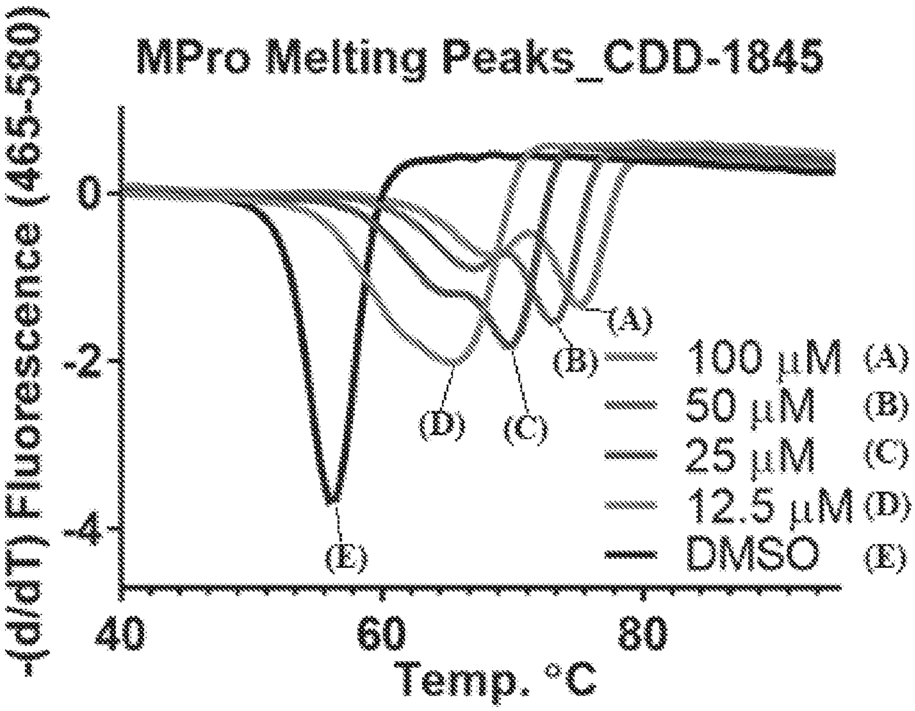
FIG. 22 contains tables of the metabolic stability of CDD-1733, CDD-1819 and CDD-1845 in HLM and MLM. Final concentrations are as follows: Liver microsomes: 0.5 mg protein/ml, Compound concentration: 2.0 μM, NADPH Concentration: 1.0 mM. JQ1 was used as the short half-life control. Alprazolam was used as the long half-life control. Measurements were obtained in duplicate at 0, 30, and 60 min.
Figure 23:
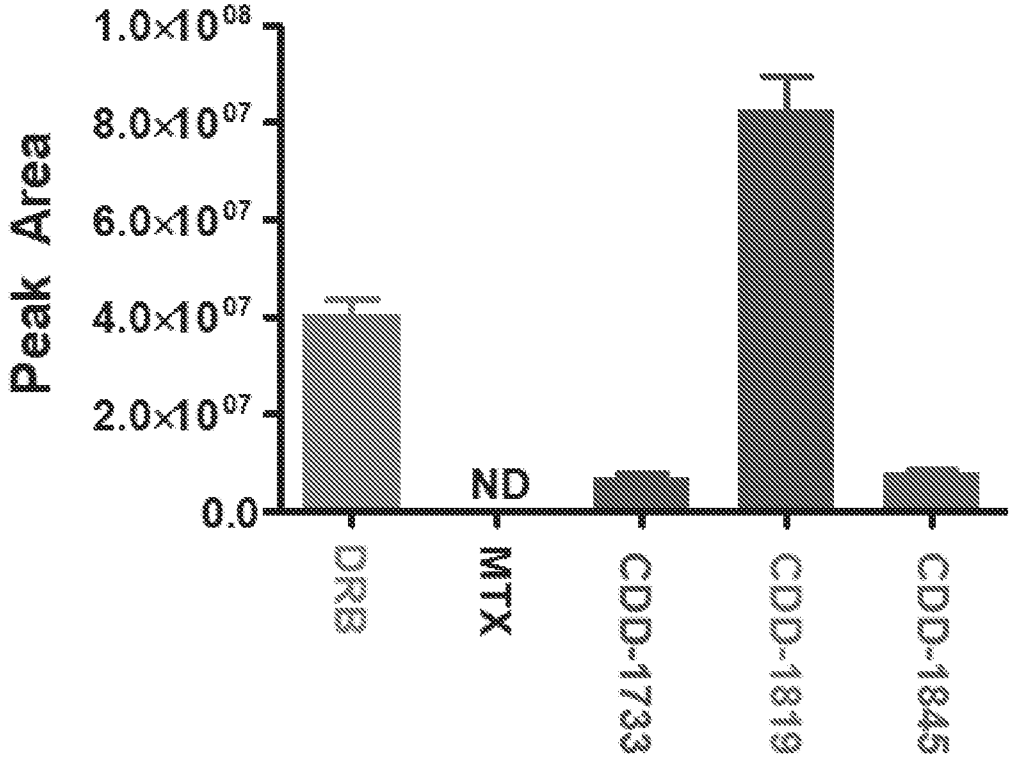
FIG. 23 depicts the HepG2 cell uptake of CDD-1733, CDD-1819, and CDD-1845. The HepG2 cell uptake capacities of CDD-1733, CDD-1819, and CDD-1845 were expressed as the intracellular concentrations (peak areas) of these compounds. Methotrexate (MTX) and doxorubicin (DRB) were used as the negative and positive controls, respectively. The HepG2 cells were incubated with the compounds and controls (final concentration 10 μM) for 2 hours at 37° C., harvested, and homogenized. The intracellular concentrations were measured with UHPLC-Q Exactive Orbitrap MS. ND stands for "not detected".
Figure 24:
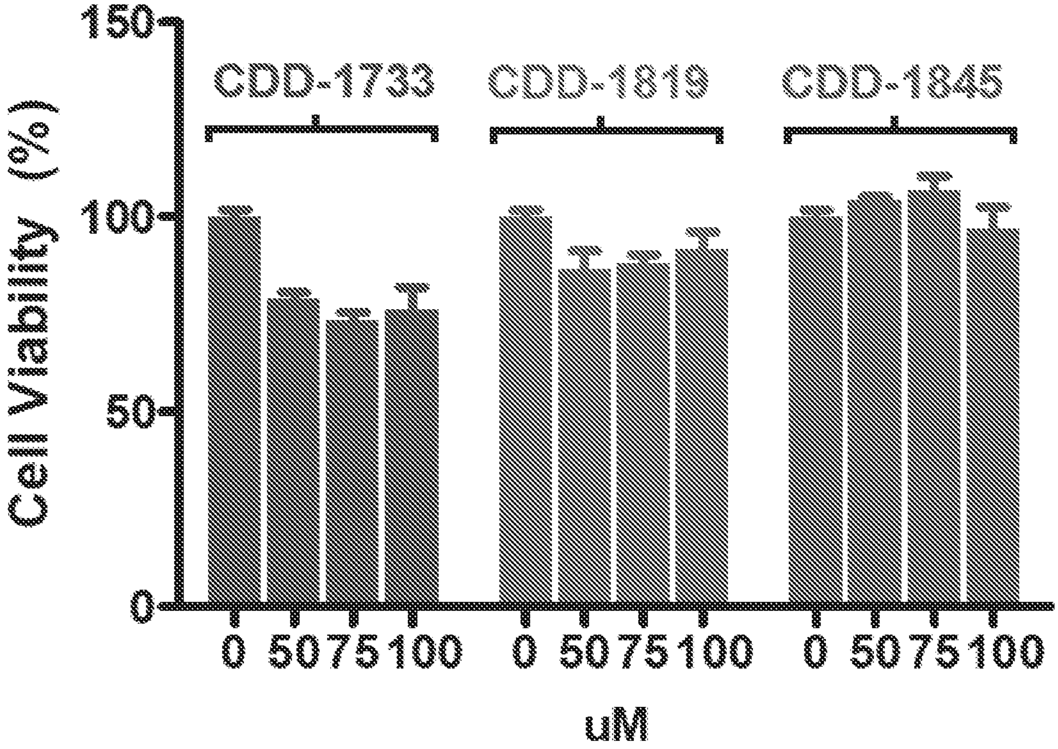
FIG. 24 depicts HepG2 cell viability after incubation with CDD-1733, CDD-1819, and CDD-1845 for 24 hours. The HepG2 cells were incubated with CDD-1733, CDD-1819, and CDD-1845 (0-100 μM) for 24 hours at 37° C. Cell viability was measured with XTT assay. XTT readings were normalized by the control group (DMSO) to give the normalized viabilities. The $IC_{50}$ values were expressed as ">100 μM" for CDD-1733, CDD-1819, and CDD-1845, as the cell viabilities were larger than 80% in the 100 μM group for these compounds.
Figure 25A:
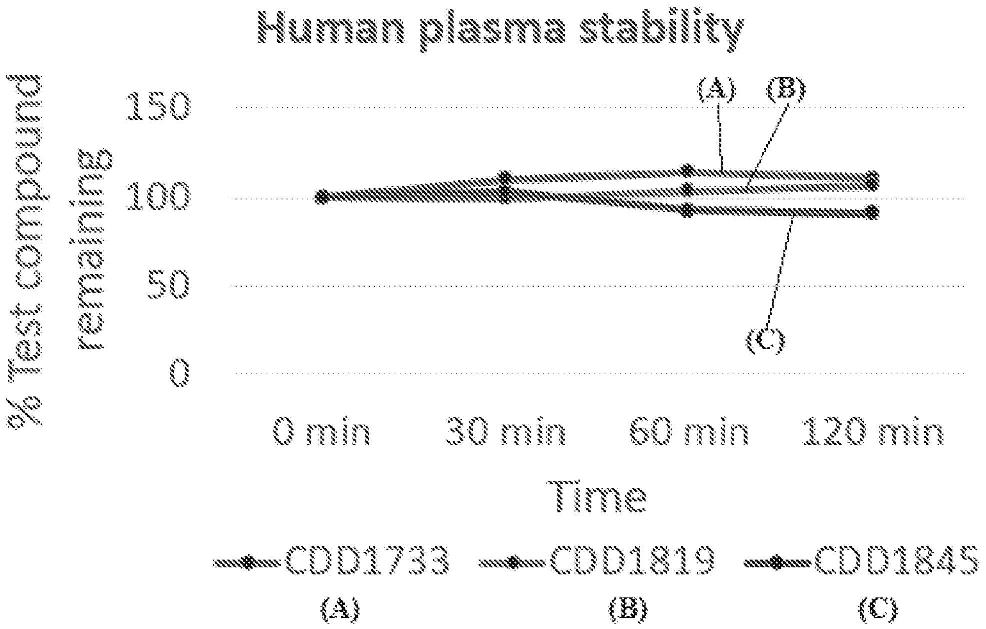
FIGS. 25A-25B depict plasma stability of CDD-1733, CDD-1819, and CDD-1845 in human (FIG. 25A) and mouse plasma (FIG. 25B), respectively.
Figure 25B:
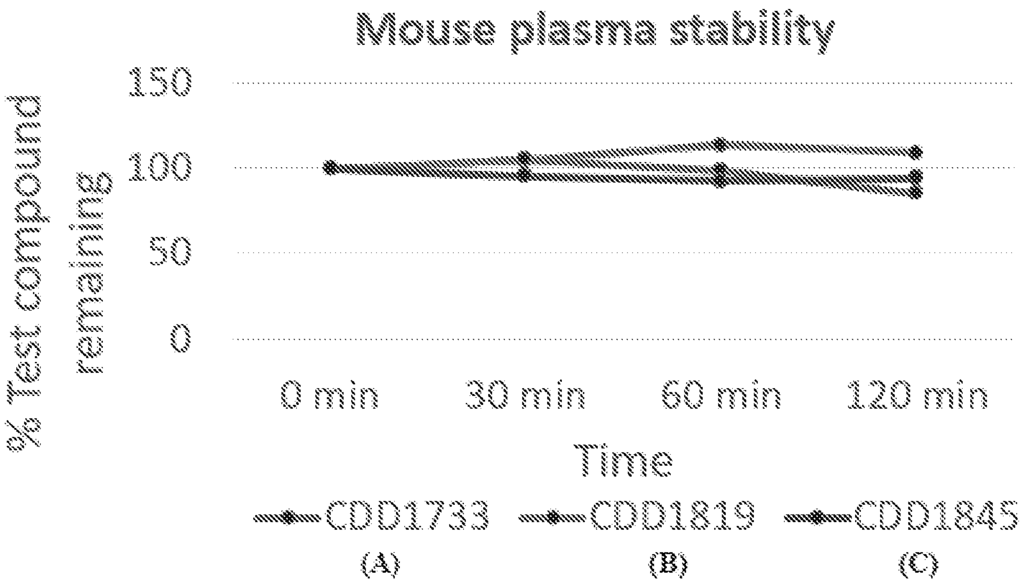
Figure 26:
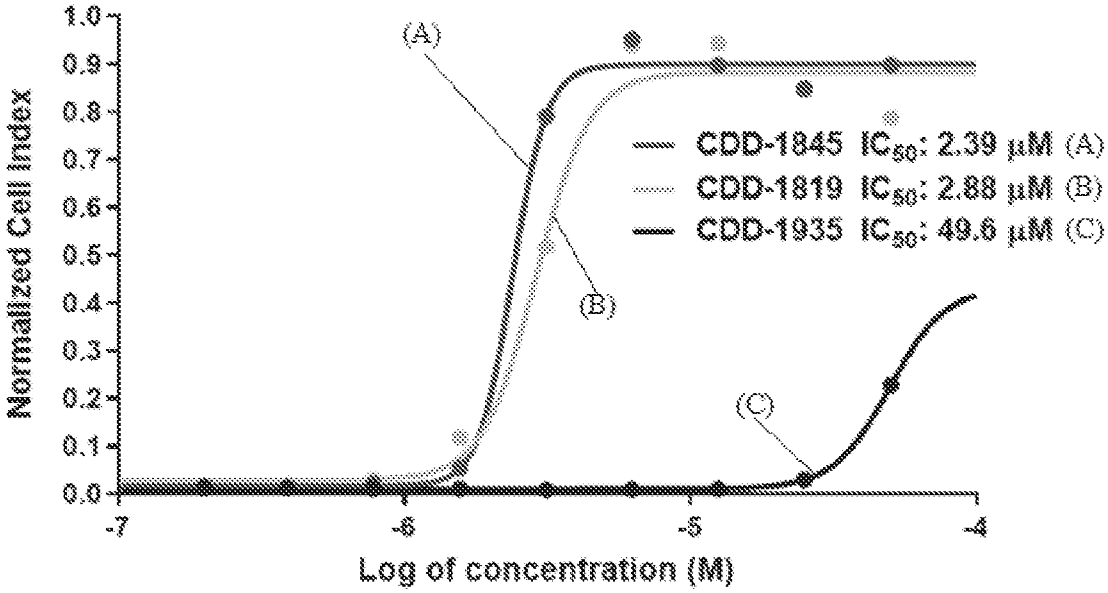
FIG. 26 depicts normalized cell index plotted versus concentration (log) of $M^{pro}$ drug compound measuring using xCELLigence RTCA. Average data points from duplicate measurements were used. A sigmoidal dose-response curve was fitted to determine $IC_{50}$ values for each compound (i.e., CDD-1845, CDD-1819, and CDD-1935).

The hits were optimized to lead compounds. Some of the generated structure-activity relationships are shown in Tables 3 and 5 for the series CDD-1733 and CDD-1713, respectively. A co-crystal structure of CDD-1713 with SARS-COV-2 $M^{pro}$ was also resolved, showing CDD-1713 directly interacting with the catalytic C145 residue (FIGS. 8A-8D). Additionally, a co-crystal structure of CDD-1733 with SARS-COV-2 $M^{pro}$ was resolved, showing CDD-1733 (FIGS. 15A-15B). CDD-1733 is located and stabilized in the active site of $M^{pro}$ through numerous hydrogen bonds and hydrophobic interactions. In contrast to CDD-1713, CDD-1733 does not form a covalent interaction with the enzyme. Rather, the indazole and isoquinoline rings of CDD-1733 make hydrophobic interactions with Cys145. The NH group of the indazole group forms a hydrogen bond with the main chain amide nitrogen of Gly 143 in the S1' site. The isoquinoline ring of CDD-1733 inserts into the S1 pocket of $M^{pro}$. The nitrogen of isoquinoline is hydrogen-bonded with the nitrogen of the imidazole side chain from residue His163. In addition, residues Thr25, Thr26, Phe140, Leu141 and Ser144 in site S1' and S1 of the enzyme participate in stabilizing the indazole and isoquinoline groups through hydrophobic interactions. The oxygen of the cyclobutane methylamide accepts a hydrogen bond from the main-chain amide nitrogen of residue Glu166 in the S3 site. Two sets of water-mediated interactions are observed between the amide group attached to the central indazole ring of CDD-1733 and residue Asn142 and His41 of $M^{pro}$, respectively. In particular, the amide oxygen is hydrogen-bonded with the oxygen of the carboxamide side chain of Asn142 in the S1' site of the enzyme. The amide nitrogen interacts with the nitrogen of the imidazole side chain and the main chain amide of residue His 41 in the S2 site of the enzyme through a hydrogen bond. Additional residues are involved in stabilization of CDD-1733 and $M^{pro}$ through hydrophobic interactions. For instance, residue Met49 in the S2 site and residue His164 in the S1' site interact with the benzyl group of the trifluoromethyl-benzene and the cyclobutane ring, respectively. The terminal methyl groups of the butyl group make hydrophobic interactions with residues Thr25, Cys44, Thr45 and Ser46. The methylamide group linked to cyclobutane and the carbon of trifluoromethyl group of CDD-1733 were further stabilized by Reside Met165 in the S1' site of $M^{pro}$. Taken together, these numerous interactions lead to high affinity binding and potent inhibition of $M^{pro}$ by CDD-1733.

TABLE 5
Structure-activity relationships of the compounds in the CDD-1713 hit series.
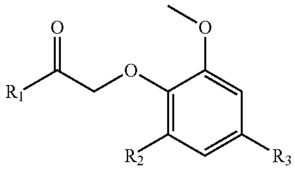
| Compound ID | $R_1$ | $R_2$ | $R_3$ | $K_{i,app}$ (nM) |
|---|---|---|---|---|
| CDD-1712 | 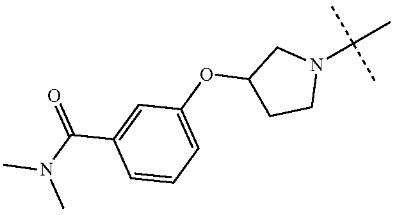 | 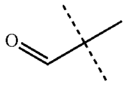 | 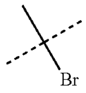 | Inactive |
| CDD-1713 | 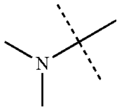 | 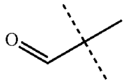 | 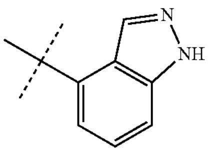 | 64.8 |
| CDD-1714 | 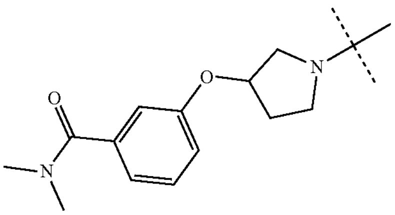 | 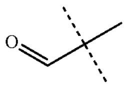 | 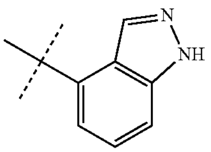 | 24.4 |
| CDD-1776 | 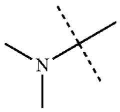 | 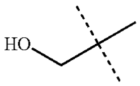 | 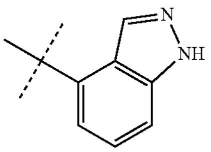 | Inactive |
| CDD-1777 | 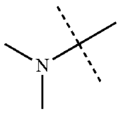 | 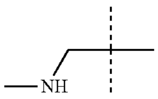 | 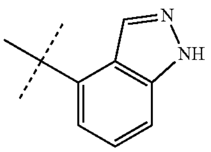 | Inactive |
| CDD-1793 | 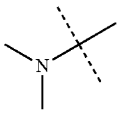 | 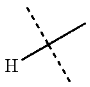 | 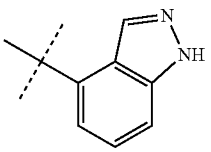 | Inactive |

A mouse model for COVID-19 infection can be used for in vivo studies of the efficacy of the lead compounds. Additionally, binding of all synthesized hits disclosed herein can be tested with thermal shift assays in addition to the FRET-based inhibition assay to capture possible allosteric binders. This can facilitate new drug development strategies other than directly inhibiting the catalytic site of SARS-COV-2 $M^{pro}$.

Example 3: Selected Pharmacokinetic Studies of CDD-1733, CDD-1819, and/or CDD-1845 in Mice The present disclosure further provides pharmacokinetic data for selected compounds disclosed herein, including compounds CDD-1733, CDD-1819, and CDD-1845 (FIGS. 27A-27C, and Tables 6-8).

TABLE 6

Figure 27A:
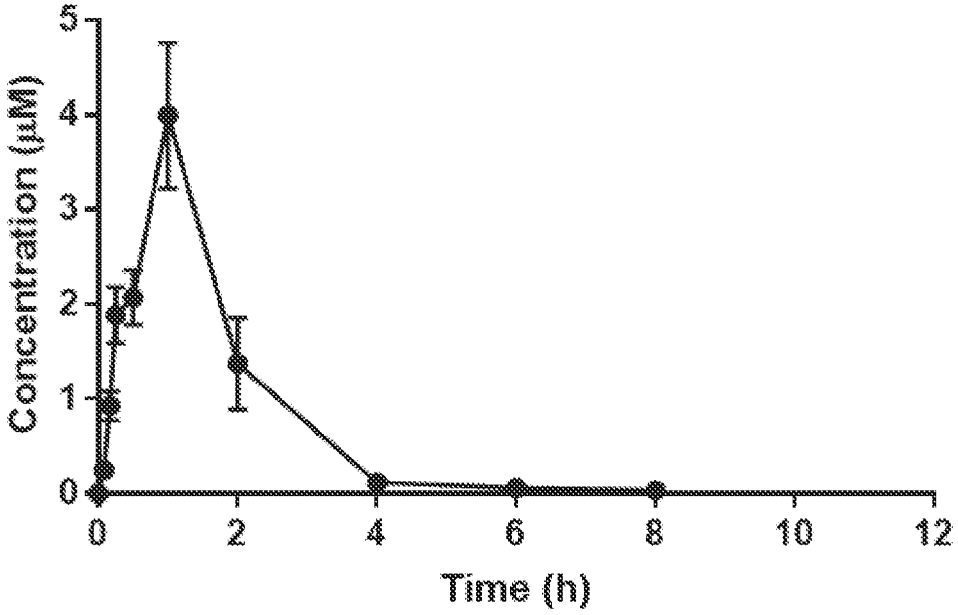
FIGS. 27A-27C provide selected mouse pharmacokinetic data for compounds CDD-1733 (FIG. 27A), CDD-1819 (FIG. 27B), and CDD-1845 (FIG. 27C).
Figure 27B:
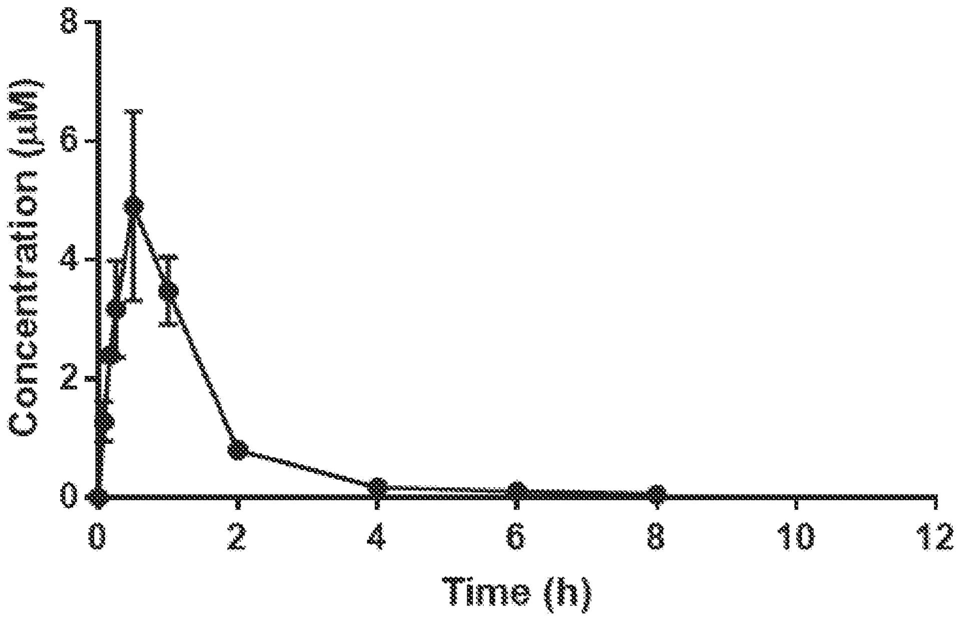
Figure 27C:
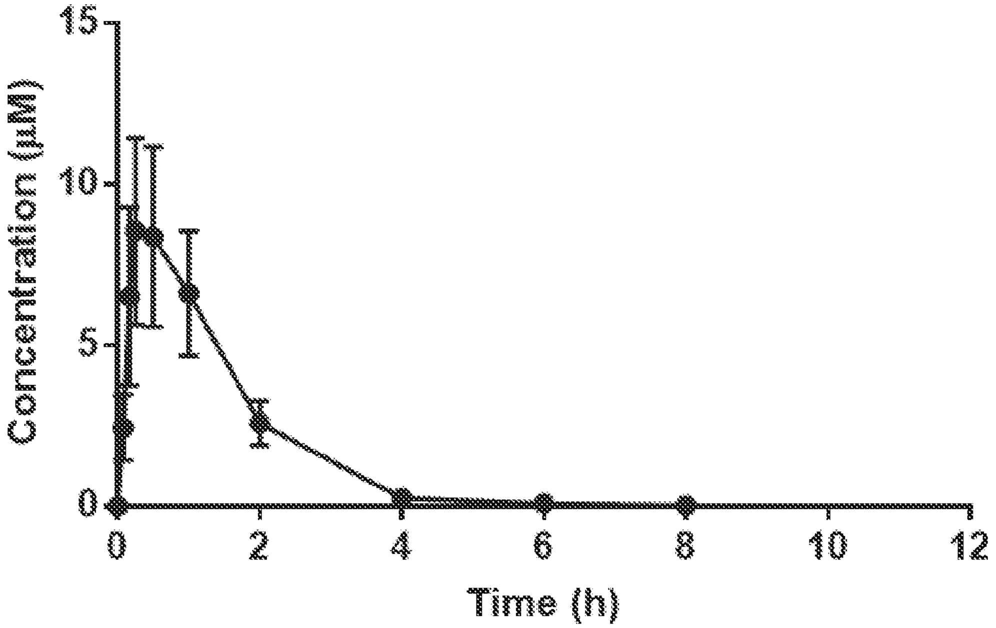

Noncompartmental parameters of CDD-1733 pharmacokinetics (n = 4; see FIG. 27A).

| Parameter | Unit | CDD-1733 |
|---|---|---|
| $T_{max}$ | hr | 1 |
| $C_{max}$ | μmol/L | 4.21 ± 1.80 |
| $T_{1/2}$ | hr | 2.15 ± 1.46 |
| $AUC_{0\text{-}t}$ | hr · μmol/L | 7.80 ± 3.22 |
| $AUC_{0\text{-}\infty}$ | hr · μmol/L | 7.22 ± 3.19 |
| CL/F | mg/(hr · μmol/L)/kg | 7.73 ± 2.75 |
| $MRT_{0\text{-}t}$ | hr | 1.48 ± 0.04 |
| $MRT_{0\text{-}\infty}$ | hr | 1.72 ± 0.36 |

TABLE 7

Noncompartmental parameters of CDD-1819 pharmacokinetics (n = 3; see FIG. 27B).

| Parameter | Unit | CDD-1819 |
|---|---|---|
| $T_{max}$ | hr | 0.33 ± 0.14 |
| $C_{max}$ | μmol/L | 5.14 ± 2.57 |
| $T_{1/2}$ | hr | 1.16 ± 0.12 |
| $AUC_{0\text{-}t}$ | hr · μmol/L | 7.09 ± 1.76 |
| $AUC_{0\text{-}\infty}$ | hr · μmol/L | 7.18 ± 1.77 |
| CL/F | mg/(hr · μmol/L)/kg | 7.26 ± 1.81 |
| $MRT_{0\text{-}t}$ | hr | 1.31 ± 0.12 |
| $MRT_{0\text{-}\infty}$ | hr | 1.42 ± 0.16 |

TABLE 8

Noncompartmental parameters of CDD-1845 pharmacokinetics (n = 3; see FIG. 27C).

| Parameter | Unit | CDD-1845 |
|---|---|---|
| $T_{max}$ | hr | 0.33 ± 0.14 |
| $C_{max}$ | μmol/L | 8.93 ± 4.55 |
| $T_{1/2}$ | hr | 1.14 ± 0.32 |
| $AUC_{0\text{-}t}$ | hr · μmol/L | 14.87 ± 7.79 |
| $AUC_{0\text{-}\infty}$ | hr · μmol/L | 14.93 ± 7.85 |
| CL/F | mg/(hr · μmol/L)/kg | 4.02 ± 1.98 |
| $MRT_{0\text{-}t}$ | hr | 1.22 ± 0.03 |
| $MRT_{0\text{-}\infty}$ | hr | 1.25 ± 0.02 |

Example 4: Compound Synthesis

General Procedure for Acylation

To a solution of on-DNA amine (51.4 μL, 0.7 mM in water) in 72 μL of pH 9.5 borate buffer (250 mM in water, 500 equivalents) was added 18 μL of carboxylic acid solution (200 mM in MeCN, 100 equivalents) and 18 μL of 4-(4,6-dimethoxy-1,3,5-triazin-2-yl)-4-methylmorpholinium chloride (DMTMM, 200 mM in water, 100 equivalents). The reaction was incubated at room temperature for 18 h and then quenched by ethanol precipitation.

General Procedure for Reductive Alkylation

An aldehyde building block (18 μL, 200 mM in MeCN, 100 equivalents) was added to a solution of DNA-conjugated amine (27.7 μL, 1.3 mM in water, 1 equivalent) in 36 μL of pH 5.8 MES buffer (2-(N-morpholino) ethanesulfonic acid, 500 mM in water, 500 equivalents). The mixture was added a solution of $NaCNBH_3$ (18 μL, 200 mM in water, 200 equivalents) and 36 μL MeCN to give final 40% v/v MeCN. The reaction mixture was heated at 40° C. for 16 hours, followed by being quenched by ethanol precipitation.

General Procedure for Reverse Acylation

To a solution of on-DNA carboxylic acid (40.5 μL, 0.9 mM in water) in 72 μL of pH 5.8 MES buffer (250 mM in water, 500 equivalents) was added 18 μL of amine solution (200 mM in MeCN, 100 equivalents), 18 μL of 4-(4,6-dimethoxy-1,3,5-triazin-2-yl)-4-methylmorpholinium chloride (DMTMM, 200 mM in water, 100 equivalents) and 36 μL MeCN to give final 40% v/v MeCN. The reaction was incubated at room temperature for 18 h and then quenched by ethanol precipitation.

General Procedure for Nitro Reduction (Hypodiboric Acid)

To a solution of nitro-containing DNA conjugate (50 μL, 0.7 mM in water) was added 22 μL of NaOH solution (818 mM in water, 500 equivalents), and ethanol (54 μL), followed by the addition of 54 μL of $B_2(OH)_4$ (100 mM in water, 150 equivalents). The reaction mixture was incubated at room temperature for 2 h prior to ethanol precipitation. Second ethanol precipitation was performed after reconstitution the DNA pellet with water to remove residual building blocks. The solution of $B_2(OH)_4$ in neutral water was prepared freshly from vortexing or brief sonication before use.

General Procedure for Nucleophilic Aromatic Substitution (Heating)

To a solution of on-DNA amine (29.1 μL, 1.0 mM in water) in 58.2 μL of pH 9.5 borate buffer (250 mM in water, 500 equivalents) was added 5 μL of aryl halide (200 mM in MeCN, 100 equivalents) and 32 μL MeCN to give final 32% v/v MeCN. The reaction was heated at 40° C. for 18 h before being quenched by EtOH precipitation.

General Procedure for Nucleophilic Aromatic Substitution (DABCO)

To a solution of on-DNA amine (29.1 μL, 1.0 mM in water) in 5.8 μL of sodium hydroxide solution (5000 mM in water, 1000 equivalents), 64 μL of water and 1.5 μL of MeCN was added 43.7 μL of aryl halide (200 mM in MeCN, 300 equivalents), followed by 1.5 μL of DABCO (1,4-diazabicyclo[2,2,2]octane, 100 mM in MeCN, 5 equivalents) to give final 32% v/v MeCN. The reaction was incubated at room temperature for 18 h and then quenched by ethanol precipitation.

General Procedure for Suzuki Coupling

To the halogenated DNA conjugate (6.8 μL, 0.7 mM in water) was added 5 μL of CsOH (400 mM in water, 400 equivalents) and 2.5 μL of boronic acid (200 mM in 1,4-dioxane: water 1:1, 100 equiv), followed by adding 2 μL of freshly prepared sSPhos-Pd-G2 (5 mM in DMA, 2 equivalents). The reaction mixture was heated at 80° C. for 20 min and was cooled to room temperature. Sodium cysteine was added (2.5 μL, 200 mM in water, 100 equivalents) and heated at 80° C. for 20 min. The reaction mixture was cooled to room temperature prior to ethanol precipitation.

General Procedure for Sonogashira Coupling

To the halogenated DNA conjugate (6.8 μL, 0.7 mM in water) was added 5 μL of CsOH (1000 mM in water, 1000 equivalents) and 2.5 μL of terminal alkyne (200 mM in DMA, 100 equiv), followed by adding 4 μL of freshly prepared sSPhos-Pd-G2 (5 mM in DMA, 4 equivalents). The reaction mixture was heated at 80° C. for 20 min and was cooled to room temperature. Sodium cysteine was added (2.5 μL, 200 mM in water, 100 equivalents) and heated at 80° C. for 20 min. The reaction mixture was cooled to room temperature prior to ethanol precipitation.

Synthesis of a DNA-Encoded Chemical Library (DECL)

Architecture of the main library build and Building block diversity analysis.

Figure 29:
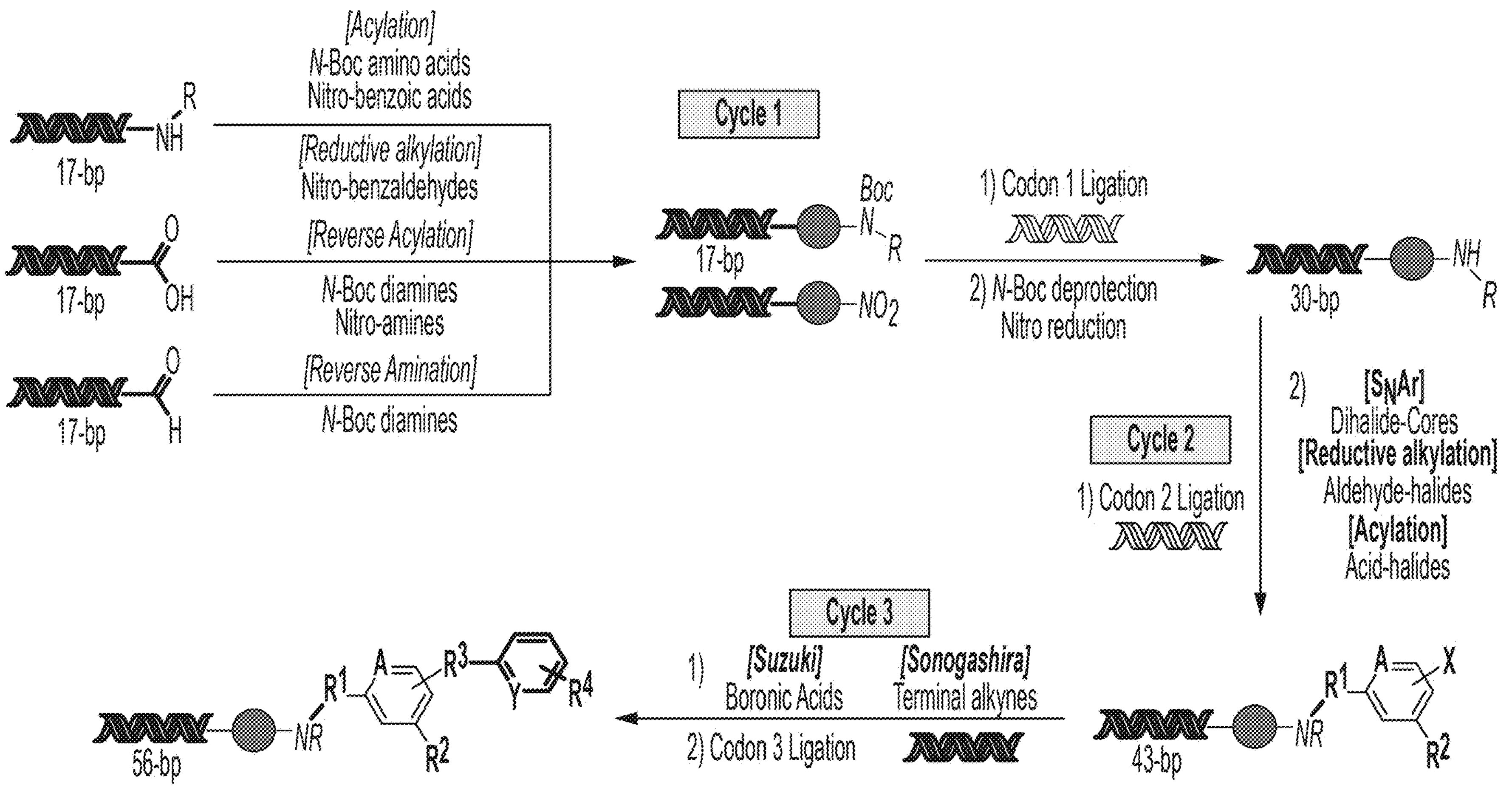
FIG. 29 depicts the synthetic scheme for FIG. 4. Cycles 1-3 are indicated. This library comprised 925 combinations in cycle 1, 585 building block in cycle 2 and 685 building blocks in cycle 3, which resulted in a library size of 370.7 million.

Similar strategy for the two aspects were adopted from previous reported literature. Synthetic sequence of the library build (FIG. 29):

Procedure for Cycle 1

Various linker-functionalized S2 (36 nmol/well) were plated individually into wells in 96-well plates. N-Boc amino acids (237) and nitro benzoic acids (44) were used for acylation with two different amine-terminating DNA substrates. Nitro benzaldehydes (42) were attached through reductive alkylation onto two different amine-terminating DNA substrates. N-Boc diamines (269) and nitro amines (46) were attached by reverse acylation to two different carboxylic acid terminated DNA substrates. N-Boc secondary diamines (177) were attached via reductive amination to one aldehyde terminated DNA substrate. Blanks were included as controls of building block-free and/or reagent-free conditions. Each well was carefully analyzed by LC-MS and 925 wells were proceeded to further step after removing those with low reaction conversions. After ethanol precipitation, each well was encoded with enzymatic ligation to unique DNA oligonucleotides (codon 1, 13-mer duplexed). Finally, N-Boc deprotection or nitro reduction was applied to the corresponding wells before pooling all wells. After pooling, additional ethanol precipitation was conducted to yield approximately 35.7 μmol of cycle 1 library pool.

Procedure for Cycle 2

After splitting the cycle 1 pool into 1178 wells (29.1 nmol/well), each well underwent codon 2 ligation with the general procedure. A variety of carboxylate aryl halides (380) were used for acylation with DEPBT and DMTMM methods; a variety of aryl dihalides (114) were attached by nucleophilic aromatic substitution using both heating and DABCO-promoted methods; a variety of aldehyde aryl halides (95) was used for reductive amination using both $NaCNBH_3$ and $NaBH_4$ methods. The conditions of these methods are described in previous sections and all methods were encoded separately. In addition, blanks were included with the same reaction conditions in the absence of building blocks or reagents. After pooling and additional ethanol precipitation, approximately 31.5 μmol of the cycle 2 pool was recovered. Procedure for Cycle 3. After splitting a portion of the cycle 2 pool into 691 wells (5 nmol/well), a series of boronic acids and pinacol esters (497) and terminal alkynes (188) were attached by Suzuki coupling and Sonogashira coupling. In addition, several blanks were included without building block and/or reagents to incorporate possible side-products. After ethanol precipitation, unique DNA oligonucleotides were used to encode each wells (codon 3). Each well was carefully analyzed by LC-MS to ensure the codon 3 ligation for further deconding process. After pooling and additional ethanol precipitation, approximately 3.4 μmol of the cycle 3 pool was recovered (71% recovery yield after 3 cycles of chemical transformations and ligations). Residual solids after Suzuki coupling and Sonogashira coupling need to be removed by centrifugation for further ligation to be proceeded successfully.

Preparation of Amplifiable DECL Samples for Further Selection Experiments

After completion of the main library builds, the entire library material was ligated with a duplexed pair of 12-mer DNA oligonucleotides (library ID) to encode the overall library construct. After ethanol precipitation, the DECL material underwent sequential ligation with DNA oligonucleotides, containing a region to encode selection experiment, a degenerate region as molecular identifier during amplification, and a reverse primer region for post-selection PCR amplification (the purposes/design of these components are discussed in a previous publication).

Methods for off DNA Synthesis

General Procedure-1 (Amidation)

The acid compound (1 equiv.) was dissolved in DMF under nitrogen in a round bottom flask equipped with a magnetic stir bar and a septum. Amine (1.1 equiv.) was added followed by DIPEA (1.5 equiv.) and HATU (1.1 equiv.) at room temperature. The reaction was allowed to stir for 16 h, after which time TLC and LCMS indicated complete consumption of starting material. The reaction was worked up by diluting with ethyl acetate and washed with sat. aq $NaHCO_3$ and brine. The organic phase was collected and dried over anhydrous Na2SO4. Filtered and the solvent was removed under reduced pressure to give the crude product, which was used in next reaction without further purification.

General Procedure-2 (-Boc-Removal)

The Boc-compound (1 equiv.) was dissolved in dichloromethane under nitrogen in a round bottom flask equipped with a magnetic stir bar and a septum. TFA (10% TFA in DCM, V/V, 10 mL/mmol) was added and allowed to stir at room temperature under nitrogen. After 2 h the starting material was consumed according to TLC and LCMS. The volatiles were evaporated under reduced pressure and then redissolved in toluene and evaporated to remove excess TFA. The crude product as TFA salt was used in next reaction without further purification.

General Procedure-3 (O-Alkylation)

The phenol compound (1 equiv.) was dissolved in acetone under nitrogen in a microwave vial equipped with magnetic stir bar and septum. 2-bromo-N,N-dimethylacetamide (1.1 equiv.) was added followed by $K_2CO_3$ (1.5 equiv.) and tetrabutylammonium iodide (TBAI; 0.1 equiv.). The reaction vial was sealed and allowed to heat at 65° C. for 2 h, after which time TLC and LCMS indicated complete consumption of starting material. The reaction was worked up by diluting with ethyl acetate and washed with water and brine. The organic phase was collected and dried over anhydrous $Na_2SO_4$. Filtered and the solvent was removed under reduced pressure to give the crude residue. Purification by silica gel chromatography (ethyl acetate/hexanes) provided the pure product.

General Procedure-4 (Hydroxy Ketone Synthesis)

The methyl ketone (1 equiv.) was dissolved in methanol at 0° C. in a round bottom flask equipped with magnetic stir bar and septum. Powdered potassium hydroxide (6 equiv.) was added followed by iodobenzene diacetate (1.1 equiv.). The mixture was warmed to room temperature, stirred for 3 h, and then evaporated to dryness under reduced pressure. The reaction was worked up by diluting with ethyl acetate and washed with water. The organic phase was collected and dried over anhydrous $Na_2SO_4$. The organic phase was filtered and the solvent was removed under reduced pressure to give the crude residue. The residue was dissolved in a mixture of methanol and aqueous hydrochloric acid (2M) and stirred overnight at rt before the reaction mixture was evaporated to dryness under reduced pressure. The reaction was worked up by diluting with ethyl acetate and washed with water. The organic phase was collected and dried over anhydrous $Na_2SO_4$. The organic phase was filtered and the solvent was removed under reduced pressure to give the crude residue. Purification by silica gel chromatography (ethyl acetate/hexanes) provided the pure product.

General Procedure-5 (Suzuki Reaction)

The arylbromide (1 equiv.), boronic acid (1.3 equiv.), $K_2CO_3$ (1.5 equiv.) and Pd(dppf)$Cl_2$ DCM complex (0.1 equiv.) were placed in a vial equipped with a stir bar. The vial was sealed with a septum screw-cap, and then it was evacuated and filled with nitrogen (three cycles). 1,4-dioxane and water (5:1 ratio) was added, and the resulting homogeneous reaction mixture was stirred vigorously at 110° C. for 1 h, after which time TLC and LCMS indicated complete consumption of starting material. The reaction was worked up by diluting with ethyl acetate and washed with water and brine. The organic phase was collected and dried over anhydrous $Na_2SO_4$. The organic phase was filtered and the solvent was removed under reduced pressure to give the crude residue. Purification by silica gel chromatography (ethyl acetate/hexanes) provided the pure product.

General Procedure-6 (Aldehyde Reduction)

The aldehyde compound (1 equiv.) was dissolved in dry THF under nitrogen in a round bottom flask equipped with a magnetic stir bar and a septum. Solid $NaBH_4$ (1.5 equiv.) was added at 0° C. After addition the reaction was allowed to stir at rt for 3 h, after which time TLC and LCMS indicated complete consumption of starting material. The reaction was worked up by diluting with EtOAc and washed with water and brine. The organic phase was collected and dried over anhydrous $Na_2SO_4$. The organic phase was filtered and the solvent was removed under reduced pressure to give the crude residue. Purification by silica gel chromatography (ethyl acetate/hexanes) provided the pure product.

General Procedure-7 (Reductive Amination)

The aldehyde compound (1 equiv.) was dissolved in DCM under nitrogen in a round bottom flask equipped with a magnetic stir bar and a septum. Methylamine (2M solution in THF, 1.5 equiv.) was added followed by AcOH (0.2 equiv.) at rt. The solution was stirred at rt for 20 minutes and then treated with sodium triacetoxyborohydride (STAB, 1.5 equiv.). The reaction was stirred at rt for 16 h. LCMS confirmed complete consumption of starting material. The reaction was worked up by diluting with DCM and washed with aq. sodium bicarbonate. The organic phase was collected and dried over anhydrous $Na_2SO4$. Filtered and the solvent was removed under reduced pressure to give the crude residue. Purification by silica gel chromatography (ethyl acetate/hexanes) provided the pure product.

General Procedure-8 (Wittig)

The aldehyde compound (1 equiv.) was dissolved in dry DCM under nitrogen in a round bottom flask equipped with a magnetic stir bar and a septum. (Ethoxycarbonylmethylene) triphenylphosphorane (1.1 equiv.) was added at rt. The reaction was allowed to stir for 16 h, after which time TLC and LCMS indicated complete consumption of starting material. The reaction was worked up by diluting with DCM and washed with water and brine. The organic phase was collected and dried over anhydrous $Na_2SO_4$. The organic phase was filtered and the solvent was removed under reduced pressure to give the crude residue. Purification by silica gel chromatography (ethyl acetate/hexanes) provided the pure product.

Syntheses of Compounds

Synthesized by Following General Procedure-1 & 2

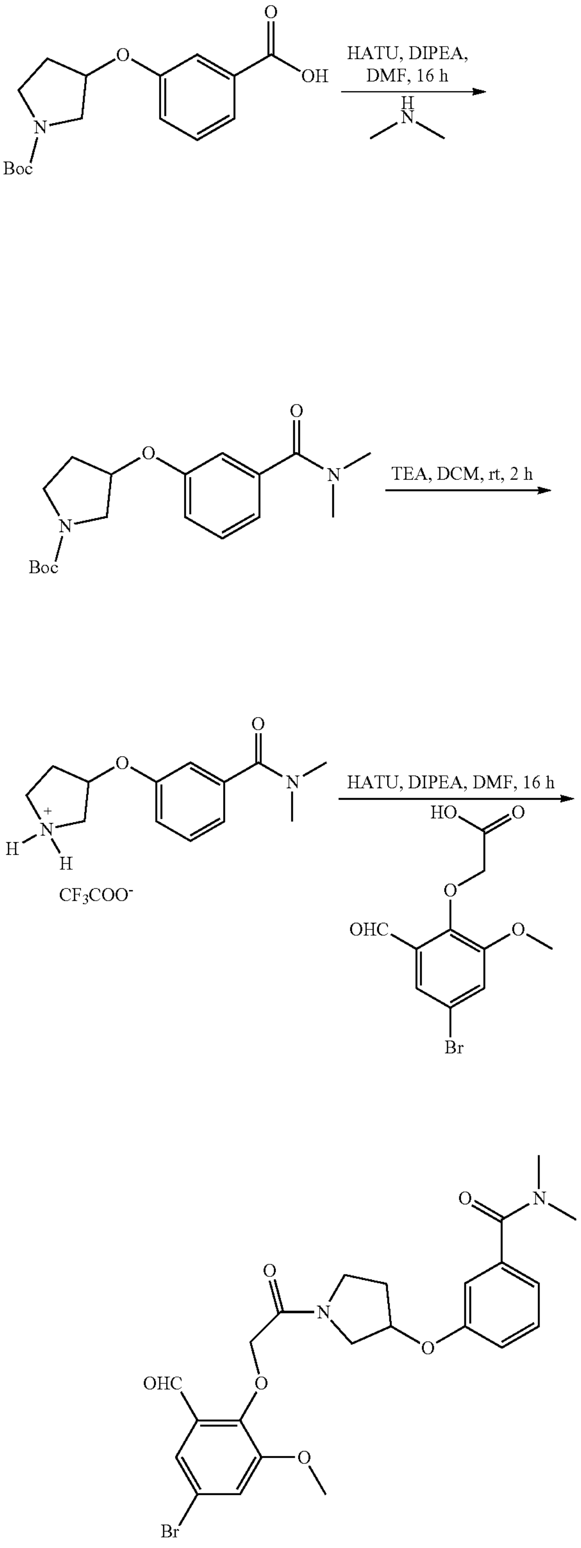

-continued

CDD-1712

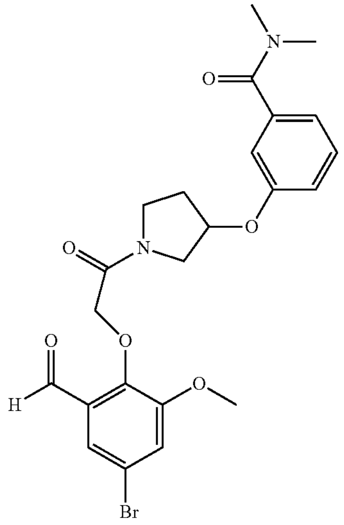

3-((1-(2-(4-bromo-2-formyl-6-methoxyphenoxy) acetyl) pyrrolidin-3-yl)oxy)-N,N-dimethylbenzamide Molecular Formula: $C_{23}H_{25}BrN_2O_6$; $^1H$ NMR (600 MHz, $CDCl_3$) δ 10.54 (s, 1H), 10.53 (s, 1H), 7.55 (t, J=2.4 Hz, 2H), 7.34-7.29 (m, 2H), 7.21 (dd, J=10.2, 2.4 Hz, 2H), 7.00 (dd, J=17.9, 7.6 Hz, 2H), 6.93-6.88 (m, 2H), 5.05-5.04 (m, 1H), 4.97-4.96 (m, 1H), 4.86 (d, J=4.2 Hz, 2H), 4.82-4.75 (m, 2H), 3.90 (s, 2H), 3.86 (s, 2H), 3.81-3.77 (m, 1H), 3.74-3.60 (m, 4H), 3.17-3.03 (m, 1H), 3.11 (d, J=3.9 Hz, 3H), 2.98-2.97 (m, 3H), 2.38-2.34 (3, 1H), 2.26-2.18 (m, 1H), 2.12-2.07 (m, 1H), 1.43-1.39 (m, 6H), 1.25 (s, 11H). $^{13}C$ NMR (151 MHz, $CDCl_3$) δ 189.3, 189.2, 171.1, 171.0, 166.8, 166.7, 156.8, 152.9, 152.9, 149.4, 149.4, 137.9, 130.9, 129.9, 129.7, 122.0, 122.0, 120.7, 120.0, 119.8, 117.2, 117.1, 116.7, 114.0, 113.8, 74.3, 70.8, 70.5, 56.5, 56.5, 55.5, 51.6, 51.0, 44.1, 43.5, 43.5, 39.6, 35.4, 31.9, 18.6, 17.2, 14.1, 12.5. HRMS (HESI-TOF) m/z calcd for $(M+H)^+$ 505.0974 and 507.0954, found 505.0968 and 507.0946.

Synthesized by Following General Procedure-3

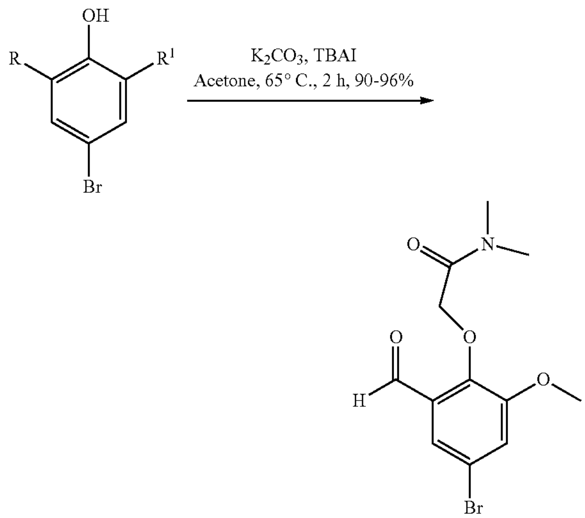

-continued

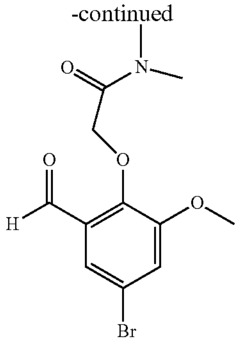

2-(4-bromo-2-formyl-6-methoxyphenoxy)-N,N-dimethylacetamide

Molecular Formula: $C_{12}H_{14}BrNO_4$; $^1H$ NMR (600 MHZ, $CDCl_3$) δ 10.52 (s, 1H), 7.55 (d, J=2.2 Hz, 1H), 7.20 (d, J=2.3 Hz, 1H), 4.89 (s, 2H), 3.89 (s, 3H), 3.00 (s, 3H), 2.95 (s, 3H). $^{13}C$ NMR (151 MHZ, $CDCl_3$) δ 189.3, 167.7, 152.9, 149.5, 131.0, 122.1, 120.7, 117.1, 70.3, 56.5, 36.0, 35.5.

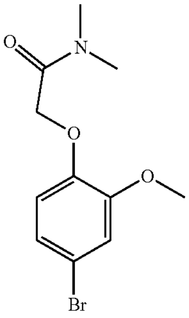 [SMILES: COc1cc(Br)ccc1OCC(=O)N(C)C]

2-(4-bromo-2-methoxyphenoxy)-N,N-dimethylacetamide

Molecular Formula: $C_{11}H_{14}BrNO_3$: $^1H$ NMR (600 MHz, $CDCl_3$) δ 6.99-6.98 (m, 2H), 6.81-6.80 (m, 1H), 4.72 (s, 2H), 3.85 (s, 3H), 3.08 (s, 3H), 2.96 (s, 3H). $^{13}C$ NMR (151 MHZ, $CDCl_3$) δ 167.6, 150.4, 146.8, 123.5, 115.7, 115.4, 114.2, 68.7, 56.1, 36.5, 35.7.

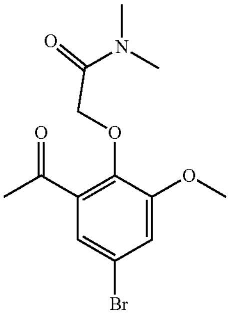 [SMILES: COc1cc(Br)cc(C(C)=O)c1OCC(=O)N(C)C]

2-(2-acetyl-4-bromo-6-methoxyphenoxy)-N,N-dimethylacetamide

Molecular Formula: $C_{13}H_{16}BrNO_4$; $^1H$ NMR (600 MHZ, $CDCl_3$) δ 7.34 (dd, J=2.3, 1.2 Hz, 1H), 7.13 (d, J=2.6 Hz, 1H), 4.75 (s, 2H), 3.87 (s, 3H), 3.01 (s, 3H), 2.98 (s, 3H), 2.65 (s, 3H). $^{13}C$ NMR (151 MHZ, $CDCl_3$) δ 198.9, 167.4, 153.3, 145.6, 135.3, 123.7, 118.8, 116.9, 70.9, 56.4, 36.2, 35.5, 31.4.

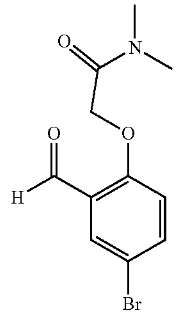 [SMILES: CN(C)C(=O)COc1ccc(Br)cc1C=O]

2-(4-bromo-2-formylphenoxy)-N,N-dimethylacetamide

Molecular Formula: $C_{11}H_{12}BrNO_3$; $^1H$ NMR (600 MHZ, $CDCl_3$) δ 10.45 (s, 1H), 7.92 (d, J=2.6 Hz, 1H), 7.59-7.57 (m, 1H), 6.88 (d, J=8.9 Hz, 1H), 4.84 (s, 2H), 3.08 (s, 3H), 2.98 (s, 3H). $^{13}C$ NMR (151 MHz, $CDCl_3$) δ 188.0, 166.6, 159.3, 138.2, 131.2, 126.5, 115.1, 114.4, 67.4, 36.3, 35.7.

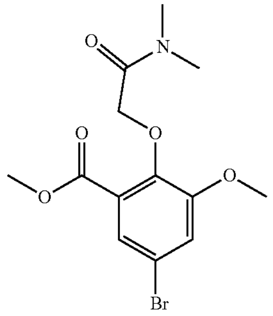

Methyl 5-bromo-2-(2-(dimethylamino)-2-oxoethoxy)-3-methoxybenzoate

Molecular Formula: $C_{13}H_{16}BrNO_5$; $^1H$ NMR (600 MHZ, $CDCl_3$) δ 7.45 (dd, J=2.4, 1.0 Hz, 1H), 7.14 (d, J=2.4 Hz, 1H), 4.67 (s, 2H), 3.87 (s, 3H), 3.85 (s, 3H), 3.08 (s, 3H), 2.98 (s, 3H). $^{13}C$ NMR (151 MHz, $CDCl_3$) δ 167.6, 165.1, 154.0, 146.5, 127.6, 124.9, 119.1, 116.8, 72.0, 56.4, 52.5, 36.5, 35.5.

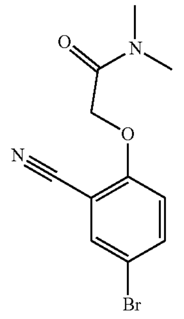 [SMILES: CN(C)C(=O)COc1ccc(Br)cc1C#N]

2-(4-bromo-2-cyanophenoxy)-N,N-dimethylacetamide

Molecular Formula: $C_{11}H_{11}BrN_2O_2$; $^1H$ NMR (600 MHz, $CDCl_3$) δ 7.66 (dd, J=2.6, 1.2 Hz, 1H), 7.59 (ddd, J=9.1, 2.6, 1.2 Hz, 1H), 6.94 (dd, J=9.0, 1.3 Hz, 1H), 4.84 (s, 2H), 3.11 (s, 2H), 2.96 (s, 1H). $^{13}C$ NMR (151 MHz, $CDCl_3$) δ 166.3, 158.8, 137.3, 135.9, 114.7, 114.7, 113.3, 104.0, 68.2, 36.7, 35.7.

Synthesized by Following General Procedure-3 & 4

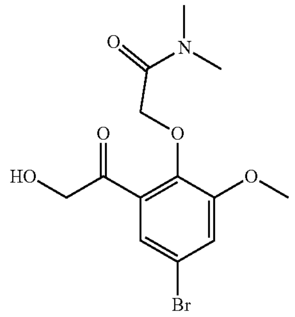 [SMILES: COc1cc(Br)cc(C(=O)CO)c1OCC(=O)N(C)C]

2-(4-bromo-2-(2-hydroxyacetyl)-6-methoxyphenoxy)-N,N-dimethylacetamide

Molecular Formula: $C_{13}H_{16}BrNO_5$; $^1H$ NMR (600 MHZ, $CDCl_3$) δ 7.55 (d, J=2.3 Hz, 1H), 7.17 (d, J=2.4 Hz, 1H), 4.89 (s, 2H), 4.81 (s, 2H), 3.88 (s, 3H), 2.98 (s, 3H), 2.96 (s, 3H). 13C NMR (151 MHz, $CDCl_3$) δ 199.9, 167.5, 152.7, 146.6, 130.7, 124.2, 119.9, 116.7, 69.9, 69.6, 56.5, 36.0, 35.5.

Synthesized by Following General Procedure-5

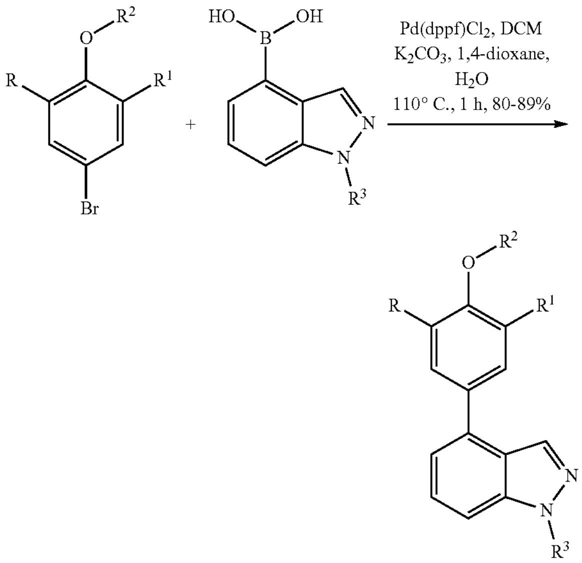

-continued

CDD-1714

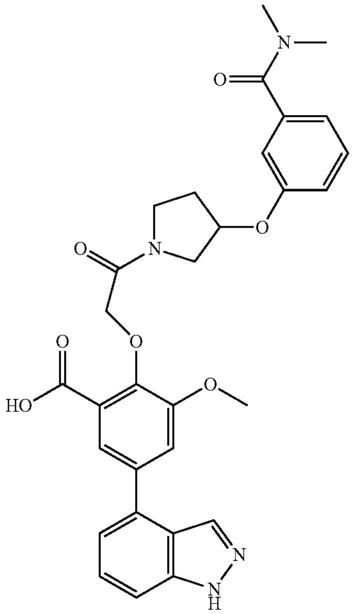

3-((1-(2-(2-formyl-4-(1H-indazol-4-yl)-6-methoxyphenoxy) acetyl) pyrrolidin-3-yl)oxy)-N,N-dimethylbenzamide Molecular Formula: $C_{30}H_{30}N_4O_6$; $^1$H NMR (600 MHZ, $CDCl_3$) δ 10.70 (s, 1H), 10.67 (s, 1H), 8.18 (d, J=3.6 Hz, 1H), 7.76 (dd, J=6.2, 2.1 Hz, 1H), 7.49 (d, J=8.4 Hz, 1H), 7.47-7.41 (m, 1H), 7.34-7.29 (m, 1H), 7.23 (dd, J=7.0, 4.1 Hz, 1H), 7.03-6.99 (m, 1H), 6.96-6.89 (m, 2H), 5.06-5.04 (m, 1H), 4.97-4.96 (m, 2H), 4.88 (q, J=14.4 Hz, 1H), 3.97-3.92 (m, 4H), 3.86-3.79 (m, 1H), 3.74-3.67 (m, 2H), 3.12-3.11 (m, 3H), 2.99-2.98 (m, 3H), 2.39-2.35 (m, 1H), 2.28-2.18 (m, 1H), 2.13-2.07 (m, 1H), 2.02-2.00 (m, 1H). $^{13}$C NMR (151 MHz, $CDCl_3$) δ 190.5, 171.1, 167.1, 156.8, 150.0, 140.6, 137.9, 134.1, 133.8, 130.2, 129.7, 127.0, 120.4, 119.8, 119.1, 117.8, 117.2, 116.8, 114.0, 109.2, 71.0, 56.4, 51.8, 51.2, 44.2, 43.6, 39.6, 35.4, 31.9, 14.2. HRMS (HESI-TOF) m/z calcd for $(M+H)^+$ 543.2244, found 543.2241.

CDD-1713

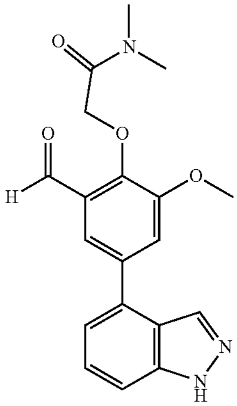

2-(2-formyl-4-(1H-indazol-4-yl)-6-methoxyphenoxy)-N,N-dimethylacetamide

Molecular Formula: $C_{19}H_{19}N_3O_4$; $^1$H NMR (600 MHz, $CDCl_3$) δ 10.68 (s, 1H), 8.20 (s, 1H), 7.76 (d, J=2.1 Hz, 1H), 7.51 (d, J=8.4 Hz, 1H), 7.49-7.41 (m, 2H), 7.24 (d, J=7.0 Hz, 1H), 5.00 (s, 2H), 3.97 (s, 3H), 3.08 (s, 3H), 3.01 (s, 3H). $^{13}$C NMR (151 MHZ, $CDCl_3$) δ 190.5, 168.0, 152.4, 150.1, 136.1, 130.3, 127.1, 120.5, 119.2, 117.9, 109.2, 70.9, 56.4, 36.2, 35.6, 29.7. HRMS (HESI-TOF) m/z calcd for $(M+H)^+$ 354.1454, found 354.1443.

CDD-1793

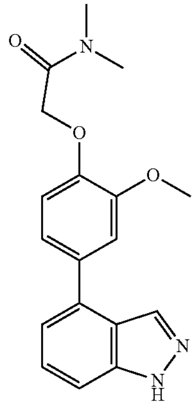

2-(4-(1H-indazol-4-yl)-2-methoxyphenoxy)-N,N-dimethylacetamide

Molecular Formula: $C_{18}H_{19}N_3O_3$; $^1$H NMR (600 MHZ, $CDCl_3$) δ 8.23 (s, 1H), 7.51-7.40 (m, 2H), 7.25-7.18 (m, 3H), 7.07 (d, J=8.1 Hz, 1H), 4.85 (s, 2H), 3.94 (s, 3H), 3.16 (s, 3H), 3.02 (s, 3H). $^{13}$C NMR (151 MHz, $CDCl_3$) δ 168.0, 149.7, 147.3, 134.0, 127.0, 120.9, 120.0, 114.4, 112.3, 108.6, 68.6, 56.1, 36.7, 35.9. HRMS (HESI-TOF) m/z calcd for $(M+H)^+$ 326.1505, found 326.1487.

CDD-1847

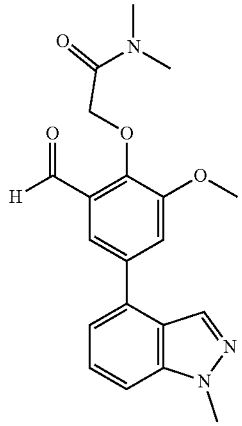

2-(2-formyl-6-methoxy-4-(1-methyl-1H-indazol-4-yl)phenoxy)-N,N-dimethylacetamide Molecular Formula: $C_{20}H_{21}N_3O_4$; $^1$H NMR (600 MHZ, $CDCl_3$) δ 10.67 (s, 1H), 8.09 (d, J=0.9 Hz, 1H), 7.78 (d, J=2.1 Hz, 1H), 7.48-7.43 (m, 2H), 7.40 (d, J=8.4 Hz, 1H), 7.23 (d, J=7.0 Hz, 1H), 4.99 (s, 2H), 4.13 (s, 3H), 3.97 (s, 3H), 3.07 (s, 3H), 3.00 (s, 3H). 13C NMR (151 MHz, $CDCl_3$) δ 190.5, 168.0, 152.4, 150.0, 140.4, 136.1, 134.0, 132.0, 130.3, 126.5, 122.3, 120.0, 119.2, 117.9, 108.4, 70.8, 56.4, 36.2, 35.8, 35.6. HRMS (HESI-TOF) m/z calcd for $(M+H)^+$ 368.1610, found 368.1604.

CDD-1883

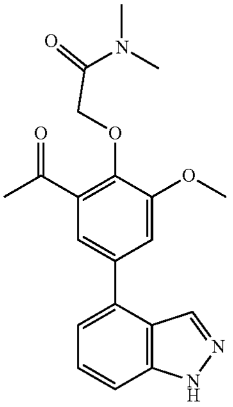

2-(2-acetyl-4-(1H-indazol-4-yl)-6-methoxyphenoxy)-N,N-dimethylacetamide

Molecular Formula: $C_{20}H_{21}N_3O_4$; $^1H$ NMR (600 MHZ, $CDCl_3$) δ 8.20 (s, 1H), 7.54 (d, J=2.1 Hz, 1H), 7.51 (d, J=8.4 Hz, 1H), 7.45 (dd, J=8.4, 7.0 Hz, 1H), 7.37 (d, J=2.1 Hz, 1H), 7.24 (d, J=7.0 Hz, 1H), 4.87 (s, 2H), 3.95 (s, 3H), 3.09 (s, 3H), 3.03 (s, 3H), 2.74 (s, 3H). 13C NMR (151 MHz, $CDCl_3$) δ 200.3, 167.8, 152.8, 146.1, 136.1, 134.6, 120.9, 120.4, 115.7, 71.3, 56.4, 36.4, 35.6, 31.6. HRMS (HESI-TOF) m/z calcd for $(M+H)^+$ 368.1610, found 368.1606.

CDD-1886

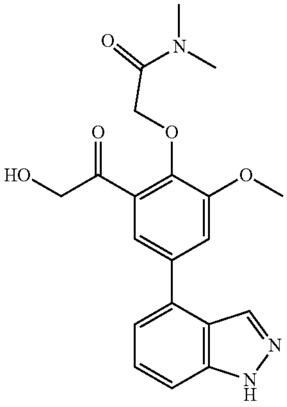

2-(2-(2-hydroxyacetyl)-4-(1H-indazol-4-yl)-6-methoxyphenoxy)-N,N-dimethylacetamide Molecular Formula: $C_{20}H_{21}N_3O_5$; $^1H$ NMR (600 MHz, $CDCl_3$) δ 8.20 (s, 1H), 7.77 (d, J=2.1 Hz, 1H), 7.51 (d, J=8.3 Hz, 1H), 7.47 (dd, J=8.4, 7.0 Hz, 1H), 7.42 (d, J=2.1 Hz, 1H), 7.24 (s, 1H), 4.99 (s, 2H), 4.91 (s, 2H), 3.96 (s, 3H), 3.05 (s, 3H), 3.00 (s, 3H). 13C NMR (151 MHz, $CDCl_3$) δ 200.8, 167.7, 134.2, 129.9, 127.1, 121.6, 121.4, 120.5, 116.9, 109.1, 70.3, 69.7, 56.4, 36.1, 35.6. HRMS (HESI-TOF) m/z calcd for $(M+H)^+$ 384.1559, found 384.1553.

CDD-1976

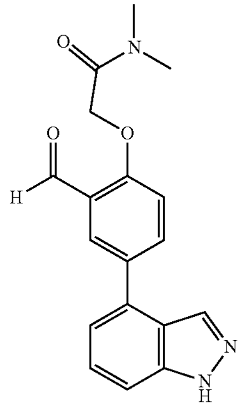

2-(2-formyl-4-(1H-indazol-4-yl) phenoxy)-N,N-dimethylacetamide

Molecular Formula: $C_{18}H_{17}N_3O_3$; $^1H$ NMR (600 MHZ, MeOD) δ 10.58 (s, 1H), 8.11 (s, 2H), 7.94 (d, J=8.8 Hz, 1H), 7.53-7.43 (m, 2H), 7.24-7.20 (m, 2H), 5.10 (s, 2H), 3.13 (s, 3H), 3.00 (s, 3H). 13C NMR (151 MHz, $CDCl_3$) δ 193.7, 172.2, 164.3, 144.9, 139.3, 137.0, 136.4, 131.1, 130.7, 125.0, 123.5, 117.7, 113.0, 69.9, 38.9, 38.5. HRMS (HESI-TOF) m/z calcd for $(M+H)^+$ 324.1348, found 324.1346.

CDD-1982

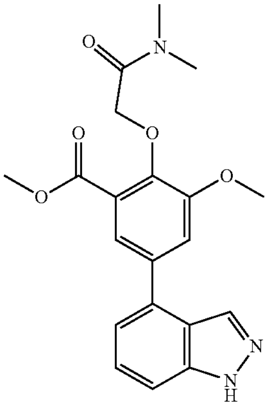

Methyl 2-(2-(dimethylamino)-2-oxoethoxy)-5-(1H-indazol-4-yl)-3-methoxybenzoate

Molecular Formula: $C_{20}H_{21}N_3O_5$; $^1H$ NMR (600 MHz, $CDCl_3$) δ 8.23 (s, 1H), 7.66 (s, 1H), 7.53 (d, J=8.3 Hz, 1H), 7.44 (t, J=7.7 Hz, 1H), 7.36 (d, J=2.2 Hz, 1H), 7.22 (d, J=7.0 Hz, 1H), 4.82 (s, 2H), 3.91 (d, J=8.0 Hz, 6H), 3.17 (s, 3H), 3.05 (s, 3H). 13C NMR (151 MHZ, $CDCl_3$) δ 168.1, 166.3, 153.5, 146.8, 136.3, 133.9, 127.0, 126.7, 122.2, 120.4, 115.9, 109.5, 72.3, 56.4, 52.4, 36.7, 35.7. HRMS (HESI-TOF) m/z calcd for $(M+H)^+$ 384.1559, found 384.1559.

CDD-2037

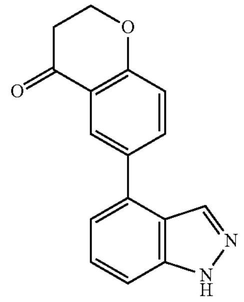

6-(1H-indazol-4-yl)chroman-4-one

Molecular Formula $C_{16}H_{12}N_2O_2$; $^1H$ NMR (600 MHz, $CDCl_3$) δ 8.27 (s, 1H), 8.24 (d, J=2.4 Hz, 1H), 7.84-7.83 (m, 1H), 7.58 (d, J=8.5 Hz, 1H), 7.53 (t, J=7.8 Hz, 1H), 7.28 (d, J=7.2 Hz, 1H), 7.16 (d, J=8.5 Hz, 1H), 4.63 (t, J=6.5 Hz, 2H), 2.90 (t, J=6.5 Hz, 2H). 13C NMR (151 MHz, $CDCl_3$) δ 191.6, 161.6, 135.9, 133.0, 127.7, 126.7, 121.6, 120.7, 118.6, 67.2, 37.8, 29.7. HRMS (HESI-TOF) m/z calcd for $(M+H)^+$ 265.0977, found 265.0967.

CDD-2038

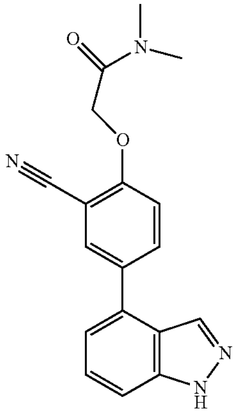

2-(2-cyano-4-(1H-indazol-4-yl) phenoxy)-N,N-dimethylacetamide

Molecular Formula: $C_{18}H_{16}N_4O_2$; $^1H$ NMR (600 MHZ, $CDCl_3$) δ 8.13 (s, 1H), 7.84 (d, J=2.1 Hz, 1H), 7.79 (dd, J=8.7, 2.4 Hz, 1H), 7.54 (d, J=8.4 Hz, 1H), 7.45 (t, J=7.7 Hz, 1H), 7.18 (d, J=8.7 Hz, 1H), 7.14 (d, J=7.1 Hz, 1H), 4.95 (s, 2H), 3.20 (s, 3H), 3.03 (s, 3H). 13C NMR (151 MHZ, $CDCl_3$) δ 166.8, 159.1, 140.7, 134.3, 133.7, 133.6, 133.3, 132.4, 127.3, 121.4, 120.4, 116.0, 113.4, 109.6, 102.7, 68.3, 36.9, 35.9. HRMS (HESI-TOF) m/z calcd for $(M+H)^+$ 321.1352, found 321.1338.

Synthesized by Following General Procedure-6

CDD-1776

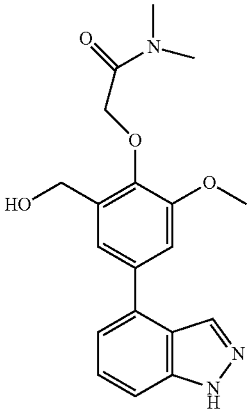

2-(2-(hydroxymethyl)-4-(1H-indazol-4-yl)-6-methoxyphenoxy)-N,N-dimethylacetamide Molecular Formula: $C_{19}H_{21}N_3O_4$; $^1H$ NMR (600 MHz, $CDCl_3$) δ 8.21 (s, 1H), 7.48-7.42 (m, 2H), 7.22-7.20 (m, 3H), 5.02 (s, 2H), 4.78 (s, 2H), 3.94 (s, 3H), 3.02 (d, J=2.7 Hz, 6H). 13C NMR (151 MHz, $CDCl_3$) δ 169.9, 151.4, 146.3, 140.6, 135.5, 135.4, 134.9, 134.5, 127.1, 122.4, 121.8, 120.2, 112.7, 108.6, 69.4, 61.9, 56.2, 35.9, 35.8. HRMS (HESI-TOF) m/z calcd for $(M+H)^+$ 356.1610, found 356.1602.

Synthesized by Following General Procedure-7

CDD-1777

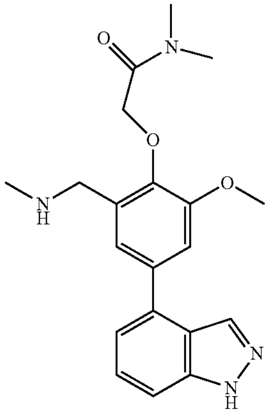

2-(4-(1H-indazol-4-yl)-2-methoxy-6-((methylamino) methyl)phenoxy)-N,N-dimethylacetamide Molecular Formula: $C_{20}H_{24}N_4O_3$; $^1H$ NMR (800 MHZ, $CDCl_3$) δ 8.22 (s, 1H), 7.55 (d, J=8.3 Hz, 1H), 7.44 (dd, J=8.3, 7.0 Hz, 1H), 7.31 (d, J=5.4 Hz, 2H), 7.21 (d, J=7.1 Hz, 1H), 5.24 (s, 2H), 4.29 (s, 2H), 3.96 (s, 3H), 3.03 (s, 3H), 3.01 (s, 3H), 2.78 (s, 3H). 13C NMR (201 MHz, $CDCl_3$) δ 170.4, 150.9, 145.4, 135.8, 133.6, 127.0, 124.4, 124.3, 120.3, 114.6, 109.4, 68.6, 56.2, 49.0, 36.0, 35.8, 32.3. HRMS (HESI-TOF) m/z calcd for $(M+H)^+$ 369.1927, found 369.1912.

Synthesized by Following General Procedure-8

CDD-1971

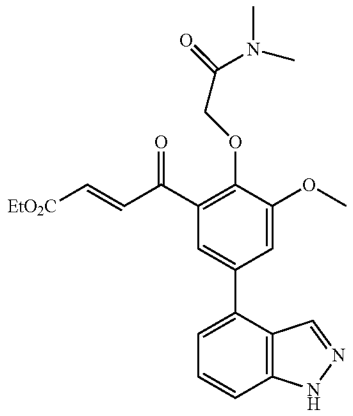

ethyl (E)-4-(2-(2-(dimethylamino)-2-oxoethoxy)-5-(1H-indazol-4-yl)-3-methoxyphenyl)-4-oxobut-2-enoate Molecular Formula: $C_{24}H_{25}N_3O_6$; $^1H$ NMR (600 MHZ, $CDCl_3$) δ 8.13 (d, J=16.1 Hz, 1H), 7.51-7.43 (m, 4H), 7.24 (s, 3H), 6.53 (d, J=16.1 Hz, 1H), 4.81 (s, 2H), 4.27 (q, J=7.1 Hz, 2H), 3.94-3.93 (s, 3H), 3.22 (s, 3H), 3.03 (s, 3H), 1.34 (t, J=7.1 Hz, 3H). 13C NMR (151 MHz, $CDCl_3$) δ 167.0, 152.6, 139.2, 129.0, 120.2, 114.2, 72.0, 60.5, 56.2, 36.8, 35.6, 29.7, 14.4. HRMS (HESI-TOF) m/z calcd for $(M+H)^+$ 452.1822, found 424.1853.

Syntheses

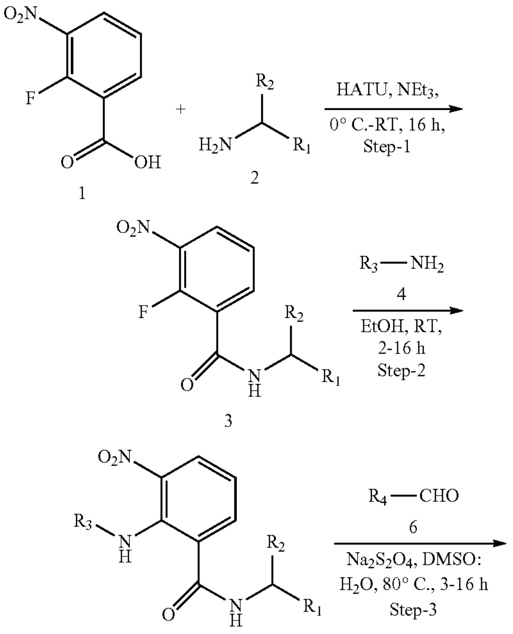

1 2 3 5

-continued

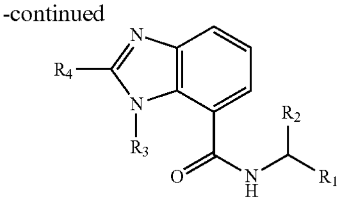

7

General Procedure—Step-1

The acid compound (1 equiv.) was dissolved in DMF under nitrogen in a round bottom flask equipped with a magnetic stir bar and a septum. Amine 2 (1.1 equiv.) was added followed by HATU (1.2 equiv.) and DIPEA (1.5 equiv.) at 0° C. and allowed to warm to room temperature. The reaction was allowed to stir for 16 h, after which time TLC and LCMS indicated complete consumption of starting material. The reaction was worked up by diluted with ethyl acetate and washed with sat. aq $NaHCO_3$ and brine. The organic phase was collected and dried over anhydrous $Na_2SO_4$, filtered, and concentrated reduced pressure to give the crude product. Purification of the crude product by silica gel chromatography (ethyl acetate/hexanes) provided the desired product 3.

General Procedure—Step-2

The compound 3 (1 equiv.) was dissolved in ethanol under nitrogen in a round bottom flask equipped with a magnetic stir bar and a septum. Amine 4 (1.2 equiv.) and NEts (1.5 equiv.) was added at RT. The reaction was allowed to stir for 2-16 h, after which time TLC and LCMS indicated complete consumption of starting material. Then solvent was removed under reduced pressure to give the crude residue which was purification by silica gel chromatography (ethyl acetate/hexanes) provided the desired product 5.

General Procedure—Step-3

The compound 5 (1 equiv.) was dissolved in DMSO: water (5:1) under nitrogen in a round bottom flask equipped with a magnetic stir bar and a septum. Aldehyde 6 (1.3 equiv.) was added followed by $Na_2S_2O_4$ (6.0 equiv.) at room temperature. The reaction was allowed to stir for 3-16 h at 80° C., after which time TLC and LCMS indicated complete consumption of starting material. The reaction was worked up by diluted with ethyl acetate and washed with sat. aq $NaHCO_3$ and brine. The organic phase was collected and dried over anhydrous $Na_2SO_4$, filtered, and concentrated under reduced pressure to give the crude product. The crude product was purified by reverse phase column chromatography (water/ACN) provided the desired product 7.

Synthesized by Following General Procedure—Step-1

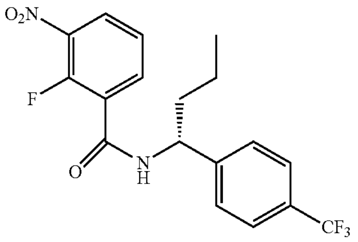 [SMILES: CCC[C@@H](NC(=O)c1cccc([N+](=O)[O-])c1F)c1ccc(C(F)(F)F)cc1]

(R)-2-fluoro-3-nitro-N-(1-(4-(trifluoromethyl)phenyl)butyl)benzamide

Molecular Formula: $C_{18}H_{16}F_4N_2O_3$; yield 72%; $^1H$ NMR (600 MHZ, $CDCl_3$) δ 8.32 (t, J=7.0 Hz, 1H), 8.17 (dd, J=11.0, 4.1 Hz, 1H), 7.63 (d, J=8.1 Hz, 2H), 7.49 (d, J=8.1 Hz, 2H), 7.42 (t, J=8.0 Hz, 1H), 7.02-6.95 (m, 1H), 5.22 (q, J=7.1 Hz, 1H), 1.97-1.83 (m, 2H), 1.52-1.43 (m, 1H), 1.43-1.35 (m, 1H), 0.99 (t, J=7.4 Hz, 3H). $^{13}C$ NMR (151 MHz, $CDCl_3$) δ 160.8, 160.8, 154.3, 152.6, 146.1, 138.1, 138.1, 137.7, 137.7, 130.2, 130.0, 129.8, 129.6, 129.2, 127.0, 125.9, 125.9, 125.9, 125.9, 125.1, 125.0, 124.1, 124.0, 123.2, 54.3, 38.5, 19.5, 13.8.

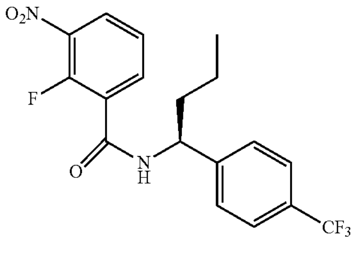 [SMILES: CCC[C@H](NC(=O)c1cccc([N+](=O)[O-])c1F)c1ccc(C(F)(F)F)cc1]

(S)-2-fluoro-3-nitro-N-(1-(4-(trifluoromethyl)phenyl)butyl)benzamide

Molecular Formula: $C_{18}H_{16}F_4N_2O_3$; yield 75%; $^1H$ NMR (600 MHz, $CDCl_3$) δ 8.33 (ddd, J=8.1, 6.6, 1.9 Hz, 1H), 8.17 (td, J=8.1, 1.9 Hz, 1H), 7.62 (d, J=8.1 Hz, 2H), 7.47 (d, J=8.2 Hz, 2H), 7.42 (t, J=7.8 Hz, 1H), 6.93-6.88 (m, 1H), 5.22-5.18 (m, 1H), 1.95-1.83 (m, 2H), 1.48 (d, J=7.4 Hz, 1H), 1.36 (dd, J=27.0, 9.8 Hz, 1H), 0.98 (t, J=7.4 Hz, 3H). $^{13}C$ NMR (151 MHz, $CDCl_3$) δ 160.8, 160.8, 154.3, 152.6, 146.1, 138.1, 138.1, 137.7, 137.7, 130.2, 130.0, 129.8, 129.6, 129.2, 127.0, 125.9, 125.9, 125.9, 125.9, 125.1, 125.0, 124.1, 124.0, 123.2, 54.3, 38.5, 19.5, 13.8.

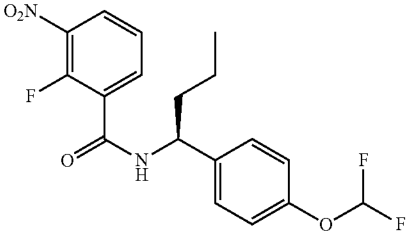 [SMILES: CCC[C@H](NC(=O)c1cccc([N+](=O)[O-])c1F)c1ccc(OC(F)F)cc1]

(S)—N-(1-(4-(difluoromethoxy)phenyl)butyl)-2-fluoro-3-nitrobenzamide

Molecular Formula: $C_{18}H_{17}F_3N_2O_4$; yield 60%; $^1H$ NMR (600 MHZ, $CD_3OD$) δ 9.11 (d, J=8.0 Hz, 1H), 8.20-8.15 (m, 1H), 7.84 (dd, J=9.6, 3.7 Hz, 1H), 7.43 (d, J=8.5 Hz, 3H), 7.14 (d, J=8.6 Hz, 2H), 6.81 (t, J=74.2 Hz, 1H), 5.17-5.05 (m, 1H), 1.93-1.86 (m, 1H), 1.85-1.73 (m, 1H), 1.56-1.48 (m, 1H), 1.48-1.37 (m, 1H), 1.00 (t, J=7.4 Hz, 3H). $^{13}C$ NMR (151 MHz, $CD_3OD$) δ 164.7, 164.6, 154.5, 152.7, 151.9, 151.9, 151.9, 141.2, 139.2, 139.2, 136.1, 136.1, 129.2, 128.9, 128.5, 128.5, 128.4, 128.4, 125.9, 125.9, 120.3, 119.5, 117.8, 116.1, 55.0, 54.9, 39.4, 20.7, 14.0.

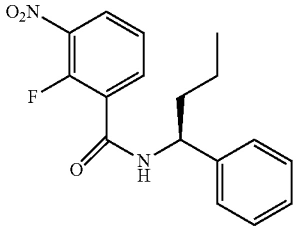 [SMILES: CCC[C@H](NC(=O)c1cccc([N+](=O)[O-])c1F)c1ccccc1]

(S)-2-fluoro-3-nitro-N-(1-phenylbutyl)benzamide

Molecular Formula: $C_{17}H_{17}FN_2O_3$; yield 62%; $^1H$ NMR (600 MHZ, $CDCl_3$) δ 8.11 (dd, J=10.1, 3.8 Hz, 1H), 8.00 (t, J=6.8 Hz, 1H), 7.25-7.24 (m, 5H), 7.17 (dd, J=8.6, 4.3 Hz, 1H), 6.96 (t, J=7.9 Hz, 1H), 5.12-5.01 (m, 1H), 1.88-1.72 (m, 2H), 1.37-1.22 (m, 2H), 0.86 (t, J=7.4 Hz, 3H). $^{13}C$ NMR (151 MHZ, $CDCl_3$) δ 160.7, 154.0, 152.3, 141.9, 137.9, 137.9, 137.3, 137.3, 128.8, 128.7, 127.6, 126.6, 124.8, 124.7, 54.4, 38.5, 19.5, 13.8.

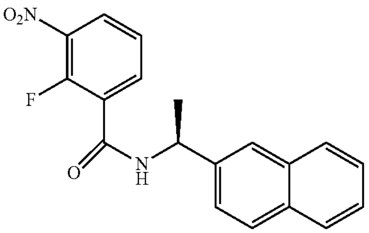 [SMILES: C[C@H](NC(=O)c1cccc([N+](=O)[O-])c1F)c1ccc2ccccc2c1]

(S)-2-fluoro-N-(1-(naphthalen-2-yl)ethyl)-3-nitrobenzamide

Molecular Formula: $C_{19}H_{15}FN_2O_3$; yield 82%; $^1H$ NMR (600 MHZ, $CDCl_3$) δ 8.37 (t, J=7.2 Hz, 1H), 8.15 (t, J=7.6 Hz, 1H), 7.86 (dd, J=13.9, 8.9 Hz, 4H), 7.52-7.45 (m, 3H), 7.41 (t, J=8.0 Hz, 1H), 6.96 (s, 1H), 5.55-5.48 (m, 1H), 1.72 (d, J=6.9 Hz, 3H). $^{13}C$ NMR (151 MHz, $CDCl_3$) δ 160.5, 154.3, 152.6, 139.9, 138.2, 137.7, 137.6, 133.5, 133.0, 129.0, 128.9, 128.1, 127.8, 126.5, 126.2, 124.9, 124.9, 124.9, 124.5, 124.4, 77.4, 77.2, 76.9, 50.3, 22.0.

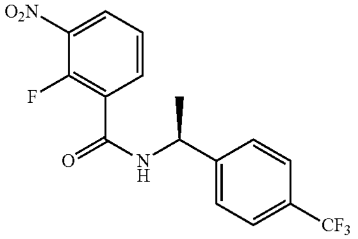 [SMILES: C[C@H](NC(=O)c1cccc([N+](=O)[O-])c1F)c1ccc(C(F)(F)F)cc1]

(S)-2-fluoro-3-nitro-N-(1-(4-(trifluoromethyl)phenyl)ethyl)benzamide

Molecular Formula: $C_{16}H_{12}F_4N_2O_3$; yield 82%; $^1H$ NMR (600 MHZ, $CDCl_3$) δ 8.34 (ddd, J=8.1, 6.6, 1.9 Hz, 1H), 8.17 (td, J=8.1, 1.8 Hz, 1H), 7.63 (d, J=8.2 Hz, 2H), 7.50 (d, J=8.2 Hz, 2H), 7.45-7.39 (m, 1H), 6.96-6.88 (m, 1H), 5.36 (p, J=6.9 Hz, 1H), 1.63 (d, J=7.0 Hz, 3H). $^{13}C$ NMR (151

MHz, $CDCl_3$) δ 160.7, 160.7, 154.2, 152.5, 146.8, 138.1, 138.0, 137.5, 137.5, 130.2, 130.0, 129.8, 129.6, 129.2, 129.1, 126.5, 125.9, 125.9, 125.9, 125.9, 125.0, 125.0, 124.2, 124.1, 123.2, 49.9, 22.1.

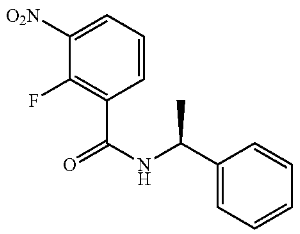 [SMILES: C[C@H](NC(=O)c1cccc([N+](=O)[O-])c1F)c1ccccc1]

(S)-2-fluoro-3-nitro-N-(1-phenylethyl)benzamide

Molecular Formula: $C_{15}H_{13}FN_2O_3$; yield 64%; $^1$H NMR (600 MHZ, $CDCl_3$) δ 8.35 (ddd, J=8.1, 6.6, 1.9 Hz, 1H), 8.14 (td, J=8.1, 1.8 Hz, 1H), 7.43-7.34 (m, 5H), 7.30 (td, J=6.1, 3.3 Hz, 1H), 6.88 (s, 1H), 5.34 (ddd, J=14.1, 7.1, 1.9 Hz, 1H), 1.62 (d, J=6.9 Hz, 3H). $^{13}$C NMR (151 MHz, $CDCl_3$) δ 160.4, 160.4, 154.3, 152.5, 142.6, 137.7, 137.7, 129.0, 127.9, 126.3, 124.9, 124.9, 124.5, 124.4, 50.2, 22.1.

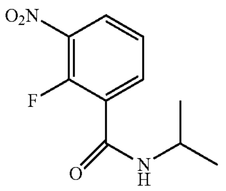 [SMILES: CC(C)NC(=O)c1cccc([N+](=O)[O-])c1F]

2-fluoro-N-isopropyl-3-nitrobenzamide

Molecular Formula: $C_{10}H_{11}FN_2O_3$; yield 47%; $^1$H NMR (600 MHZ, $CDCl_3$) δ 8.37-8.27 (m, 1H), 8.16-8.08 (m, 1H), 7.40 (t, J=8.0 Hz, 1H), 6.45 (s, 1H), 4.30 (dd, J=12.5, 6.5 Hz, 1H), 1.28 (d, J=6.6 Hz, 6H). $^{13}$C NMR (151 MHz, $CDCl_3$) δ 160.4, 160.4, 154.2, 152.4, 137.5, 137.5, 128.8, 128.8, 124.9, 124.8, 42.7, 22.7.

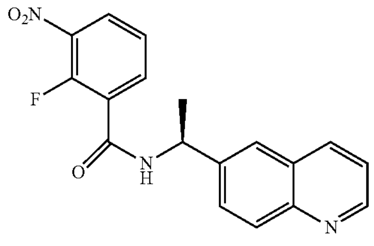 [SMILES: C[C@H](NC(=O)c1cccc([N+](=O)[O-])c1F)c1ccc2ncccc2c1]

(S)-2-fluoro-3-nitro-N-(1-(quinolin-6-yl)ethyl)benzamide

Molecular Formula: $C_{18}H_{14}FN_3O_3$; yield 70%; $^1$H NMR (600 MHz, $CDCl_3$) δ 8.91 (dd, J=4.1, 1.4 Hz, 1H), 8.37-8.33 (m, 1H), 8.18-8.14 (m, 2H), 8.12 (d, J=8.7 Hz, 1H), 7.82 (d, J=1.5 Hz, 1H), 7.74 (dd, J=8.7, 2.0 Hz, 1H), 7.44-7.40 (m, 2H), 7.06-6.99 (m, 1H), 5.53 (d, J=6.9 Hz, 1H), 1.73 (d, J=7.0 Hz, 3H). $^{13}$C NMR (151 MHz, $CDCl_3$) δ 160.6, 154.4, 152.6, 150.7, 148.0, 140.9, 137.7, 137.7, 136.2, 130.5, 129.2, 128.3, 128.0, 125.0, 125.0, 124.8, 124.3, 124.2, 121.7, 50.1, 22.1.

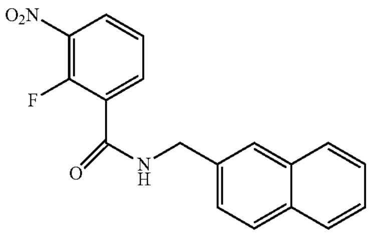 [SMILES: O=C(NCc1ccc2ccccc2c1)c1cccc([N+](=O)[O-])c1F]

2-fluoro-N-(naphthalen-2-ylmethyl)-3-nitrobenzamide

Molecular Formula: $C_{18}H_{13}FN_2O_3$; yield 68%; $^1$H NMR (600 MHz, $CDCl_3$) δ 8.44-8.40 (m, 1H), 8.18-8.14 (m, 1H), 7.88-7.79 (m, 4H), 7.52-7.46 (m, 3H), 7.43 (t, J=8.0 Hz, 1H), 7.01 (s, 1H), 4.85 (d, J=5.6 Hz, 2H). $^{13}$C NMR (151 MHz, $CDCl_3$) δ 161.4, 154.3, 152.6, 137.7, 137.7, 134.8, 133.5, 133.1, 129.2, 129.0, 127.9, 127.9, 126.8, 126.6, 126.3, 125.9, 125.0, 125.0, 124.3, 124.2, 44.8.

Synthesized by Following General Procedure—Step-2

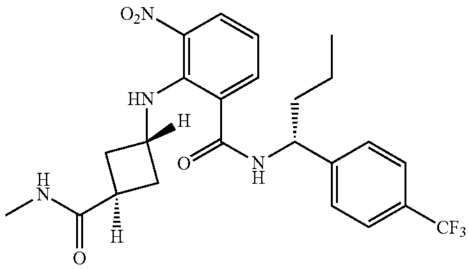 [SMILES: CCC[C@@H](NC(=O)c1cccc([N+](=O)[O-])c1N[C@H]1C[C@H](C(=O)NC)C1)c1ccc(C(F)(F)F)cc1]

2-(((1r,3R)-3-(methylcarbamoyl)cyclobutyl)amino)-3-nitro-N—((R)-1-(4-(trifluoro methyl)phenyl)butyl) benzamide Molecular Formula: $C_{24}H_{27}F_3N_4O_4$; yield 78%; $^1$H NMR (600 MHz, DMSO-$d_6$) δ 9.11 (d, J=7.4 Hz, 1H), 8.23 (d, J=7.0 Hz, 1H), 8.01 (d, J=8.2 Hz, 1H), 7.71 (d, J=7.5 Hz, 2H), 7.61 (d, J=6.1 Hz, 4H), 6.80 (t, J=7.6 Hz, 1H), 5.01 (d, J=7.0 Hz, 1H), 3.96 (dd, J=13.6, 6.7 Hz, 1H), 2.83 (bs, 1H), 2.56 (d, J=3.6 Hz, 3H), 2.34 (bs, 2H), 2.05-1.96 (m, 2H), 1.88 (d, J=8.6 Hz, 1H), 1.71 (bs, 1H), 1.37 (bs, 1H), 1.26 (d, J=22.5 Hz, 1H), 0.91 (t, J=6.9 Hz, 3H). $^{13}$C NMR (151 MHz, DMSO-$d_6$) δ 174.8, 167.6, 148.8, 142.6, 136.1, 135.6, 128.6, 127.8, 125.7, 125.7, 124.8, 116.0, 53.4, 49.7, 38.1, 34.6, 34.5, 33.2, 26.0, 19.7, 14.1.

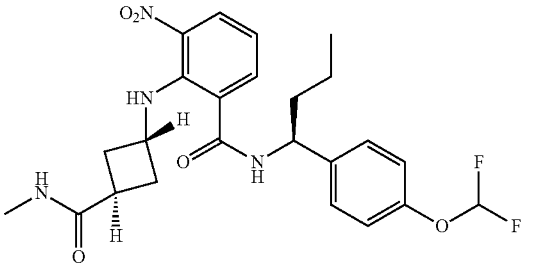 [SMILES: CCC[C@H](NC(=O)c1cccc([N+](=O)[O-])c1N[C@H]1C[C@H](C(=O)NC)C1)c1ccc(OC(F)F)cc1]

N—((S)-1-(4-(difluoromethoxy)phenyl)butyl)-2-(((1r,3S)-3-(methylcarbamoyl)cyclobutyl)amino)-3-nitrobenzamide Molecular Formula: $C_{24}H_{28}F_2N_4O_5$; yield 67%; $^1H$ NMR (600 MHz, $CDCl_3$) δ 9.26 (bs, 1H), 8.62 (bs, 1H), 8.00 (d, J=7.6 Hz, 1H), 7.89 (d, J=7.7 Hz, 1H), 7.70 (s, 1H), 7.63 (t, J=7.0 Hz, 1H), 7.41 (d, J=6.9 Hz, 1H), 7.35 (d, J=8.0 Hz, 2H), 7.27 (d, J=6.8 Hz, 1H), 7.03 (d, J=7.9 Hz, 2H), 6.40 (d, J=73.8 Hz, 1H), 5.12 (dd, J=14.9, 7.4 Hz, 2H), 2.61 (d, J=2.5 Hz, 3H), 2.20 (bs, 1H), 2.04-1.94 (m, 3H), 1.83-1.81 (m, 3H), 1.42-1.41 (d, J=7.6 Hz, 1H), 1.36-1.26 (m, 1H), 0.93 (t, J=7.3 Hz, 3H). $^{13}C$ NMR (151 MHZ, $CDCl_3$) δ 174.4, 167.0, 166.9, 150.5, 142.2, 139.4, 128.7, 128.3, 126.3, 126.2, 119.9, 117.7, 117.1, 115.9, 114.2, 53.5, 53.4, 53.3, 51.9, 48.6, 38.2, 35.4, 35.4, 30.9, 30.7, 19.7, 13.8.

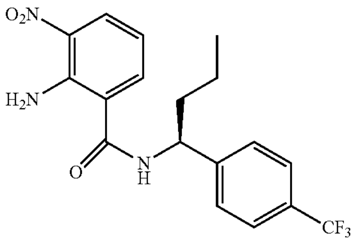 [SMILES: CCC[C@H](NC(=O)c1cccc([N+](=O)[O-])c1N)c1ccc(C(F)(F)F)cc1]

(S)-2-amino-3-nitro-N-(1-(4-(trifluoromethyl)phenyl)butyl)benzamide

Molecular Formula: $C_{18}H_{18}F_3N_3O_3$; yield 50%; $^1H$ NMR (600 MHZ, $CDCl_3$) δ 8.30 (dd, J=8.5, 1.4 Hz, 1H), 8.11 (s, 2H), 7.63 (d, J=8.3 Hz, 3H), 7.46 (d, J=8.1 Hz, 2H), 6.64 (dd, J=8.5, 7.6 Hz, 1H), 6.25 (d, J=7.3 Hz, 1H), 5.14 (q, J=7.4 Hz, 1H), 1.94-1.83 (m, 2H), 1.47-1.40 (m, 1H), 1.40-1.32 (m, 1H), 0.98 (t, J=7.4 Hz, 3H). $^{13}C$ NMR (151 MHz, $CDCl_3$) δ 167.6, 146.3, 146.2, 134.1, 133.4, 130.4, 130.1, 129.9, 126.9, 126.0, 126.0, 125.1, 123.2, 119.9, 114.1, 53.7, 38.4, 19.6, 13.9.

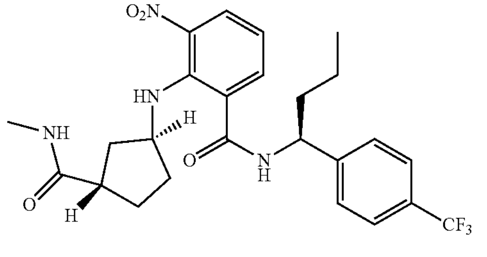 [SMILES: CCC[C@H](NC(=O)c1cccc([N+](=O)[O-])c1N[C@H]1CC[C@H](C(=O)NC)C1)c1ccc(C(F)(F)F)cc1]

2-(((1S,3S)-3-(methylcarbamoyl)cyclopentyl)amino)-3-nitro-N—((S)-1-(4-(trifluoromethyl)phenyl)butyl)benzamide Molecular Formula: $C_{25}H_{29}F_3N_4O_4$; yield 98%; $^1H$ NMR (600 MHz, $CDCl_3$) δ 8.13 (dd, J=8.4, 1.6 Hz, 1H), 7.80 (dd, J=7.5, 1.6 Hz, 1H), 7.64 (d, J=8.1 Hz, 2H), 7.48 (d, J=8.1 Hz, 2H), 7.19 (dd, J=17.0, 8.7 Hz, 2H), 6.95-6.91 (m, 1H), 5.43 (d, J=2.5 Hz, 1H), 5.20 (q, J=7.6 Hz, 1H), 3.83 (dt, J=14.4, 7.2 Hz, 1H), 2.78 (d, J=4.8 Hz, 3H), 2.65-2.55 (m, 1H), 2.09-1.99 (m, 1H), 2.00-1.80 (m, 3H), 1.66 (dt, J=22.7, 15.2 Hz, 3H), 1.43-1.24 (m, 4H), 0.96 (t, J=7.4 Hz, 3H). $^{13}C$ NMR (151 MHZ, $CDCl_3$) δ 176.0, 167.4, 146.1, 142.7, 137.8, 136.2, 129.8, 129.6, 128.5, 127.3, 127.2, 125.6, 125.6, 124.9, 123.1, 117.7, 117.5, 58.1, 53.6, 49.4, 49.3, 49.1, 49.0, 42.9, 37.7, 37.1, 33.1, 28.0, 19.5, 13.6.

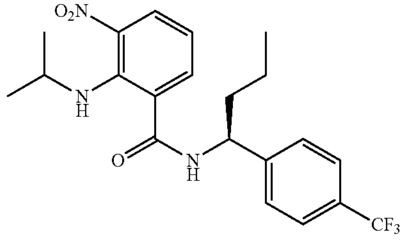 [SMILES: CCC[C@H](NC(=O)c1cccc([N+](=O)[O-])c1NC(C)C)c1ccc(C(F)(F)F)cc1]

(S)-2-(isopropylamino)-3-nitro-N-(1-(4-(trifluoromethyl)phenyl)butyl)benzamide

Molecular Formula: $C_{21}H_{24}F_3N_3O_3$; yield 90%; $^1H$ NMR (600 MHZ, $CDCl_3$) δ 8.13 (dd, J=8.3, 1.7 Hz, 1H), 7.90 (dd, J=7.5, 1.7 Hz, 1H), 7.62 (d, J=8.1 Hz, 3H), 7.48 (d, J=8.1 Hz, 2H), 6.98 (t, J=7.9 Hz, 1H), 5.19 (q, J=7.6 Hz, 1H), 3.34 (dt, J=12.6, 6.3 Hz, 1H), 1.98-1.90 (m, 1H), 1.88-1.80 (m, 1H), 1.41-1.35 (m, 1H), 1.34-1.27 (m, 1H), 1.03 (d, J=6.3 Hz, 3H), 0.96 (t, J=7.4 Hz, 3H), 0.85 (d, J=6.3 Hz, 3H). $^{13}C$ NMR (151 MHZ, $CDCl_3$) δ 166.1, 146.0, 142.8, 140.9, 137.0, 130.4, 130.1, 129.9, 129.7, 129.0, 128.6, 127.4, 125.9, 125.9, 125.9, 125.9, 125.0, 123.2, 120.0, 53.7, 50.9, 38.0, 23.2, 23.1, 19.6, 13.9.

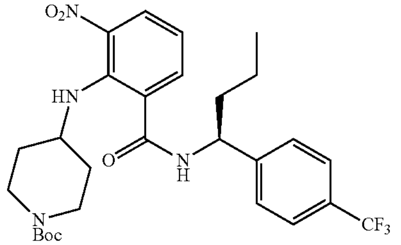 [SMILES: CCC[C@H](NC(=O)c1cccc([N+](=O)[O-])c1NC1CCN(C(=O)OC(C)(C)C)CC1)c1ccc(C(F)(F)F)cc1]

tert-butyl(S)-4-((2-nitro-6-((1-(4-(trifluoromethyl)phenyl)butyl)carbamoyl)phenyl)amino)piperidine-1-carboxylate Molecular Formula: $C_{28}H_{35}F_3N_4O_5$; yield 95%; $^1H$ NMR (600 MHz, $CDCl_3$) δ 8.13 (dd, J=8.3, 1.7 Hz, 1H), 7.87 (dd, J=7.5, 1.7 Hz, 1H), 7.64 (d, J=8.1 Hz, 2H), 7.50 (d, J=8.1 Hz, 2H), 7.41 (d, J=8.2 Hz, 1H), 7.03-6.97 (m, 1H), 5.22 (dd, J=15.0, 7.4 Hz, 1H), 3.84 (d, J=62.1 Hz, 2H), 3.12-3.03 (m, 1H), 2.52 (t, J=12.0 Hz, 1H), 2.36-2.28 (m, 1H), 1.91

(tdd, J=13.3, 5.9, 3.8 Hz, 1H), 1.88-1.80 (m, 1H), 1.71 (d, J=11.0 Hz, 1H), 1.41 (s, 9H), 1.39-1.35 (m, 1H), 1.35-1.28 (m, 2H), 1.20-1.09 (m, 2H), 0.95 (t, J=7.4 Hz, 3H). $^{13}$C NMR (151 MHz, $CDCl_3$) δ 166.2, 154.5, 145.9, 142.0, 140.6, 136.9, 128.8, 128.7, 127.4, 126.1, 126.1, 120.1, 79.9, 60.5, 55.8, 53.6, 38.1, 32.7, 28.5, 19.7, 13.9.

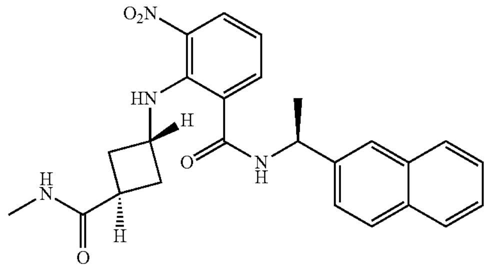 [SMILES: CNC(=O)[C@H]1C[C@H](Nc2c(C(=O)N[C@@H](C)c3ccc4ccccc4c3)cccc2[N+](=O)[O-])C1]

2-(((1r,3S)-3-(methylcarbamoyl)cyclobutyl)amino)-N—((S)-1-(naphthalen-2-yl)ethyl)-3-nitrobenzamide Molecular Formula: $C_{25}H_{26}N_4O_4$; yield 64%; $^1$H NMR (600 MHZ, DMSO-$d_6$) δ 9.15 (d, J=7.7 Hz, 1H), 8.30 (d, J=7.4 Hz, 1H), 8.01 (dd, J=8.4, 1.3 Hz, 1H), 7.96-7.87 (m, 4H), 7.68 (d, J=4.5 Hz, 1H), 7.64-7.56 (m, 2H), 7.54-7.45 (m, 2H), 6.79 (t, J=7.9 Hz, 1H), 5.32-5.23 (m, 1H), 4.13-4.04 (m, 1H), 2.86-2.78 (m, 1H), 2.56 (d, J=4.6 Hz, 3H), 2.47-2.35 (m, 2H), 2.06 (ddd, J=24.7, 17.8, 10.2 Hz, 2H), 1.58 (d, J=7.0 Hz, 3H). $^{13}$C NMR (151 MHZ, DMSO-$d_6$) δ 174.5, 174.1, 166.8, 142.2, 141.9, 135.4, 135.3, 132.9, 132.1, 128.0, 128.0, 127.8, 127.5, 126.1, 125.7, 124.9, 124.8, 124.2, 115.5, 49.2, 48.8, 34.5, 34.2, 32.8, 25.6, 21.8.

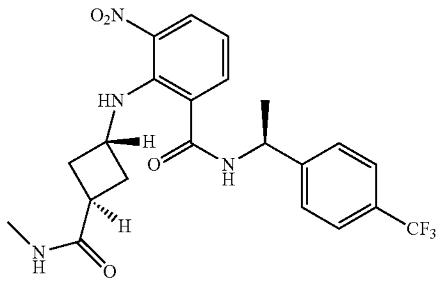 [SMILES: CNC(=O)[C@H]1C[C@H](Nc2c(C(=O)N[C@@H](C)c3ccc(C(F)(F)F)cc3)cccc2[N+](=O)[O-])C1]

2-(((1r,3S)-3-(methylcarbamoyl)cyclobutyl)amino)-3-nitro-N—((S)-1-(4-(trifluoromethyl)phenyl)ethyl) benzamide Molecular Formula: $C_{22}H_{23}F_3N_4O_4$; yield 92%; $^1$H NMR (600 MHz, DMSO-$d_6$) δ 9.15 (d, J=7.5 Hz, 1H), 8.26 (d, J=7.5 Hz, 1H), 8.03 (dd, J=8.4, 1.3 Hz, 1H), 7.70 (dd, J=21.3, 6.3 Hz, 3H), 7.62 (dd, J=12.7, 4.8 Hz, 3H), 6.81-6.77 (m, 1H), 5.17 (p, J=6.9 Hz, 1H), 4.10-4.02 (m, 1H), 2.83 (dt, J=13.6, 4.5 Hz, 1H), 2.57 (d, J=4.6 Hz, 3H), 2.44-2.34 (m, 2H), 2.10-2.01 (m, 2H), 1.50 (d, J=7.1 Hz, 3H). $^{13}$C NMR (151 MHZ, DMSO-$d_6$) δ 174.5, 166.9, 149.3, 142.1, 135.5, 135.3, 128.0, 127.5, 127.3, 126.9, 125.3, 125.3, 125.3, 124.7, 123.4, 115.5, 115.5, 49.3, 48.5, 34.4, 34.2, 32.7, 25.5, 21.8.

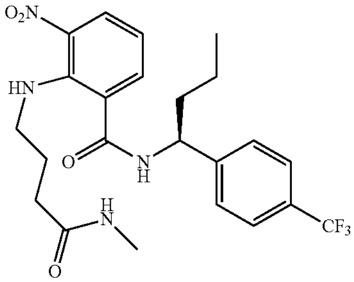 [SMILES: CCC[C@H](NC(=O)c1cccc([N+](=O)[O-])c1NCCCC(=O)NC)c1ccc(C(F)(F)F)cc1]

(S)-2-((4-(methylamino)-4-oxobutyl)amino)-3-nitro-N-(1-(4-(trifluoromethyl)phenyl)butyl)benzamide Molecular Formula: $C_{23}H_{27}F_3N_4O_4$; yield 80%; $^1$H NMR (600 MHz, $CD_3OD$) δ 8.08 (d, J=8.5 Hz, 1H), 7.57 (d, J=7.7 Hz, 2H), 7.48 (d, J=7.6 Hz, 2H), 7.44-7.40 (m, 1H), 6.67 (t, J=7.9 Hz, 1H), 4.99-4.95 (m, 1H), 2.94-2.88 (m, 1H), 2.86-2.80 (m, 1H), 2.56 (s, 3H), 1.95-1.87 (m, 2H), 1.85-1.80 (m, 1H), 1.74-1.67 (m, 1H), 1.60 (dd, J=9.5, 5.2 Hz, 2H), 1.44-1.37 (m, 1H), 1.28 (d, J=6.4 Hz, 1H), 0.90 (t, J=7.3 Hz, 3H). $^{13}$C NMR (151 MHZ, $CD_3OD$) δ 175.3, 170.8, 148.6, 144.9, 137.3, 136.7, 130.6, 130.4, 129.4, 128.7, 127.0, 126.6, 126.6, 124.8, 116.6, 55.1, 46.7, 39.0, 33.9, 27.3, 26.3, 20.9, 14.0.

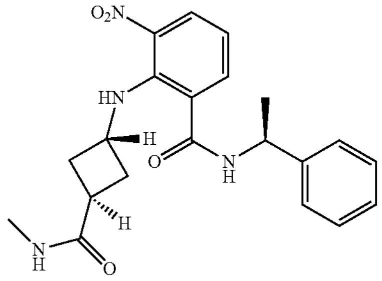 [SMILES: CNC(=O)[C@H]1C[C@H](Nc2c(C(=O)N[C@@H](C)c3ccccc3)cccc2[N+](=O)[O-])C1]

2-(((1r,3S)-3-(methylcarbamoyl)cyclobutyl)amino)-3-nitro-N—((S)-1-phenylethyl)benzamide Molecular Formula: $C_{12}H_{24}N_4O_4$; yield 40%; $^1$H NMR (600 MHz, DMSO-$d_6$) δ 9.05 (d, J=7.8 Hz, 1H), 8.27 (d, J=7.4 Hz, 1H), 8.01 (d, J=8.3 Hz, 1H), 7.68 (d, J=4.3 Hz, 1H), 7.59 (d, J=7.2 Hz, 1H), 7.41 (d, J=7.5 Hz, 2H), 7.35 (t, J=7.6 Hz, 2H), 7.24 (d, J=7.2 Hz, 1H), 6.78 (t, J=7.9 Hz, 1H), 5.15-5.07 (m, 1H), 4.05 (dd, J=14.4, 7.2 Hz, 1H), 2.87-2.79 (m, 1H), 2.57 (d, J=4.6 Hz, 3H), 2.47-2.34 (m, 2H), 2.05 (ddd, J=20.9, 17.7, 10.3 Hz, 2H), 1.48 (d, J=7.0 Hz, 3H). $^{13}$C NMR (151 MHZ, DMSO-$d_6$) δ 174.4, 166.7, 144.5, 142.1, 135.3, 135.3, 128.3, 127.9, 126.7, 126.0, 124.9, 115.4, 49.2, 48.5, 34.4, 34.1, 32.8, 25.6, 22.0.

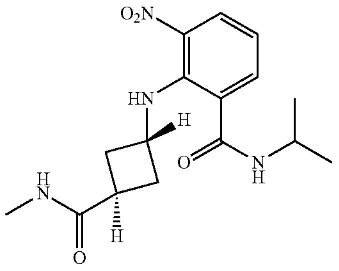 [SMILES: CNC(=O)[C@H]1C[C@H](Nc2c(C(=O)NC(C)C)cccc2[N+](=O)[O-])C1]

N-isopropyl-2-(((1r,3r)-3-(methylcarbamoyl)cyclobutyl)amino)-3-nitrobenzamide

Molecular Formula: $C_{16}H_{22}N_4O_4$; yield 100%; $^1$H NMR (600 MHZ, $CD_3OD$) δ 8.50 (d, J=7.3 Hz, 1H), 8.15 (dd, J=8.5, 1.4 Hz, 2H), 7.75 (s, 1H), 7.50 (dd, J=7.3, 1.3 Hz, 2H), 6.80-6.74 (m, 2H), 4.27 (p, J=7.1 Hz, 2H), 4.16 (dq, J=13.1, 6.5 Hz, 2H), 3.00-2.94 (m, 2H), 2.71 (d, J=4.7 Hz, 6H), 2.66-2.59 (m, 4H), 2.20 (ddd, J=10.7, 8.6, 5.8 Hz, 4H), 1.27 (d, J=6.6 Hz, 12H). $^{13}$C NMR (151 MHz, $CD_3OD$) δ 178.0, 170.1, 143.7, 137.2, 129.2, 127.5, 117.0, 50.9, 43.2, 35.9, 34.8, 26.4, 22.4.

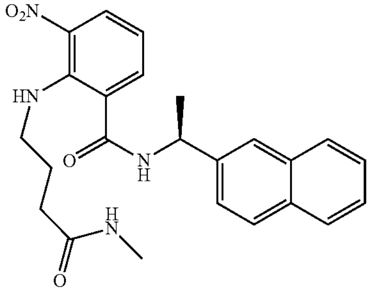 [SMILES: CNC(=O)CCCNc1c(C(=O)N[C@@H](C)c2ccc3ccccc3c2)cccc1[N+](=O)[O-]]

(S)-2-((4-(methylamino)-4-oxobutyl)amino)-N-(1-(naphthalen-2-yl)ethyl)-3-nitro benzamide Molecular Formula: $C_{24}H_{26}N_4O_4$; yield 84%; $^1$H NMR (600 MHz, DMSO-$d_6$) δ 9.18 (s, 1H), 8.07 (s, 2H), 7.90 (s, 4H), 7.62 (d, J=24.8 Hz, 3H), 7.50 (bs, 2H), 6.77 (bs, 1H), 5.27 (bs, 1H), 2.99 (bs, 2H), 2.53 (s, 3H), 1.98 (bs, 2H), 1.67 (bs, 2H), 1.56 (s, 3H). $^{13}$C NMR (151 MHZ, DMSO-$d_6$) δ 171.5, 167.1, 143.4, 141.7, 135.9, 134.7, 132.9, 132.1, 128.0, 127.9, 127.7, 127.5, 126.1, 125.7, 125.2, 124.9, 124.3, 115.0, 48.8, 45.0, 32.3, 25.7, 25.4, 21.9.

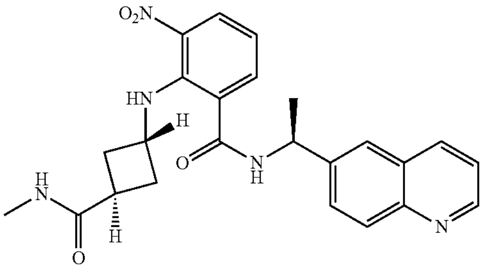 [SMILES: CNC(=O)[C@H]1C[C@H](Nc2c(C(=O)N[C@@H](C)c3ccc4ncccc4c3)cccc2[N+](=O)[O-])C1]

2-(((1r,3S)-3-(methylcarbamoyl)cyclobutyl)amino)-3-nitro-N—((S)-1-(quinolin-6-yl)ethyl)benzamide Molecular Formula: $C_{24}H_{25}N_5O_4$; yield 79%; $^1$H NMR (600 MHZ, DMSO-$d_6$) δ 9.20 (d, J=7.6 Hz, 1H), 8.88 (d, J=2.8 Hz, 1H), 8.39 (d, J=8.1 Hz, 1H), 8.29 (d, J=7.4 Hz, 1H), 8.03 (d, J=8.4 Hz, 2H), 7.96 (s, 1H), 7.85 (d, J=8.8 Hz, 1H), 7.69 (d, J=4.3 Hz, 1H), 7.66 (d, J=7.0 Hz, 1H), 7.53 (dd, J=8.2, 4.1 Hz, 1H), 6.79 (t, J=7.9 Hz, 1H), 5.35-5.27 (m, 1H), 4.09 (dd, J=14.5, 7.3 Hz, 1H), 2.83 (dd, J=9.0, 4.7 Hz, 1H), 2.57 (d, J=4.5 Hz, 3H), 2.44-2.37 (m, 2H), 2.10-2.02 (m, 2H), 1.59 (d, J=7.0 Hz, 3H). $^{13}$C NMR (151 MHZ, $CDCl_3$) δ 174.1, 167.7, 154.3, 150.3, 147.4, 144.9, 144.3, 141.7, 136.7, 134.2, 132.2, 129.9, 128.7, 128.4, 128.3, 125.3, 124.5, 123.2, 122.7, 122.3, 121.6, 51.7, 49.9, 33.7, 29.8, 26.5, 22.1.

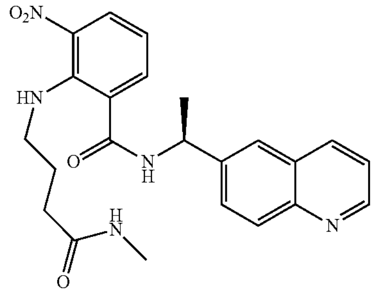 [SMILES: CNC(=O)CCCNc1c(C(=O)N[C@@H](C)c2ccc3ncccc3c2)cccc1[N+](=O)[O-]]

(S)-2-((4-(methylamino)-4-oxobutyl)amino)-3-nitro-N-(1-(quinolin-6-yl)ethyl)benzamide Molecular Formula: $C_{23}H_{25}N_5O_4$; yield 81%; $^1$H NMR (600 MHz, DMSO-$d_6$) δ 9.22 (d, J=7.8 Hz, 1H), 8.88 (dd, J=4.0, 1.4 Hz, 1H), 8.39 (d, J=8.1 Hz, 1H), 8.07 (td, J=8.0, 3.2 Hz, 2H), 8.03 (d, J=8.7 Hz, 1H), 7.95 (bs, 1H), 7.84 (dd, J=8.7, 1.7 Hz, 1H), 7.70-7.63 (m, 2H), 7.53 (dd, J=8.3, 4.2 Hz, 1H), 6.78 (t, J=7.9 Hz, 1H), 5.30 (d, J=7.1 Hz, 1H), 3.03-2.96 (m, 2H), 2.53 (d, J=4.6 Hz, 3H), 1.98 (t, J=7.4 Hz, 2H), 1.67 (d, J=14.2 Hz, 2H), 1.57 (d, J=7.0 Hz, 3H). $^{13}$C NMR (151 MHz, DMSO-$d_6$) δ 171.5, 167.2, 150.2, 147.0, 143.4, 142.3, 135.9, 134.7, 129.1, 128.4, 127.9, 127.7, 125.1, 124.5, 121.6, 115.0, 48.6, 45.0, 32.3, 25.6, 25.4, 21.8.

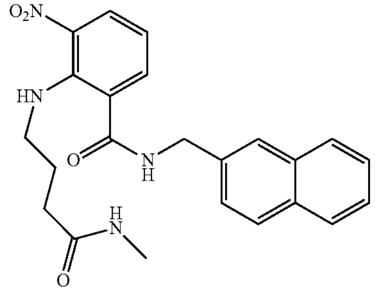 [SMILES: CNC(=O)CCCNc1c(C(=O)NCc2ccc3ccccc3c2)cccc1[N+](=O)[O-]]

2-((4-(methylamino)-4-oxobutyl)amino)-N-(naphthalen-2-ylmethyl)-3-nitrobenzamide Molecular Formula: $C_{23}H_{24}N_4O_4$; yield 80%; $^1$H NMR (600 MHZ, DMSO-$d_6$) δ 9.25 (t, J=5.9 Hz, 1H), 8.15 (t, J=5.0 Hz, 1H), 8.05 (dd, J=8.4, 1.5 Hz, 1H), 7.91 (dd, J=7.8, 5.5 Hz, 3H), 7.84 (s, 1H), 7.69 (dd, J=7.3, 1.5 Hz, 2H), 7.52-7.47 (m, 3H), 6.77 (dd, J=8.2, 7.6 Hz, 1H), 4.61 (d, J=5.9 Hz, 2H), 3.01 (dd, J=12.1, 6.8 Hz, 2H), 2.53 (d, J=4.6 Hz, 3H), 2.02 (t, J=7.4 Hz, 2H), 1.71 (m, 2H). $^{13}$C NMR (151 MHz, DMSO-$d_6$) δ 171.6, 167.9, 143.5, 136.5, 135.5, 135.0, 132.9, 132.1, 128.1, 128.0, 127.6, 127.5, 126.2, 126.0, 125.7, 125.7, 124.6, 115.0, 45.1, 42.9, 32.4, 25.7, 25.4.

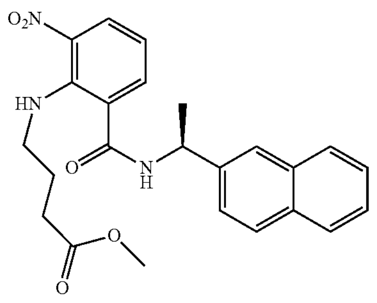 [SMILES: COC(=O)CCCNc1c(C(=O)N[C@@H](C)c2ccc3ccccc3c2)cccc1[N+](=O)[O-]]

methyl(S)-4-((2-((1-(naphthalen-2-yl)ethyl)carbamoyl)-6-nitrophenyl)amino) butanoate Molecular Formula: $C_{24}H_{25}N_3O_5$; yield 83%; $^1$H NMR (600 MHz, DMSO-$d_6$) δ 9.19 (d, J=8.0 Hz, 1H), 8.07 (dd, J=8.4, 1.2 Hz, 1H), 7.99 (t, J=5.2 Hz, 1H), 7.94-7.87 (m, 4H), 7.64 (dd, J=7.2, 1.0 Hz, 1H), 7.59 (dd, J=8.5, 1.0 Hz, 1H), 7.54-7.45 (m, 2H), 6.82-6.75 (m, 1H), 5.27 (s, 1H), 3.51 (s, 3H), 3.00-2.89 (m, 2H), 2.09 (t, J=7.4 Hz, 2H), 1.68-1.61 (m, 2H), 1.55 (d, J=7.1 Hz, 3H). $^{13}$C NMR (151 MHz, DMSO-$d_6$) δ 172.0, 166.4, 142.7, 141.0, 135.3, 134.3, 132.3, 131.5, 127.4, 127.3, 127.1, 126.9, 125.6, 125.1, 124.8, 124.3, 123.8, 114.6, 50.7, 48.2, 44.0, 29.8, 24.3, 21.3.

Synthesized by Following General Procedure—Step-3

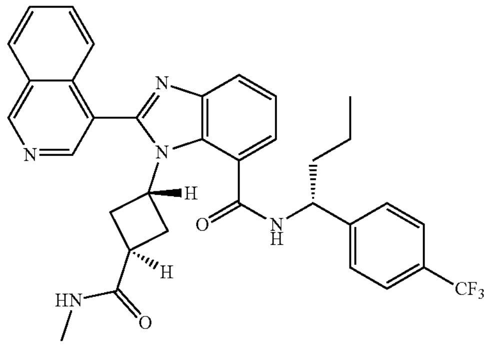 [SMILES: CCC[C@@H](NC(=O)c1cccc2nc(-c3cncc4ccccc34)n([C@H]3C[C@H](C(=O)NC)C3)c12)c1ccc(C(F)(F)F)cc1]

2-(isoquinolin-4-yl)-1-((1r,3R)-3-(methylcarbamoyl)cyclobutyl)-N—((R)-1-(4-(trifluoromethyl)phenyl)butyl)-1H-benzo[d]imidazole-7-carboxamide Molecular Formula: $C_{34}H_{32}F_3N_5O_2$; yield 63%; $^1$H NMR (600 MHZ, $CDCl_3$) δ 9.34 (bs, 1H), 8.70 (bs, 1H), 8.07 (d, J=7.9 Hz, 1H), 7.97 (d, J=7.8 Hz, 2H), 7.76 (d, J=7.4 Hz, 1H), 7.70 (s, 1H), 7.62 (d, J=8.0 Hz, 2H), 7.55 (d, J=8.0 Hz, 2H), 7.48 (d, J=7.3 Hz, 1H), 7.34 (t, J=7.7 Hz, 1H), 6.67 (d, J=6.5 Hz, 1H), 5.39 (bs, 1H), 5.31-5.24 (m, 1H), 5.16 (bs, 1H), 2.66 (d, J=3.8 Hz, 3H), 2.27 (bs, 1H), 2.14-1.98 (m, 4H), 1.94-1.84 (m, 2H), 1.52-1.45 (m, 1H), 1.39 (d, J=7.0 Hz, 1H), 1.00 (t, J=7.3 Hz, 3H). $^{13}$C NMR (151 MHZ, $CD_3OD$) δ 176.9, 170.1, 155.6, 148.9, 148.7, 145.1, 144.7, 135.5, 134.0, 133.1, 129.8, 129.8, 128.7, 126.5, 126.5, 125.1, 124.2, 123.7, 55.2, 53.2, 39.3, 34.4, 26.3, 20.9, 14.1. HRMS (HESI-TOF) m/z calcd for $(M+H)^+$ 600.2586, found 600.2564.

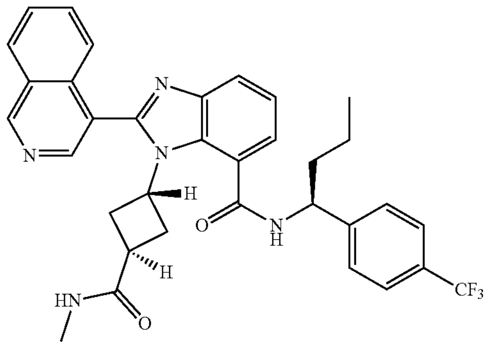 [SMILES: CCC[C@H](NC(=O)c1cccc2nc(-c3cncc4ccccc34)n([C@H]3C[C@H](C(=O)NC)C3)c12)c1ccc(C(F)(F)F)cc1]

2-(isoquinolin-4-yl)-1-((1r,3S)-3-(methylcarbamoyl)cyclobutyl)-N—((S)-1-(4-(trifluoromethyl)phenyl)butyl)-1H-benzo[d]imidazole-7-carboxamide Molecular Formula: $C_{34}H_{32}F_3N_5O_2$; yield 66%; $^1$H NMR (600 MHZ, $CDCl_3$) δ 9.31 (bs, 1H), 8.65 (bs, 1H), 8.05 (d, J=8.1 Hz, 1H), 7.95 (d, J=8.0 Hz, 1H), 7.74 (t, J=7.5 Hz, 1H), 7.68 (t, J=7.5 Hz, 1H), 7.60 (d, J=8.1 Hz, 2H), 7.54 (d, J=8.1 Hz, 2H), 7.47 (d, J=7.4 Hz, 1H), 7.31 (t, J=7.8 Hz, 1H), 6.79 (d, J=7.0 Hz, 1H), 5.37 (bs, 1H), 5.26 (td, J=13.7, 5.8 Hz, 2H), 2.65 (d, J=4.5 Hz, 3H), 2.25 (s, 1H), 2.11-2.00 (m, 4H), 1.89 (ddd, J=20.5, 11.7, 6.6 Hz, 2H), 1.50-1.43 (m, 1H), 1.42-1.34 (m, 1H), 0.99 (t, J=7.3 Hz, 3H). $^{13}$C NMR (151 MHZ, $CD_3OD$) δ 176.9, 170.1, 155.6, 152.2, 148.9, 145.1, 144.7, 135.5, 134.0, 133.1, 130.5, 130.3, 128.7, 126.5, 126.5, 125.1, 124.8, 124.2, 123.7, 123.1, 55.2, 53.2, 39.4, 34.4, 26.3, 20.9, 14.1. HRMS (HESI-TOF) m/z calcd for $(M+H)^+$ 600.2586, found 600.2569.

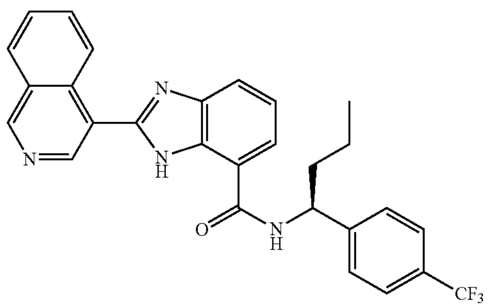 [SMILES: CCC[C@H](NC(=O)c1cccc2nc(-c3cncc4ccccc34)[nH]c12)c1ccc(C(F)(F)F)cc1]

(S)-2-(isoquinolin-4-yl)-N-(1-(4-(trifluoromethyl)phenyl)butyl)-1H-benzo[d]imidazole-7-carboxamide Molecular Formula: $C_{28}H_{23}F_3N_4O$; yield 58%; $^1$H NMR (600 MHZ, $CDCl_3$) δ 12.29 (s, 1H), 10.65 (s, 1H), 9.32 (s, 1H), 9.08 (d, J=17.1 Hz, 2H), 8.18-8.06 (m, 2H), 7.77 (d, J=6.8 Hz, 2H), 7.62 (d, J=5.0 Hz, 1H), 7.46 (t, J=14.5 Hz, 4H), 7.33 (t, J=7.7 Hz, 1H), 5.34 (d, J=6.3 Hz, 1H), 1.98-1.92 (m, 1H), 1.87-1.83 (m, 1H), 1.47-1.37 (m, 2H), 0.88 (d, J=5.5 Hz, 3H). $^{13}$C NMR (151 MHz, $CDCl_3$) δ

165.8, 154.3, 149.6, 147.5, 143.4, 142.0, 134.7, 133.6, 132.1, 128.8, 128.5, 128.4, 126.9, 125.5, 125.3, 125.1, 124.1, 123.5, 123.3, 122.6, 121.7, 121.7, 115.3, 53.7, 39.4, 19.5, 14.0. HRMS (HESI-TOF) m/z calcd for $(M+H)^+$ 489.1890, found 489.1882.

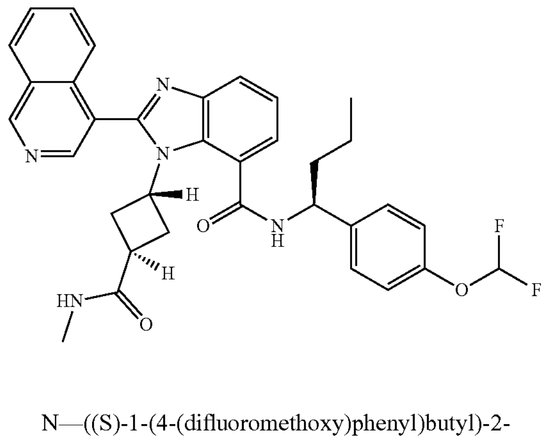

N—((S)-1-(4-(difluoromethoxy)phenyl)butyl)-2-(isoquinolin-4-yl)-1-((1r,3S)-3-(methylcarbamoyl)cyclobutyl)-1H-benzo[d]imidazole-7-carboxamide Molecular Formula: $C_{34}H_{33}F_2N_5O_3$; yield 60%; $^1H$ NMR (600 MHZ, $CD_3OD$) δ 9.46 (bs, 1H), 8.76 (bs, 1H), 8.29 (d, J=8.2 Hz, 1H), 8.04 (d, J=21.8 Hz, 1H), 7.93 (dd, J=17.0, 7.7 Hz, 2H), 7.85 (t, J=7.6 Hz, 1H), 7.58 (bs, 1H), 7.50 (d, J=8.4 Hz, 2H), 7.45 (t, J=7.8 Hz, 1H), 7.13 (d, J=6.8 Hz, 2H), 6.81 (t, J=74.3 Hz, 1H), 5.35 (s, 1H), 5.16 (t, J=7.6 Hz, 1H), 2.60 (bs, 3H), 2.41 (bs, 1H), 2.17-1.98 (m, 4H), 1.89-1.82 (m, 1H), 1.76 (d, J=48.2 Hz, 1H), 1.52 (bs, 1H), 1.41 (bs, 1H), 1.02 (t, J=7.3 Hz, 3H). $^{13}C$ NMR (151 MHZ, $CD_3OD$) δ 176.8, 169.7, 152.1, 134.6, 130.2, 130.1, 129.7, 125.5, 124.6, 124.2, 122.5, 120.2, 119.6, 117.9, 116.2, 54.9, 53.5, 34.4, 26.4, 21.0, 14.1. HRMS (HESI-TOF) m/z calcd for $(M+H)^+$ 598.2630, found 598.2613.

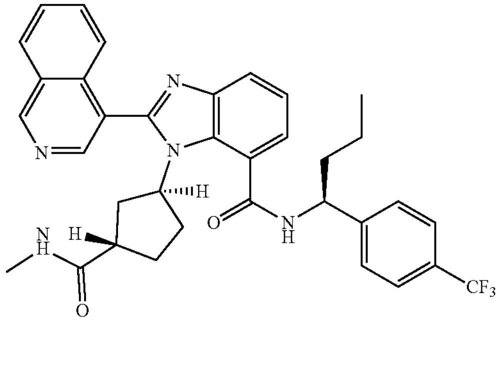 [SMILES: CCC[C@H](NC(=O)c1cccc2nc(-c3cncc4ccccc34)n([C@H]3CC[C@H](C(=O)NC)C3)c12)c1ccc(C(F)(F)F)cc1]

2-(isoquinolin-4-yl)-1-((1S,3S)-3-(methylcarbamoyl)cyclopentyl)-N—((S)-1-(4-(trifluoromethyl)phenyl)butyl)-1H-benzo[d]imidazole-7-carboxamide Molecular Formula: $C_{34}H_{33}F_2N_5O_3$; yield 75%; $^1H$ NMR (600 MHz, $CDCl_3$) δ 9.39 (s, 1H), 8.63 (s, 1H), 8.12-8.06 (m, 1H), 7.92 (d, J=7.8 Hz, 1H), 7.72-7.66 (m, 2H), 7.63 (d, J=8.0 Hz, 2H), 7.54 (dd, J=18.1, 8.2 Hz, 3H), 7.39-7.31 (m, 2H), 6.57 (d, J=4.4 Hz, 1H), 5.27 (dd, J=15.3, 7.7 Hz, 1H), 5.11-4.96 (m, 1H), 2.64 (d, J=4.5 Hz, 3H), 2.21 (s, 1H), 1.96 (dd, J=30.2, 12.5 Hz, 2H), 1.87 (dd, J=26.5, 9.9 Hz, 4H), 1.60 (s, 1H), 1.53-1.45 (m, 1H), 1.39 (dd, J=21.5, 15.3 Hz, 1H), 1.34-1.26 (m, 1H), 1.00 (t, J=7.3 Hz, 3H). $^{13}C$ NMR (151 MHZ, $CDCl_3$) δ 174.9, 168.5, 154.4, 150.9, 146.6, 144.4, 144.2, 135.2, 132.0, 131.7, 130.0, 129.8, 128.4, 128.2, 127.1, 126.0, 125.9, 125.9, 125.9, 125.0, 124.7, 123.2, 123.1, 122.7, 122.5, 122.1, 58.2, 53.9, 43.5, 38.5, 29.1, 26.3, 19.7, 13.9. HRMS (HESI-TOF) m/z calcd for $(M+H)^+$ 614.2743, found 614.2726.

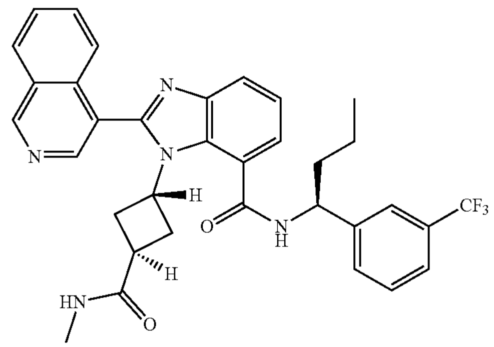 [SMILES: CCC[C@H](NC(=O)c1cccc2nc(-c3cncc4ccccc34)n([C@H]3C[C@H](C(=O)NC)C3)c12)c1cccc(C(F)(F)F)c1]

2-(isoquinolin-4-yl)-1-((1r,3S)-3-(methylcarbamoyl)cyclobutyl)-N—((S)-1-(3-(trifluoromethyl)phenyl)butyl)-1H-benzo[d]imidazole-7-carboxamide Molecular Formula: $C_{34}H_{32}F_3N_5O_2$; yield 60%; $^1H$ NMR (600 MHZ, $CD_3OD$) δ 9.42 (bs, 1H), 8.72 (bs, 1H), 8.25 (d, J=8.3 Hz, 1H), 8.03 (d, J=8.1 Hz, 1H), 7.90 (d, J=7.4 Hz, 2H), 7.79 (dd, J=14.8, 6.9 Hz, 2H), 7.72 (d, J=3.9 Hz, 1H), 7.60-7.51 (m, 3H), 7.45-7.39 (m, 1H), 5.36 (d, J=11.0 Hz, 1H), 5.21 (t, J=7.5 Hz, 1H), 2.56 (bs, 3H), 2.39 (bs, 1H), 2.20-1.95 (m, 4H), 1.85 (ddd, J=9.7, 6.9, 3.4 Hz, 1H), 1.73 (bs, 1H), 1.52 (bs, 1H), 1.39 (d, J=13.6 Hz, 1H), 1.00 (t, J=7.3 Hz, 3H). $^{13}C$ NMR (151 MHZ, $CD_3OD$) δ 176.8, 170.0, 155.5, 152.1, 145.8, 145.0, 144.6, 135.4, 134.0, 133.0, 132.0, 131.9, 131.7, 130.4, 128.4, 126.6, 125.2, 125.1, 125.0, 124.9, 124.8, 124.6, 124.6, 124.1, 123.6, 123.0, 55.2, 39.4, 34.4, 26.3, 20.9, 14.1. HRMS (HESI-TOF) m/z calcd for $(M+H)^+$ 600.2586, found 600.2572.

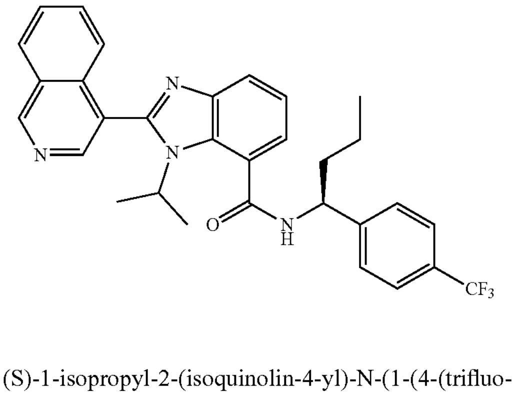

(S)-1-isopropyl-2-(isoquinolin-4-yl)-N-(1-(4-(trifluoromethyl)phenyl)butyl)-1H-benzo[d]imidazole-7-carboxamide Molecular Formula: $C_{31}H_{29}F_3N_4O$; yield 70%; $^1H$ NMR (600 MHZ, $CDCl_3$) δ 9.34 (s, 1H), 8.59 (s, 1H), 8.08-8.02 (m, 1H), 7.88 (d, J=7.3 Hz, 1H), 7.68-7.62 (m, 2H), 7.59 (d, J=8.1 Hz, 2H), 7.50 (d, J=8.1 Hz, 3H), 7.34 (d, J=6.6 Hz, 1H), 7.29 (t, J=7.7 Hz, 1H), 6.68 (d, J=8.1 Hz, 1H), 5.24 (q, J=7.9 Hz, 1H), 4.75 (s, 1H), 1.97-1.92 (m, 1H), 1.90-1.83 (m, 1H), 1.53-1.45 (m, 1H), 1.43-1.34 (m, 1H), 0.99 (t, J=7.4 Hz, 9H). $^{13}$C NMR (151 MHZ, $CDCl_3$) δ 168.4, 154.3, 150.7, 146.4, 144.4, 144.2, 135.4, 131.7, 131.6, 130.0, 129.8, 128.2, 128.1, 128.0, 127.2, 125.8, 125.8, 125.0, 123.2, 122.6, 122.5, 122.3, 121.9, 53.8, 49.9, 38.0, 19.7, 13.9.

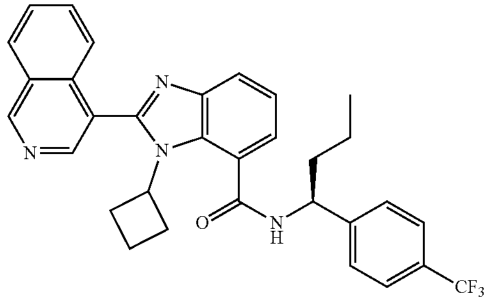 [SMILES: CCC[C@H](NC(=O)c1cccc2nc(-c3cncc4ccccc34)n(C3CCC3)c12)c1ccc(C(F)(F)F)cc1]

(S)-1-cyclobutyl-2-(isoquinolin-4-yl)-N-(1-(4-(trifluoromethyl)phenyl)butyl)-1H-benzo[d]imidazole-7-carboxamide Molecular Formula: $C_{32}H_{29}F_3N_4O$; yield 65%; $^1$H NMR (600 MHZ, $CDCl_3$) δ 9.31 (bs, 1H), 8.70 (bs, 1H), 8.04 (d, J=8.1 Hz, 1H), 7.96 (dd, J=19.6, 8.0 Hz, 2H), 7.73 (bs, 1H), 7.67 (t, J=7.4 Hz, 1H), 7.60 (d, J=8.1 Hz, 2H), 7.54 (d, J=8.0 Hz, 2H), 7.46 (d, J=7.4 Hz, 1H), 7.30 (t, J=7.7 Hz, 1H), 6.79 (bs, 1H), 5.19 (q, J=7.6 Hz, 1H), 4.95 (d, J=6.5 Hz, 1H), 2.00 (ddd, J=7.8, 6.2, 2.8 Hz, 1H), 1.94-1.87 (m, 1H), 1.49-1.44 (m, 1H), 1.38 (ddd, J=10.1, 9.2, 4.8 Hz, 1H), 1.24-1.15 (m, 4H), 0.98 (dd, J=9.4, 5.3 Hz, 3H), 0.96 (t, J=3.4 Hz, 1H), 0.88 (d, J=6.8 Hz, 1H). $^{13}$C NMR (151 MHZ, $CDCl_3$) δ 167.6, 154.2, 151.3, 146.4, 144.5, 134.4, 132.4, 132.0, 128.2, 128.1, 127.4, 125.8, 124.5, 123.2, 122.9, 122.5, 122.1, 54.0, 53.0, 38.2, 19.7, 15.1, 13.9. HRMS (HESI-TOF) m/z calcd for $(M+H)^+$ 543.2372, found 543.2351.

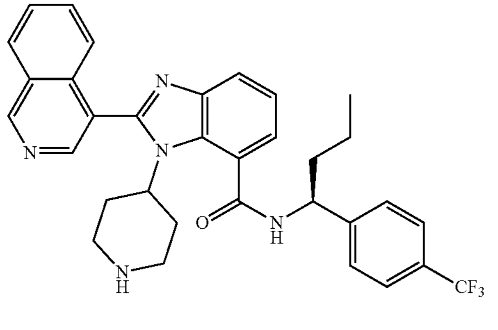 [SMILES: CCC[C@H](NC(=O)c1cccc2nc(-c3cncc4ccccc34)n(C3CCNCC3)c12)c1ccc(C(F)(F)F)cc1]

(S)-2-(isoquinolin-4-yl)-1-(piperidin-4-yl)-N-(1-(4-(trifluoromethyl)phenyl)butyl)-1H-benzo[d]imidazole-7-carboxamide Molecular Formula: $C_{33}H_{32}F_3N_5O$; yield 43%; $^1$H NMR (600 MHZ, $CDCl_3$) δ 9.34 (s, 1H), 8.57 (s, 1H), 8.05 (dd, J=6.5, 2.8 Hz, 1H), 7.88 (d, J=7.9 Hz, 1H), 7.64 (ddd, J=25.9, 14.1, 4.9 Hz, 4H), 7.54-7.46 (m, 3H), 7.38 (d, J=6.9 Hz, 1H), 7.30 (t, J=7.7 Hz, 1H), 6.79 (s, 1H), 5.24 (q, J=7.8 Hz, 1H), 4.49 (d, J=43.7 Hz, 1H), 2.75 (d, J=119.2 Hz, 2H), 2.20 (t, J=11.8 Hz, 1H), 1.99-1.67 (m, 6H), 1.54-1.34 (m, 3H), 0.99 (t, J=7.3 Hz, 3H). $^{13}$C NMR (151 MHz, $CDCl_3$) δ 168.3, 154.4, 150.8, 146.8, 144.4, 144.1, 135.4, 132.0, 131.7, 130.1, 129.9, 128.2, 128.1, 128.1, 127.2, 125.9, 125.9, 124.9, 123.2, 123.0, 122.8, 122.0, 57.2, 53.9, 46.4, 46.1, 38.7, 19.8, 13.9. HRMS (HESI-TOF) m/z calcd for $(M+H)^+$ 572.2637, found 572.2631.

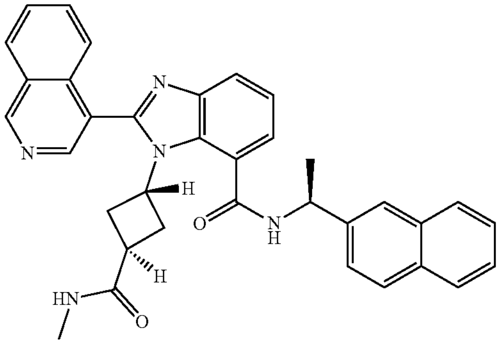

2-(isoquinolin-4-yl)-1-((1r,3S)-3-(methylcarbamoyl)cyclobutyl)-N—((S)-1-(naphth alen-2-yl)ethyl)-1H-benzo[d]imidazole-7-carboxamide Molecular Formula: $C_{35}H_{31}N_5O_2$; yield 64%; $^1$H NMR (600 MHZ, $CDCl_3$) δ 9.25 (s, 1H), 8.60 (s, 1H), 8.00 (d, J=8.6 Hz, 1H), 7.94 (d, J=7.7 Hz, 1H), 7.87 (s, 1H), 7.85-7.77 (m, 3H), 7.64 (dd, J=17.1, 9.2 Hz, 2H), 7.52 (dd, J=8.5, 1.6 Hz, 1H), 7.49 (dd, J=7.5, 0.8 Hz, 1H), 7.47-7.43 (m, 2H), 7.30 (t, J=7.8 Hz, 1H), 6.97 (d, J=5.8 Hz, 1H), 5.50 (dd, J=14.4, 7.1 Hz, 1H), 4.90 (s, 1H), 2.38 (s, 3H), 2.23-2.19 (m, 1H), 2.11 (t, J=9.5 Hz, 2H), 2.01 (s, 2H), 1.75 (d, J=6.9 Hz, 3H). $^{13}$C NMR (151 MHZ, $CDCl_3$) δ 173.9, 167.7, 154.4, 151.6, 145.0, 144.4, 140.8, 134.3, 133.4, 132.9, 132.1, 128.8, 128.3, 128.2, 128.0, 127.8, 126.7, 126.3, 125.0, 124.7, 123.3, 123.2, 122.7, 122.2, 51.7, 50.1, 33.5, 26.4, 22.5. HRMS (HESI-TOF) m/z calcd for $(M+H)^+$ 572.2556, found 554.2551.

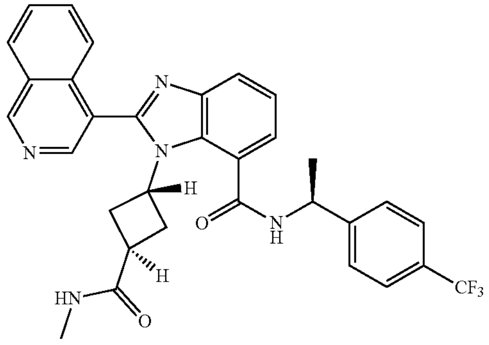 [SMILES: CNC(=O)[C@H]1C[C@H](n2c(-c3cncc4ccccc34)nc3cccc(C(=O)N[C@@H](C)c4ccc(C(F)(F)F)cc4)c32)C1]

2-(isoquinolin-4-yl)-1-((1r,3S)-3-(methylcarbamoyl)cyclobutyl)-N—((S)-1-(4-(trifluoromethyl)phenyl)ethyl)-1H-benzo[d]imidazole-7-carboxamide Molecular Formula: $C_{32}H_{28}F_3N_5O_2$; yield 100%; $^1$H NMR (600 MHz, $CDCl_3$) δ 9.30 (d, J=15.6 Hz, 1H), 8.65 (d, J=25.2 Hz, 1H), 8.05 (t, J=7.3 Hz, 1H), 7.99 (s, 1H), 7.94 (t, J=8.6 Hz, 1H), 7.82-7.72 (m, 1H), 7.69 (dd, J=7.5, 3.4 Hz, 1H), 7.61 (d, J=6.9 Hz, 2H), 7.57 (t, J=6.6 Hz, 2H), 7.46 (t, J=6.3 Hz, 1H), 7.34-7.29 (m, 1H), 6.74 (d, J=79.3 Hz, 1H), 5.46-5.41 (m, 1H), 5.31 (d, J=43.4 Hz, 1H), 2.67 (d, J=5.4 Hz, 3H), 2.31 (d, J=7.0 Hz, 2H), 2.07 (dd, J=22.5, 11.1 Hz, 3H), 1.71 (t, J=5.7 Hz, 3H). $^{13}$C NMR (151 MHz, $CDCl_3$) δ 174.0, 167.5, 154.4, 151.4, 147.3, 145.0, 144.5, 134.2, 132.2, 128.3, 126.9, 126.0, 125.9, 125.1, 124.5, 123.7, 123.4, 123.1, 122.4, 122.3, 51.8, 49.6, 33.8, 29.8, 26.5, 22.2. HRMS (HESI-TOF) m/z calcd for $(M+H)^+$ 572.2268, found 572.2261.

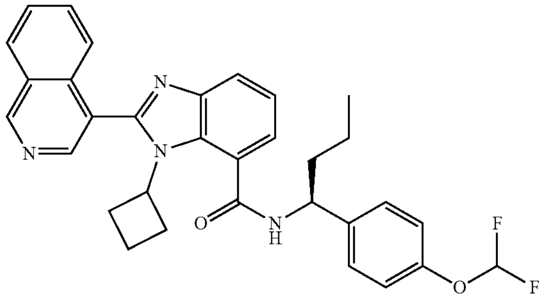 [SMILES: CCC[C@H](NC(=O)c1cccc2nc(-c3cncc4ccccc34)n(C3CCC3)c12)c1ccc(OC(F)F)cc1]

(S)-1-cyclobutyl-N-(1-(4-(difluoromethoxy)phenyl)butyl)-2-(isoquinolin-4-yl)-1H-benzo[d]imidazole-7-carboxamide Molecular Formula: $C_{32}H_{30}F_2N_4O_2$; yield 62%; $^1$H NMR (600 MHZ, $CDCl_3$) δ 9.29 (s, 1H), 8.66 (s, 1H), 8.04 (d, J=8.1 Hz, 1H), 7.94 (dd, J=14.2, 8.2 Hz, 2H), 7.71 (s, 1H), 7.66 (t, J=7.4 Hz, 1H), 7.44 (d, J=7.4 Hz, 1H), 7.40 (d, J=8.6 Hz, 2H), 7.27 (dd, J=14.5, 6.8 Hz, 1H), 7.08 (d, J=8.5 Hz, 2H), 7.03 (d, J=7.8 Hz, 1H), 6.48 (t, J=73.8 Hz, 1H), 5.21-5.10 (m, 1H), 4.96 (s, 1H), 2.02-1.94 (m, 1H), 1.91-1.83 (m, 1H), 1.56 (s, 1H), 1.50-1.40 (m, 2H), 1.40-1.32 (m, 2H), 1.26-1.16 (m, 3H), 0.97 (t, J=7.4 Hz, 3H). $^{13}$C NMR (151 MHZ, $CD_3OD$) δ 170.0, 155.4, 152.0, 151.9, 145.0, 141.2, 133.8, 133.1, 129.8, 129.7, 129.5, 125.2, 125.2, 124.3, 123.6, 122.8, 120.4, 119.4, 117.6, 115.9, 54.9, 54.2, 39.0, 20.9, 15.8, 14.1. HRMS (HESI-TOF) m/z calcd for $(M+H)^+$ 572.2268, found 572.2261.

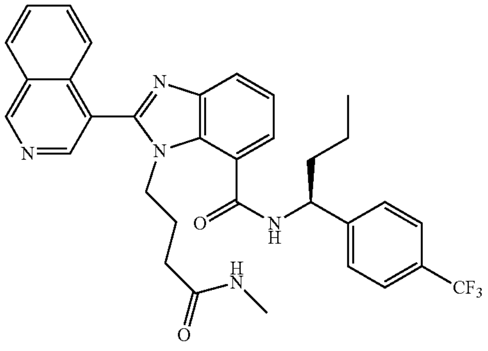 [SMILES: CCC[C@H](NC(=O)c1cccc2nc(-c3cncc4ccccc34)n(CCCC(=O)NC)c12)c1ccc(C(F)(F)F)cc1]

(S)-2-(isoquinolin-4-yl)-1-(4-(methylamino)-4-oxobutyl)-N-(1-(4-(trifluoromethyl)phenyl)butyl)-1H-benzo[d]imidazole-7-carboxamide Molecular Formula: $C_{33}H_{32}F_3N_5O_2$; yield 82%; $^1$H NMR (600 MHZ, $CD_3OD$) δ 9.38 (s, 1H), 8.67 (s, 1H), 8.10 (d, J=7.9 Hz, 1H), 7.97 (d, J=8.0 Hz, 1H), 7.72 (dd, J=14.3, 6.9 Hz, 3H), 7.60 (d, J=8.2 Hz, 2H), 7.55 (d, J=8.1 Hz, 2H), 7.49 (d, J=7.4 Hz, 1H), 7.37 (t, J=7.8 Hz, 1H), 6.94 (s, 1H), 5.18 (q, J=7.6 Hz, 1H), 4.26-4.18 (m, 1H), 4.12-4.04 (m, 1H), 2.51 (d, J=4.8 Hz, 3H), 2.04-1.96 (m, 1H), 1.89 (ddd, J=16.8, 8.4, 5.0 Hz, 2H), 1.62 (dd, J=13.3, 6.0 Hz, 1H), 1.53-1.47 (m, 3H), 1.42-1.35 (m, 1H), 0.99 (t, J=7.3 Hz, 3H). $^{13}$C NMR (151 MHZ, $CD_3OD$) δ 171.6, 167.6, 154.6, 151.9, 146.6, 144.9, 144.6, 134.6, 132.2, 131.4, 129.8, 129.6, 128.4, 128.3, 127.4, 125.8, 125.8, 125.1, 124.4, 123.3, 123.1, 122.3, 122.2, 54.2, 45.8, 38.4, 32.5, 26.1, 25.9, 19.7, 13.9. HRMS (HESI-TOF) m/z calcd for $(M+H)^+$ 572.2586, found 588.2573.

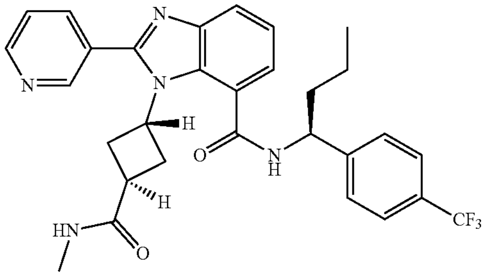 [SMILES: CCC[C@H](NC(=O)c1cccc2nc(-c3cccnc3)n([C@H]3C[C@H](C(=O)NC)C3)c12)c1ccc(C(F)(F)F)cc1]

1-((1r,3S)-3-(methylcarbamoyl)cyclobutyl)-2-(pyridin-3-yl)-N—((S)-1-(4-(trifluoro methyl)phenyl)butyl)-1H-benzo[d]imidazole-7-carboxamide Molecular Formula: $C_{30}H_{30}F_3N_5O_2$; yield 58%; $^1$H NMR (600 MHZ, $CD_3OD$) δ 8.89 (bs, 1H), 8.70 (bs, 1H), 8.17 (bs, 1H), 7.85 (d, J=8.2 Hz, 1H), 7.78-7.47 (m, 6H), 7.40 (dd, J=7.4, 3.0 Hz, 1H), 5.17 (s, 1H), 4.93 (d, J=6.7 Hz, 1H), 2.54 (dd, J=6.8, 3.1 Hz, 3H), 2.42-2.23 (m, 2H), 2.03 (bs, 1H), 1.83 (d, J=41.9 Hz, 4H), 1.47 (d, J=72.9 Hz, 2H), 1.10-0.86 (m, 3H). $^{13}$C NMR (151 MHz, $CD_3OD$) δ 175.2, 170.0, 153.4, 151.7, 150.4, 148.7, 145.0, 138.8, 133.5, 130.6, 130.4, 129.4, 128.9, 126.6, 126.5, 126.5, 125.3, 124.8, 124.0, 123.7, 123.2, 55.1, 50.5, 39.0, 36.4, 35.3, 33.7, 26.2, 20.9, 14.0. HRMS (HESI-TOF) m/z calcd for $(M+H)^+$ 550.2430, found 550.2412.

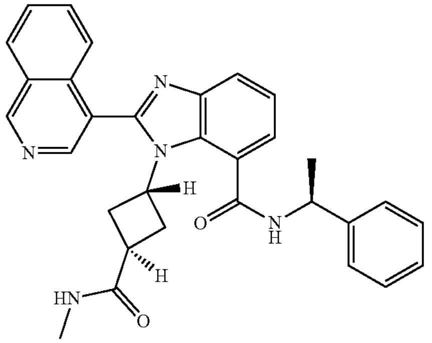 [SMILES: CNC(=O)[C@H]1C[C@H](n2c(-c3cncc4ccccc34)nc3cccc(C(=O)N[C@@H](C)c4ccccc4)c32)C1]

2-(isoquinolin-4-yl)-1-((1r,3S)-3-(methylcarbamoyl)cyclobutyl)-N—((S)-1-phenyl ethyl)-1H-benzo[d]imidazole-7-carboxamide Molecular Formula: $C_{13}H_{29}N_5O_2$; yield 65%; $^1$H NMR (600 MHZ, $CD_3OD$) δ 9.45 (s, 1H), 9.23 (d, J=7.4 Hz, 1H), 8.76 (s, 1H), 8.28 (d, J=8.2 Hz, 1H), 8.05 (d, J=8.2 Hz, 1H), 7.91 (t, J=9.0 Hz, 2H), 7.83 (t, J=7.5 Hz, 1H), 7.56 (d, J=7.2 Hz, 1H), 7.49-7.39 (m, 4H), 7.35 (t, J=7.4 Hz, 2H), 7.24 (t, J=7.1 Hz, 1H), 5.42-5.32 (m, 1H), 5.35-5.27 (m, 1H), 2.60 (s, 3H), 2.45 (bs, 1H), 2.18 (dd, J=71.4, 32.9 Hz, 3H), 1.84 (dd, J=67.4, 3.8 Hz, 1H), 1.64 (d, J=7.0 Hz, 3H). $^{13}$C NMR (151 MHz, $CD_3OD$) δ 175.5, 168.4, 154.2, 143.6, 143.3, 132.6, 128.5, 128.4, 128.2, 126.8, 126.0, 123.0, 122.3, 121.4, 51.9, 49.8, 49.7, 33.1, 25.0, 21.1. HRMS (HESI-TOF) m/z calcd for $(M+H)^+$ 504.2400, found 504.2379.

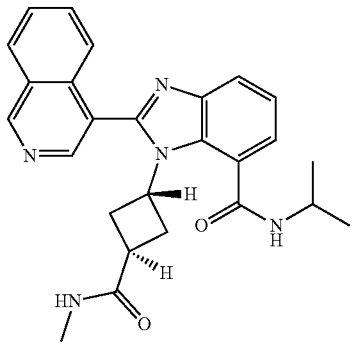 [SMILES: CNC(=O)[C@H]1C[C@H](n2c(-c3cncc4ccccc34)nc3cccc(C(=O)NC(C)C)c32)C1]

N-isopropyl-2-(isoquinolin-4-yl)-1-((1r,3r)-3-(methylcarbamoyl)cyclobutyl)-1H-benzo[d]imidazole-7-carboxamide Molecular Formula: $C_{26}H_{27}N_5O_2$; yield 86%; $^1$H NMR (600 MHZ, $CDCl_3$) δ 9.32 (s, 1H), 8.69 (s, 1H), 8.04 (dd, J=16.2, 8.3 Hz, 2H), 7.92 (d, J=7.9 Hz, 1H), 7.77 (t, J=7.4 Hz, 1H), 7.69 (t, J=7.5 Hz, 1H), 7.44 (d, J=7.3 Hz, 1H), 7.32 (t, J=7.7 Hz, 1H), 6.18 (d, J=7.7 Hz, 1H), 5.61 (d, J=3.8 Hz, 1H), 5.44 (q, J=8.2 Hz, 1H), 4.35-4.28 (m, J=13.1, 6.6 Hz, 1H), 2.68 (d, J=4.8 Hz, 3H), 2.40 (d, J=9.8 Hz, 1H), 2.31-2.00 (m, 4H), 1.35 (d, J=6.5 Hz, 6H). $^{13}$C NMR (151 MHz, $CDCl_3$) δ 174.1, 167.6, 154.3, 151.1, 144.8, 144.4, 134.3, 132.2, 132.1, 128.3, 124.6, 123.2, 123.2, 122.9, 122.3, 51.8, 42.5, 33.9, 26.5, 22.9. HRMS (HESI-TOF) m/z calcd for $(M+H)^+$ 442.2243, found 442.2220.

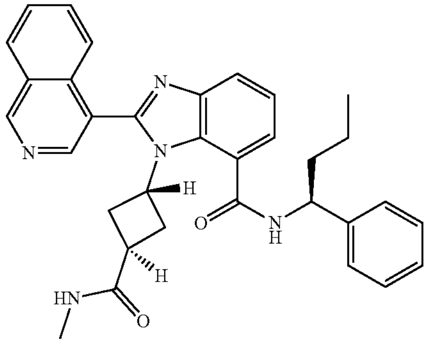 [SMILES: CCC[C@H](NC(=O)c1cccc2nc(-c3cncc4ccccc34)n([C@H]3C[C@H](C(=O)NC)C3)c12)c1ccccc1]

2-(isoquinolin-4-yl)-1-((1r,3S)-3-(methylcarbamoyl)cyclobutyl)-N—((S)-1-phenylbutyl)-1H-benzo[d]imidazole-7-carboxamide Molecular Formula: $C_{33}H_{33}N_5O_2$; yield 78%; $^1$H NMR (600 MHZ, $CDCl_3$) δ 9.21 (bs, 1H), 8.58 (d, J=40.6 Hz, 1H), 7.99 (t, J=62.1 Hz, 3H), 7.63 (dd, J=22.0, 14.6 Hz, 2H), 7.46 (d, J=7.0 Hz, 1H), 7.35 (d, J=7.3 Hz, 2H), 7.23 (dd, J=31.5, 25.2 Hz, 6H), 5.41 (d, J=18.3 Hz, 1H), 5.10 (dd, J=15.0, 7.3 Hz, 1H), 4.78 (d, J=41.7 Hz, 1H), 2.43 (d, J=53.3 Hz, 4H), 2.02-1.77 (m, 4H), 1.69 (bs, 1H), 1.55 (d, J=38.4 Hz, 2H), 1.41 (bs, 1H), 1.32 (d, J=6.4 Hz, 1H), 0.91 (t, J=6.7 Hz, 3H). $^{13}$C NMR (151 MHZ, $CDCl_3$) δ 172.5, 167.5, 154.1, 151.0, 144.8, 144.4, 142.4, 132.2, 132.1, 128.6, 128.1, 128.0, 127.2, 127.1, 123.0, 122.5, 122.0, 54.1, 49.0, 38.2, 33.1, 26.1, 19.7, 13.8.

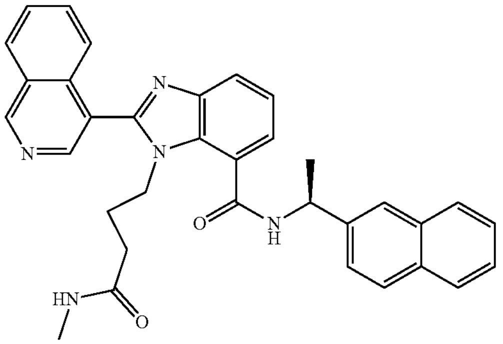 [SMILES: CNC(=O)CCCn1c(-c2cncc3ccccc23)nc2cccc(C(=O)N[C@@H](C)c3ccc4ccccc4c3)c21]

(S)-2-(isoquinolin-4-yl)-1-(4-(methylamino)-4-oxobutyl)-N-(1-(naphthalen-2-yl)ethyl)-1H-benzo[d]imidazole-7-carboxamide Molecular Formula: $C_{34}H_{31}N_5O_2$; yield 63%; $^1$H NMR (600 MHz, $CDCl_3$) δ 9.31 (s, 1H), 8.54 (s, 1H), 8.04 (d, J=7.8 Hz, 1H), 7.94-7.87 (m, 2H), 7.83 (dd, J=17.4, 8.3 Hz, 3H), 7.71-7.64 (m, 3H), 7.55 (d, J=8.5 Hz, 1H), 7.47 (dd, J=11.5, 6.5 Hz, 3H), 7.31 (t, J=7.8 Hz, 1H), 7.01 (d, J=7.8 Hz, 1H), 5.50 (p, J=7.0 Hz, 1H), 5.12 (d, J=14.0 Hz, 1H), 4.21-4.10 (m, 2H), 2.38 (d, J=4.7 Hz, 3H), 2.03 (d, J=7.7 Hz, 1H), 1.75 (d, J=6.9 Hz, 3H), 1.71-1.63 (m, 1H), 1.52 (dt, J=20.9, 7.2 Hz, 1H), 1.42 (ddd, J=22.5, 15.1, 7.7 Hz, 2H). $^{13}$C NMR (151 MHz, $CDCl_3$) δ 171.5, 167.4, 144.9, 140.5, 133.5, 132.9, 132.1, 131.5, 128.9, 128.3, 128.0, 127.8, 126.6, 126.2, 125.2, 124.7, 124.4, 123.0, 122.4, 122.2, 50.1, 45.9, 32.5, 26.2, 26.1, 22.0. HRMS (HESI-TOF) m/z calcd for $(M+H)^+$ 542.2556, found 542.2540. HRMS (HESI-TOF) m/z calcd for $(M+H)^+$ 542.2556, found 542.2540.

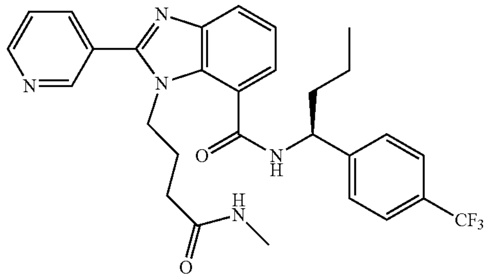 [SMILES: CCC[C@H](NC(=O)c1cccc2nc(-c3cccnc3)n(CCCC(=O)NC)c12)c1ccc(C(F)(F)F)cc1]

(S)-1-(4-(methylamino)-4-oxobutyl)-2-(pyridin-3-yl)-N-(1-(4-(trifluoro methyl)phenyl)butyl)-1H-benzo[d]imidazole-7-carboxamide Molecular Formula: $C_{29}H_{30}F_3N_5O_2$; yield 51%; $^1$H NMR (600 MHZ, $CD_3OD$ δ 8.89 (s, 2H), 8.75 (d, J=3.9 Hz, 2H), 8.17 (d, J=7.9 Hz, 2H), 7.91 (s, 1H), 7.87 (d, J=8.1 Hz, 2H), 7.66 (did, J=19.3, 8.3 Hz, 10H), 7.55 (d, J=7.3 Hz, 2H), 7.43 (t, J=7.8 Hz, 2H), 5.18 (dd, J=8.4, 6.9 Hz, 2H), 4.42-4.22 (m, 4H), 2.50 (s, 6H), 2.06-1.95 (m, 2H), 1.91-1.78 (m, 2H), 1.69-1.38 (m, 13H), 1.02 (t, J=7.4 Hz, 6H). $^{13}$C NMR (151 MHZ, $CD_3OD$) δ 174.2, 169.7, 154.0, 151.7, 150.9, 149.0, 144.9, 139.2, 132.5, 128.7, 126.6, 126.6, 125.1, 123.9, 123.8, 122.9, 55.3, 46.5, 39.3, 32.6, 26.2, 21.0, 14.1. HRMS (HESI-TOF) m/z calcd for $(M+H)^+$ 542.2430, found 538.2424.

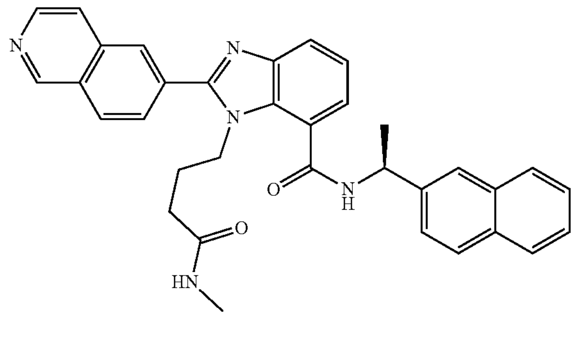 [SMILES: CNC(=O)CCCn1c(-c2ccc3cnccc3c2)nc2cccc(C(=O)N[C@@H](C)c3ccc4ccccc4c3)c21]

(S)-2-(isoquinolin-6-yl)-1-(4-(methylamino)-4-oxobutyl)-N-(1-(naphthalen-2-yl)ethyl)-1H-benzo[d]imidazole-7-carboxamide Molecular Formula: $C_{34}H_{31}N_5O_2$; yield 77%; $^1$H NMR (600 MHz, $CDCl_3$) δ 9.32 (s, 1H), 8.60 (d, J=5.7 Hz, 1H), 8.26 (s, 1H), 8.11 (d, J=8.5 Hz, 1H), 7.98-7.92 (m, 3H), 7.90-7.84 (m, 3H), 7.82 (d, J=5.7 Hz, 1H), 7.56 (dd, J=8.5, 1.7 Hz, 1H), 7.53-7.48 (m, 2H), 7.45 (dd, J=7.4, 0.9 Hz, 1H), 7.32 (t, J=7.8 Hz, 1H), 6.68 (d, J=7.9 Hz, 1H), 5.51 (p, J=7.1 Hz, 1H), 4.70 (d, J=3.9 Hz, 1H), 4.48-4.32 (m, 2H), 2.41 (d, J=4.8 Hz, 3H), 1.92-1.83 (m, 1H), 1.76 (d, J=7.0 Hz, 3H), 1.67 (d, J=2.6 Hz, 1H), 1.49 (dt, J=14.4, 7.1 Hz, 1H), 1.38-1.31 (m, 1H). $^{13}$C NMR (151 MHz, $CDCl_3$) δ 171.6, 167.4, 154.7, 152.5, 144.8, 143.9, 140.7, 135.6, 133.5, 133.0, 132.2, 132.0, 129.0, 128.6, 128.4, 128.3, 128.3, 128.0, 127.9, 126.7, 126.3, 125.4, 124.7, 123.1, 122.9, 122.3, 122.2, 121.2, 50.1, 45.8, 32.1, 26.1, 26.0, 22.2. HRMS (HESI-TOF) m/z calcd for $(M+H)^+$ 542.2542, found 542.2541.

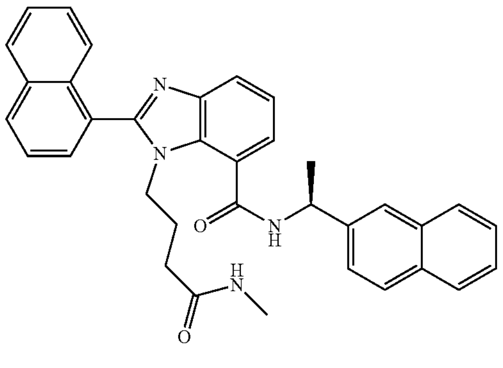

(S)-1-(4-(methylamino)-4-oxobutyl)-2-(naphthalen-1-yl)-N-(1-(naphthalen-2-yl)ethyl)-1H-benzo[d]imidazole-7-carboxamide Molecular Formula: $C_{34}H_{31}N_5O_2$; yield 93%; $^1$H NMR (600 MHz, $CDCl_3$) δ 7.99 (d, J=8.2 Hz, 1H), 7.93 (t, J=8.6 Hz, 2H), 7.89 (s, 1H), 7.83 (dd, J=16.5, 8.0 Hz, 3H), 7.63 (d, J=7.7 Hz, 2H), 7.58-7.50 (m, 3H), 7.50-7.43 (m, 4H), 7.30 (t, J=7.8 Hz, 1H), 6.78 (d, J=7.2 Hz, 1H), 5.49 (p, J=7.0 Hz, 1H), 4.87 (s, 1H), 4.11 (s, 2H), 2.35 (d, J=4.7 Hz, 3H), 1.76-1.65 (m, 4H), 1.59-1.52 (m, 1H), 1.42 (dd, J=15.4, 7.7 Hz, 2H). $^{13}$C NMR (151 MHZ, $CDCl_3$) δ 171.7, 167.4, 154.6, 144.8, 140.5, 133.6, 133.4, 132.9, 132.2, 131.3, 130.7, 129.1, 128.9, 128.6, 128.0, 127.8, 127.7, 127.5, 126.6, 126.6, 126.2, 125.3, 125.2, 125.1, 124.7, 122.9, 122.6, 122.1, 121.9, 50.0, 45.7, 32.7, 26.1, 26.1, 22.0. HRMS (HESI-TOF) m/z calcd for $(M+H)^+$ 541.2589, found 541.2587.

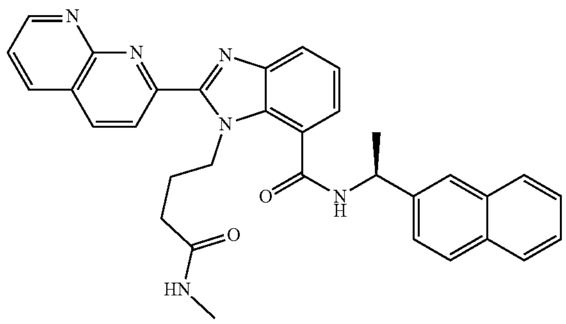 [SMILES: CNC(=O)CCCn1c(-c2ccc3cccnc3n2)nc2cccc(C(=O)N[C@@H](C)c3ccc4ccccc4c3)c21]

(S)-1-(4-(methylamino)-4-oxobutyl)-N-(1-(naphthalen-2-yl)ethyl)-2-(1,8-naphthyridin-2-yl)-1H-benzo[d]imidazole-7-carboxamide Molecular Formula: $C_{33}H_{30}N_6O_2$; yield 16%; $^1$H NMR (600 MHZ, DMSO-$d_6$) δ 9.41 (d, J=7.9 Hz, 1H), 9.18 (dd, J=4.1, 1.9 Hz, 1H), 8.68 (d, J=8.5 Hz, 1H), 8.60-8.54 (m, 2H), 7.98-7.93 (m, 4H), 7.93-7.89 (m, 2H), 7.74 (dd, J=8.1, 4.2 Hz, 1H), 7.67 (d, J=8.5 Hz, 1H), 7.54-7.47 (m, 3H), 7.45 (d, J=7.3 Hz, 1H), 7.39 (t, J=7.7 Hz, 1H), 5.46-5.40 (m, 1H), 5.21 (dd, J=13.9, 7.4 Hz, 1H), 5.08-5.00 (m, 1H), 2.34 (d, J=4.5 Hz, 3H), 1.92-1.81 (m, 4H), 1.61 (d, J=7.0 Hz, 3H). $^{13}$C NMR (151 MHz, DMSO-$d_6$) δ 171.1, 166.5, 154.5, 154.4, 152.7, 150.3, 143.3, 142.0, 138.8, 137.6, 132.9, 132.2, 132.1, 128.1, 127.8, 127.5, 126.1, 125.7, 125.0, 124.3, 124.0, 123.6, 123.2, 123.0, 122.4, 122.1, 121.7, 48.9, 45.3, 32.1, 26.5, 25.3, 22.0. HRMS (HESI-TOF) m/z calcd for $(M+H)^+$ 542.2499, found 542.2498.

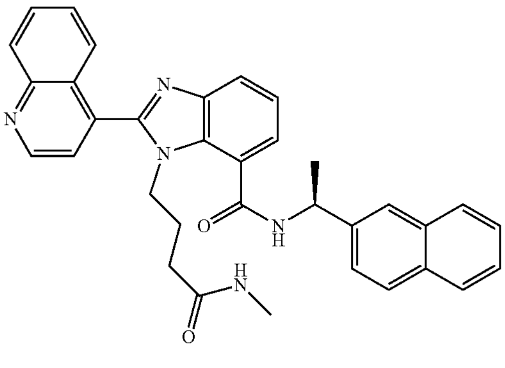 [SMILES: CNC(=O)CCCn1c(-c2ccnc3ccccc23)nc2cccc(C(=O)N[C@@H](C)c3ccc4ccccc4c3)c21]

(S)-1-(4-(methylamino)-4-oxobutyl)-N-(1-(naphthalen-2-yl)ethyl)-2-(quinolin-4-yl)-1H-benzo[d]imidazole-7-carboxamide Molecular Formula: $C_{34}H_{31}N_5O_2$; yield 29%; $^1$H NMR (600 MHz, $CDCl_3$) δ 9.05 (d, J=4.3 Hz, 1H), 8.24 (d, J=8.4

Hz, 1H), 7.98 (d, J=8.0 Hz, 1H), 7.91 (s, 1H), 7.87-7.81 (m, 3H), 7.80-7.75 (m, 2H), 7.60 (d, J=4.2 Hz, 1H), 7.56 (t, J=7.3 Hz, 2H), 7.49 (dt, J=20.7, 6.7 Hz, 3H), 7.36 (t, J=7.8 Hz, 1H), 6.70 (d, J=7.4 Hz, 1H), 5.54-5.47 (m, 1H), 4.75 (s, 1H), 4.15 (ddt, J=20.5, 8.6, 6.0 Hz, 2H), 2.38 (d, J=4.8 Hz, 3H), 1.76 (d, J=6.9 Hz, 3H), 1.74-1.68 (m, 1H), 1.54 (d, J=7.0 Hz, 1H), 1.44-1.34 (m, 2H). $^{13}$C NMR (151 MHz, $CDCl_3$) δ 171.4, 167.2, 140.4, 133.5, 131.5, 130.5, 129.0, 128.3, 128.0, 127.8, 126.7, 126.3, 125.5, 125.3, 124.7, 123.4, 123.2, 122.9, 122.4, 50.2, 45.9, 32.3, 26.2, 26.1, 22.0. HRMS (HESI-TOF) m/z calcd for $(M+H)^+$ 542.2533, found 542.2532.

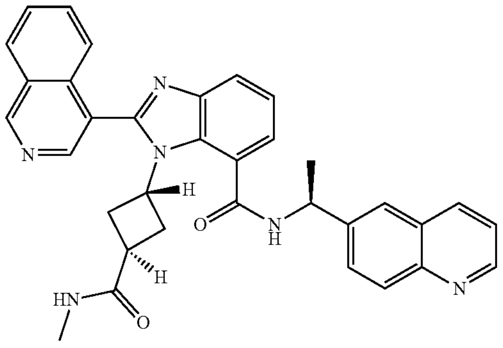 [SMILES: CNC(=O)[C@H]1C[C@H](n2c(-c3cncc4ccccc34)nc3cccc(C(=O)N[C@@H](C)c4ccc5ncccc5c4)c32)C1]

2-(isoquinolin-4-yl)-1-((1r,3S)-3-(methylcarbamoyl)cyclobutyl)-N—((S)-1-(quinolin-6-yl)ethyl)-1H-benzo[d]imidazole-7-carboxamide Molecular Formula: $C_{34}H_{30}N_6O_2$; yield 35%; $^1$H NMR (600 MHZ, $CDCl_3$) δ 9.23 (s, 1H), 8.80 (s, 1H), 8.15 (dd, J=24.9, 8.4 Hz, 2H), 8.07-7.88 (m, 4H), 7.84 (d, J=8.6 Hz, 1H), 7.72 (s, 1H), 7.66 (t, J=7.3 Hz, 1H), 7.51 (d, J=7.4 Hz, 1H), 7.39 (dd, J=8.2, 4.1 Hz, 1H), 7.34 (d, J=7.7 Hz, 1H), 7.12 (d, J=44.4 Hz, 1H), 5.60 (p, J=6.8 Hz, 1H), 5.41 (s, 1H), 5.28 (d, J=17.3 Hz, 1H), 2.57 (d, J=4.6 Hz, 3H), 2.25 (bs, 1H), 2.14 (bs, 1H), 2.02 (d, J=22.5 Hz, 3H), 1.82 (d, J=5.7 Hz, 3H). $^{13}$C NMR (151 MHZ, $CDCl_3$) δ 174.10, 167.70, 154.33, 150.31, 147.43, 144.90, 144.27, 141.71, 136.67, 134.21, 132.21, 129.88, 128.67, 128.36, 128.26, 125.29, 124.51, 123.21, 122.73, 122.30, 121.65, 51.73, 49.85, 33.70, 29.84, 26.47, 22.12. HRMS (HESI-TOF) m/z calcd for $(M+H)^+$ 555.2508, found 555.2510.

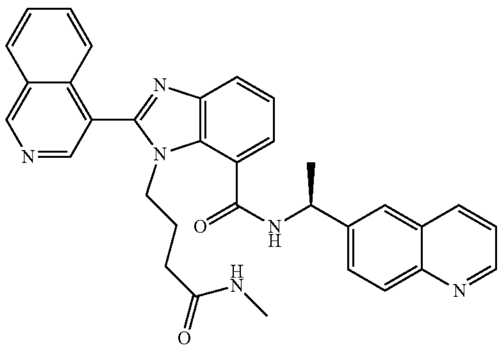 [SMILES: CNC(=O)CCCn1c(-c2cncc3ccccc23)nc2cccc(C(=O)N[C@@H](C)c3ccc4ncccc4c3)c21]

(S)-2-(isoquinolin-4-yl)-1-(4-(methylamino)-4-oxobutyl)-N-(1-(quinolin-6-yl)ethyl)-1H-benzo[d]imidazole-7-carboxamide Molecular Formula: $C_{33}H_{30}N_6O_2$; yield 31%; $^1$H NMR (600 MHz, $CDCl_3$) δ 9.36 (s, 1H), 8.89 (d, J=3.0 Hz, 1H), 8.65 (s, 1H), 8.22 (d, J=8.1 Hz, 1H), 8.15 (d, J=8.7 Hz, 1H), 8.08 (d, J=8.0 Hz, 1H), 7.96 (d, J=8.0 Hz, 1H), 7.92 (s, 1H), 7.85 (d, J=8.7 Hz, 1H), 7.75-7.67 (m, 3H), 7.51 (d, J=7.4 Hz, 1H), 7.43 (dd, J=8.2, 4.2 Hz, 1H), 7.35 (t, J=7.8 Hz, 1H), 6.88 (d, J=7.1 Hz, 1H), 5.53 (d, J=7.1 Hz, 1H), 5.20 (bs, 1H), 4.20 (bs, 2H), 2.49 (d, J=4.7 Hz, 3H), 1.78 (d, J=6.9 Hz, 3H), 1.75-1.71 (m, 1H), 1.57-1.47 (m, 3H). $^{13}$C NMR (151 MHz, $CDCl_3$) δ 171.4, 167.3, 154.5, 151.8, 150.1, 144.9, 144.5, 136.7, 134.6, 132.1, 131.4, 129.8, 128.5, 128.2, 128.2, 125.0, 124.3, 123.1, 122.9, 122.1, 121.5, 49.8, 45.8, 32.5, 26.1, 26.0, 21.9. HRMS (HESI-TOF) m/z calcd for $(M+H)^+$ 543.2508, found 543.2499.

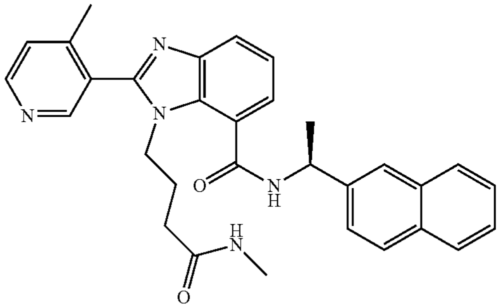 [SMILES: CNC(=O)CCCn1c(-c2cnccc2C)nc2cccc(C(=O)N[C@@H](C)c3ccc4ccccc4c3)c21]

(S)-1-(4-(methylamino)-4-oxobutyl)-2-(4-methylpyridin-3-yl)-N-(1-(naphthalen-2-yl)ethyl)-1H-benzo[d]imidazole-7-carboxamide Molecular Formula: $C_{31}H_{31}N_5O_2$; yield 60%; $^1$H NMR (600 MHZ, $CDCl_3$) δ 8.57 (d, J=4.5 Hz, 1H), 8.52 (s, 1H), 7.90 (d, J=5.6 Hz, 2H), 7.85 (dd, J=19.1, 9.8 Hz, 3H), 7.55 (d, J=8.4 Hz, 1H), 7.52-7.47 (m, 2H), 7.45 (d, J=7.4 Hz, 1H), 7.31 (t, J=7.7 Hz, 2H), 6.74 (d, J=6.8 Hz, 1H), 5.54-5.46 (m, 1H), 5.04 (bs, 1H), 4.11 (dd, J=13.9, 5.9 Hz, 1H), 4.06 (d, J=7.1 Hz, 1H), 2.50-2.46 (m, 3H), 2.26 (bs, 3H), 1.76-1.75 (m, 4H), 1.57-1.42 (m, 3H). $^{13}$C NMR (151 MHz, $CDCl_3$) δ 171.6, 167.3, 152.2, 150.8, 150.4, 147.8, 144.8, 140.6, 133.5, 132.9, 131.2, 128.9, 128.0, 127.8, 127.0, 126.7, 126.3, 125.5, 125.2, 124.6, 123.0, 122.7, 122.1, 122.0, 50.1, 45.4, 32.5, 26.2, 26.1, 22.1, 19.5. HRMS (HESI-TOF) m/z calcd for $(M+H)^+$ 506.2556, found 506.2550.

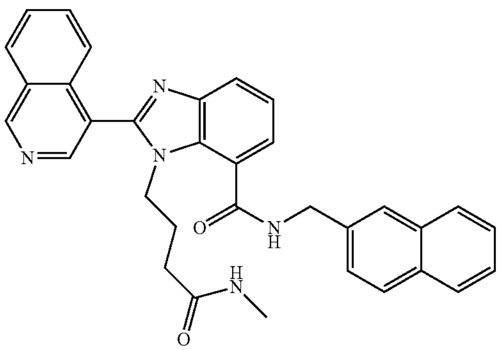 [SMILES: CNC(=O)CCCn1c(-c2cncc3ccccc23)nc2cccc(C(=O)NCc3ccc4ccccc4c3)c21]

2-(isoquinolin-4-yl)-1-(4-(methylamino)-4-oxobutyl)-N-(naphthalen-2-ylmethyl)-1H-benzo[d]imidazole-7-carboxamide Molecular Formula: $C_{33}H_{29}N_5O_2$; yield 80%; $^1$H NMR (600 MHZ, $CDCl_3$) δ 9.30 (s, 1H), 8.53 (s, 1H), 8.04 (d, J=8.0 Hz, 1H), 7.93 (d, J=7.6 Hz, 1H), 7.88-7.81 (m, 4H), 7.75-7.66 (m, 3H), 7.56-7.45 (m, 4H), 7.32 (t, J=7.8 Hz, 1H), 7.07 (t, J=5.7 Hz, 1H), 5.24 (d, J=4.0 Hz, 1H), 4.85 (d, J=5.8 Hz, 2H), 4.26 (t, J=6.9 Hz, 2H), 2.44 (d, J=4.8 Hz, 3H), 1.74-1.69 (m, 2H), 1.61 (t, J=7.6 Hz, 2H). $^{13}$C NMR (151 MHz, $CDCl_3$) δ 171.6, 168.1, 154.6, 151.8, 144.9, 144.5, 135.4, 134.7, 133.5, 132.9, 132.1, 131.4, 128.9, 128.3, 128.2, 127.9, 127.9, 127.1, 126.6, 126.3, 126.2, 124.5, 123.0, 123.0, 122.3, 122.2, 122.0, 45.9, 44.7, 32.7, 26.3, 26.1. HRMS (HESI-TOF) m/z calcd for $(M+H)^+$ 528.2388, found 528.2387.

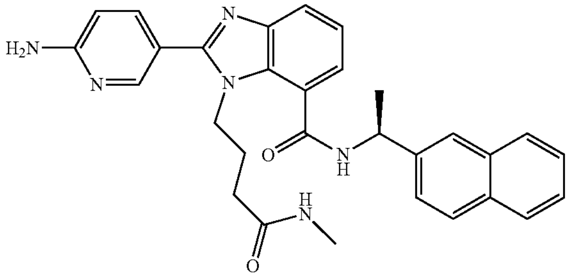 [SMILES: CNC(=O)CCCn1c(-c2ccc(N)nc2)nc2cccc(C(=O)N[C@@H](C)c3ccc4ccccc4c3)c21]

(S)-2-(6-aminopyridin-3-yl)-1-(4-(methylamino)-4-oxobutyl)-N-(1-(naphthalen-2-yl)ethyl)-1H-benzo[d]imidazole-7-carboxamide Molecular Formula: $C_{30}H_{30}N_6O_2$; yield 43%; $^1$H NMR (600 MHZ, $CD_3OD$) δ 8.22 (s, 1H), 7.93 (s, 1H), 7.90-7.82 (m, 3H), 7.79 (d, J=7.8 Hz, 1H), 7.71 (d, J=8.1 Hz, 1H), 7.61 (d, J=8.1 Hz, 1H), 7.48 (dd, J=19.2, 7.1 Hz, 3H), 7.36 (t, J=7.5 Hz, 1H), 6.69 (d, J=8.5 Hz, 1H), 5.45 (d, J=6.7 Hz, 1H), 4.29 (dd, J=33.3, 6.5 Hz, 2H), 2.48 (s, 3H), 1.69 (d, J=6.6 Hz, 4H), 1.54-1.48 (m, 3H). $^{13}$C NMR (151 MHZ, $CD_3OD$) δ 174.4, 169.7, 161.9, 155.5, 149.8, 144.8, 142.6, 139.9, 134.9, 134.2, 132.4, 129.5, 128.9, 128.7, 127.3, 126.9, 126.0, 125.8, 124.4, 123.8, 123.4, 122.1, 115.5, 109.7, 51.2, 46.4, 32.8, 26.9, 26.2, 22.3. HRMS (HESI-TOF) m/z calcd for $(M+H)^+$ 507.2508, found 507.2498.

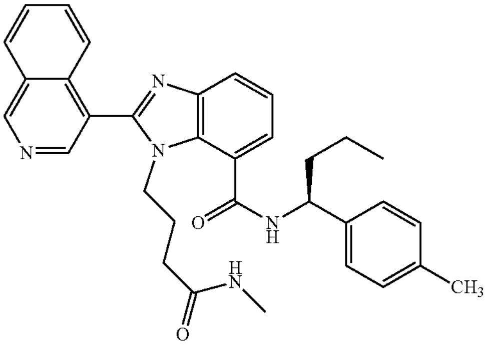 [SMILES: CCC[C@H](NC(=O)c1cccc2nc(-c3cncc4ccccc34)n(CCCC(=O)NC)c12)c1ccc(C)cc1]

(S)-2-(isoquinolin-4-yl)-1-(4-(methylamino)-4-oxobutyl)-N-(1-(p-tolyl)butyl)-1H-benzo[d]imidazole-7-carboxamide Molecular Formula: $C_{33}H_{35}N_5O_2$; yield 73%; $^1$H NMR (600 MHZ, $CDCl_3$) δ 9.37 (s, 1H), 8.60 (s, 1H), 8.08 (d, J=7.8 Hz, 1H), 7.93 (d, J=8.0 Hz, 1H), 7.70 (dt, J=12.2, 3.8 Hz, 3H), 7.44 (d, J=7.4 Hz, 1H), 7.32 (t, J=7.7 Hz, 1H), 7.29-7.26 (m, 3H), 7.15 (d, J=7.8 Hz, 2H), 6.75 (t, J=10.9 Hz, 1H), 5.39 (s, 1H), 5.13 (q, J=7.6 Hz, 1H), 4.20 (dd, J=13.7, 6.3 Hz, 1H), 4.10 (d, J=7.1 Hz, 1H), 2.48 (d, J=4.5 Hz, 3H), 2.32 (s, 3H), 2.00-1.93 (m, 1H), 1.89-1.85 (m, 2H), 1.68 (dd, J=12.2, 5.5 Hz, 1H), 1.55 (d, J=3.5 Hz, 3H), 1.51-1.40 (m, 1H), 1.42-1.33 (m, 1H), 0.97 (t, J=7.3 Hz, 3H). $^{13}$C NMR (151 MHZ, $CDCl_3$) δ 171.7, 167.4, 154.6, 151.8, 145.0, 144.6, 139.3, 137.4, 134.7, 132.1, 131.5, 129.6, 128.3, 128.3, 126.8, 124.5, 123.0, 122.8, 122.5, 122.1, 54.2, 45.9, 38.6, 32.8, 26.3, 26.2, 21.2, 19.8, 14.0. HRMS (HESI-TOF) m/z calcd for $(M+H)^+$ 534.2869, found 534.2853.

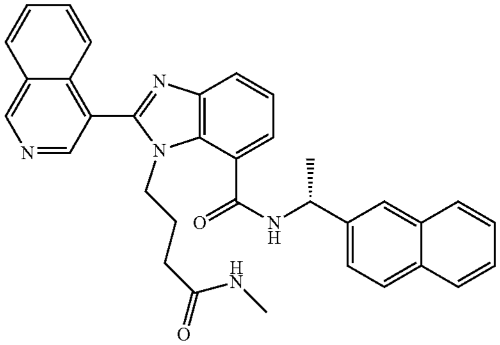 [SMILES: CNC(=O)CCCn1c(-c2cncc3ccccc23)nc2cccc(C(=O)N[C@H](C)c3ccc4ccccc4c3)c21]

(R)-2-(isoquinolin-4-yl)-1-(4-(methylamino)-4-oxobutyl)-N-(1-(naphthalen-2-yl)ethyl)-1H-benzo[d]imidazole-7-carboxamide Molecular Formula: $C_{34}H_{31}N_5O_2$; yield 71%; $^1$H NMR (600 MHZ, $CDCl_3$) δ 9.36 (s, 1H), 8.62 (s, 1H), 8.06 (d, J=7.9 Hz, 1H), 7.95 (d, J=8.0 Hz, 1H), 7.91 (s, 1H), 7.87-7.80 (m, 3H), 7.72-7.70 (m, 2H), 7.68 (dd, J=7.9, 2.8 Hz, 1H), 7.56 (dd, J=8.4, 1.6 Hz, 1H), 7.48 (ddd, J=9.3, 6.5, 2.2 Hz, 3H), 7.33 (t, J=7.8 Hz, 1H), 6.85 (d, J=7.8 Hz, 1H), 5.51 (p, J=7.0 Hz, 1H), 5.03 (s, 1H), 4.18 (dt, J=14.5, 7.2 Hz, 2H), 2.41 (d, J=4.7 Hz, 3H), 1.76 (d, J=6.9 Hz, 5H), 1.70 (dd, J=14.3, 6.9 Hz, 1H), 1.61-1.49 (m, 1H), 1.49-1.37 (m, 2H). $^{13}$C NMR (151 MHZ, $CDCl_3$) δ 171.4, 167.2, 144.9, 140.4, 134.6, 133.3, 132.8, 131.9, 131.4, 128.8, 128.2, 128.1, 127.9, 127.7, 126.5, 126.1, 125.1, 124.6, 124.4, 123.0, 122.8, 122.2, 122.0, 50.0, 45.7, 32.4, 26.0, 26.0, 21.9. HRMS (HESI-TOF) m/z calcd for $(M+H)^+$ 542.2556, found 542.2543.

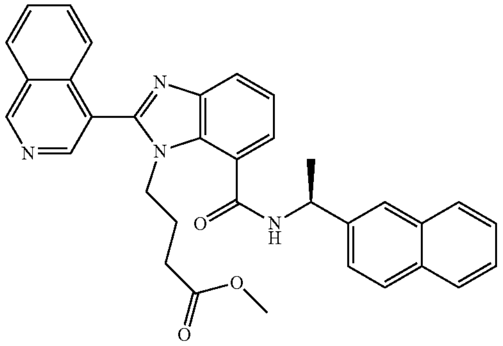 [SMILES: COC(=O)CCCn1c(-c2cncc3ccccc23)nc2cccc(C(=O)N[C@@H](C)c3ccc4ccccc4c3)c21]

Methyl(S)-4-(2-(isoquinolin-4-yl)-7-((1-(naphthalen-2-yl)ethyl)carbamoyl)-1H-benzo[d]imidazol-1-yl) butanoate Molecular Formula: $C_{34}H_{30}N_4O_3$; yield 53%; $^1$H NMR (600 MHZ, $CDCl_3$) δ 9.41 (s, 1H), 8.73 (s, 1H), 8.11 (d, J=8.0 Hz, 1H), 8.00 (d, J=8.0 Hz, 1H), 7.90-7.81 (m, 4H), 7.74 (d, J=3.6 Hz, 2H), 7.71 (dd, J=8.3, 3.9 Hz, 1H), 7.55 (d, J=8.4 Hz, 1H), 7.51-7.45 (m, 3H), 7.37 (t, J=7.8 Hz, 1H), 6.59 (d, J=7.2 Hz, 1H), 5.56-5.49 (m, 1H), 4.29 (s, 2H), 3.30 (s, 2H), 1.76 (d, J=6.9 Hz, 3H), 1.71 (d, J=11.0 Hz, 2H), 1.62-1.56 (m, 2H). $^{13}$C NMR (151 MHZ, $CDCl_3$) δ 172.4, 167.1, 154.6, 152.0, 145.1, 144.7, 140.2, 134.8, 133.5, 133.0, 132.1, 131.5, 128.9, 128.3, 128.2, 128.0, 127.8, 126.6, 126.2, 125.1, 124.7, 124.5, 123.2, 122.8, 122.4, 122.2, 122.0, 51.6, 49.9, 45.6, 30.3, 25.5, 21.9.

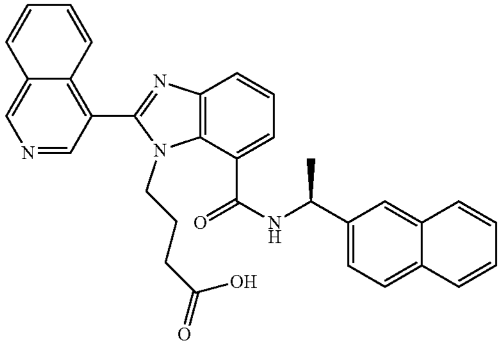 [SMILES: C[C@H](NC(=O)c1cccc2nc(-c3cncc4ccccc34)n(CCCC(=O)O)c12)c1ccc2ccccc2c1]

(S)-4-(2-(isoquinolin-4-yl)-7-((1-(naphthalen-2-yl) ethyl)carbamoyl)-1H-benzo[d]imidazol-1-yl)butanoic acid Molecular Formula: $C_{33}H_{28}N_4O_3$; yield 11%; $^1$H NMR (600 MHZ, $CD_3OD$) δ 9.39 (s, 1H), 8.63 (s, 1H), 8.20 (d, J=8.0 Hz, 1H), 7.88 (d, J=8.2 Hz, 2H), 7.84-7.70 (m, 5H), 7.63 (d, J=8.3 Hz, 1H), 7.57 (d, J=7.6 Hz, 2H), 7.43-7.35 (m, 3H), 5.42 (q, J=6.8 Hz, 1H), 4.09 (s, 2H), 3.27 (s, 2H), 1.65 (d, J=7.0 Hz, 3H), 1.58 (d, J=6.9 Hz, 2H), 1.50-1.46 (m, 2H). $^{13}$C NMR (151 MHZ, $CD_3OD$) δ 168.0, 154.5, 151.4, 143.7, 141.1, 134.6, 133.5, 132.8, 132.5, 130.8, 128.5, 128.4, 128.2, 127.5, 127.3, 125.9, 125.5, 124.6, 124.4, 123.7, 123.5, 122.6, 122.4, 121.9, 121.3, 49.8, 48.5, 45.3, 25.3, 20.9. HRMS (HESI-TOF) m/z calcd for $(M+H)^+$ 529.2261, found 529.2216.

```
Sequence Listing
                                   SEQ ID NO: 1
GGTGGCTCATATGTCGGCAGTGCTGCAATCCGGCTTTCGCAAAATGGC

                                   SEQ ID NO: 2
GCCACCTGGATCCTTAATGATGATGATGATGATGGGGACCCTGGAAGG

TTACACCAGAG

                                   SEQ ID NO: 3
SAVLQSGFRK

                                   SEQ ID NO: 4
SGFTFQGP

                                   SEQ ID NO: 5
KTSAVLQSGFRKME

                                   SEQ ID NO: 6
ACACTTGCTGGT

                                   SEQ ID NO: 7
CAGCAAGTGTGA

                                   SEQ ID NO: 8
TATGATACTAAAGTAAGTCACACACAATTGGAGCAGTCCTGAGTGAAT

ACCTGCAT

                                   SEQ ID NO: 9
ATGCAGGTATTCACTGAGGACTGCTCCAATTGTGTGTGACTTACTTTA

GTATCATATC
```

Enumerated Embodiments

The following exemplary embodiments are provided, the number of which is not to be construed as designating levels of importance:

Embodiment 1 provides a compound of formula (I), or a salt, solvate, stereoisomer, tautomer, isotopically labelled derivative, or geometric isomer thereof:

(I)

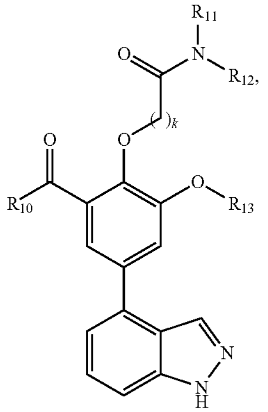

wherein:

$R_{10}$ is selected from the group consisting of H, D, OH, and $C_1$-$C_6$ hydroxyalkyl; and $R_{11}$ and $R_{12}$ are each independently $C_1$-$C_6$ alkyl; or $R_{11}$ and $R_{12}$ combine with the N atom to which they are bound to form an optionally substituted heterocyclyl;

$R_{13}$ is $C_1$-$C_6$ alkyl; and k is an integer from 1 to 10.

Embodiment 2 provides the compound of Embodiment 1, wherein k is 1.

Embodiment 3 provides the compound of Embodiment 1 or 2, wherein $R_{10}$ is $(CH_2)_n$—OH and n is 1.

Embodiment 4 provides the compound of any one of Embodiments 1-3, wherein $R_{11}$ and $R_{12}$ combine with the N atom to which they are bound to form a pyrrolidine ring substituted with

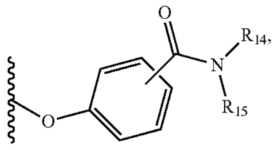

wherein $R_{14}$ and $R_{15}$ are each independently $C_1$-$C_6$ alkyl.

Embodiment 5 provides the compound of any one of Embodiments 1-4, wherein one of the following applies:

(i) $R_{11}$ and $R_{12}$ are each methyl; or (ii) $R_{11}$ and $R_{12}$, together with the nitrogen atom to which they are attached, combine to form

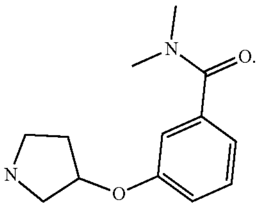 [SMILES: CN(C)C(=O)c1cccc(OC2CCNC2)c1]

Embodiment 6 provides the compound of any one of Embodiments 1-5, wherein $R_{13}$ is methyl.

Embodiment 7 provides the compound of any one of Embodiments 1-6, wherein the compound is selected from the group consisting of:

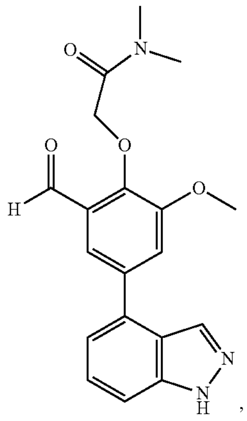

-continued

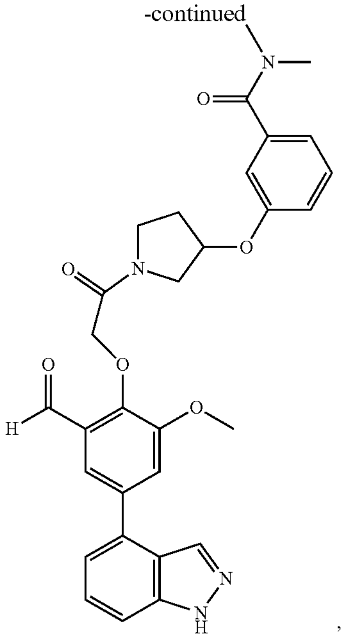

, and

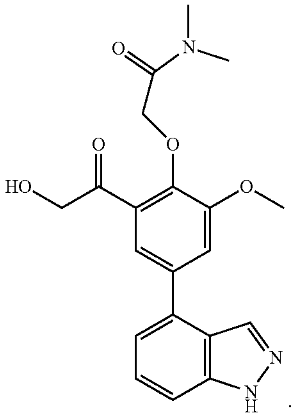

Embodiment 8 provides a compound of formula (II), or a salt, solvate, stereoisomer, tautomer, isotopically labelled derivative, or geometric isomer thereof:

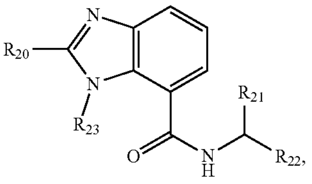

(II)

wherein:

$R_{20}$ is selected from the group consisting of

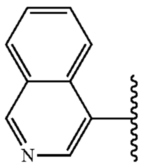 [SMILES: *c1cncc2ccccc12]

and $C_5$ heteroaryl optionally substituted with $C_1$-$C_6$ alkyl;

$R_{21}$ is selected from the group consisting of H, D, and $C_1$-$C_{12}$ alkyl;

$R_{22}$ is selected from the group consisting of unsubstituted $C_6$-$C_{12}$ aryl, unsubstituted $C_4$-$C_{10}$ heteroaryl, and phenyl substituted with one or more substituents selected from the group consisting of $CF_3$, $CCl_3$, $CBr_3$, $CI_3$, $C_1$-$C_6$ alkyl, and $C_1$-$C_6$ haloalkoxy;

$R_{23}$ is selected from $(CH_2)_mC(=O)NHR_{24}$, $(CH_2)_nC(=O)OH$, $(CH_2)_pC(=O)OR_{24}$, $C_3$-$C_7$ cycloalkyl, and $C_3$-$C_7$ heterocyclyl, wherein the $C_3$-$C_7$ cycloalkyl and the $C_3$-$C_7$ heterocyclyl are each optionally substituted with $C(=O)NHR_{25}$;

$R_{24}$ and $R_{25}$ are each independently a $C_1$-$C_6$ alkyl;

m, n, and p are each independently an integer from 1 to 10;

wherein, when $R_{20}$ is an unsubstituted $C_5$ heteroaryl, $R_{23}$ is $(CH_2)_nC(=O)NHR_{24}$; and wherein, when $R_{22}$ is unsubstituted $C_6$ aryl, $R_{21}$ is methyl.

Embodiment 9 provides the compound of Embodiment 8, wherein $R_{20}$ is selected from the group consisting of

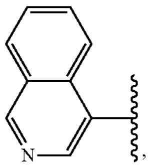
,
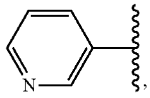
, and
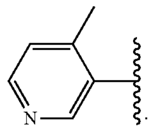
.

Embodiment 10 provides the compound of Embodiment 8 or 9, wherein $R_{21}$ is selected from methyl, ethyl, or propyl.

Embodiment 11 provides the compound of any one of Embodiments 8-10, wherein $R_{22}$ is phenyl monosubstituted with $CF_3$, methyl, or $OCHF_2$.

Embodiment 12 provides the compound of any one of Embodiments 8-11, wherein one of the following applies:

(i) $R_{22}$ is phenyl;

(ii) $R_{22}$ is 2-naphthyl;

(iii) $R_{22}$ is

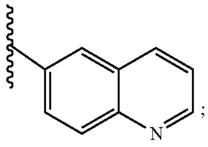 [SMILES: *c1ccc2ncccc2c1]

(iv) $R_{22}$ is

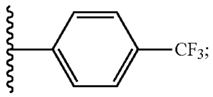 [SMILES: *c1ccc(C(F)(F)F)cc1]

(v) $R_{22}$ is

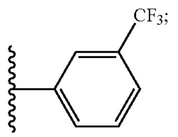 [SMILES: *c1cccc(C(F)(F)F)c1]

(vi) $R_{22}$ is or

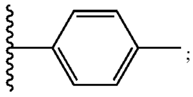 [SMILES: *c1ccc(C)cc1]

(vii) $R_{22}$ is

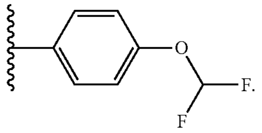 [SMILES: *c1ccc(OC(F)F)cc1]

Embodiment 13 provides the compound of any one of Embodiments 8-12, wherein one of the following applies:

(i) $R_{23}$ is $(CH_2)_mC(=O)NHR_{24}$ wherein m is 3;

(ii) $R_{23}$ is $CH_2)_pC(=O)OR_{24}$ wherein p is 3;

(iii) $R_{23}$ is cyclobutyl monosubstituted with $C(=O)NHR_{25}$ wherein $R_{25}$ is methyl;

(iv) $R_{23}$ is cyclopentyl monosubstituted with $C(=O)NHR_{25}$ wherein $R_{25}$ is methyl; or (v) $R_{23}$ is a saturated $C_5$ heterocyclyl comprising one nitrogen atom.

Embodiment 14 provides the compound of any one of Embodiments 8-13, wherein one of the following applies:

(i) $R_{23}$ is $(CH_2)_mC(=O)NHR_{24}$ wherein m is 3 and $R_{24}$ is methyl;

(ii) $R_{23}$ is $CH_2)_pC(=O)OR_{24}$ wherein p is 3 and $R_{24}$ is methyl;

(iii) $R_{23}$ is $(CH_2)_nC(=O)OH$ wherein n is 3;

(iv) $R_{23}$ is cyclobutyl;

(v) $R_{23}$ is

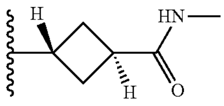
or
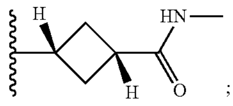
;

(vi) $R_{23}$ is or

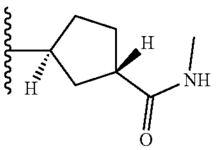
or
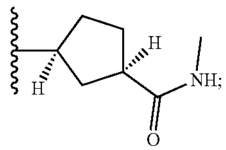

(vii) $R_{23}$ is

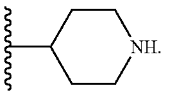 [SMILES: *C1CCNCC1]

Embodiment 15 provides the compound of any one of Embodiments 8-14, wherein the compound is selected from the group consisting of:

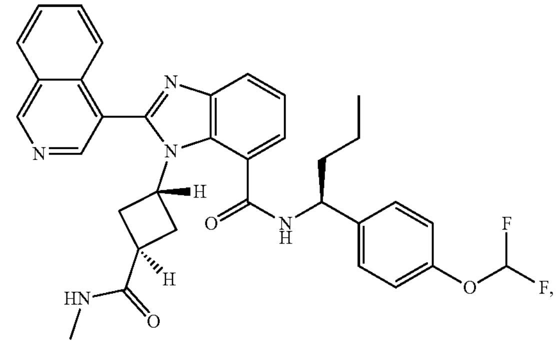
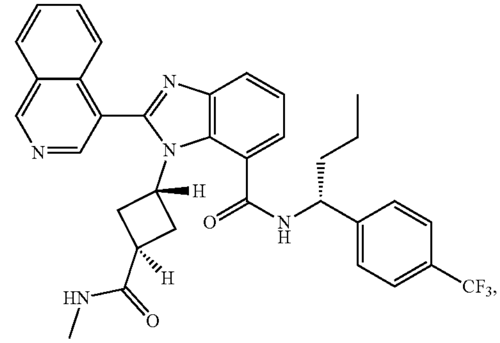
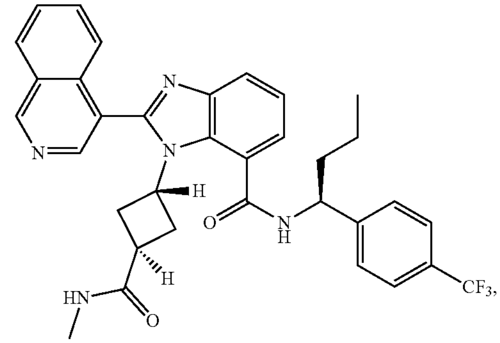
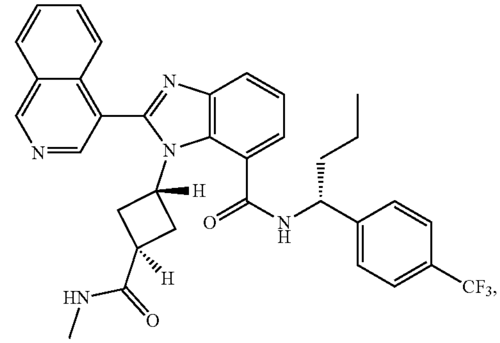
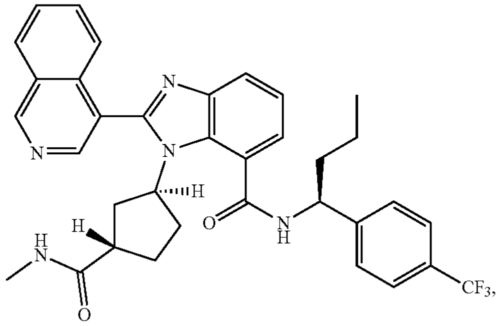
-continued
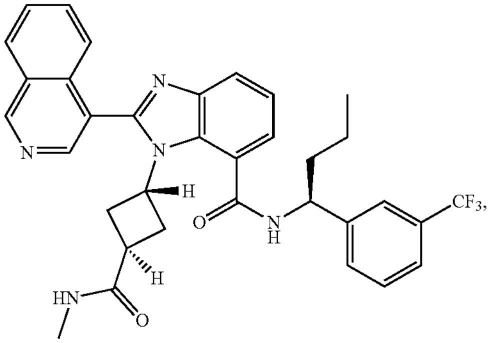
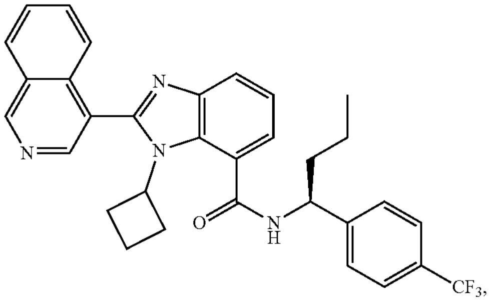
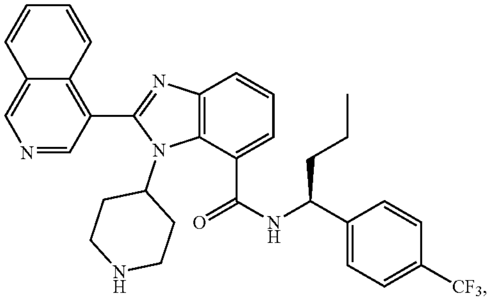
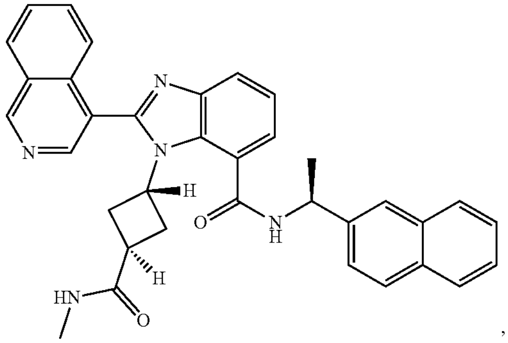
,
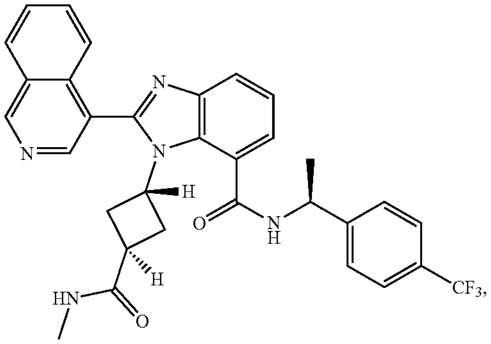

-continued
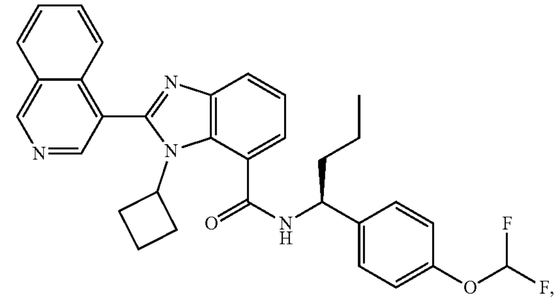
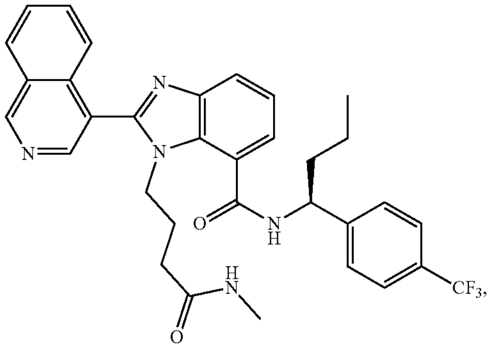
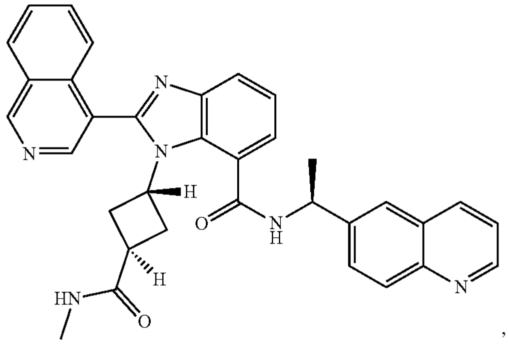
,
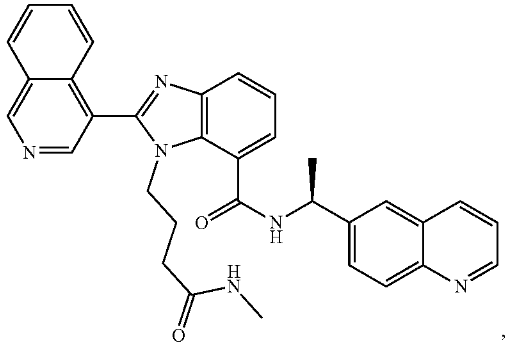
,
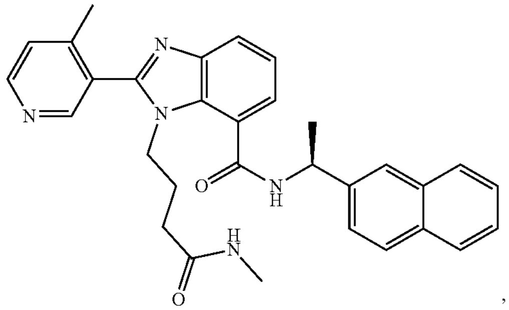
,
-continued
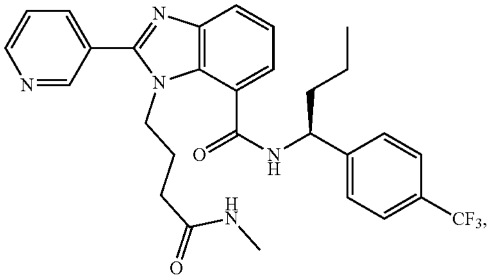
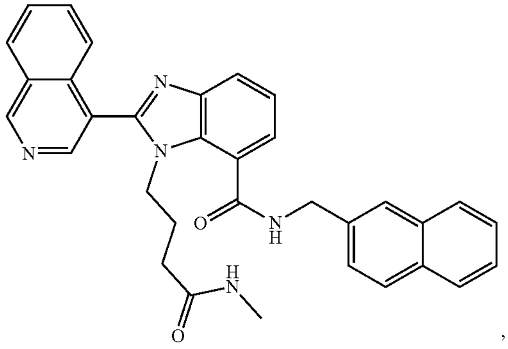
,
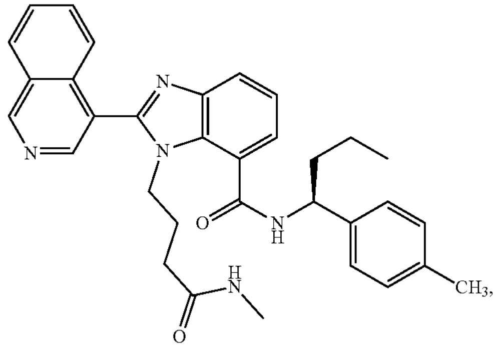
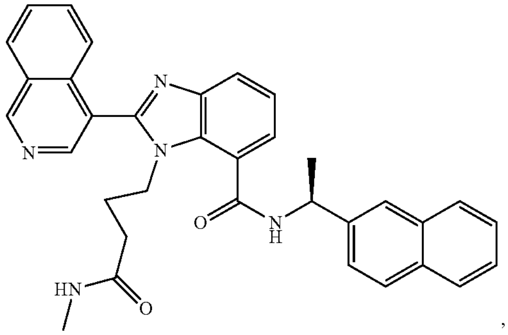
,
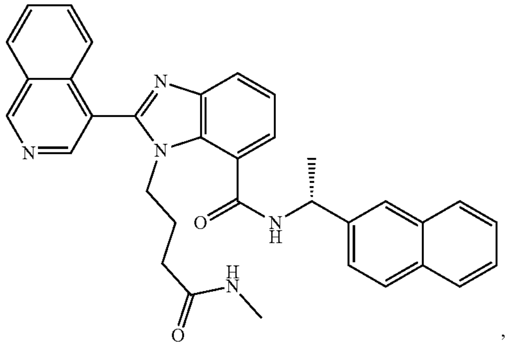
, -continued

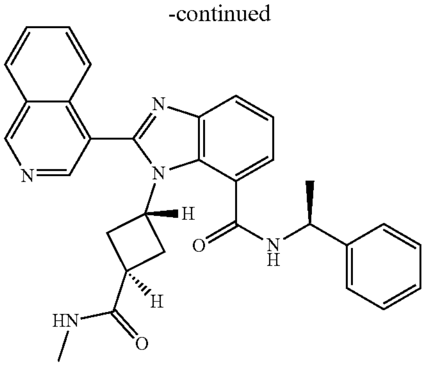

,

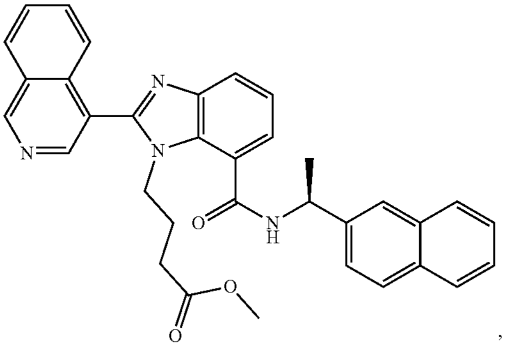

, and

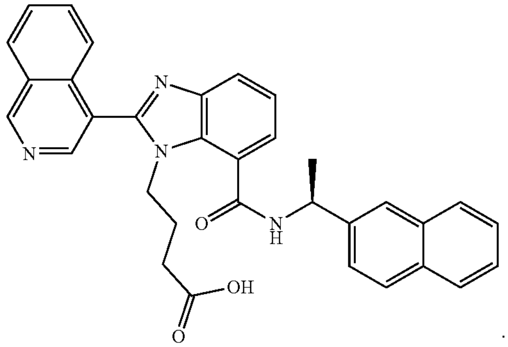

.

Embodiment 16 provides a pharmaceutical composition comprising at least one compound of any one of Embodiments 1-15 and a pharmaceutically acceptable carrier.

Embodiment 17 provides the pharmaceutical composition of Embodiment 16, further comprising at least one additional agent useful for treating, ameliorating, and/or preventing a coronavirus infection.

Embodiment 18 provides a method of treating, ameliorating, and/or preventing a coronavirus infection in a subject, the method comprising administering to the subject a therapeutically effective amount of at least one compound of any one of Embodiments 1-15 and/or at least one pharmaceutical composition of any one of Embodiments 16-17.

Embodiment 19 provides the method of Embodiment 18, wherein the coronavirus is at least one of 229E, NL63, OC43, HKU1, MERS-COV, SARS-COV, and SARS-COV-2.

Embodiment 20 provides the method of Embodiment 18 or 19, wherein the coronavirus is SARS-COV-2.

Embodiment 21 provides the method of any one of Embodiments 18-20, wherein the compound is administered orally or intravenously to the subject.

Embodiment 22 provides the method of any one of Embodiments 18-21, wherein the compound inhibits the coronavirus main protease ($M^{pro}$).

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A compound of formula (I), or a salt, solvate, stereoisomer, tautomer, isotopically labelled derivative, or geometric isomer thereof:

(I)

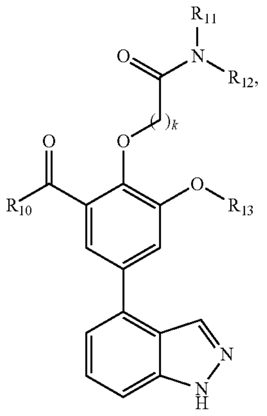

wherein:

$R_{10}$ is selected from the group consisting of H, D, OH, and $C_1$-$C_6$ hydroxyalkyl; and $R_{11}$ and $R_{12}$ are each independently $C_1$-$C_6$ alkyl; or $R_{11}$ and $R_{12}$ combine with the N atom to which they are bound to form an optionally substituted heterocyclyl;

$R_{13}$ is $C_1$-$C_6$ alkyl; and k is 1, 2, 3, 4, 5, 6, 7, 8, 9, or 10.

2. The compound of claim 1, wherein k is 1.

3. The compound of claim 1, wherein $R_{10}$ is $(CH_2)_n$-OH and n is 1.

4. The compound of claim 1, wherein $R_{11}$ and $R_{12}$ combine with the N atom to which they are bound to form a pyrrolidine ring substituted with

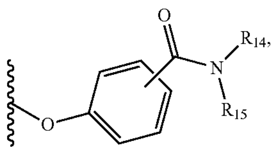

wherein $R_{14}$ and $R_{15}$ are each independently $C_1$-$C_6$ alkyl.

5. The compound of claim 1, wherein one of the following applies:

(i) $R_{11}$ and $R_{12}$ are each methyl; or (ii) $R_{11}$ and $R_{12}$, together with the nitrogen atom to which they are attached, combine to form

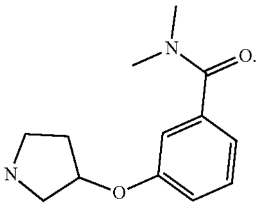 [SMILES: CN(C)C(=O)c1cccc(OC2CCNC2)c1]

6. The compound of claim 1, wherein $R_{13}$ is methyl.

7. The compound of claim 1, wherein the compound is selected from the group consisting of:

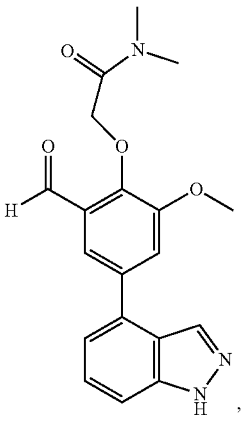

,

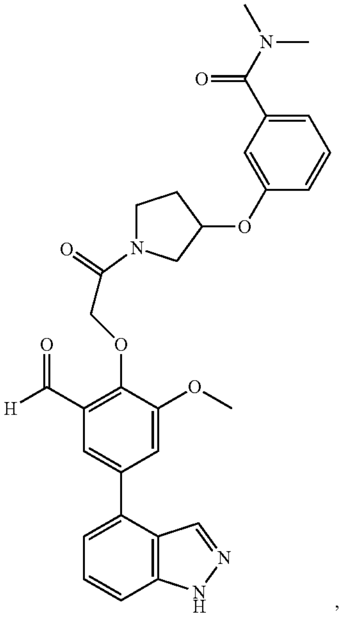

, and

-continued

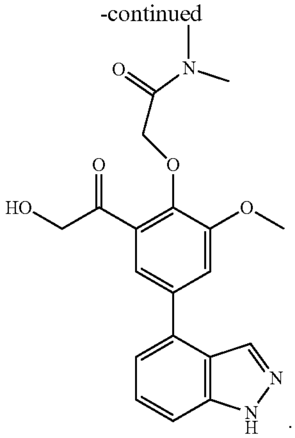

.

8. A compound of formula (II), or a salt, solvate, stereoisomer, tautomer, isotopically labelled derivative, or geometric isomer thereof:

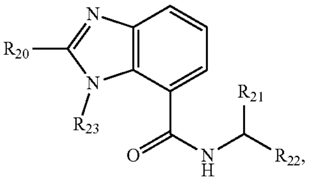

(II)

wherein:

$R_{20}$ is selected from the group consisting of

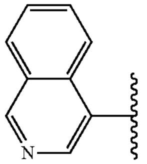 [SMILES: *c1cncc2ccccc12]

and $C_5$ heteroaryl optionally substituted with $C_1$-$C_6$ alkyl;

$R_{21}$ is selected from the group consisting of H, D, and $C_1$-$C_{12}$ alkyl;

$R_{22}$ is selected from the group consisting of unsubstituted $C_6$-$C_{12}$ aryl, unsubstituted $C_4$-$C_{10}$ heteroaryl, and phenyl substituted with one or more substituents selected from the group consisting of $CF_3$, $CCl_3$, $CBr_3$, $Cl_3$, $C_1$-$C_6$ alkyl, and $C_1$-$C_6$ haloalkoxy;

$R_{23}$ is selected from the group consisting of $(CH_2)_mC({=}O)NHR_{24}$, $(CH_2)_nC({=}O)OH$, $(CH_2)_pC({=}O)OR_{24}$, $C_3$-$C_7$ cycloalkyl, and $C_3$-$C_7$ heterocyclyl, wherein the $C_3$-$C_7$cycloalkyl and the $C_3$-$C_7$ heterocyclyl are each optionally substituted with $C({=}O)NHR_{25}$;

$R_{24}$ and $R_{25}$ are each independently a-$C_1$-$C_6$ alkyl;

m, n, and p are each independently 1, 2, 3, 4, 5, 6, 7, 8, 9, or 10;

wherein, when $R_{20}$ is an unsubstituted Cs heteroaryl, $R_{23}$ is $(CH_2)_nC({=}O)NHR_{24}$; and wherein, when $R_{22}$ is unsubstituted $C_6$ aryl, $R_{21}$ is methyl.

9. The compound of claim 8, wherein $R_{20}$ is selected from the group consisting of:

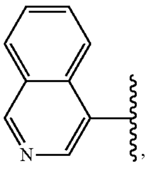, 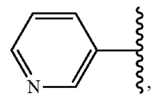, and 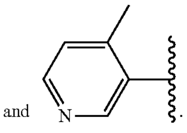.

10. The compound of claim 8 er 9, wherein at least one of the following applies:

(a) $R_{21}$ is selected from the group consisting of methyl, ethyl, or propyl; and (b) $R_{22}$ is phenyl monosubstituted with $CF_3$, methyl, or $OCHF_2$.

11. The compound of claim 8, wherein one of the following applies:

(i) $R_{22}$ is phenyl;

(ii) $R_{22}$ is 2-naphthyl;

(iii) $R_{22}$ is

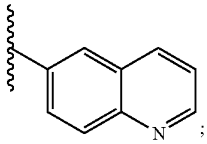 [SMILES: *c1ccc2ncccc2c1];

(iv) $R_{22}$ is

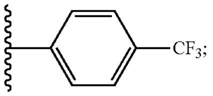 [SMILES: *c1ccc(C(F)(F)F)cc1]

(v) $R_{22}$ is

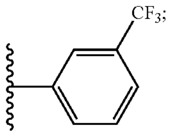 [SMILES: *c1cccc(C(F)(F)F)c1]

(v) $R_{22}$ is

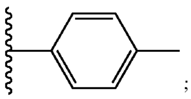;

or (vii) $R_{22}$ is

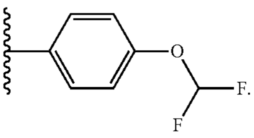 [SMILES: *c1ccc(OC(F)F)cc1]

12. The compound of claim 8, wherein one of the following applies:

(i) $R_{23}$ is $(CH_2)_mC(=O)NHR_{24}$ wherein m is 3;

(ii) $R_{23}$ is $(CH_2)_pC(=O)OR_{24}$ wherein p is 3;

(iii) $R_{23}$ is cyclobutyl monosubstituted with $C(=O)NHR_{25}$ wherein $R_{25}$ is methyl;

(iv) $R_{23}$ is cyclopentyl monosubstituted with $C(=O)NHR_{25}$ wherein $R_{25}$ is methyl; or (v) $R_{23}$ is a-saturated Cs heterocyclyl comprising one nitrogen atom.

13. The compound of claim 8, wherein one of the following applies:

(i) $R_{23}$ is $(CH_2)_mC(=O)NHR_{24}$ wherein m is 3 and $R_{24}$ is methyl;

(ii) $R_{23}$ is $(CH_2)_pC(=O)OR_{24}$ wherein p is 3 and $R_{24}$ is methyl;

(iii) $R_{23}$ is $(CH_2)_nC(=O)OH$ wherein n is 3;

(iv) $R_{23}$ is cyclobutyl;

(v) $R_{23}$ is

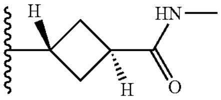 or 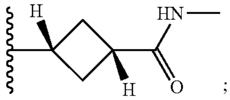;

(vi) $R_{23}$ is

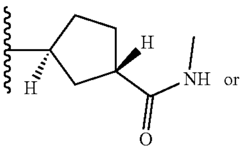 or 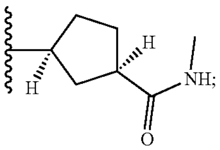;

or (vii) $R_{23}$ is

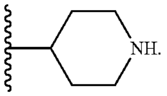 [SMILES: *C1CCNCC1].

14. The compound of claim 8, wherein the compound is selected from the group consisting of:

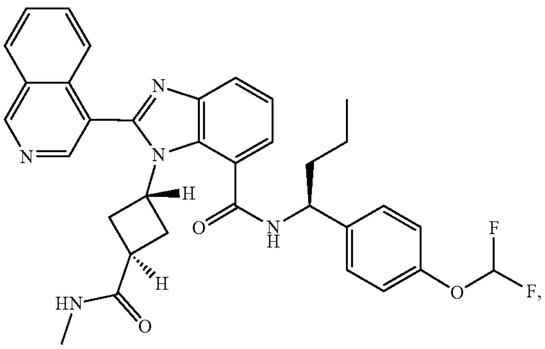,

-continued
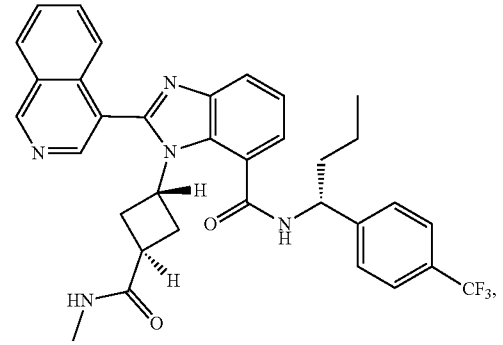
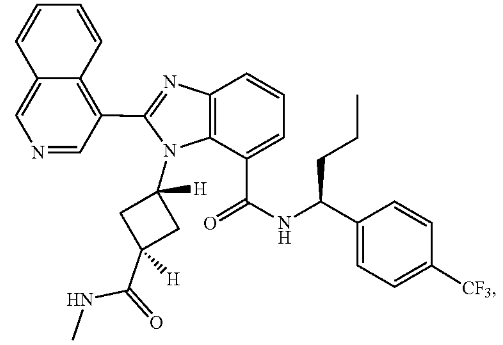
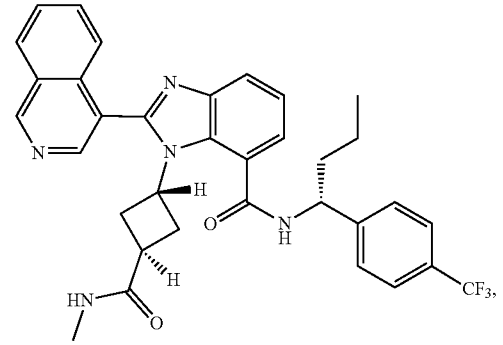
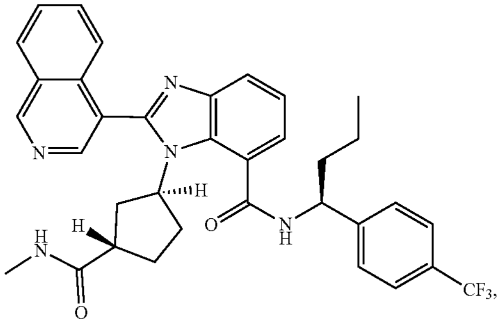
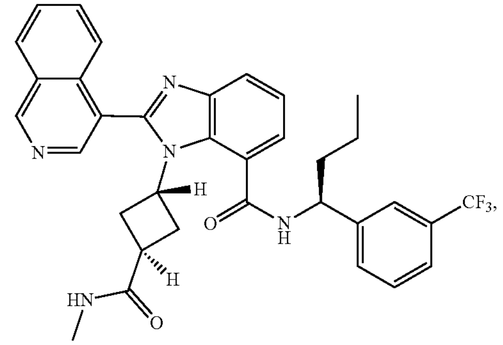
-continued
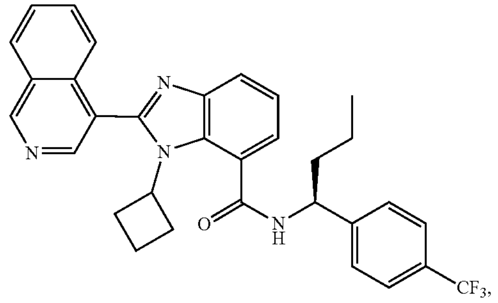
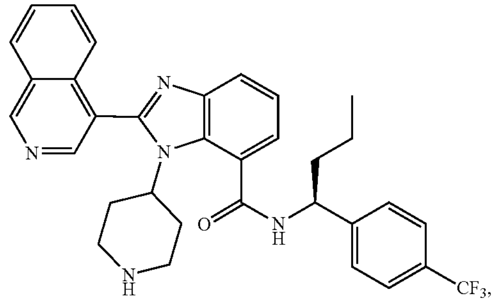
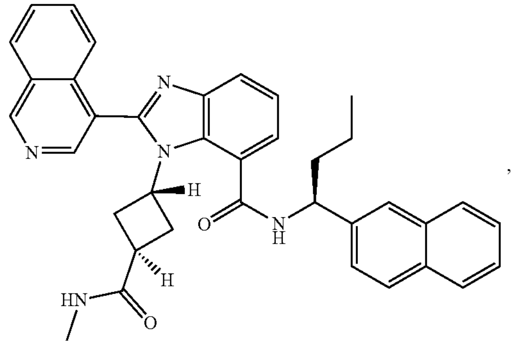
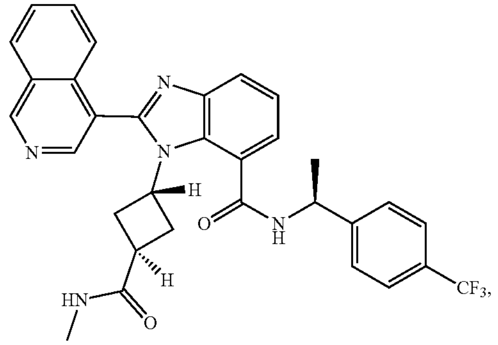
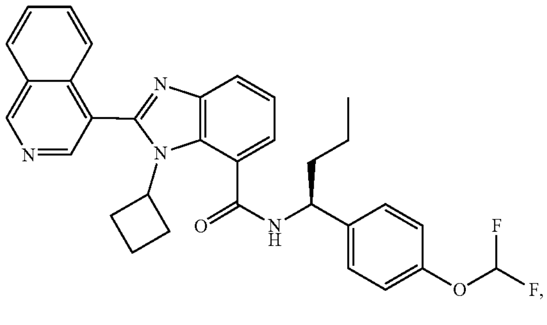

-continued
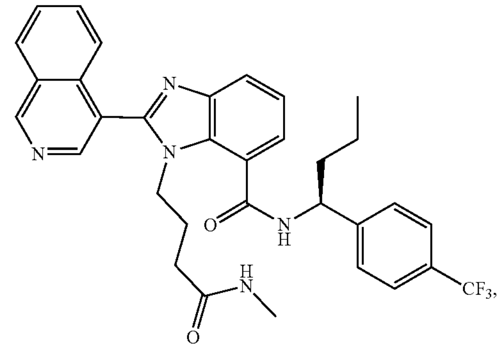
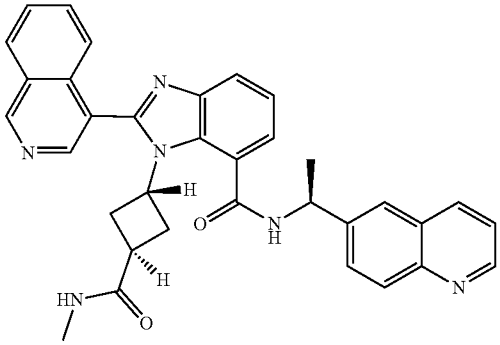
,
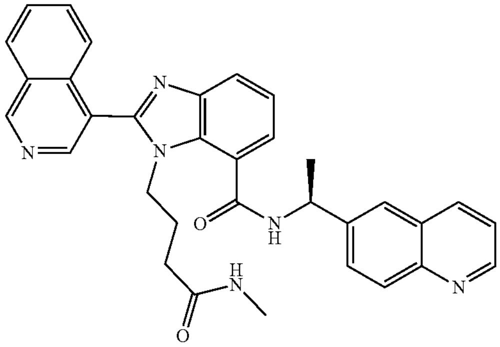
,
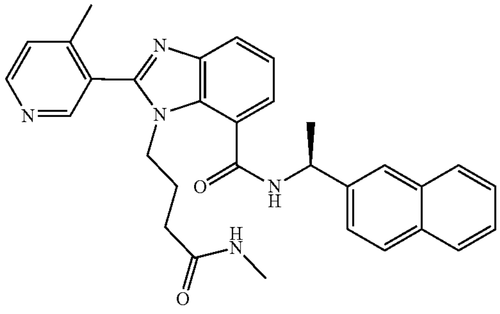
,
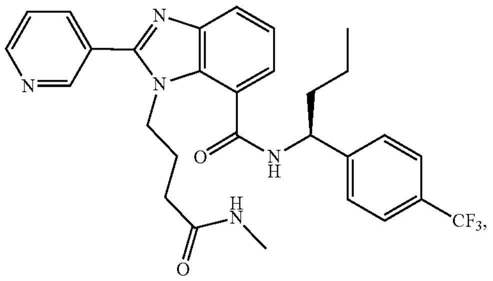
-continued
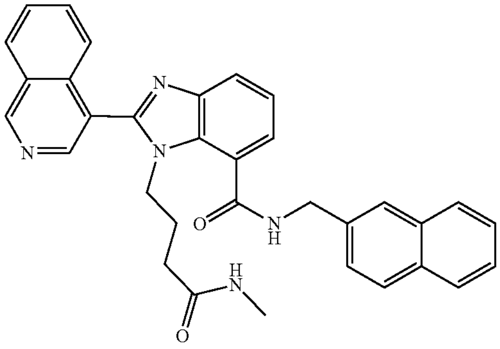
,
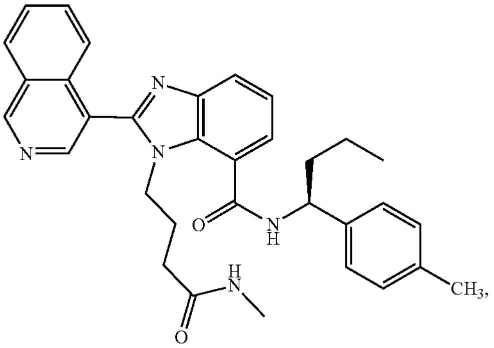
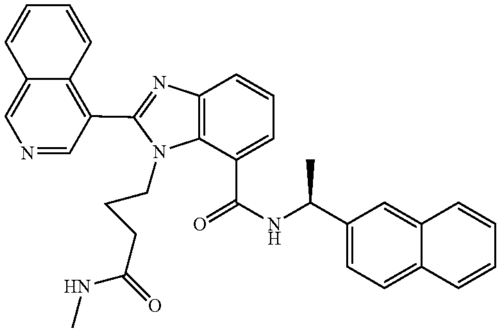
,
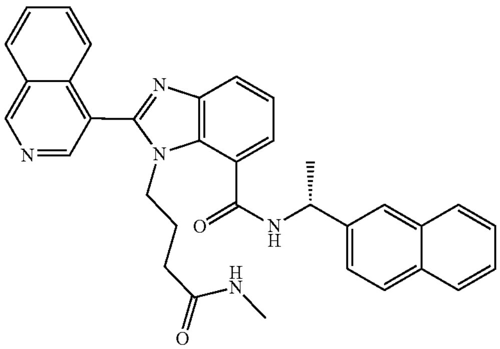
, -continued

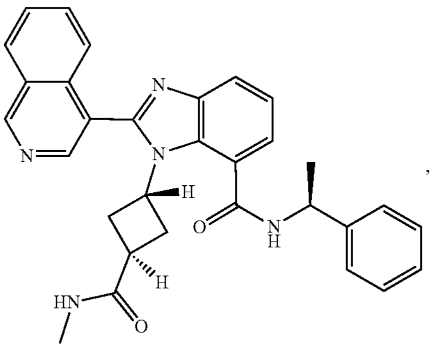

,

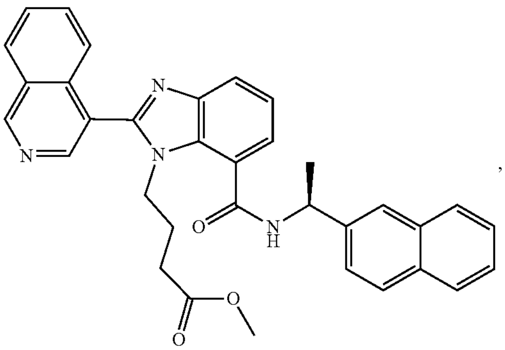

, and

-continued

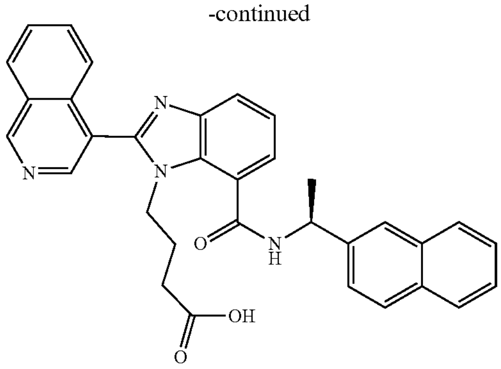

.

15. A pharmaceutical composition comprising at least one compound of claim 1 and a pharmaceutically acceptable carrier.

16. The pharmaceutical composition of claim 15, further comprising at least one additional agent useful for treating, ameliorating, or preventing a coronavirus infection.

17. A method of treating, ameliorating, or preventing a coronavirus infection in a subject, the method comprising administering to the subject a therapeutically effective amount of at least one compound of 1 and/or a pharmaceutical composition thereof.

18. The method of claim 17, wherein the coronavirus is at least one of 229E, NL63, OC43, HKU1, MERS-COV, SARS-COV, and SARS-COV-2.

19. The method of claim 17, wherein the compound is administered orally or intravenously to the subject.

20. The compound of claim 17, wherein the compound inhibits the coronavirus main protease ($M^{pro}$).

* * * * *